(12) United States Patent
Koike et al.

(10) Patent No.: US 8,110,585 B2
(45) Date of Patent: Feb. 7, 2012

(54) BICYCLIC COMPOUND AND PHARMACEUTICAL USE THEREOF

(75) Inventors: Tatsuki Koike, Osaka (JP); Takafumi Takai, Osaka (JP); Yasutaka Hoashi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 119 days.

(21) Appl. No.: 12/451,090

(22) PCT Filed: Apr. 25, 2008

(86) PCT No.: PCT/JP2008/058020
§ 371 (c)(1),
(2), (4) Date: Oct. 26, 2009

(87) PCT Pub. No.: WO2008/136382
PCT Pub. Date: Nov. 13, 2008

(65) Prior Publication Data
US 2010/0130538 A1    May 27, 2010

(30) Foreign Application Priority Data
Apr. 26, 2007  (JP) ................ 2007/117676

(51) Int. Cl.
*A61K 31/416*  (2006.01)
*A61K 31/428*  (2006.01)
*A61K 31/437*  (2006.01)
*C07D 231/54*  (2006.01)
*C07D 277/64*  (2006.01)
*C07D 471/04*  (2006.01)

(52) U.S. Cl. ..... 514/300; 514/367; 514/406; 548/362.5; 548/180; 546/121

(58) Field of Classification Search .......... None
See application file for complete search history.

(56) References Cited

U.S. PATENT DOCUMENTS

| | | | |
|---|---|---|---|
| 5,856,529 A | 1/1999 | Catt et al. | |
| 5,981,571 A | 11/1999 | Catt et al. | |
| 6,060,506 A | 5/2000 | Catt et al. | |
| 6,211,225 B1 | 4/2001 | Takaki et al. | |
| 6,214,869 B1 | 4/2001 | Chen et al. | |
| 6,569,894 B1 | 5/2003 | Takaki et al. | |
| 2003/0216456 A1 | 11/2003 | Takaki et al. | |
| 2007/0021426 A1 | 1/2007 | Abouabdellah et al. | |

FOREIGN PATENT DOCUMENTS

| | | |
|---|---|---|
| RU | 2 364 586 | 4/2008 |
| WO | 97/43272 | 11/1997 |
| WO | 98/25606 | 6/1998 |
| WO | 99/62515 | 12/1999 |
| WO | 02/083863 | 10/2002 |
| WO | 03/086393 | 10/2003 |
| WO | 2004/037250 | 5/2004 |
| WO | 2007/036733 | 4/2007 |
| WO | 2008/104055 | 9/2008 |

OTHER PUBLICATIONS

Arendt, et al. Brit. J. Psy. 193:267-9 (2008).*
Hardeland, et al. Arzneimittelforschung, 58:1-10 (2008) (Abstract).*
Altun, et al. Int. J. Clin. Prac. 5:835-45 (2007) (Abstract).*
English translation of the International Preliminary Report on Patentability, Nov. 10, 2009.
Supplementary European Search Report issued Mar. 1, 2011 in European Application No. 08752094.6.
International Search Report issued May 27, 2008 in International (PCT) Application No. PCT/JP2008/058020.
L. Sun et al., "Design and synthesis of benzoxazole derivatives as novel melatoninergic ligands", Bioorganic & Medicinal Chemistry Letters, vol. 14, No. 5, pp. 1197-1200, 2004.
C. Marot et al., "Pharmacophoric Search and 3D-QSAR Comparative Molecular Field Analysis Studies on Agonists of Melatonin Sheep Receptors", J. Med. Chem., vol. 41, pp. 4453-4465, 1998.
P. A. Witt-Enderby et al., "Melatonin Receptors and Ligands", Vitamins and Hormones, vol. 58, pp. 321-354, 2000.
L. Sun et al., "Synthesis and structure-activity relationship of novel benzoxazole derivatives as melatonin receptor agonists", Bioorganic & Medicinal Chemistry Letters, vol. 14, No. 14, pp. 3799-3802, 2004.
Notice of Opposition dated Apr. 23, 2010 in corresponding Costa Rican Patent Application No. 11084.
Search Report issued in the Georgian Patent Application No. AP 2008 011573 and its English translation, Oct. 13, 2010.

* cited by examiner

*Primary Examiner* — Yong Chu
*Assistant Examiner* — Michael Barker
(74) *Attorney, Agent, or Firm* — Wenderoth, Lind & Ponack, L.L.P.

(57) ABSTRACT

The present invention provides a compound represented by the formula

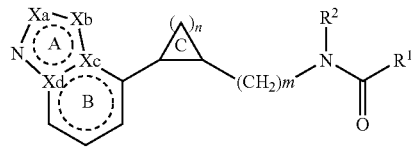

wherein $R^1$ is a hydrocarbon group optionally having substituent(s), amino optionally having substituent(s), hydroxy optionally having a substituent or a heterocyclic group optionally having substituent(s); $R^2$ is a hydrogen atom or a hydrocarbon group optionally having substituent(s); Xa and Xb are each C, N, O or S; Xc and Xd are each C or N; m is 0-2; n is 1-3; ring A is a 5-membered ring optionally having substituent(s); ring B is a 6-membered ring optionally having substituent(s); and ring C is a 3- to 5-membered ring optionally having substituent(s), provided that when Xa, Xc and Xd are each C, then Xb is N or S, or a salt thereof, which is useful as an agent for the prophylaxis or treatment of a disease relating to an action of melatonin, and the like.

17 Claims, No Drawings

BICYCLIC COMPOUND AND PHARMACEUTICAL USE THEREOF

This application is a U.S. national stage of International Application No. PCT/JP2008/058020 filed Apr. 25, 2008.

TECHNICAL FIELD

The present invention relates to a bicyclic compound having superior affinity for melatonin receptor, and useful as an agent for the prophylaxis or treatment of a disease related to the action of melatonin.

BACKGROUND OF THE INVENTION

Melatonin (N-acetyl-5-methoxytryptamine), which is a hormone synthesized and secreted principally in the pineal gland, increases in dark environments and decreases in light environments. Melatonin acts suppressively on pigment cells and the female gonads, and acts as a synchronous factor of biological clock while taking part in transmittance of photoperiodic code. Therefore, melatonin is expected to be usable for the treatment of diseases related to melatonin activity, such as reproductive and endocrinic disorders, sleep-awake rhythm disorders, jet-lag syndrome, various disorders related to aging and the like. It has been clarified that the production amount of melatonin decreases with aging and there is a report documenting that retention of the production amount of melatonin could prevent aging itself [Ann. N.Y. Acad. Sci., vol. 719, pages 456-460, (1994) (non-patent document 1)]. However, since melatonin is easily metabolized by metabolic enzymes in vivo [Clinical Examinations, vol. 38, No. 11, pages 282-284 (1994) (non-patent document 2)]. Therefore, melatonin is not entirely suitable as a drug.

WO 98/25606 (patent document 1) describes a compound represented by the formula

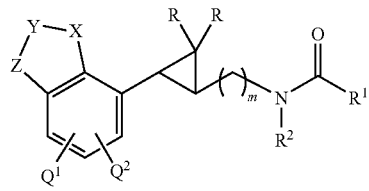

wherein $Q^1$ and $Q^2$ are each independently hydrogen or halogen; X is $CH_2$, CH or oxygen; Y is $CR^3$, $CR^3R^4$ or $(CH_2)n$; n is 1-4; Z is $CH_2$, CH or oxygen; R is hydrogen, halogen or $C_{1-4}$ alkyl in both cases; m is 1 or 2; $R^1$ is $C_{1-6}$ alkyl, $C_{3-6}$ cycloalkyl, $C_{1-3}$ haloalkyl, $C_{1-6}$ alkylamino, $C_{2-6}$ alkenyl, $C_{1-6}$ alkoxy($C_{1-4}$)alkyl, $C_{1-4}$ alkylthio($C_{1-4}$)alkyl or $C_{1-4}$ trifluoromethylalkyl; $R^2$ is hydrogen or $C_{1-4}$ alkyl; and $R^3$ and $R^4$ are each independently hydrogen or $C_{1-4}$ alkyl, or a pharmaceutically acceptable solvate thereof and the like, which is useful as a melatonergic agent.

US 2003/0216456 (patent document 2) describes a compound represented by the formula

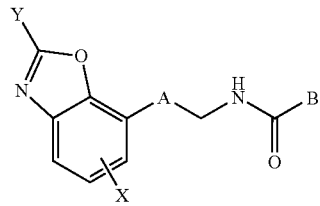

wherein A is $C_{1-4}$ alkylene or 1,2 disubstituted cyclopropyl; B is $C_{1-6}$ alkyl, $C_{3-6}$ cycloalkyl, $C_{1-6}$ alkoxy or $C_{1-4}$ alkylamino; X is hydrogen, halogen, $C_{2-4}$ alkenyl, $C_{1-6}$ alkyl, furyl, or phenyl optionally substituted with halogen, $C_{1-6}$ alkoxy or haloalkyl; and Y is hydrogen, phenyl, or $C_{1-6}$ alkyl optionally substituted with phenyl, or a salt thereof or a pharmaceutically acceptable solvate thereof and the like, which is useful as a melatonergic agent.

Bioorg. Med. Chem. Lett. 2004, vol. 14, pages 1197-1200 (non-patent document 3) describes a compound represented by the formula

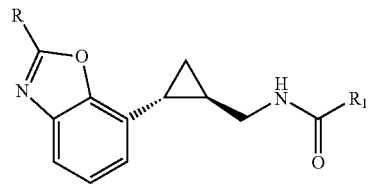

wherein R is $Ph(CH_2)_4$ etc., and $R_1$ is Et etc., and the like, as a melatonergic ligand.

U.S. Pat. No. 6,569,894 (patent document 3) describes a compound represented by the formula

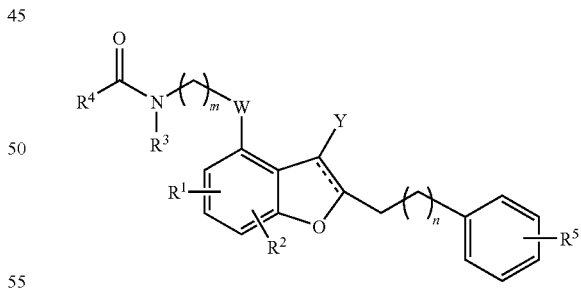

wherein $R^1$ and $R^2$ are each hydrogen or halogen; $R^3$ is hydrogen or $C_{1-4}$ alkyl; $R^4$ is $C_{1-4}$ alkyl, $C_{3-6}$ cycloalkyl, $C_{1-3}$ haloalkyl, $C_{2-6}$ alkenyl, $C_{1-4}$ alkoxy, $C_{1-2}$ trifluoromethylalkyl or $C_{1-4}$ alkylamino; $R^5$ is hydrogen, halogen, $C_{1-4}$ alkyl or $C_{1-4}$ alkoxy; Y is hydrogen or halogen; W is ethylene or 1,2 disubstituted cyclopropyl; m is 1 or 2; and n is 1-9, and the like, which is useful as a melatonergic agent.

Bioorg. Med. Chem. Lett. 2004, vol. 14, pages 3799-3802 (non-patent document 4) describes a compound represented by the formula

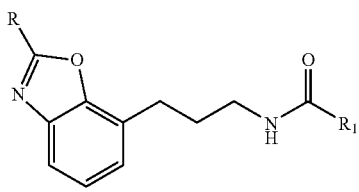

wherein R is Me etc., and $R_1$ is Et, c-Pr etc., and the like, as a melatonin receptor agonist.

WO 99/62515 (patent document 4) describes a compound represented by the formula

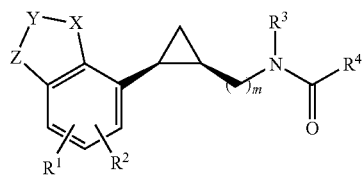

wherein $R^1$ and $R^2$ are each independently hydrogen or halogen; X is $CH_2$, CH or oxygen; Y is $CR^5$, $CR^5R^6$ or $(CH_2)n$; n is 1-2; Z is $CH_2$, CH or oxygen; m is 1 or 2; $R^3$ is hydrogen or $C_{1-4}$ alkyl; $R^4$ is $C_{1-6}$ alkyl, $C_{3-6}$ cycloalkyl, $C_{1-3}$ haloalkyl, $C_{2-6}$ alkenyl, $C_{1-4}$ alkoxy($C_{1-4}$)alkyl, $C_{1-4}$ alkylthio($C_{1-4}$) alkyl or $C_{1-4}$ trifluoromethylalkyl; and $R^5$ and $R^6$ are each independently hydrogen or $C_{1-4}$ alkyl, or a pharmaceutically acceptable solvate thereof and the like, which is useful as a melatonergic agent.

WO 97/32871 (patent document 5) and U.S. Pat. No. 6,034,239 (patent document 6) disclose a compound represented by the formula:

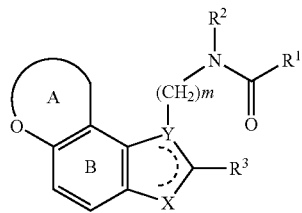

wherein $R^1$ represents an optionally substituted hydrocarbon group, optionally substituted amino or an optionally substituted heterocyclic group; $R^2$ represents a hydrogen atom or an optionally substituted hydrocarbon group; $R^3$ represents a hydrogen atom, an optionally substituted hydrocarbon group or an optionally substituted heterocyclic group; X represents $CHR^4$, $NR^4$, O or S wherein $R^4$ represents a hydrogen atom or an optionally substituted hydrocarbon group; Y represents C, CH or N, provided that when X is $CH_2$, Y is C or CH;
-----is a single bond or a double bond,
ring A represents an optionally substituted 5- to 7-membered oxygen-containing heterocyclic ring; ring B represents an optionally substituted benzene ring; and m represents an integer of 1 to 4, or a salt thereof and the like, which has an affinity for melatonin receptor and is useful as a therapeutic agent for sleep disorder and the like.

patent document 1: WO 98/25606
patent document 2: US 2003/0216456
patent document 3: U.S. Pat. No. 6,569,894
patent document 4: WO 99/62515
patent document 5: WO 97/32871
patent document 6: U.S. Pat. No. 6,034,239
non-patent document 1: Ann. N. Y. Acad. Sci., vol. 719, pages 456-460, 1994
non-patent document 2: Clinical Examinations, vol. 38, No. 11, pages 282-284, 1994
non-patent document 3: Bioorg. Med. Chem. Lett. 2004, vol. 14, pages 1197-1200
non-patent document 4: Bioorg. Med. Chem. Lett. 2004, vol. 14, pages 3799-3802

DISCLOSURE OF THE INVENTION

Melatonin receptor agonists having different structures from that of melatonin, and having superior affinity for melatonin receptor, superior intracerebral mobility and superior metabolic stability are expected to be more effective for the treatment of sleep disorder and the like than melatonin. While the above-mentioned compounds and the like have been reported as melatonin receptor agonists, the development of a novel compound, which is different from the above-mentioned known compounds in the chemical structure, has superior agonistic activity for melatonin receptor, and is useful as a pharmaceutical product, is desired.

The present inventors have conducted various studies and first succeeded in the production of a novel compound represented by the following formula (I) and a salt thereof. They have further found that the compound and a salt thereof unexpectedly have superior properties as melatonin receptor agonists and are useful as pharmaceutical agents and, based on these findings, completed the present invention.

Accordingly, the present invention relates to [1] a compound represented by the formula:

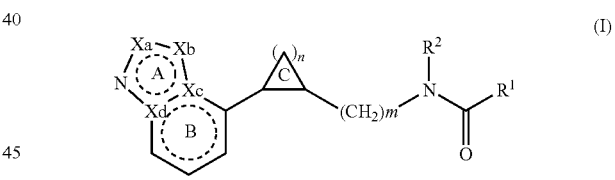

wherein
$R^1$ is a hydrocarbon group optionally having substituent(s), amino optionally having substituent(s), hydroxy optionally having a substituent or a heterocyclic group optionally having substituent(s),
$R^2$ is a hydrogen atom or a hydrocarbon group optionally having substituent(s),
Xa and Xb are each a carbon atom, a nitrogen atom, an oxygen atom or a sulfur atom,
Xc and Xd are each a carbon atom or a nitrogen atom,
m is 0, 1 or 2,
n is 1, 2 or 3,
ring A is a 5-membered ring optionally having substituent(s),
ring B is a 6-membered ring optionally having substituent(s),
ring C is a 3- to 5-membered ring optionally having substituent(s), and
-----is a single bond or a double bond,
provided that when Xa, Xc and Xd are carbon atoms, then Xb is a nitrogen atom or a sulfur atom, or a salt thereof (hereinafter sometimes to be abbreviated as compound (I));

[2] the compound of the aforementioned [1], wherein the bicyclic ring consisting of ring A and ring B is a ring represented by the formula

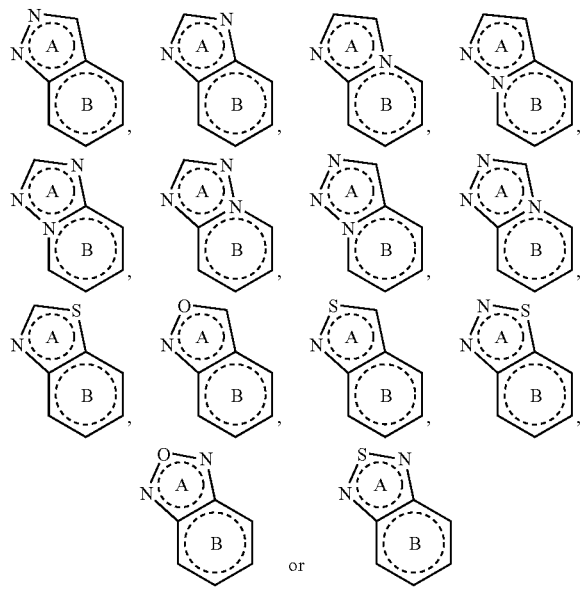

or wherein each symbol is as defined above;

[3] the compound of the aforementioned [1], wherein $R^1$ is $C_{1-6}$ alkyl optionally having substituent(s), $C_{3-6}$ cycloalkyl optionally having substituent(s), $C_{2-6}$ alkenyl optionally having substituent(s), $C_{6-14}$ aryl optionally having substituent(s), amino optionally having substituent(s) or hydroxy optionally having a substituent;

[4] the compound of the aforementioned [1], wherein $R^2$ is a hydrogen atom or $C_{1-6}$ alkyl optionally having substituent(s);

[5] the compound of the aforementioned [1], wherein m is 1;

[6] the compound of the aforementioned [1], wherein n is 1;

[7] the compound of the aforementioned [1], wherein ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;

[8] the compound of the aforementioned [1], wherein ring B is a 6-membered ring optionally having 1 to 3 substituents selected from a halogen atom, cyano, a hydrocarbon group optionally having substituent(s), amino optionally having substituent(s), hydroxy optionally having a substituent, mercapto optionally having a substituent and a heterocyclic group optionally having substituent(s);

[9] the compound of the aforementioned [1], wherein ring C is $C_{3-5}$ cycloalkane optionally having 1 to 4 substituents selected from a hydrocarbon group optionally having substituent(s) and a halogen atom;

[10] N-{[2-(2-methyl-2H-indazol-4-yl)cyclopropyl]methyl}acetamide,
N-{[2-(2-methyl-2H-indazol-4-yl)cyclopropyl]methyl}propanamide,
N-{[2-(2-methylpyrazolo[1,5-a]pyridin-4-yl)cyclopropyl]methyl}acetamide,
N-{[2-(2-methylpyrazolo[1,5-a]pyridin-4-yl)cyclopropyl]methyl}propanamide,
N-{[2-(3-fluoro-2-methyl-2H-indazol-4-yl)cyclopropyl]methyl}acetamide,
N-{[2-(5-fluoro-2-methyl-2H-indazol-4-yl)cyclopropyl]methyl}acetamide,
N-{[2-(7-fluoro-2-methyl-2H-indazol-4-yl)cyclopropyl]methyl}acetamide,
N-{[2-(2-methylpyrazolo[1,5-a]pyridin-4-yl)cyclopropyl]methyl}cyclopropanecarboxamide, or
N-{[2-(2-methyl-1,3-benzothiazol-7-yl)cyclopropyl]methyl}acetamide, or a salt thereof;

[11] a prodrug of the compound of the aforementioned [1];

[12] a pharmaceutical composition comprising the compound of the aforementioned [1] or a prodrug thereof;

[13] the pharmaceutical composition of the aforementioned [12], which is a melatonin receptor agonist;

[14] the pharmaceutical composition of the aforementioned [12], which is an agent for the prophylaxis or treatment of sleep disorder;

[15] a compound represented by the formula

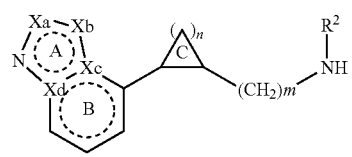

wherein each symbol is as defined in the aforementioned [1], or a salt thereof;

[16] a method for preventing or treating sleep disorder in a mammal, comprising administering an effective amount of the compound of the aforementioned [1] or a salt thereof or a prodrug thereof to the mammal;

[17] use of the compound of the aforementioned [1] or a salt thereof or a prodrug thereof for producing an agent for the prophylaxis or treatment of sleep disorder, and the like.

Since compound (I) shows superior affinity for melatonin receptors, superior pharmacokinetics (e.g., metabolic stability) and the like, a clinically useful agent for the prophylaxis or treatment of diseases related to the action of melatonin in the living body can be provided.

The formula (I) encompasses the following formulas.

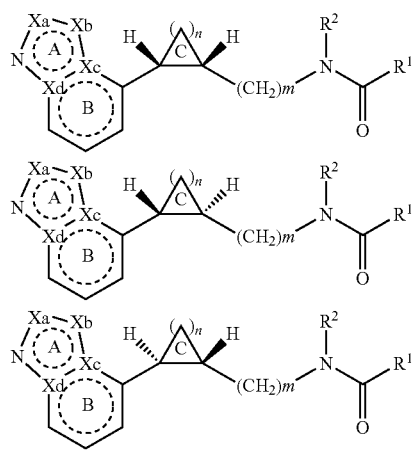

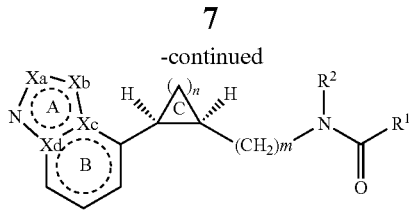

The term "halogen atom" used in the present specification includes fluorine, chlorine, bromine and iodine.

Examples of the term "$C_{1-6}$ alkyl" used in the present specification include methyl, ethyl, propyl, isopropyl, butyl, isobutyl, sec-butyl, tert-butyl, pentyl, hexyl and the like.

Examples of the term "$C_{2-6}$ alkenyl" used in the present specification include vinyl, 1-propenyl, allyl, isopropenyl, butenyl, isobutenyl and the like.

Examples of the term "$C_{2-6}$ alkynyl" used in the present specification include ethynyl, propargyl, 1-propynyl and the like.

Examples of the term "$C_{3-6}$ cycloalkyl" used in the present specification include cyclopropyl, cyclobutyl, cyclopentyl and cyclohexyl.

Examples of the term "$C_{6-14}$ aryl" used in the present specification include phenyl, 1-naphthyl, 2-naphthyl, biphenylyl, 2-anthryl and the like.

Examples of the term "$C_{6-10}$ aryl" used in the present specification include phenyl, 1-naphthyl, 2-naphthyl and the like.

Examples of the term "$C_{1-6}$ alkoxy" used in the present specification include methoxy, ethoxy, propoxy, isopropoxy, butoxy, isobutoxy, sec-butoxy, tert-butoxy, pentyloxy, hexyloxy and the like.

Examples of the term "mono-$C_{1-6}$ alkylamino" used in the present specification include methylamino, ethylamino, propylamino, isopropylamino, butylamino, isobutylamino, sec-butylamino, tert-butylamino, pentylamino, hexylamino and the like.

Examples of the term "di-$C_{1-6}$ alkylamino" used in the present specification include dimethylamino, diethylamino, dipropylamino, diisopropylamino, dibutylamino, N-ethyl-N-methylamino and the like.

Examples of the term "$C_{1-6}$ alkyl-carbonyl" used in the present specification include acetyl, ethylcarbonyl, propylcarbonyl, isopropylcarbonyl, butylcarbonyl, tert-butylcarbonyl and the like.

Examples of the term "$C_{1-6}$ alkoxy-carbonyl" used in the present specification include methoxycarbonyl, ethoxycarbonyl, propoxycarbonyl, isopropoxycarbonyl, butoxycarbonyl, tert-butoxycarbonyl and the like.

Examples of the term "mono-$C_{1-6}$ alkyl-carbamoyl" used in the present specification include methylcarbamoyl, ethylcarbamoyl, propylcarbamoyl, isopropylcarbamoyl, butylcarbamoyl, tert-butylcarbamoyl and the like.

Examples of the term "di-$C_{1-6}$ alkyl-carbamoyl" used in the present specification include dimethylcarbamoyl, diethylcarbamoyl, dipropylcarbamoyl, diisopropylcarbamoyl and the like.

Examples of the term "$C_{6-14}$ aryl-carbamoyl" used in the present specification include phenylcarbamoyl, 1-naphthylcarbamoyl, 2-naphthylcarbamoyl, biphenylylcarbamoyl, 2-anthrylcarbamoyl and the like.

Examples of the term "$C_{6-14}$ aryloxy" used in the present specification include phenoxy, 1-naphthoxy, 2-naphthoxy, biphenylyloxy, 2-anthryloxy and the like.

Examples of the term "$C_{1-6}$ alkyl-carbonylamino" used in the present specification include acetylamino, ethylcarbonylamino, propylcarbonylamino, isopropylcarbonylamino, butylcarbonylamino, tert-butylcarbonylamino and the like.

Examples of the term "$C_{7-12}$ aralkyl" used in the present specification include benzyl, α-methylbenzyl, phenethyl and the like.

Examples of the term "$C_{1-6}$ alkyl-carbonyloxy" used in the present specification include acetyloxy, ethylcarbonyloxy, propylcarbonyloxy, isopropylcarbonyloxy, butylcarbonyloxy, tert-butylcarbonyloxy and the like.

Examples of the term "$C_{6-14}$ aryl-carbonyloxy" used in the present specification include benzoyloxy, naphthoyloxy and the like.

Examples of the term "$C_{7-12}$ aralkyloxy-carbonyl" used in the present specification include benzyloxycarbonyl and the like.

Examples of the term "3- to 6-membered cyclic amino optionally containing, besides a carbon atom and one nitrogen atom, 1 to 3 hetero atoms selected from a nitrogen atom, an oxygen atom and a sulfur atom" used in the present specification include aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like.

Examples of the term "$C_{1-3}$ alkylenedioxy" used in the present specification include methylenedioxy, ethylenedioxy and the like.

Examples of the term "mono-$C_{1-6}$ alkylsulfamoyl" used in the present specification include N-methylsulfamoyl, N-ethylsulfamoyl, N-propylsulfamoyl, N-isopropylsulfamoyl, N-butylsulfamoyl and the like.

Examples of the term "di-$C_{1-6}$ alkylsulfamoyl" used in the present specification include N,N-dimethylsulfamoyl, N,N-diethylsulfamoyl, N,N-dipropylsulfamoyl, N,N-dibutylsulfamoyl and the like.

Examples of the term "$C_{1-6}$ alkylthio" used in the present specification include methylthio, ethylthio, propylthio, isopropylthio, butylthio, sec-butylthio, tert-butylthio and the like.

Examples of the term "$C_{6-14}$ arylthio" used in the present specification include phenylthio, naphthylthio and the like.

Examples of the term "$C_{1-6}$ alkylsulfinyl" used in the present specification include methylsulfinyl, ethylsulfinyl, propylsulfinyl, butylsulfinyl and the like.

Examples of the term "$C_{6-14}$ arylsulfinyl" used in the present specification include phenylsulfinyl, naphthylsulfinyl and the like.

Examples of the term "$C_{1-6}$ alkylsulfonyl" used in the present specification include methylsulfonyl, ethylsulfonyl, propylsulfonyl, butylsulfonyl and the like.

Examples of the term "$C_{6-14}$ arylsulfonyl" used in the present specification include phenylsulfonyl, naphthylsulfonyl and the like.

Examples of the term "hydrocarbon group" of the "hydrocarbon group optionally having substituent(s)" used in the present specification include an aliphatic hydrocarbon group, a monocyclic saturated hydrocarbon group, an aromatic hydrocarbon group and the like, and one having a carbon number of 1 to 16 is preferable. Specifically, for example, alkyl, alkenyl, alkynyl, cycloalkyl, aryl and the like are used.

As "alkyl", for example, lower alkyl ($C_{1-6}$ alkyl) and the like are preferable.

As "alkenyl", for example, lower alkenyl ($C_{2-6}$ alkenyl) and the like are preferable.

As "alkynyl", for example, lower alkynyl ($C_{2-6}$ alkynyl) and the like are preferable.

As "cycloalkyl", for example, lower cycloalkyl ($C_{3-6}$ cycloalkyl) and the like are preferable.

As "aryl", for example, $C_{6-14}$ aryl and the like are preferable, $C_{6-10}$ aryl is more preferable, and, for example, phenyl and the like are widely used.

Examples of the substituent that the "hydrocarbon group" of the "hydrocarbon group optionally having substituent(s)" optionally has include (1) a halogen atom,
(2) nitro,
(3) cyano,
(4) hydroxy,
(5) $C_{1-6}$ alkyl optionally having 1 to 5 substituents selected from the substituent group consisting of (a) a halogen atom, (b) nitro, (c) cyano, (d) hydroxy, (e) $C_{1-6}$ alkoxy optionally having 1 to 3 halogen atoms, (f) amino, (g) mono-$C_{1-6}$ alkylamino, (h) di-$C_{1-6}$ alkylamino, (i) carboxy, (j) $C_{1-6}$ alkyl-carbonyl, (k) $C_{1-6}$ alkoxy-carbonyl, (l) carbamoyl, (m) mono-$C_{1-6}$ alkyl-carbamoyl, (n) di-$C_{1-6}$ alkyl-carbamoyl, (o) $C_{6-14}$ aryl-carbamoyl, (p) $C_{6-14}$ aryl, (q) $C_{6-14}$ aryloxy, and (r) $C_{1-6}$ alkyl-carbonylamino optionally having 1 to 3 halogen atoms (hereinafter sometimes to be abbreviated as substituent group A),
(6) $C_{1-6}$ alkoxy optionally having 1 to 5 substituents selected from the aforementioned substituent group A,
(7) amino,
(8) mono-$C_{1-6}$ alkylamino optionally having 1 to 5 substituents selected from the aforementioned substituent group A,
(9) di-$C_{1-6}$ alkylamino optionally having 1 to 5 substituents selected from the aforementioned substituent group A,
(10) carboxy,
(11) $C_{1-6}$ alkyl-carbonyl optionally having 1 to 5 substituents selected from the aforementioned substituent group A,
(12) $C_{1-6}$ alkoxy-carbonyl optionally having 1 to 5 substituents selected from the aforementioned substituent group A,
(13) carbamoyl,
(14) mono-$C_{1-6}$ alkyl-carbamoyl optionally having 1 to 5 substituents selected from the aforementioned substituent group A,
(15) di-$C_{1-6}$ alkyl-carbamoyl optionally having 1 to 5 substituents selected from the aforementioned substituent group A,
(16) $C_{6-14}$ aryl-carbamoyl optionally having 1 to 5 substituents selected from (a) substituent group A and (b) $C_{1-6}$ alkyl optionally having 1 to 3 halogen atoms,
(17) $C_{6-14}$ aryl optionally having 1 to 5 substituents selected from (a) substituent group A and (b) $C_{1-6}$ alkyl optionally having 1 to 3 halogen atoms,
(18) $C_{6-14}$ aryloxy optionally having 1 to 5 substituents selected from (a) substituent group A and (b) $C_{1-6}$ alkyl optionally having 1 to 3 halogen atoms,
(19) $C_{1-6}$ alkyl-carbonylamino optionally having 1 to 5 substituents selected from the aforementioned substituent group A,
(20) oxo,
(21) $C_{6-14}$ aryl-carbonyloxy,
(22) $C_{1-6}$ alkoxy-carbonyl,
(23) $C_{7-12}$ aralkyloxy-carbonyl,
(24) amidino,
(25) imino,
(26) 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituents selected from (a) substituent group A, (b) $C_{1-6}$ alkyl optionally having 1 to 3 halogen atoms and (c) oxo,
(27) $C_{1-3}$ alkylenedioxy,
(28) mercapto,
(29) sulfo,
(30) sulfino,
(31) phosphono,
(32) sulfamoyl,
(33) mono-$C_{1-6}$ alkylsulfamoyl,
(34) di-$C_{1-6}$ alkylsulfamoyl,
(35) $C_{1-6}$ alkylthio,
(36) $C_{6-14}$ arylthio,
(37) $C_{1-6}$ alkylsulfinyl,
(38) $C_{6-14}$ arylsulfinyl,
(39) $C_{1-6}$ alkylsulfonyl, and
(40) $C_{6-14}$ arylsulfonyl and the like. The "hydrocarbon group" of the "hydrocarbon group optionally having substituent(s)" may have 1 to 5, preferably 1 to 3, substituents mentioned above at substitutable position(s) of the hydrocarbon group. When the number of the substituents is two or more, the substituents may be the same or different.

The substituent(s) that the "hydrocarbon group" optionally has is(are) preferably 1 to 5 (preferably 1 to 3) substituents selected from (1) a halogen atom, (2) nitro, (3) cyano, (4) hydroxy, (5) $C_{1-6}$ alkyl optionally having 1 to 3 halogen atoms, (6) $C_{1-6}$ alkoxy optionally having 1 to 3 halogen atoms, (7) amino, (8) mono-$C_{1-6}$ alkylamino, (9) di-$C_{1-6}$ alkylamino, (10) carboxy, (11) $C_{1-6}$ alkyl-carbonyl, (12) $C_{1-6}$ alkoxy-carbonyl, (13) carbamoyl, (14) mono-$C_{1-6}$ alkyl-carbamoyl, (15) di-$C_{1-6}$ alkyl-carbamoyl, (16) $C_{6-14}$ aryl-carbamoyl, (17) $C_{6-14}$ aryl, (18) $C_{6-14}$ aryloxy, (19) $C_{1-6}$ alkyl-carbonylamino, (20) oxo and the like.

As the "heterocyclic group" of the term "heterocyclic group optionally having substituent(s)" used in the present specification, for example, a 5- to 14-membered (preferably 5- to 10-membered) (monocyclic, bicyclic or tricyclic, preferably monocyclic or bicyclic) heterocyclic group containing, besides a carbon atom, 1 to 4 (preferably 1 to 3) hetero atoms of one or two kinds selected from a nitrogen atom, an oxygen atom and a sulfur atom, can be mentioned. For example, a 5-membered ring group containing, besides a carbon atom, 1 to 4 hetero atoms selected from a nitrogen atom, an oxygen atom and a sulfur atom, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 2- or 4-imidazolinyl, 1,2,3-triazolyl, 1,2,4-triazolyl, 1H- or 2H-tetrazolyl and the like; for example, a 6-membered ring group containing, besides a carbon atom, 1 to 4 hetero atoms selected from a nitrogen atom, an oxygen atom and a sulfur atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, 1- or 2-piperazinyl, triazinyl, 3- or 4-pyridazinyl, pyrazinyl, N-oxido-3- or 4-pyridazinyl and the like; for example, a bicyclic or tricyclic fused ring group containing, besides a carbon atom, 1 to 4 hetero atoms selected from a nitrogen atom, an oxygen atom and a sulfur atom (preferably, a group formed by condensation of the aforementioned 5- or 6-membered ring with one or two 5- or 6-membered ring group(s) optionally containing, besides a carbon atom, 1 to 4 hetero atoms selected from a nitrogen atom, an oxygen atom and a sulfur atom), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl and the like; and the like are used. Of these, a 5- to 7-membered (preferably 5- or 6-membered) heterocyclic group containing, besides a carbon atom, 1 to 3 hetero atoms selected from a nitrogen atom, an oxygen atom and a sulfur atom is preferable.

As the substituent that the "heterocyclic group" of the "heterocyclic group optionally having substituent(s)" may have, the aforementioned "hydrocarbon group optionally having substituent(s)", and the groups recited as examples of the substituents that the "hydrocarbon group optionally having substituent(s)" may have can be mentioned. Particularly preferably, for example,
(1) a halogen atom,
(2) $C_{1-6}$ alkyl optionally having 1 to 3 halogen atoms,
(3) $C_{3-6}$ cycloalkyl,
(4) $C_{2-6}$ alkynyl,
(5) $C_{2-6}$ alkenyl,
(6) $C_{7-12}$ aralkyl,
(7) $C_{6-14}$ aryl,
(8) $C_{1-6}$ alkoxy,
(9) $C_{6-14}$ aryloxy,
(10) $C_{1-6}$ alkyl-carbonyl,
(11) arylcarbonyl (e.g., $C_{6-14}$ aryl-carbonyl such as benzoyl, naphthoyl etc., and the like),
(12) $C_{1-6}$ alkyl-carbonyloxy,
(13) $C_{6-14}$ aryl-carbonyloxy,
(14) carboxy,
(15) $C_{1-6}$ alkoxy-carbonyl,
(16) $C_{7-12}$ aralkyloxy-carbonyl,
(17) carbamoyl,
(18) oxo,
(19) amidino,
(20) imino,
(21) amino,
(22) mono-$C_{1-6}$ alkylamino,
(23) di-$C_{1-6}$ alkylamino,
(24) 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituents selected from (a) substituent group A, (b) $C_{1-6}$ alkyl optionally having 1 to 3 halogen atoms and (c) oxo,
(25) $C_{1-3}$ alkylenedioxy,
(26) hydroxy,
(27) nitro,
(28) cyano,
(29) mercapto,
(30) sulfo,
(31) sulfino,
(32) phosphono,
(33) sulfamoyl,
(34) mono-$C_{1-6}$ alkylsulfamoyl,
(35) di-$C_{1-6}$ alkylsulfamoyl,
(36) $C_{1-6}$ alkylthio,
(37) $C_{6-14}$ arylthio,
(38) $C_{1-6}$ alkylsulfinyl,
(39) $C_{6-14}$ arylsulfinyl,
(40) $C_{1-6}$ alkylsulfonyl,
(41) $C_{6-14}$ arylsulfonyl and the like are used. The "heterocyclic group" of the "heterocyclic group optionally having substituent(s)" may have 1 to 5, preferably 1 to 3, substituents mentioned above at substitutable position(s) of the heterocyclic group. When the number of the substituents is two or more, the substituents may be the same or different.

The term used in the present specification "amino optionally having substituent(s)" means amino optionally having, as substituent, 1 or 2, the same or different groups selected from, for example, the aforementioned "hydrocarbon group optionally having substituent(s)", and the groups recited as examples of the substituent that the "hydrocarbon group optionally having substituent(s)" may have and the like. Preferable examples of the substituent that the "amino" may have include $C_{1-6}$ alkyl optionally having substituent(s), $C_{6-14}$ aryl optionally having substituent(s) and the like. As the substituent that the "$C_{1-6}$ alkyl" and "$C_{6-14}$ aryl" may have, those similar to the substituents that the aforementioned "hydrocarbon group" may have are used.

The term used in the present specification "hydroxy optionally having a substituent" means (1) hydroxy or (2) hydroxy having, instead of the hydrogen atom of hydroxy, one group selected from, for example, the aforementioned "hydrocarbon group optionally having substituent(s)", the groups recited as examples of the substituent that the "hydrocarbon group optionally having substituent(s)" may have and the like. As the "hydroxy optionally having a substituent", for example, hydroxy, $C_{1-6}$ alkoxy optionally having substituent(s), $C_{2-6}$ alkenyloxy optionally having substituent(s), $C_{2-6}$ alkynyloxy optionally having substituent(s), $C_{3-6}$ cycloalkyloxy optionally having substituent(s), $C_{6-14}$ aryloxy optionally having substituent(s) and the like can be mentioned. Preferred are hydroxy, $C_{1-6}$ alkoxy optionally having substituent(s), $C_{6-14}$ aryloxy optionally having substituent(s) and the like. As the substituent that the "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, those similar to the substituents that the aforementioned "hydrocarbon group" may have are used.

The term used in the present specification "mercapto optionally having a substituent" means (1) mercapto or (2) mercapto having, instead of the hydrogen atom of mercapto, one group selected from, for example, the aforementioned "hydrocarbon group optionally having substituent(s)", the groups recited as examples of the substituent that the "hydrocarbon group optionally having substituent(s)" may have and the like. As the "mercapto optionally having a substituent", for example, mercapto, $C_{1-6}$ alkylthio optionally having substituent(s), $C_{2-6}$ alkenylthio optionally having substituent(s), $C_{2-6}$ alkynylthio optionally having substituent(s), $C_{3-6}$ cycloalkylthio optionally having substituent(s), $C_{6-14}$ arylthio optionally having substituent(s) and the like can be mentioned. Preferred are mercapto, $C_{1-6}$ alkylthio optionally having substituent(s), $C_{6-14}$ arylthio optionally having substituent(s) and the like. As the substituent that the "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, those similar to the substituents that the aforementioned "hydrocarbon group" may have are used.

In the aforementioned formulas, $R^1$ is a hydrocarbon group optionally having substituent(s), amino optionally having substituent(s), hydroxy optionally having a substituent or a heterocyclic group optionally having substituent(s).

Preferable examples of the "hydrocarbon group" of the "hydrocarbon group optionally having substituent(s)" for $R^1$ include $C_{1-6}$ alkyl, $C_{2-6}$ alkenyl, $C_{2-6}$ alkynyl, $C_{3-6}$ cycloalkyl and $C_{6-14}$ aryl and the like. Preferably, $C_{1-6}$ alkyl, $C_{3-6}$ cycloalkyl, $C_{2-6}$ alkenyl, $C_{6-14}$ aryl and the like can be mentioned. More preferable examples include $C_{1-6}$ alkyl, $C_{3-6}$ cycloalkyl, $C_{2-6}$ alkenyl, phenyl and the like. The "$C_{1-6}$ alkyl", "$C_{2-6}$ alkenyl", "$C_{2-6}$ alkynyl", "$C_{3-6}$ cycloalkyl" and "$C_{6-14}$ aryl" optionally have, for example, 1 to 5, preferably 1 to 3, substituents that the aforementioned "hydrocarbon group" optionally has (preferably, a halogen atom, $C_{1-6}$ alkoxy, hydroxy and the like) and the like.

As the substituent of the "amino optionally having substituent(s)" for $R^1$, preferably 1 or 2 from, for example, $C_{1-6}$ alkyl optionally having substituent(s), $C_{6-14}$ aryl optionally having substituent(s) and the like is(are) used, and particularly, one from $C_{1-6}$ alkyl optionally having substituent(s) and the like is used. The "$C_{1-6}$ alkyl" optionally has, for example, 1 to 3 substituents that the aforementioned "hydrocarbon group" optionally has and the like. The "$C_{6-14}$ aryl" may have 1 to 5, preferably 1 to 3, substituents that the aforementioned "hydrocarbon group" optionally has (preferably, a halogen atom, $C_{1-6}$ alkoxy and the like). As the "amino optionally having substituent(s)", $C_{6-14}$ arylamino (e.g., phenylamino and the like) optionally having 1 to 3 $C_{1-6}$ alkoxy (e.g., methoxy and the like), mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like are widely used.

Preferable examples of the "hydroxy optionally having a substituent" for $R^1$ include hydroxy, $C_{1-6}$ alkoxy optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like, particularly, $C_{1-6}$ alkoxy optionally having substituent(s), $C_{2-6}$ alkenyloxy (e.g., vinyloxy and the like) optionally having substituent(s), $C_{3-6}$ cycloalkyloxy (e.g., cyclopropyloxy and the like) optionally having substituent(s) and the like can be mentioned. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" optionally have, for example, 1 to 5, preferably 1 to 3, substituents that the aforementioned "hydrocarbon group" optionally has (preferably, a halogen atom, $C_{1-6}$ alkoxy and the like) and the like.

Preferable examples of the "heterocyclic group" of the "heterocyclic group optionally having substituent(s)" for $R^1$ include a 5- or 6-membered heterocyclic group containing, besides a carbon atom, 1 to 3 hetero atoms selected from a nitrogen atom, an oxygen atom and a sulfur atom, and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like are used. Preferable examples of the substituent of the "heterocyclic group optionally having substituent(s)" for $R^1$ include a halogen atom, $C_{1-6}$ alkyl, $C_{1-6}$ alkoxy, $C_{7-12}$ aralkyloxy-carbonyl, and the like.

$R^1$ is preferably, for example, (i) $C_{1-6}$ alkyl optionally having substituent(s), (ii) $C_{3-6}$ cycloalkyl optionally having substituent(s), (iii) $C_{2-6}$ alkenyl optionally having substituent(s), (iv) $C_{6-14}$ aryl optionally having substituent(s), (v) amino optionally having substituent(s), (vi) hydroxy optionally having a substituent or the like.

As $R^1$, (i) $C_{1-6}$ alkyl optionally having substituent(s), (ii) $C_{3-6}$ cycloalkyl optionally having substituent(s), (iii) $C_{2-6}$ alkenyl optionally having substituent(s) or the like is more preferable.

As $R^1$, (i) $C_{1-6}$ alkyl optionally having 1 to 3 halogen atoms or (ii) $C_{3-6}$ cycloalkyl is preferable, and methyl, ethyl, trifluoromethyl or cyclopropyl is particularly preferable.

As $R^1$, (i) $C_{6-14}$ aryl optionally having 1 to 3 halogen atoms, (ii) $C_{1-6}$ alkoxy and (iii) mono-$C_{1-6}$ alkylamino are also preferable, and 4-bromophenyl, tert-butoxy and ethylamino can be specifically mentioned.

In the aforementioned formula, $R^2$ is a hydrogen atom or a hydrocarbon group optionally having substituent(s).

Preferable examples of the "hydrocarbon group" of the "hydrocarbon group optionally having substituent(s)" for $R^2$ include $C_{1-6}$ alkyl, $C_{2-6}$ alkenyl, $C_{2-6}$ alkynyl, $C_{3-6}$ cycloalkyl and $C_{6-14}$ aryl and the like, particularly $C_{1-6}$ alkyl and $C_{6-14}$ aryl and the like. The "$C_{1-6}$ alkyl", "$C_{2-6}$ alkenyl", "$C_{2-6}$ alkynyl", "$C_{3-6}$ cycloalkyl" and "$C_{6-14}$ aryl" optionally have, for example, 1 to 5, preferably 1 to 3, substituents that the aforementioned "hydrocarbon group" optionally has (preferably, a halogen atom, $C_{1-6}$ alkoxy and the like) and the like.

$R^2$ is preferably a hydrogen atom or $C_{1-6}$ alkyl optionally having substituent(s), more preferably a hydrogen atom or $C_{1-6}$ alkyl, particularly preferably a hydrogen atom.

In the aforementioned formula, ring A is a 5-membered ring optionally having substituent(s).

Examples of the substituent of the "5-membered ring optionally having substituent(s)" include a halogen atom, a hydrocarbon group optionally having substituent(s), amino optionally having substituent(s), hydroxy optionally having a substituent, mercapto optionally having a substituent, a heterocyclic group optionally having substituent(s) and the like. Ring A optionally has 1 or 2 of the above-mentioned substituents at substitutable position(s).

Preferable examples of the "hydrocarbon group" of the "hydrocarbon group optionally having substituent(s)" include $C_{1-6}$ alkyl, $C_{2-6}$ alkenyl, $C_{2-6}$ alkynyl, $C_{3-6}$ cycloalkyl and $C_{6-14}$ aryl and the like. Of these, $C_{1-6}$ alkyl, $C_{2-6}$ alkenyl and the like are preferable. The "$C_{1-6}$ alkyl", "$C_{2-6}$ alkenyl", "$C_{2-6}$ alkynyl", "$C_{3-6}$ cycloalkyl" and "$C_{6-14}$ aryl" optionally have, for example, 1 to 5, preferably 1 to 3, substituents that the aforementioned "hydrocarbon group" optionally has (preferably, a halogen atom, $C_{1-6}$ alkoxy and the like) and the like.

Preferable examples of the "amino optionally having substituent(s)" include amino, $C_{1-6}$ alkylamino optionally having substituent(s), $C_{6-14}$ arylamino optionally having substituent(s) and the like. Of these, amino, mono-$C_{1-6}$ alkylamino, di-$C_{1-6}$ alkylamino, $C_{6-14}$ arylamino and the like can be mentioned.

Preferable examples of the "hydroxy optionally having a substituent" include hydroxy, $C_{1-6}$ alkoxy optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy optionally having substituent(s) and the like. Of these, hydroxy, $C_{1-6}$ alkoxy optionally having substituent(s), $C_{6-14}$ aryloxy optionally having substituent(s) and the like are preferable. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" optionally have, for example, 1 to 5, preferably 1 to 3, substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "mercapto optionally having substituent(s)" include mercapto, $C_{1-6}$ alkylthio optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio optionally having substituent(s) and the like. Of these, mercapto, $C_{1-6}$ alkylthio (e.g., methylthio and the like) optionally having substituent(s), $C_{6-14}$ arylthio optionally having substituent(s) and the like are preferable. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" optionally have, for example, 1 to 5, preferably 1 to 3, substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "heterocyclic group" of the "heterocyclic group optionally having substituent(s)" include a 5- or 6-membered heterocyclic group containing, besides a carbon atom, 1 to 3 hetero atoms selected from a nitrogen atom, an oxygen atom and a sulfur atom, and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like are used. Preferable examples of the substituent of the "heterocyclic group optionally having substituent(s)" include a halogen atom, $C_{1-6}$ alkyl, $C_{1-6}$ alkoxy, $C_{7-12}$ aralkyloxy-carbonyl, amino, mono-$C_{1-6}$ alkylamino, di-$C_{1-6}$ alkylamino and the like.

Ring A is preferably a 5-membered ring optionally having 1 or 2 substituents selected from a halogen atom, a hydrocarbon group optionally having substituent(s), amino optionally having substituent(s), hydroxy optionally having a substituent and mercapto optionally having a substituent.

Ring A is, more preferably, a 5-membered ring optionally having 1 or 2 substituents selected from $C_{1-6}$ alkyl optionally having substituent(s), $C_{2-6}$ alkenyl optionally having substituent(s) and $C_{3-6}$ cycloalkyl optionally having substituent(s). Particularly, a 5-membered ring optionally having 1 or 2 $C_{1-6}$ alkyl optionally having substituent(s) is preferable. Moreover, a 5-membered ring optionally having one $C_{1-6}$ alkyl optionally having substituent(s) is preferable.

Further specifically, ring A is a 5-membered ring optionally having 1 or 2 (more preferably 1) substituents selected from (1) methyl optionally having 1 to 3 halogen atoms and (2) ethyl is preferable.

In the aforementioned formula, ring B is a 6-membered ring optionally having substituent(s).

The substituent of the "6-membered ring optionally having substituent(s)" is a halogen atom, cyano, a hydrocarbon group optionally having substituent(s), amino optionally having substituent(s), hydroxy optionally having a substituent, mercapto optionally having a substituent, a heterocyclic group optionally having substituent(s) and the like. Ring B optionally has, at substitutable position, 1 to 3 (preferably 1 or 2) of the above-mentioned substituents.

Ring B is preferably a 6-membered ring optionally having 1 or 2 substituents selected from a halogen atom, cyano, a hydrocarbon group optionally having substituent(s), hydroxy optionally having a substituent and a heterocyclic group optionally having substituent(s).

Ring B is, more preferably, a 6-membered ring optionally having 1 or 2 substituents selected from a halogen atom, cyano, $C_{1-6}$ alkyl, $C_{3-6}$ cycloalkyl, $C_{6-14}$ aryl, $C_{1-6}$ alkoxy and a 6-membered heterocyclic group (e.g., a 6-membered nitrogen-containing heterocyclic group such as pyridyl and the like), particularly, a 6-membered ring optionally having 1 or 2 halogen atoms is preferable. Moreover, an unsubstituted 6-membered ring is preferable.

In the aforementioned formula, ring C is a 3- to 5-membered ring optionally having substituent(s).

As the "3- to 5-membered ring" of the "3- to 5-membered ring optionally having substituent(s)", a 3- to 5-membered saturated or unsaturated cyclic hydrocarbon can be mentioned, for example, $C_{3-5}$ cycloalkane (e.g., cyclopropane, cyclobutane, cyclopentane), $C_{3-5}$ cycloalkene (e.g., cyclopropene, cyclobutene, cyclopentene, cyclobutadiene, cyclopentadiene) and the like can be mentioned.

Examples of the substituent of the "3- to 5-membered ring optionally having substituent(s)" include a halogen atom, a hydrocarbon group optionally having substituent(s), a heterocyclic group optionally having substituent(s) and the like. Ring C optionally has 1 to 4 (preferably 1 or 2) substituents mentioned above at substitutable position(s).

Preferable examples of the "halogen atom" include fluorine, chlorine and bromine.

Preferable examples of the "hydrocarbon group" of the "hydrocarbon group optionally having substituent(s)" include $C_{1-6}$ alkyl, $C_{2-6}$ alkenyl, $C_{2-6}$ alkynyl, $C_{3-6}$ cycloalkyl and $C_{6-14}$ aryl and the like, particularly $C_{1-6}$ alkyl and $C_{6-14}$ aryl and the like. The "$C_{1-6}$ alkyl", "$C_{2-6}$ alkenyl", "$C_{2-6}$ alkynyl", "$C_{3-6}$ cycloalkyl" and "$C_{6-14}$ aryl" optionally have, for example, 1 to 5, preferably 1 to 3, substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "heterocyclic group" of the "heterocyclic group optionally having substituent(s)" include a 5- or 6-membered heterocyclic group containing, besides a carbon atom, 1 to 3 hetero atoms selected from a nitrogen atom, an oxygen atom and a sulfur atom and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like can be mentioned. Preferable examples of the substituent of the "heterocyclic group optionally having substituent(s)" include a halogen atom, $C_{1-6}$ alkyl, $C_{1-6}$ alkoxy, $C_{7-12}$ aralkyloxy-carbonyl, amino, mono-$C_{1-6}$ alkylamino, di-$C_{1-6}$ alkylamino and the like.

Ring C is preferably a $C_{3-5}$ cycloalkane optionally having 1 to 4 substituents selected from a hydrocarbon group optionally having substituent(s) and a halogen atom.

Ring C is, more preferably, cyclopropane optionally having 1 or 2 substituents selected from a halogen atom, $C_{1-6}$ alkyl optionally having substituent(s), $C_{3-6}$ cycloalkyl optionally having substituent(s) and $C_{6-14}$ aryl optionally having substituent(s). The substituent that the "$C_{1-6}$ alkyl", "$C_{3-6}$ cycloalkyl" and "$C_{6-14}$ aryl" optionally have include 1 or 2 substituents selected from a halogen atom, $C_{1-6}$ alkyl, $C_{6-14}$ aryl, $C_{1-6}$ alkoxy, amino, mono-$C_{1-6}$ alkylamino, di-$C_{1-6}$ alkylamino and the like. Ring C is more preferably cyclopropane.

Examples of the bicyclic ring consisting of ring A and ring B include rings represented by the formulas

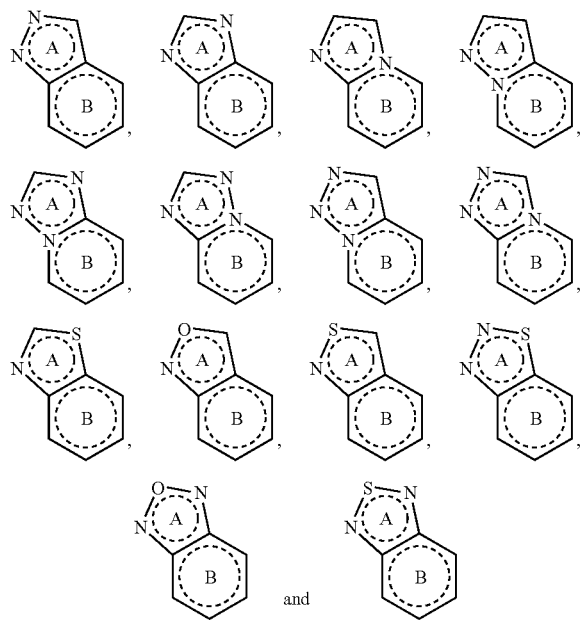

wherein each symbol is as defined above, and the like.

Preferable examples include rings represented by the formulas

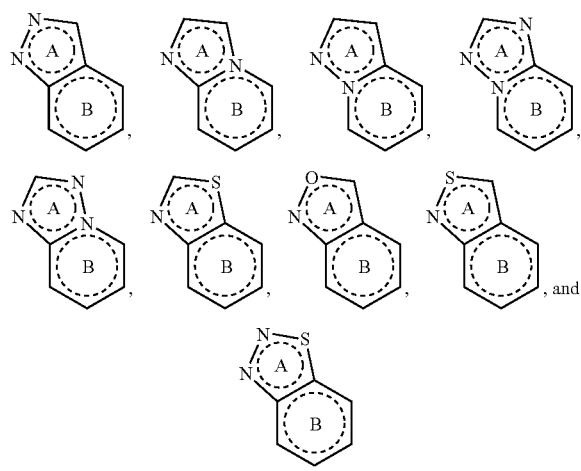

wherein each symbol is as defined above, and the like.

More preferable examples include rings represented by the formulas

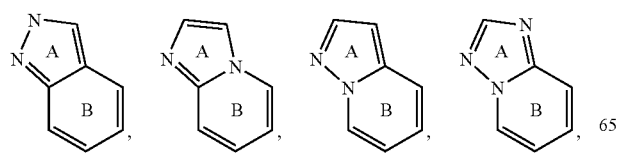

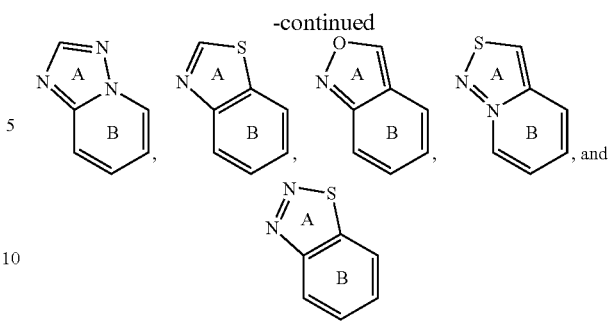

wherein each symbol is as defined above, and the like. Of these, a ring of the above-mentioned formula wherein ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent; and ring B is a 6-membered ring optionally having 1 to 3 substituents selected from a halogen atom, cyano, a hydrocarbon group optionally having substituent(s), amino optionally having substituent(s), hydroxy optionally having a substituent, mercapto optionally having a substituent and a heterocyclic group optionally having substituent(s), or the like is preferable.

Compound (I) is preferably a compound wherein $R^1$ is $C_{1-6}$ alkyl optionally having substituent(s), $C_{3-6}$ cycloalkyl optionally having substituent(s), $C_{2-6}$ alkenyl optionally having substituent(s), $C_{6-14}$ aryl optionally having substituent(s), amino optionally having substituent(s) or hydroxy optionally having a substituent;

$R^2$ is a hydrogen atom or $C_{1-6}$ alkyl optionally having substituent(s);

m is 1;

ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;

ring B is a 6-membered ring optionally having 1 or 2 substituents selected from a halogen atom, cyano, a hydrocarbon group optionally having substituent(s), amino optionally having substituent(s), hydroxy optionally having a substituent, mercapto optionally having a substituent and a heterocyclic group optionally having substituent(s); and ring C is $C_{3-5}$ cycloalkane optionally having 1 to 4 substituents selected from a hydrocarbon group optionally having substituent(s) and a halogen atom or the like, more preferably, a compound wherein $R^1$ is $C_{1-6}$ alkyl optionally having substituent(s), $C_{3-6}$ cycloalkyl optionally having substituent(s) or $C_{2-6}$ alkenyl optionally having substituent(s);

$R^2$ is a hydrogen atom or $C_{1-6}$ alkyl optionally having substituent(s);

m is 1;

ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;

ring B is 6-membered ring optionally having 1 or 2 substituents selected from a halogen atom, a hydrocarbon group optionally having substituent(s), amino optionally having substituent(s), hydroxy optionally having a substituent and mercapto optionally having a substituent; and ring C is $C_{3-5}$ cycloalkane optionally having 1 to 4 substituents selected from a hydrocarbon group optionally having substituent(s) and a halogen atom, or the like.

More preferably, a compound wherein $R^1$ is $C_{1-6}$ alkyl or $C_{1-6}$ alkoxy; $R^2$ is a hydrogen atom; m is 1; ring A is a 5-membered ring optionally having 1 or 2 substituents selected from a halogen atom and $C_{1-6}$ alkyl optionally having 1 to 3 halogen atoms; ring B is a 6-membered ring optionally having 1 or 2 substituents selected from a halogen atom and $C_{1-6}$ alkyl optionally having 1 to 3 halogen atoms; and ring C is an unsubstituted cyclopropane and the like can be mentioned.

Preferable examples of compound (I) include a compound represented by the formula

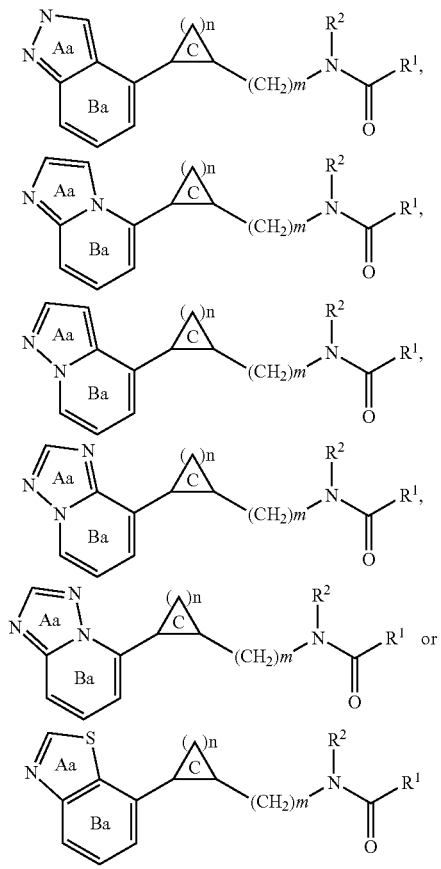

wherein ring Aa is as defined for the above-mentioned ring A, ring Ba is as defined for the above-mentioned ring B, and other symbols are as defined above, and the like.

Particularly, a compound wherein $R^1$ is $C_{1-6}$ alkyl or $C_{1-6}$ alkoxy; $R^2$ is a hydrogen atom; m is 1; ring Aa is a 5-membered ring optionally having 1 or 2 substituents selected from a halogen atom and $C_{1-6}$ alkyl optionally having 1 to 3 halogen atoms; ring Ba is a 6-membered ring optionally having 1 or 2 substituents selected from a halogen atom and $C_{1-6}$ alkyl optionally having 1 to 3 halogen atoms; and ring C is an unsubstituted cyclopropane and the like can be mentioned.

Moreover, a compound wherein $R^1$ is $C_{1-6}$ alkyl; $R^2$ is a hydrogen atom; m is 1; ring Aa is a 5-membered ring optionally having $C_{1-6}$ alkyl; ring Ba is an unsubstituted 6-membered ring; and ring C is an unsubstituted cyclopropane and the like can also be mentioned as an example.

As preferable examples of compound (I), a compound wherein the bicyclic ring consisting of ring A and ring B is a ring represented by the formula

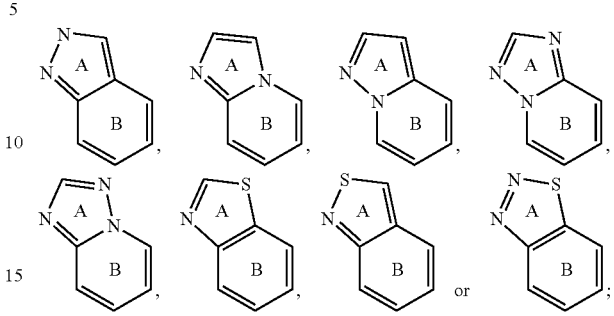

$R^1$ is (i) $C_{1-6}$ alkyl optionally having 1 to 3 halogen atoms, (ii) $C_{3-6}$ cycloalkyl, (iii) $C_{6-14}$ aryl optionally having 1 to 3 halogen atoms, (iv) $C_{1-6}$ alkoxy or (v) mono-$C_{1-6}$ alkylamino;

$R^2$ is a hydrogen atom;

m is 1;

ring A is a 5-membered ring optionally having 1 or 2 substituents selected from a halogen atom and $C_{1-6}$ alkyl optionally having 1 to 3 halogen atoms;

ring B is a 6-membered ring optionally having 1 or 2 substituents selected from a halogen atom, cyano, $C_{1-6}$ alkyl, $C_{3-6}$ cycloalkyl, $C_{6-14}$ aryl, $C_{1-6}$ alkoxy and a 6-membered heterocyclic group (e.g., a 6-membered nitrogen-containing heterocyclic group such as pyridyl and the like); and ring C is an unsubstituted cyclopropane and the like can also be mentioned.

More specifically, the compounds of Examples 1 to 63 are preferable, particularly, the following compounds are preferable.

N-{[2-(2-methyl-2H-indazol-4-yl)cyclopropyl]methyl}acetamide,

N-{[2-(2-methyl-2H-indazol-4-yl)cyclopropyl]methyl}propanamide,

N-{[2-(2-methylpyrazolo[1,5-a]pyridin-4-yl)cyclopropyl]methyl}acetamide,

N-{[2-(2-methylpyrazolo[1,5-a]pyridin-4-yl)cyclopropyl]methyl}propanamide,

N-{[2-(3-fluoro-2-methyl-2H-indazol-4-yl)cyclopropyl]methyl}acetamide,

N-{[2-(5-fluoro-2-methyl-2H-indazol-4-yl)cyclopropyl]methyl}acetamide,

N-{[2-(7-fluoro-2-methyl-2H-indazol-4-yl)cyclopropyl]methyl}acetamide,

N-{[2-(2-methylpyrazolo[1,5-a]pyridin-4-yl)cyclopropyl]methyl}cyclopropanecarboxamide, or N-{[2-(2-methyl-1,3-benzothiazol-7-yl)cyclopropyl]methyl}acetamide, or a salt thereof.

As a salt of compound (I), for example, a pharmaceutically acceptable salt and the like are used. For example, a salt with inorganic base, a salt with organic base, a salt with inorganic acid, a salt with organic acid, a salt with basic or acidic amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like. Of these, a pharmaceutically acceptable salt is preferable. Examples thereof when compound (I) has a basic functional group include salts with inorganic acid such as hydrochloric acid, hydrobromic acid, nitric acid, sulfuric acid, phosphoric acid and the like, and salts with organic acid such as acetic acid, phthalic acid, fumaric acid, tartaric acid, maleic acid, citric acid, succinic acid, methanesulfonic acid, p-toluenesulfonic acid and the like. Examples thereof when compound (I) has an acidic functional group include alkali metal salts such as sodium salt, potassium salt and the like, alkaline earth metal salts such as calcium salt, magnesium salt and the like, ammonium salt and the like.

The production methods of compound (I) are described in the following.

The following compounds (II)-(LV) include salts thereof. As the salt, for example, one similar to the salt of compound (I) and the like are used.

The compound obtained in each step can be directly used as a reaction mixture or a crude product for the next reaction. It can be isolated from a reaction mixture according to a conventional method, and can be easily purified by a separation means such as recrystallization, distillation, chromatography and the like.

The reaction schemes thereof are shown below, wherein each symbol in the compound is as defined above. In the formulas, $R^{3a-3n}$ are each a hydrogen atom, a hydrocarbon group optionally having substituent(s) or a heterocyclic group optionally having substituent(s), $R^{3o}$ is a hydrocarbon group optionally having substituent(s) or a heterocyclic group optionally having substituent(s), $R^{4a-4h}$ are each a hydrogen atom or a hydrocarbon group optionally having substituent(s), Y is a halogen atom, $R^5$ is a hydrogen atom, $-CO_2R^{4a}$, $-CHO$, $-Y$ or $-CH_2OH$, $R^8$ is a hydrogen atom, $-CO_2R^{4g}$ or $-CN$, $R^9$ is a hydrogen atom, $-CO_2R^{4h}$, $-CN$, $-CH_2OH$, $-CH_2NHR^2$, $-CHO$ or $-C\equiv N-OH$, and $P^{1-8}$ are each a hydrogen atom or an amino-protecting group.

As the solvent used for the production method of compound (I), the following solvents are recited.

Alcohols:
methanol, ethanol, 1-propanol, 2-propanol, tert-butyl alcohol and the like Ethers:
diethyl ether, diisopropyl ether, diphenyl ether, tetrahydrofuran, 1,4-dioxane, 1,2-dimethoxyethane, diethylene glycol dimethyl ether and the like Halogenated Hydrocarbons:
dichloromethane, chloroform, carbon tetrachloride, 1,2-dichloroethane and the like Acid Anhydrides:
acetic anhydride and the like Organic Acids:
formic acid, acetic acid, propionic acid, trifluoroacetic acid, methanesulfonic acid and the like Inorganic Acids:
sulfuric acid and the like Esters:
methyl acetate, ethyl acetate, butyl acetate and the like Ketones:
acetone, methyl ethyl ketone and the like Aromatic Hydrocarbons:
benzene, toluene, xylene and the like Saturated Hydrocarbons:
cyclohexane, hexane and the like Amides:
N,N-dimethylformamide, N,N-dimethylacetamide, hexamethylphosphoric triamide and the like Nitriles:
acetonitrile, propionitrile and the like Sulfoxides:
dimethyl sulfoxide and the like Aromatic Organic Bases:
pyridine, lutidine and the like As the base used for the production method of compound (I), the following bases are recited.

Inorganic Bases:
sodium hydroxide, potassium hydroxide, magnesium hydroxide and the like Basic Salts:
sodium carbonate, potassium carbonate, cesium carbonate, calcium carbonate, sodium hydrogen carbonate and the like Organic Bases:
triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like Metal Alkoxides:
sodium methoxide, sodium ethoxide, potassium tert-butoxide and the like Alkali Metal Hydrides:
sodium hydride, potassium hydride and the like Metal Amides:
sodium amide, lithium diisopropylamide, lithium hexamethyldisilazide and the like Organic Lithiums:
methyllithium, n-butyllithium, sec-butyllithium, tert-butyllithium and the like Aromatic Amines:
pyridine, lutidine and the like Tertiary Amines:
triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like As the acid used for the production method of compound (I), the following acids are recited.

Inorganic Acids:
hydrochloric acid, sulfuric acid, nitric acid, hydrobromic acid, phosphoric acid and the like Organic Acids:
acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like As nitrite salts and nitrous acid esters as a diazotizing reagent used for the production method of compound (I), the following compounds are recited.

Nitrite Salts:
  sodium nitrite, potassium nitrite and the like
Nitrous Acid Esters:
  ethyl nitrite, amyl nitrite and the like As phosphorus halide, succinimides, halogen, hydrogen halide and halide salt as a halogenating agent used for the production method of compound (I), the following compounds are recited.

Phosphorus Halide:
  phosphorus trichloride, phosphorus oxychloride, phosphorus pentachloride, phosphorus tribromide, phosphorus triiodide and the like
Succinimides:
  bromosuccinimide, iodosuccinimide and the like
Halogen:
  chlorine, bromine, iodine, iodine monofluoride, iodine monochloride and the like
Hydrogen Halide:
  hydrochloric acid, hydrobromic acid, hydroiodic acid and the like
Halide Salt:
  sodium chloride, sodium bromide, potassium iodide and the like As the metal catalyst used for the production method of compound (I), various metal complexes having ligand are used, and as palladium compound, nickel compound, rhodium compound and copper compound, the following compounds are specifically used.

Palladium Compound:
  palladium(II) acetate, tetrakis(triphenylphosphine)palladium(0), bis(triphenylphosphine)palladium(II) chloride, dichlorobis(triethylphosphine)palladium(II), tris(dibenzylideneacetone)dipalladium(0), [2,2'-bis(diphenylphosphino)-1,1'-binaphthyl]palladium(II) chloride, complex of palladium(II) acetate and 1,1'-bis(diphenylphosphino)ferrocene, and the like
Nickel Compound:
  tetrakis(triphenylphosphine)nickel(0), bis(triethylphosphine)nickel(II) chloride, bis(triphenylphosphine)nickel(II) chloride and the like
Rhodium Compound:
  tris(triphenylphosphine)rhodium(III) chloride and the like
Copper Compound:
  copper oxide, copper(II) chloride and the like (Reaction 01)

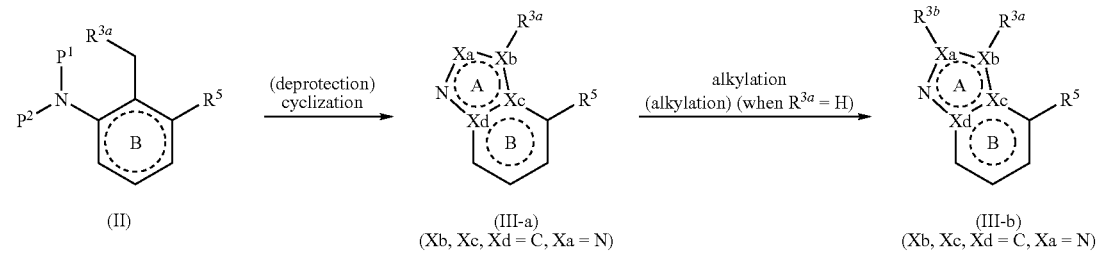

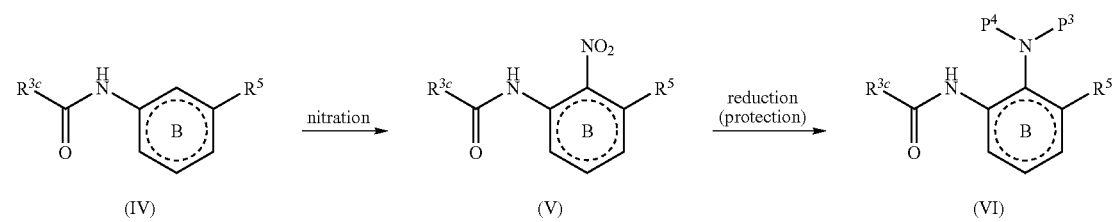

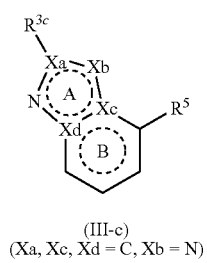

-continued
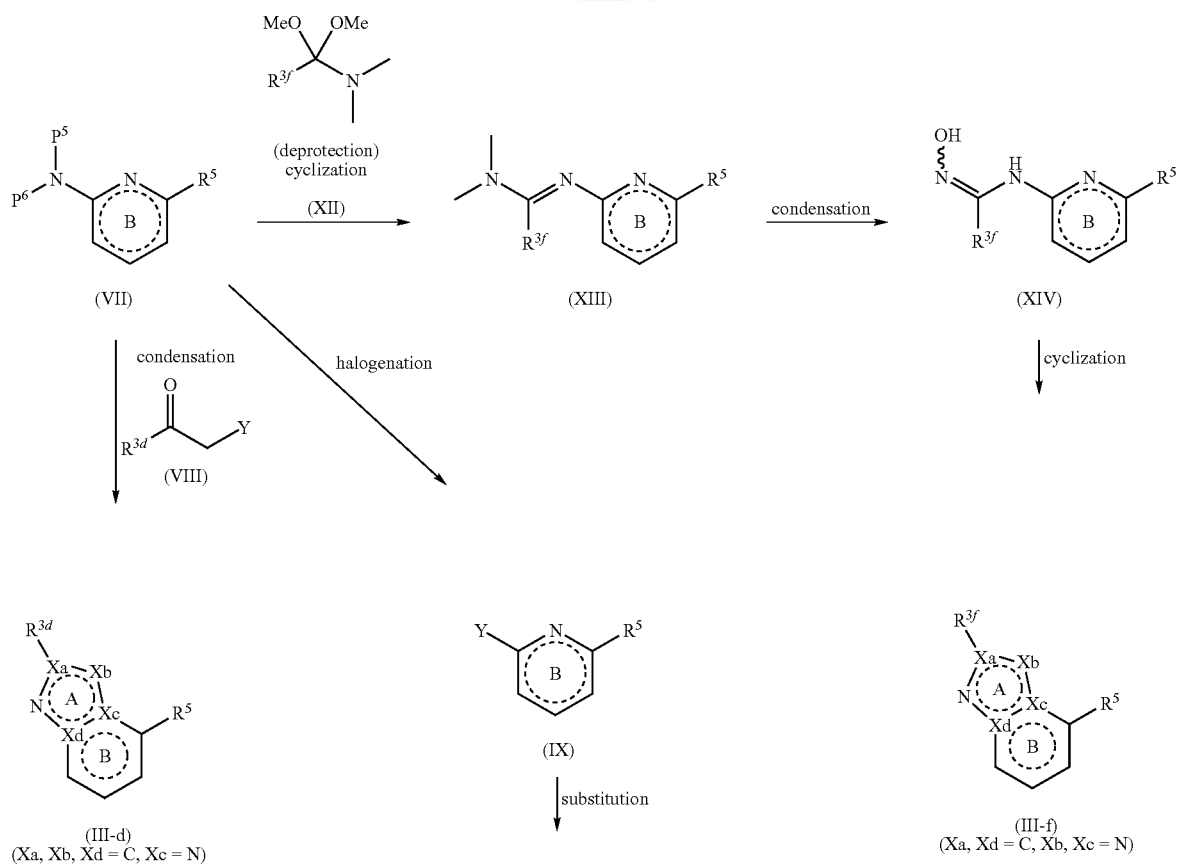
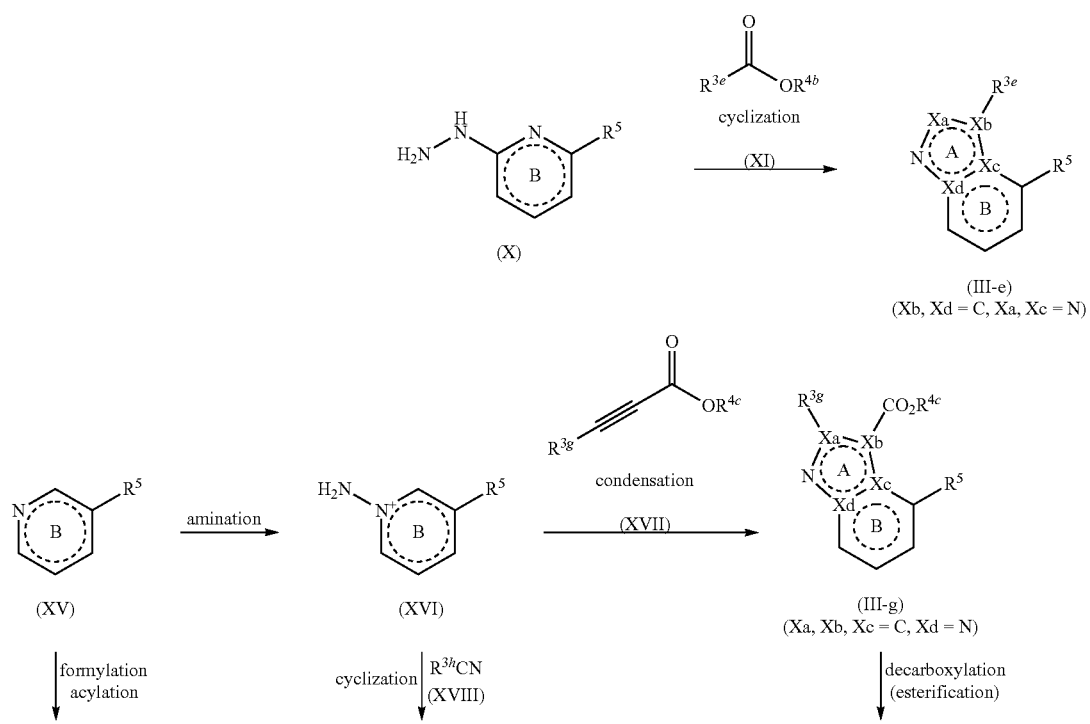

-continued
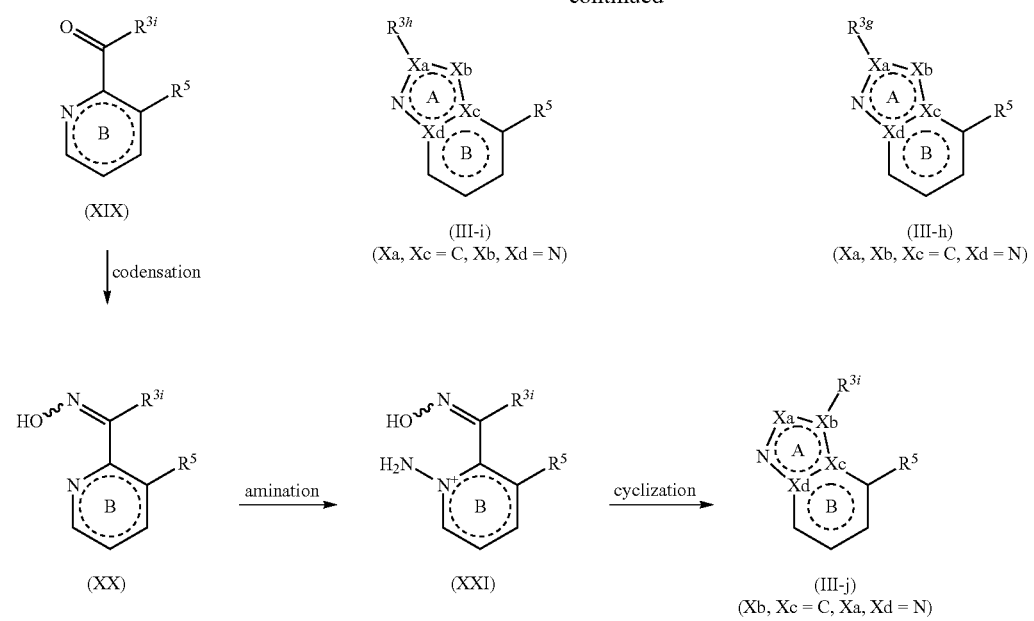
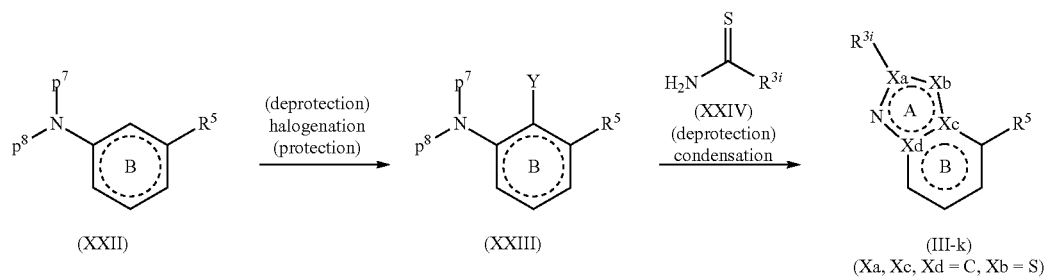
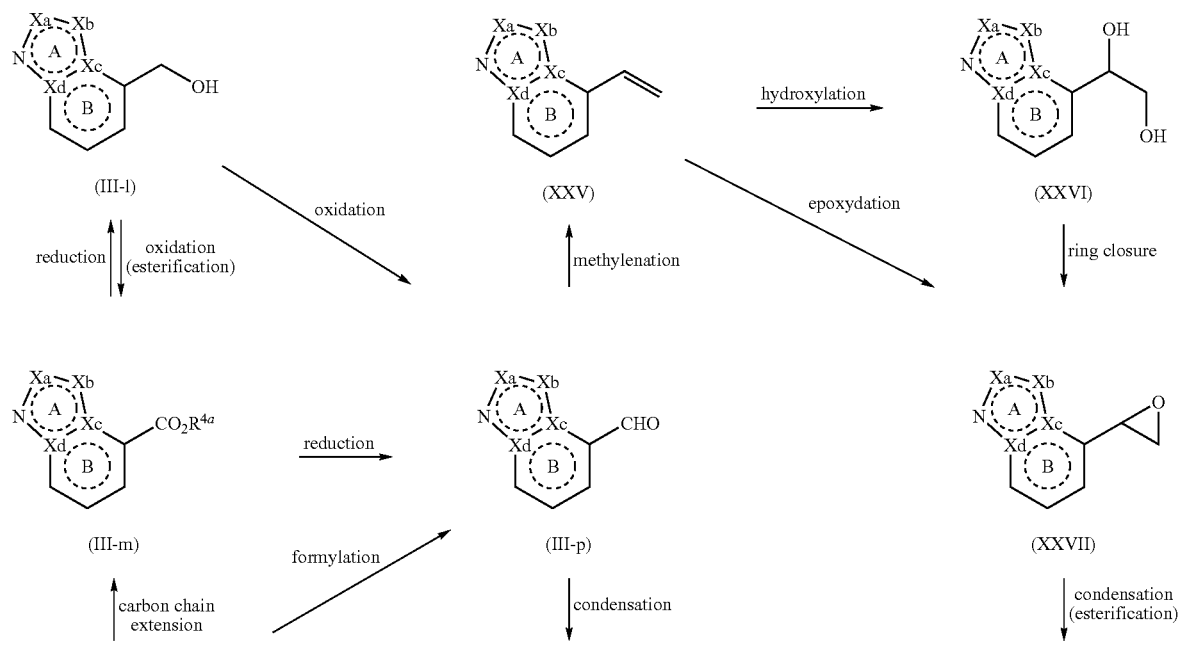

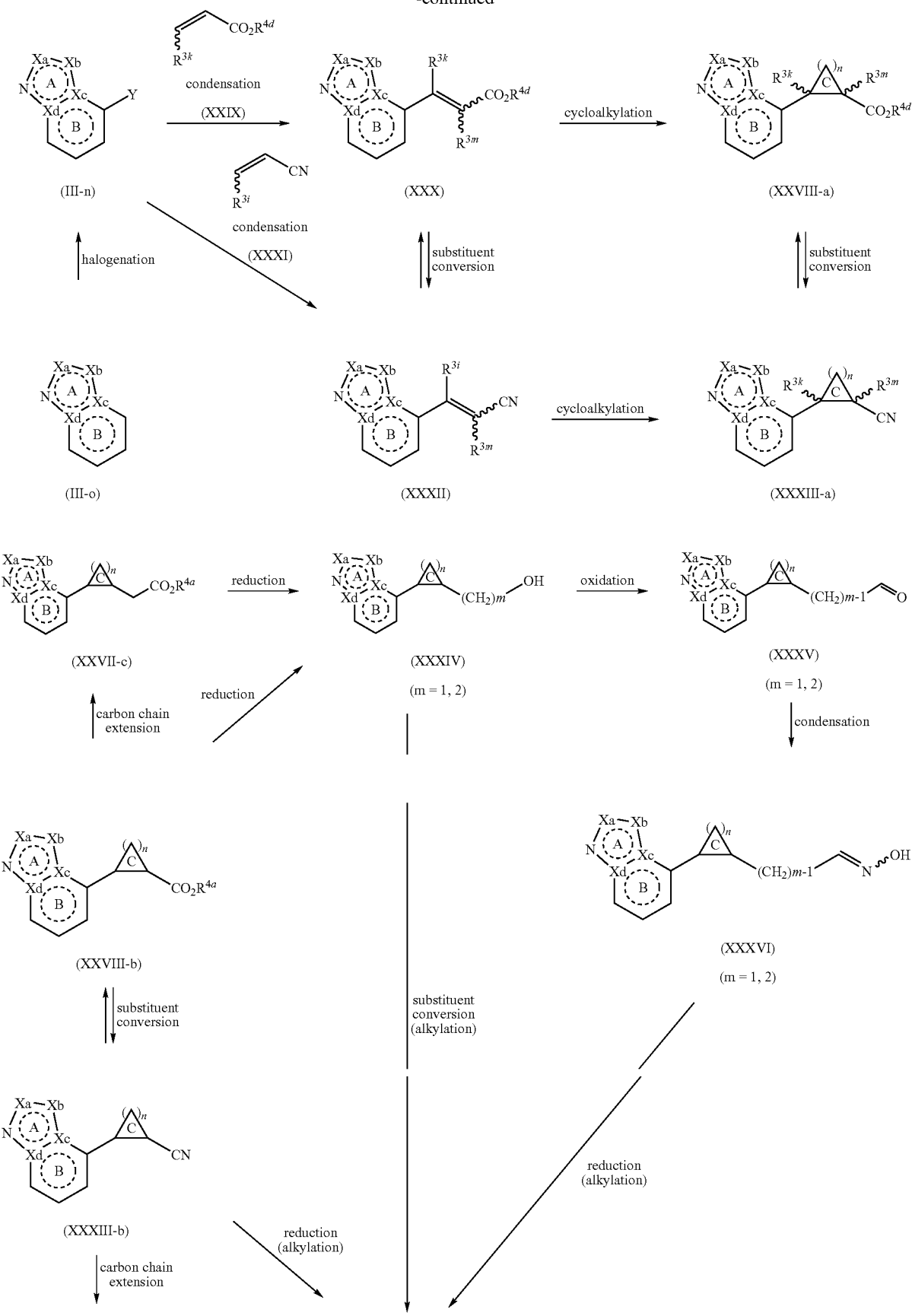

-continued

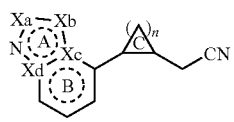
(XXXIII-c)

reduction (alkylation) →

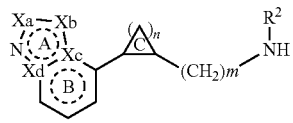
(XXXVII)

acylation ureation carbonation (alkylation) →

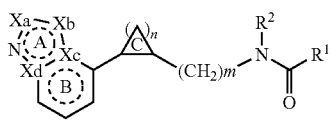
(I)

Compound (III-l) can be produced by a method known per se, for example, the method described in J. Med. Chem., vol. 44, page 2691 (2001) and the like, or a method analogous thereto.

Compound (III-m) can be produced by a method known per se, for example, the method described in J. Med. Chem., vol. 43, page 41 (2000), J. Med. Chem., vol. 43, page 4084 (2000), J. Chem. Soc. Perkin Trans. 1, page 1159 (1987), J. Heterocyclic Chem., vol. 12, page 877 (1975), Pestic. Sci., vol. 50, page 275 (1997) and the like, or a method analogous thereto.

Compound (III-n) can be produced by a method known per se, for example, the method described in J. Org. Chem., vol. 45, page 3738 (1980), Eur. J. Org. Chem., vol. 17, page 3761 (2005), J. Med. Chem., vol. 34, page 108 (1991), J. Chem. Soc., page 268 (1969), J. Chem. Soc. Perkin Trans. 1, page 1954 (1973), J. Heterocyclic Chem., vol. 7, page 629 (1970) and the like, or a method analogous thereto.

Compound (III-p) can be produced by a method known per se, for example, the method described in J. Org. Chem., vol. 57, page 5538 (1992), J. Org. Chem., vol. 61, page 5130 (1996), J. Heterocyclic Chem., vol. 23, page 897 (1986), Heterocycles, vol. 45, page 955 (1997) and the like, or a method analogous thereto.

Compounds (II), (III-o), (IV), (VII), (VIII), (IX), (XI), (XII), (XV), (XVI), (XVII), (XVIII), (XIX), (XXII), (XXIV), (XXIX) and (XXXI), and the compounds (XXXVIII-a), (XXXVIII-b), (XXXVIII-c), (XXXVIII-d) and (XXXVIII-e) described in (Reaction 02) below can be produced by a method known per se, or a method analogous thereto.

When the compound used for the explanation of the production method is commercially available, such commercially available product can also be used directly.

Compound (III-a) wherein Xb, Xc and Xd are carbon atoms, and Xa is a nitrogen atom can be produced by reacting compound (II) with a diazotizing reagent in the presence of an acid. Examples of the acid include inorganic acids, organic acids, boron trifluoride ether complex and the like. Examples of the diazotizing reagent include nitrous acid, nitrite salts, nitrous acid esters and the like. The acid is used in a proportion of about 2.0 to 200 mol, preferably about 5.0 to 100 mol, per 1 mol of compound (II). The diazotizing reagent is used in a proportion of about 1.0 to 20 mol, preferably about 1.0 to 3.0 mol, per 1 mol of compound (II). This reaction is advantageously performed using a solvent inert to the reaction. While such solvent is not particularly limited as long as the reaction proceeds, for example, a solvent such as alcohols, ethers, halogenated hydrocarbons, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 100° C., preferably 0° C. to 30° C.

In the formula of compound (II), the groups represented by $P^1$ and $P^2$ are the same or different and each is i) a hydrogen atom, ii) formyl, or iii) $C_{1-6}$ alkyl-carbonyl (e.g., acetyl, propionyl and the like), benzoyl, $C_{1-6}$ alkoxy-carbonyl (e.g., methoxycarbonyl, ethoxycarbonyl, tert-butoxycarbonyl (Boc) and the like), allyloxycarbonyl (Aloc), phenoxycarbonyl, fluorenylmethyloxycarbonyl (Fmoc), $C_{7-10}$ aralkyl-carbonyl (e.g., benzylcarbonyl and the like), $C_{7-10}$ aralkyloxycarbonyl (e.g., benzyloxycarbonyl (Z) and the like), $C_{7-10}$ aralkyl (e.g., benzyl and the like), trityl, phthaloyl or N,N-dimethylaminomethylene, each optionally having substituent(s), or the like. As these substituents, phenyl, a halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro and the like are used, and the number of substituents is about 1 to 3. A group represented by $P^1$ or $P^2$ can be used as an amino-protecting group, which can be introduced and removed by a method known per se, for example, the method described in Wiley-Interscience, 1999, "Protective Groups in Organic Synthesis, 3$^{rd}$ Ed." (by Theodora W. Greene, Peter G. M. Wuts) and the like.

Compound (III-b) wherein Xb, Xc and Xd are carbon atoms, and Xa is a nitrogen atom can be produced by reacting compound (III-a) with an alkylating agent. Examples of the alkylating agent include trimethyloxonium tetrafluoroborate, triethyloxonium hexafluorophosphate and the like. The alkylating agent is used in a proportion of about 1.0 to 50 mol, preferably about 1.0 to 3.0 mol, per 1 mol of compound (III-a). This reaction is advantageously performed using a solvent inert to the reaction. While such solvent is not particularly limited as long as the reaction proceeds, for example, a solvent such as ethers, halogenated hydrocarbons, esters, ketones and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 100° C., preferably 0° C. to 30° C.

Compound (III-b) wherein $R^{3a}$ is a hydrogen atom can be, when desired, subjected to an alkylation reaction using an alkylating agent (e.g., alkyl halide represented by $R^{3a}X$ wherein X is a halogen atom, and the like) in the presence of a base. The alkylating agent is used in a proportion of about 1.0 to 50 mol, preferably about 1.0 to 3.0 mol, per 1 mol of compound (III-b). Examples of the base include inorganic bases, basic salts, organic bases, metal alkoxides, alkali metal hydrides, metal amides and the like. The base is used in a proportion of about 1.0 to 5.0 mol, preferably about 1.0 to 2.0 mol, per 1 mol of compound (III-b). This reaction is advantageously performed using a solvent inert to the reaction. While such solvent is not particularly limited as long as the reaction proceeds, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 30 min to 48 hr, preferably 30 min to 6 hr. The reaction temperature is generally −20° C. to 200° C., preferably −10° C. to 150° C.

As alkyl halide represented by $R^{3a}X$, a commercially available product may be used, or can be produced according to a method known per se or a method analogous thereto.

Compound (V) can be produced by reacting compound (IV) with a nitrating reagent. Examples of the nitrating reagent include a metal nitrate salt such as sodium nitrate, potassium nitrate and the like, acetyl nitrate, dinitrogen pentoxide, nitronium salt, nitric acid, mixed acid (a mixture of nitric acid and sulfuric acid), and a mixture thereof. The nitrating reagent is used in a proportion of about 0.8 to 20 mol, preferably about 1.0 to 2.0 mol, per 1 mol of compound (IV). When nitric acid, mixed acid and the like are used as a nitrating reagent, an excess amount thereof can also be used as a reaction solvent. This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, acid anhydrides, organic acids, inorganic acids and the like or a mixed solvent thereof and the like are preferable. While the reaction time varies depending on the reagent and solvent to be used, it is generally 10 min to 24 hr, preferably 30 min to 12 hr. The reaction temperature is generally −20° C. to 150° C., preferably 0° C. to 80° C.

Compound (VI) wherein a group represented by $P^3$ or $P^4$ is as defined for a group represented by $P^1$ or $P^2$ can be produced by subjecting compound (V) to a reduction reaction. The reduction reaction is generally performed according to a conventional method and using a reducing agent. Examples of the reducing agent include metal hydride such as aluminum hydride, diisobutylaluminum hydride, tributyltin hydride and the like, metal hydrogen complex compounds such as sodium cyanoborohydride, sodium triacetoxyborohydride, sodium borohydride, lithium aluminum hydride and the like, borane complexes such as borane tetrahydrofuran complex, borane dimethyl sulfide complex and the like, alkylboranes such as thexylborane, disiamylborane and the like, diborane, metals such as zinc, aluminum, tin, iron and the like, alkali metal (e.g., sodium, lithium and the like)/liquid ammonia (Birch reduction) and the like. The amount of the reducing agent to be used is appropriately determined according to the kind of the reducing agent. For example, metal hydride, metal hydrogen complex compound, borane complex, alkylborane or diborane is used in a proportion of about 0.25 to 10 mol, preferably about 0.5 to 5 mol, per 1 mol of compound (V), and the metal (including alkali metal to be used for Birch reduction) is used in a proportion of about 1.0 to 20 mol, preferably about 1.0 to 5.0 mol, per 1 mol of compound (V). This reaction is advantageously performed using a solvent inert to the reaction. While such solvent is not particularly limited as long as the reaction proceeds, for example, a solvent such as alcohols, ethers, saturated hydrocarbons, amides, halogenated hydrocarbons, organic acids, water and the like or a mixed solvent thereof and the like are preferable. While the reaction time varies depending on the reagent and solvent to be used, it is generally 10 min to 100 hr, preferably 30 min to 50 hr. The reaction temperature is generally −20° C. to 100° C., preferably 0° C. to 80° C.

In addition, the reduction reaction can also be performed by a hydrogenation reaction. In this case, for example, a catalyst such as palladium carbon, platinum(IV) oxide, Raney nickel, Raney cobalt etc., and the like are used. The catalyst is used in a proportion of about 1.0 to 2000 wt %, preferably about 10 to 300 wt %, relative to compound (V). It is also possible to use various hydrogen sources instead of gaseous hydrogen. Examples of the hydrogen source include formic acid, ammonium formate, triethylammonium formate, sodium phosphinate, hydrazine and the like. The hydrogen source is used in a proportion of about 1.0 to 10 mol, preferably about 1.0 to 5.0 mol, per 1 mol of compound (V). This reaction is advantageously performed using a solvent inert to the reaction. For example, a solvent such as alcohols, ethers, aromatic hydrocarbons, saturated hydrocarbons, amides, halogenated hydrocarbons, esters, organic acids, water and the like or a mixed solvent thereof and the like are preferable. While the reaction time varies depending on the kind and amount of the reducing agent to be used, and the activity and amount of the catalyst, it is generally 30 min to 100 hr, preferably 1 hr to 50 hr. The reaction temperature is generally −20° C. to 120° C., preferably 0° C. to 80° C. When a hydrogenation catalyst is used, the pressure of hydrogen is generally 1 to 100 atm.

Compound (III-c) wherein Xa, Xc and Xd are carbon atoms, and Xb is a nitrogen atom can be produced by subjecting compound (VI) to a cyclization reaction. For the cyclization reaction, for example, a method by heating, a method using an acid, a method analogous thereto and the like are used. For ring closure by heating, the reaction is advantageously performed without solvent or in a solvent inert to the reaction. While such solvent is not particularly limited as long as the reaction proceeds, for example, a solvent such as ethers, aromatic hydrocarbons, amides, halogenated hydrocarbons, organic acids, inorganic acids, water and the like or a mixed solvent thereof and the like are preferable. While the reaction time varies depending on the reagent and solvent to be used, it is generally 10 min to 100 hr, preferably 1 hr to 10 hr. The reaction temperature is generally 50° C. to 300° C., preferably 100° C. to 200° C.

For ring closure using an acid, for example, inorganic acids, organic acids, boron trifluoride ether complex and the like are used. The acid is used in a proportion of about 0.05 to 100 mol, preferably about 0.1 to 10 mol, per 1 mol of compound (VI). This reaction is advantageously performed without solvent or in a solvent inert to the reaction. While such solvent is not particularly limited as long as the reaction proceeds, for example, a solvent such as ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 100 hr, preferably 30 min to 12 hr. The reaction temperature is generally 0° C. to 200° C., preferably 0° C. to 150° C.

Compound (III-d) wherein Xa, Xb and Xd are carbon atoms, and Xc is a nitrogen atom can be produced by condensing compound (VII) wherein a group represented by $P^5$ or $P^6$ is as defined for a group represented by $P^1$ or $P^2$ and compound (VIII) in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Compound (VIII) is used in a proportion of about 1.0 to 20 mol, preferably about 2.0 to 10 mol, per 1 mol of compound (VII); the acid is used in a proportion of about 2.0 to 200 mol, preferably about 5.0 to 100 mol, per 1 mol of compound (VII); and the base is used in a proportion of about 1.0 to 20 mol, preferably about 1.0 to 3.0 mol, per 1 mol of compound (VII). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and the solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (IX) can be produced by reacting compound (VII) with a diazotizing reagent and a halogenating agent. Examples of the diazotizing reagent include nitrous acid, nitrite salts, nitrous acid esters and the like. Examples of the halogenating agent include phosphorus halide, succinimides, halogen, hydrogen halide, halide salt, thionyl chloride and a mixture thereof and the like. The diazotizing reagent is used in a proportion of about 1.0 to 50 mol, preferably about 1.0 to 3.0 mol, per 1 mol of compound (VII). The halogenating agent is used in a proportion of about 2.0 to 200 mol, preferably about 5.0 to 100 mol, per 1 mol of compound (VII). This reaction is advantageously performed using a solvent inert to the reaction. While such solvent is not particularly limited as long as the reaction proceeds, for example, a solvent such as esters, ethers, halogenated hydrocarbons, ketones and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 150° C., preferably 0° C. to 100° C.

Compound (X) can be produced by subjecting compound (IX) to a substitution reaction with hydrazine. Examples of the hydrazine include aqueous hydrazine carbonate solution, hydrazine dihydrobromide dihydrate, hydrazine monohydrochloride, hydrazine dihydrochloride, hydrazine monohydrate, hydrazine monohydrobromide, hydrazine sulfate and the like. To promote the reaction, the reaction can also be performed in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. The hydrazine is used in a proportion of about 1.0 to 20 mol, preferably about 1.0 to 10 mol, per 1 mol of compound (IX). The acid is used in a proportion of about 0.1 to 200 mol, preferably about 1.0 to 100 mol, per 1 mol of compound (IX). The base is used in a proportion of about 0.1 to 200 mol, preferably about 1.0 to 100 mol, per 1 mol of compound (IX). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 150° C., preferably 0° C. to 100° C.

Compound (III-e) wherein Xb and Xd are carbon atoms, and Xa and Xc are nitrogen atoms can be produced by condensing compound (X) and compound (XI) in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Compound (XI) is used in a proportion of about 1.0 to 20 mol, preferably about 2.0 to 10 mol, per 1 mol of compound (X). The acid is used in a proportion of about 0.1 to 200 mol, preferably about 0.1 to 100 mol, per 1 mol of compound (X). The base is used in a proportion of about 0.1 to 200 mol, preferably about 0.1 to 100 mol, per 1 mol of compound (X). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (XIII) can be produced by condensing compound (VII) and compound (XII) in the presence of an acid or a base. Examples of the acid include inorganic acids, organic acids, boron trifluoride ether complex and the like. Examples of the base include inorganic bases, basic salts, metal alkoxides, alkali metal hydrides, metal amides, organic lithiums and the like. Compound (XII) is used in a proportion of about 1.0 to 20 mol, preferably about 2.0 to 10 mol, per 1 mol of compound (VII). The acid is used in a proportion of about 0.1 to 200 mol, preferably about 0.1 to 100 mol, per 1 mol of compound (VII). The base is used in a proportion of about 0.1 to 200 mol, preferably about 0.1 to 100 mol, per 1 mol of compound (VII). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (XIV) can be produced by condensing compound (XIII) and hydroxylamine in the presence of an acid or a base. As the hydroxylamine, aqueous hydroxylamine solution, hydroxylammonium chloride, hydroxylammonium oxalate, hydroxylammonium phosphate, hydroxylammonium sulfate and the like can be mentioned. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. The hydroxylamine is used in a proportion of about 1.0 to 20 mol, preferably about 2.0 to 10 mol, per 1 mol of compound (XIII). The acid is used in a proportion of about 0.1 to 200 mol, preferably about 0.1 to 100 mol, per 1 mol of compound (XIII). The base is used in a proportion of about 0.1 to 200 mol, preferably about 0.1 to 100 mol, per 1 mol of compound (XIII). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

In addition, compound (XIV) can also be produced according to a method known per se, for example, the method described in 4th Ed. Jikken Kagaku Koza (Courses in Experimental Chemistry), vol. 20, pages 353-354 (The Chemical Society of Japan Ed.) and the like, or a method analogous thereto.

Compound (III-f) wherein Xa and Xd are carbon atoms, and Xb and Xc are nitrogen atoms can be produced by subjecting compound (XIV) to a cyclization reaction in the presence of a dehydrating agent. Examples of the dehydrating agent include diphosphorus pentoxide, phosphorus oxychloride, phosphorus pentachloride, triphenylphosphine, phosgene, N,N'-dicyclohexylcarbodiimide, alumina, polyphosphoric acid, acetic anhydride, acetyl chloride, sodium dioxide, thionyl chloride, methanesulfonyl chloride, p-toluenesulfonyl chloride, trifluoroacetic anhydride and the like. The dehydrating agent is used in a proportion of about 1.0 to 50 mol, preferably about 1.0 to 3.0 mol, per 1 mol of compound (XIV). This reaction is advantageously performed using a solvent inert to the reaction. While such solvent is not particularly limited as long as the reaction proceeds, for example, a solvent such as ethers, halogenated hydrocarbons, esters, ketones and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 150° C., preferably 0° C. to 100° C.

Compound (XVI) can be produced by reacting compound (XV) with an aminating reagent. Examples of the aminating reagent include O-mesitylenesulfonylhydroxylamine, O-(2,4-dinitrophenyl)hydroxylamine, and a mixture thereof and the like. These reagent can be produced according to the method described in, for example, J. Org. Chem., vol. 38, page 1239 (1973), J. Org. Chem., vol. 68, page 7119 (2003) and the like, or a method analogous thereto. The aminating reagent is used in a proportion of about 1.0 to 20 mol, preferably about 1.0 to 3.0 mol, per 1 mol of compound (XV). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 150° C., preferably 20° C. to 80° C.

Compound (III-g) wherein Xa, Xb and Xc are carbon atoms, and Xd is a nitrogen atom can be produced by a condensation reaction of compound (XVI) and compound (XVII) in the presence of a base. Examples of the base include inorganic bases, basic salts, organic bases, metal alkoxides and the like. The base is used in a proportion of about 1.0 to 20 mol, preferably about 1.0 to 5.0 mol, per 1 mol of compound (XVI). Compound (XVII) is used in a proportion of about 1.0 to 20 mol, preferably about 1.0 to 5.0 mol, per 1 mol of compound (XVI). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 50 hr, preferably 1 hr to 25 hr. The reaction temperature is generally −20° C. to 150° C., preferably 0° C. to 80° C.

Compound (III-h) wherein Xa, Xb and Xc are carbon atoms, and Xd is a nitrogen atom can be produced by subjecting compound (III-g) to a decarboxylation reaction. The decarboxylation reaction can be performed according to a method known per se, or a method analogous thereto and, for example, a method using an acid, a method analogous thereto and the like can be mentioned. Examples of the acid include inorganic acids, organic acids and the like. The acid is used in a proportion of about 0.0001 to 20 mol, preferably about 0.01 to 5.0 mol, per 1 mol of compound (III-g). This reaction is advantageously performed without solvent or in a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 200 hr, preferably 30 min to 100 hr. The reaction temperature is generally 0° C. to 200° C., preferably 0° C. to 150° C.

Compound (III-h) wherein $R^5$ is carboxylic acid is subjected to esterification to give an ester form thereof. The esterification reaction can be performed according to, for example, the method described in 4th Ed. Jikken Kagaku Koza (Courses in Experimental Chemistry), vol. 22, pages 43-54 (The Chemical Society of Japan Ed.), or a method analogous thereto.

Compound (III-i) wherein Xa and Xc are carbon atoms, and Xb and Xd are nitrogen atoms can be produced by a condensation reaction of compound (XVI) and compound (XVIII) in the presence of a base. Examples of the base include inorganic bases, basic salts, organic bases, metal alkoxides and the like. The base is used in a proportion of about 1.0 to 20 mol, preferably about 1.0 to 5.0 mol, per 1 mol of compound (XVI). Compound (XVIII) is used in a proportion of about 1.0 to 20 mol, preferably about 1.0 to 5.0 mol, per 1 mol of compound (XVI). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 50 hr, preferably 1 hr to 25 hr. The reaction temperature is generally −20° C. to 150° C., preferably 0° C. to 80° C.

Compound (XIX) can be produced by reacting compound (XV) with a formylating reagent or an acylating reagent in the presence of a base. Examples of the base include organic bases, metal alkoxides, alkali metal hydrides, metal amides, organic lithiums and the like can be mentioned. Examples of the formylating reagent include N,N-dimethylformamide, N-formylpiperidine, N-formylmorpholine, formic acid esters such as ethyl formate etc., and the like, and examples of the acylating reagent include amides such as N,N-dimethylbenzamide etc., and the like. The base is used in a proportion of about 1.0 to 50 mol, preferably about 1.0 to 10 mol, per 1 mol of compound (XV). The formylating reagent or acylating reagent is used in a proportion of about 1.0 to 50 mol, preferably about 1.0 to 10 mol, per 1 mol of compound (XV). This reaction is advantageously performed using a solvent inert to the reaction. While such solvent is not particularly limited as long as the reaction proceeds, for example, a solvent such as ethers, halogenated hydrocarbons, aromatic hydrocarbons, saturated hydrocarbons and the like or a mixed solvent thereof and the like are preferable. While the reaction time varies depending on the reagent and solvent to be used, it is generally 10 min to 24 hr, preferably 30 min to 10 hr. The reaction temperature is generally −78° C. to 50° C., preferably −78° C. to 25° C.

In addition, compound (XIX) can also be produced according to a method known per se, for example, the methods described in J. Chem. Soc. Perkin Trans. 1, page 3597 (1997), J. Org. Chem., vol. 56, page 2866 (1991) and the like, or a method analogous thereto.

Compound (XX) can be produced by condensing compound (XIX) and hydroxylamine in the presence of an acid or a base. The condensation reaction can be performed by a method similar to the method of producing compound (XIV) from compound (XIII).

Compound (XXI) can be produced by reacting compound (XX) with an aminating reagent. The amination reaction can be performed by a method similar to the method of producing compound (XVI) from compound (XV).

Compound (III-j) wherein Xb and Xc are carbon atoms, and Xa and Xd are nitrogen atoms can be produced by subjecting compound (XXI) to a cyclization reaction. For the cyclization reaction, for example, a method by heating, a method using an acid, a method using a dehydrating agent, a method analogous thereto and the like are used. Cyclization by heating is advantageously performed without solvent or in a solvent inert to the reaction. While such solvent is not particularly limited as long as the reaction proceeds, for example, a solvent such as ethers, aromatic hydrocarbons, amides, halogenated hydrocarbons, organic acids, inorganic acids, water and the like or a mixed solvent thereof and the like are preferable. While the reaction time varies depending on the reagent and solvent to be used, it is generally 10 min to 100 hr, preferably 1 hr to 10 hr. The reaction temperature is generally 50° C. to 300° C., preferably 100° C. to 200° C.

For cyclization using an acid, for example, inorganic acids, organic acids, boron trifluoride ether complex and the like are used. The acid is used in a proportion of about 0.05 to 100 mol, preferably about 0.1 to 10 mol, per 1 mol of compound (XXI). This reaction is advantageously performed without solvent or in a solvent inert to the reaction. While such solvent is not particularly limited as long as the reaction proceeds, for example, a solvent such as ethers, aromatic hydrocarbons, saturated hydrocarbons, amides, halogenated hydrocarbons, sulfoxides, organic acids, inorganic acids, water and the like, or a mixed solvent thereof and the like are preferable. While the reaction time varies depending on the reagent and solvent to be used, it is generally 10 min to 100 hr, preferably 30 min to 12 hr. The reaction temperature is generally 0° C. to 200° C., preferably 0° C. to 150° C.

When a dehydrating agent is used for cyclization, Examples of the dehydrating agent include diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, p-toluenesulfonyl chloride, trifluoroacetic anhydride, acetic anhydride, acetyl chloride, polyphosphoric acid and the like. The dehydrating agent is used in a proportion of about 1.0 to 100 mol, preferably about 5.0 to 30 mol, per 1 mol of compound (XXI). This reaction is advantageously performed without solvent or in a solvent inert to the reaction. While such solvent is not particularly limited as long as the reaction proceeds, a solvent such as ethers, aromatic hydrocarbons, saturated hydrocarbons, halogenated hydrocarbons, ketones, acid anhydrides and the like or a mixed solvent thereof and the like are preferable. While the reaction time varies depending on the reagent and solvent to be used, it is generally 10 min to 100 hr, preferably 1 hr to 50 hr. The reaction temperature is generally 10° C. to 300° C., preferably 20° C. to 150° C.

Compound (XXIII) can be produced by reacting compound (XXII) wherein a group represented by $P^7$ or $P^8$ is as defined for a group represented by $P^1$ or $P^2$ with a halogenating agent. Examples of the halogenating agent include phosphorus halide, succinimides, halogen, thionyl chloride, and a mixture thereof and the like. The halogenating agent is used in a proportion of about 1.0 to 100 mol, preferably about 1.0 to 10 mol, per 1 mol of compound (XXII). To promote the reaction, the reaction can be performed in the presence of a base. Examples of the base include inorganic bases, basic salts and the like can be mentioned. This reaction is advantageously performed without solvent or in a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, acid anhydrides, organic acids, inorganic acids, water and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 200° C., preferably 10° C. to 100° C.

Compound (III-k) wherein Xa, Xc and Xd are carbon atoms, and Xb is a sulfur atom can be produced by reacting compound (XXIII) with thioamide (XXIV). The reaction is generally performed in the presence of a base. Examples of the base include inorganic bases, basic salts, aromatic amines, tertiary amines, alkali metal hydrides, metal amides, metal alkoxides and the like. It is also possible to promote the reaction by the use of a metal catalyst. As the metal catalyst, various metal complexes having ligand are used and, for example, palladium compound, nickel compound, rhodium compound, cobalt compound, copper compound, platinum compound and the like can be mentioned. Of these, palladium compound, nickel compound and copper compound are preferable. The amount of thioamide (XXIV) to be used is about 0.8 to 10 mol, preferably about 1.0 to 3.0 mol, per 1 mol of compound (XXIII). The amount of the base to be used is about 1.0 to 20 mol, preferably about 1.0 to 5.0 mol, per 1 mol of compound (XXIII). The amount of the metal catalyst to be used is about 0.000001 to 5 mol, preferably about 0.0001 to 1 mol, per 1 mol of compound (XXIII). When a metal catalyst unstable to oxygen is used for this reaction, the reaction is preferably performed, for example, in an inert gas stream such as argon gas, nitrogen gas and the like. This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, esters, sulfoxides, sulfolane, hexamethylphosphoramide, water and the like, a mixed solvent thereof and the like are preferable. The reaction temperature is generally −10° C. to 250° C., preferably 0° C. to 150° C. While the reaction time varies depending on the kind of compound (XXIII), thioamide (XXIV), base, metal catalyst and solvent, reaction temperature and the like, it is generally 10 min to 100 hr, preferably 30 min to 50 hr.

Compound (III-l) can be produced by subjecting compound (III-m) to a reduction reaction. The reduction reaction can be performed by a method similar to the method of producing compound (VI) from compound (V).

Compound (III-m) can be produced by subjecting compound (III-l) to oxidation reaction. The oxidation reaction can be performed according to a method known per se, for example, the method described in 4th Ed. Jikken Kagaku Koza (Courses in Experimental Chemistry), vol. 23, pages 1-550 (The Chemical Society of Japan Ed.) and the like, or a method analogous thereto. For example, oxidation reaction using an oxidizing agent, Swern oxidation reaction using oxalyl chloride and dimethyl sulfoxide, oxidation reaction using chromic acid, oxidation reaction using tetra-n-propylammonium perruthenate(VII) and N-methylmorpholine N-oxide and the like can be mentioned. Examples of the oxidizing agent include organic peracids such as perbenzoic acid, m-chloroperbenzoic acid (MCPBA), peracetic acid and the like, perchlorates such as lithium perchlorate, silver perchlorate, tetrabutylammonium perchlorate and the like, periodic acids such as sodium periodate, Dess-Martin periodinane, o-iodoxybenzoic acid (IBX) and the like, manganic acids such as manganese dioxide, potassium permanganate and the like, leads such as lead tetraacetate and the like, chromate such as pyridinium chlorochromate, pyridinium dichromate and the like, inorganic nitrogen compounds such as acyl nitrate, dinitrogen tetroxide and the like, halogen compounds such as halogen, N-bromosuccinimide (NBS), N-chlorosuccinimide (NCS) and the like, sulfuryl chloride, chloramine T, oxygen, hydrogen peroxide and the like. The oxidizing agent is used in a proportion of about 0.8 to 20 mol, preferably about 1.0 to 5.0 mol, per 1 mol of compound (III-l). This reaction is advantageously performed using a solvent inert to the reaction. While the solvent is not particularly limited as long as the reaction proceeds, for example, a solvent such as ethers, aromatic hydrocarbons, saturated hydrocarbons, amides, halogenated hydrocarbons, nitriles, sulfoxides, esters, water and the like or a mixed solvent thereof and the like are preferable. While the reaction time varies depending on the reagent and solvent to be used, it is generally 10 min to 100 hr, preferably 30 min to 50 hr. The reaction temperature is generally −78° C. to 150° C., preferably −78° C. to 100° C.

Compound (III-m) can also be produced from compound (III-n) according to a known carbon chain extension reaction. The carbon chain extension reaction can be performed according to a method known per se, for example, the method described in 4th Ed. Jikken Kagaku Koza (Courses in Experimental Chemistry), vol. 22, pages 14-30 (The Chemical Society of Japan Ed.) and the like, or a method analogous thereto.

Compound (III-n) can be produced by reacting compound (III-o) with a halogenating agent. The halogenation can be performed by a method similar to the method of producing compound (XXIII) from compound (XXII).

Compound (III-p) can be produced by subjecting compound (III-l) to an oxidation reaction. The oxidation reaction can be performed by a method similar to the method of producing compound (III-m) from compound (III-l).

Compound (III-p) can also be produced by subjecting compound (III-m) to a reduction reaction. The reduction reaction can be performed by a method similar to the method of producing compound (VI) from compound (V).

Compound (III-p) can also be produced from compound (III-n) according to a known formylation reaction. The formylation reaction can be performed according to a method known per se, for example, the method described in 4th Ed. Jikken Kagaku Koza (Courses in Experimental Chemistry), vol. 21, pages 23-43 (The Chemical Society of Japan Ed.) and the like, or a method analogous thereto.

Compound (XXV) can be produced by reacting compound (III-p) with a methylating agent and subjecting the compound to a dehydration reaction. Examples of the methylating agent include methyllithium, methylmagnesium bromide and the like. The methylating agent is used in a proportion of about 1.0 to 20 mol, preferably about 1.0 to 3.0 mol, per 1 mol of compound (III-p). This reaction is advantageously performed using a solvent inert to the reaction. While such solvent is not particularly limited as long as the reaction proceeds, for example, a solvent such as ethers, aromatic hydrocarbons, saturated hydrocarbons, halogenated hydrocarbons and the like or a mixed solvent thereof and the like are preferable. While the reaction time varies depending on the reagent and solvent to be used, it is generally 10 min to 30 hr, preferably 1 hr to 10 hr. The reaction temperature is generally −78° C. to 50° C., preferably −78° C. to 20° C.

For dehydration reaction, for example, a method by heating, a method using an acid, a method using a dehydrating agent, a method analogous thereto and the like are used. Dehydration by heating is advantageously performed without solvent or in a solvent inert to the reaction. While such solvent is not particularly limited as long as the reaction proceeds, for example, a solvent such as ethers, aromatic hydrocarbons, amides, halogenated hydrocarbons, organic acids, inorganic acids, water and the like or a mixed solvent thereof and the like are preferable. While the reaction time varies depending on the reagent and solvent to be used, it is generally 10 min to 100 hr, preferably 1 hr to 10 hr. The reaction temperature is generally 50° C. to 300° C., preferably 100° C. to 200° C.

When an acid is used, for example, inorganic acids, organic acids, boron trifluoride ether complex and the like are used. The acid is used in a proportion of about 0.05 to 100 mol, preferably about 0.1 to 10 mol, per 1 mol of compound (III-p). This reaction is advantageously performed without solvent or in a solvent inert to the reaction. While such solvent is not particularly limited as long as the reaction proceeds, for example, a solvent such as ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 100 hr, preferably 30 min to 12 hr. The reaction temperature is generally 0° C. to 200° C., preferably 0° C. to 150° C.

When a dehydrating agent is used, examples of the dehydrating agent include diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, p-toluenesulfonyl chloride, trifluoroacetic anhydride, acetic anhydride, acetyl chloride, polyphosphoric acid and the like. The dehydrating agent is used in a proportion of about 1.0 to 100 mol, preferably about 5.0 to 30 mol, per 1 mol of compound (III-p). This reaction advantageously performed without solvent or in a solvent inert to the reaction. While such solvent is not particularly limited as long as the reaction proceeds, a solvent such as ethers, aromatic hydrocarbons, saturated hydrocarbons, halogenated hydrocarbons, ketones, acid anhydrides and the like or a mixed solvent thereof and the like are preferable. While the reaction time varies depending on the reagent and solvent to be used, it is generally 10 min to 100 hr, preferably 1 hr to 50 hr. The reaction temperature is generally 10° C. to 300° C., preferably 20° C. to 150° C.

Compound (XXV) can also be produced by subjecting compound (III-p) to a methylenation reaction. The methylenation reaction can be performed according to a method known per se, for example, the methods described in 4th Ed. Jikken Kagaku Koza (Courses in Experimental Chemistry), vol. 19, pages 53-101 (The Chemical Society of Japan Ed.), 4th Ed. Jikken Kagaku Koza (Courses in Experimental Chemistry), vol. 25, pages 273-275 (The Chemical Society of Japan Ed.) and the like, or a method analogous thereto.

Compound (XXVI) can be produced by subjecting compound (XXV) to a hydroxylation reaction. The hydroxylation reaction can be performed according to a method known per se, for example, the methods described in 4th Ed. Jikken Kagaku Koza (Courses in Experimental Chemistry), vol. 20, pages 39-44 (The Chemical Society of Japan Ed.), 4th Ed. Jikken Kagaku Koza (Courses in Experimental Chemistry), vol. 26, pages 9-15 (The Chemical Society of Japan Ed.), Chem. Rev., vol. 94, page 2483 (1994) and the like, or a method analogous thereto.

Compound (XXVII) can be produced by subjecting compound (XXVI) to a ring closure reaction. The ring closure reaction can be performed according to a method known per se, for example, the method described in 4th Ed. Jikken Kagaku Koza (Courses in Experimental Chemistry), vol. 20, pages 218-224 (The Chemical Society of Japan Ed.) and the like, or a method analogous thereto.

Compound (XXVII) can be produced by subjecting compound (XXV) to an epoxydation reaction. The epoxydation reaction can be performed according to a method known per se, for example, the methods described in 4th Ed. Jikken Kagaku Koza (Courses in Experimental Chemistry), vol. 20, pages 213-215 (The Chemical Society of Japan Ed.), 4th Ed. Jikken Kagaku Koza (Courses in Experimental Chemistry), vol. 26, pages 8-9 (The Chemical Society of Japan Ed.) and the like, or a method analogous thereto.

Compound (XXVIII-a) can be produced by reacting compound (XXVII) with phosphonate carbanion produced by a base treatment of alkylphosphonic acid diester. As alkylphosphonic acid diester, diethyl cyanomethylphosphonate, diethyl(1-cyanoethyl)phosphonate and the like are used. The alkylphosphonic acid diester is used in a proportion of about 1.0 to 5.0 mol, preferably about 1.0 to 2.0 mol, per 1 mol of compound (XXVII). Examples of the base include metal alkoxides, alkali metal hydrides, metal amides and the like. The base is used in a proportion of about 1.0 to 5.0 mol, preferably about 1.0 to 1.5 mol, per 1 mol of compound (XXVII). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 200° C., preferably 0° C. to 150° C.

Compound (XXX) can be produced by reacting compound (III-p) with phosphonate carbanion produced by a base treatment of alkylphosphonic acid diester. As alkylphosphonic acid diester, ethyl diethylphosphonoacetate and the like are used. The alkylphosphonic acid diester is used in a proportion of about 1.0 to 5.0 mol, preferably about 1.0 to 2.0 mol, per 1 mol of compound (III-p). Examples of the base include metal alkoxides, alkali metal hydrides, metal amides and the like. The base is used in a proportion of about 1.0 to 5.0 mol, preferably about 1.0 to 1.5 mol, per 1 mol of compound (III-p). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 200° C., preferably 0° C. to 150° C.

Compound (XXX) can also be produced by reacting compound (III-p) with carbanion, produced by a base treatment of an ester represented by the formula $R^{3m}CH_2CO_2R^{4d}$, and subjecting the compound to a dehydration reaction. Examples of the ester include ethyl acetate, ethyl propionate, methyl phenoxyacetate and the like. The ester is used in a proportion of about 1.0 to 5.0 mol, preferably about 1.0 to 2.0 mol, per 1 mol of compound (III-p). Examples of the base include metal alkoxides, alkali metal hydrides, metal amides and the like. The base is used in a proportion of about 1.0 to 5.0 mol, preferably about 1.0 to 1.5 mol, per 1 mol of compound (III-p). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 200° C., preferably −78° C. to 50° C. The dehydration reaction can be performed by a method similar to the method of producing compound (XXV) from compound (III-p).

As the ester represented by the formula $R^{3m}CH_2CO_2R^{4d}$, a commercially available product may be used or can also be produced by a method known per se or a method analogous thereto.

Compound (XXX) can also be produced by condensing compound (III-n) with compound (XXIX) in the presence of a metal catalyst. As the metal catalyst, various metal complexes having ligand are used and, for example, palladium compound, nickel compound, rhodium compound, cobalt compound, copper compound, platinum compound and the like can be mentioned. Of these, palladium compound, nickel compound and copper compound are preferable. Compound (XXIX) is used in a proportion of about 0.8 to 10 mol, preferably about 1.0 to 3.0 mol, per 1 mol of compound (III-n). The metal catalyst is used in a proportion of about 0.000001 to 5 mol, preferably about 0.0001 to 1 mol, per 1 mol of compound (III-n). This reaction is preferably performed in the presence of a base. Examples of the base include inorganic bases, basic salts, organic bases, metal alkoxides, alkali metal hydrides, metal amides and the like can be mentioned. The base is used in a proportion of about 1.0 to 20 mol, preferably about 1.0 to 5.0 mol, per 1 mol of compound (III-n). When a metal catalyst unstable to oxygen is used for this reaction, the reaction is preferably performed, for example, in an inert gas stream such as argon gas, nitrogen gas and the like. This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, esters, water and the like or a mixed solvent thereof and the like are preferable. While the reaction time varies depending on the reagent and solvent to be used, it is generally 10 min to 100 hr, preferably 30 min to 50 hr. The reaction temperature is generally −10° C. to 250° C., preferably 0° C. to 150° C.

Compound (XXX) can also be produced from compound (XXXII) according to a known substituent conversion reaction. For example, a method wherein cyano is hydrolyzed under alkaline or acidic conditions to give carboxy, and the carboxy is esterified when desired and the like are employed.

Compound (XXXII) can be produced by condensing compound (III-n) and compound (XXXI) in the presence of a metal catalyst. The condensation reaction can be performed by a method similar to the method of producing compound (XXX) from compound (III-n).

Compound (XXXII) can also be produced from compound (XXX) according to a known substituent conversion reaction. For example, a method wherein ester or carboxy is amidated to give carboxamide and the carboxamide is subjected to a dehydration reaction and the like are employed.

Compound (XXVIII-a) can be produced by reacting compound (XXX) with trimethylsulfoxonium ylide produced by a base treatment of trimethylsulfoxonium. As the trimethylsulfoxonium, trimethylsulfoxonium bromide, trimethylsulfoxonium iodide and the like are used. The trimethylsulfoxonium is used in a proportion of about 1.0 to 5.0 mol, preferably about 1.0 to 2.0 mol, per 1 mol of compound (XXX). Examples of the base include metal alkoxides, alkali metal hydrides, metal amides and the like. The base is used in a proportion of about 1.0 to 5.0 mol, preferably about 1.0 to 1.5 mol, per 1 mol of compound (XXX). This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 200° C., preferably 0° C. to 150° C.

Compound (XXVIII-a) can also be produced by reacting compound (XXX) with a diazo compound. As the diazo compound, diazomethane, 2-diazopropane, diazodiphenylmethane, methyl diazoacetate and the like are used. The diazo compound is used in a proportion of about 1.0 to 5.0 mol, preferably about 1.0 to 2.0 mol, per 1 mol of compound (XXX). The reaction is performed by, for example, a method using a metal catalyst, a method using photoirradiation, a method analogous thereto and the like. Examples of the metal catalyst include palladium compound [e.g.: palladium(II) acetate], copper compound [e.g.: copper(II) acetylacetonate, copper(II) chloride and the like] and the like. The metal catalyst is used in a proportion of about 0.000001 to 5 mol, preferably about 0.0001 to 1 mol, per 1 mol of compound (XXX). When a metal catalyst unstable to oxygen is used for this reaction, the reaction is preferably performed, for example, in an inert gas stream such as argon gas, nitrogen gas and the like. This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 250° C., preferably 0° C. to 150° C.

Compound (XXVIII-a) can also be produced by subjecting compound (XXX) to a cycloalkylation reaction according to a method known per se, for example, the methods described in Synthesis, vol. 4, page 533 (2002), Tetrahedron, vol 37., page 3229 (1981), Bull. Chem. Soc. Jpn., vol. 53, page 160 (1980), Tetrahedron Lett., vol. 40, page 3225 (1999) and the like, or a method analogous thereto.

Compound (XXVIII-a) can also be produced from compound (XXXIII-a) according to a known substituent conversion reaction. The substituent conversion reaction can be performed by a method similar to the method of producing compound (XXX) from compound (XXXII).

Compound (XXXIII-a) can be produced by subjecting compound (XXXII) to a cycloalkylation reaction. The cycloalkylation reaction can be performed by a method similar to the method of producing compound (XXVIII-a) from compound (XXX).

Compound (XXXIII-a) can also be produced from compound (XXVIII-a) according to a known substituent conversion reaction. The substituent conversion reaction can be performed by a method similar to the method of producing compound (XXXII) from compound (XXX).

Compound (XXVIII-b) can be produced from compound (XXXIII-b) according to a known substituent conversion reaction. The substituent conversion reaction can be performed by a method similar to the method of producing compound (XXX) from compound (XXXII).

Compound (XXVIII-c) can be produced from compound (XXVIII-b) according to a known carbon chain extension reaction. For example, reactions wherein carboxy or alkoxycarbonyl of compound (XXVIII-b) is subjected to a reduction reaction to give an alcohol form, which is then subjected to halogenation and cyanation, and cyano is hydrolyzed under alkaline or acidic conditions to give carboxy, or the carboxy is led to an ester form and the like are employed.

Compound (XXXIII-b) can be produced from compound (XXVIII-b) according to a known substituent conversion reaction. The substituent conversion reaction can be performed by a method similar to the method of producing compound (XXXII) from compound (XXX).

Compound (XXXIII-c) can be produced from compound (XXXIII-b) according to a known carbon chain extension reaction. For example, reactions wherein cyano is hydrolyzed under alkaline or acidic conditions to give carboxy, or the carboxy is led to an ester form, subjected to a reduction reaction to give an alcohol form, then subjected to halogenation and cyanation and the like are employed.

Compound (XXXIV) wherein m is 1 or 2 can be produced by subjecting compound (XXVIII-b) or (XXVIII-c) to a reduction reaction. The reduction reaction can be performed by a method similar to the method of producing compound (VI) from compound (V).

Compound (XXXV) wherein m is 1 or 2 can be produced by subjecting compound (XXXIV) to an oxidation reaction. The oxidation reaction can be performed by a method similar to the method of producing compound (III-m) from compound (III-l).

Compound (XXXVI) wherein m is 1 or 2 can be produced by condensing compound (XXXV) and hydroxylamine in the presence of an acid or a base. The condensation reaction can be performed by a method similar to the method of producing compound (XIV) from compound (XIII).

Compound (XXXVII) can be produced by subjecting compound (XXXVI) to a reduction reaction. The reduction reaction can be performed by a method similar to the method of producing compound (VI) from compound (V).

Compound (XXXVII) can also be produced from compound (XXXIV) according to a known substituent conversion reaction. For example, a method including converting hydroxy to a leaving group, then subjecting to a substitution reaction with amine, a method including subjecting the leaving group to a substitution reaction with azide, and reducing azido to amino, a method including converting hydroxy to phthalimido by Mitsunobu reaction, and removing phthalic acid, a method including oxidizing hydroxy to aldehyde, and subjecting aldehyde to a reductive amination reaction and the like are employed.

Compound (XXXVII) can also be produced by subjecting compound (XXXIII-b) or compound (XXXIII-c) to a reduction reaction. The reduction reaction can be performed by a method similar to the method of producing compound (VI) from compound (V).

Compound (I) can be produced by reacting compound (XXXVII) with carboxylic acid, a salt thereof or a reactive derivative thereof or isocyanate. Examples of the carboxylic acid include a compound represented by the formula $R^1$—COOH. Examples of the reactive derivative of carboxylic acid include acid halides such as acid chloride, acid bromide and the like, acid amides with pyrazole, imidazole, benzotriazole and the like, acid anhydrides such as acetic anhydride, propionic anhydride, butyric anhydride and the like, acid azides, active esters such as diethoxyphosphphoric acid ester, diphenoxyphosphphoric ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester etc., and the like. Instead of using the reactive derivatives, carboxylic acid or a salt thereof may be directly reacted with compound (XXXVII) in the presence of a suitable condensation agent. Examples of the condensation agent include N,N'-disubstituted carbodiimides such as N,N'-dicyclohexylcarbodiimide, 1-ethyl-3-(3-dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide etc., and the like. When these condensation agents are used, the reaction is considered to proceed via a reactive derivative of carboxylic acid. As the isocyanate, for example, a compound represented by the formula $R^1$—NCO can be mentioned. The carboxylic acid, a salt thereof or a reactive derivative thereof, or the isocyanate is used in a proportion of generally about 1.0 to 5.0 mol, preferably about 1.0 to 2.0 mol, per 1 mol of compound (XXXVII). This reaction is advantageously performed using a solvent inert to the reaction. While such solvent is not particularly limited as long as the reaction proceeds, for example, a solvent such as ethers, aromatic hydrocarbons, saturated hydrocarbons, amides, halogenated hydrocarbons, nitriles, sulfoxides, aromatic organic bases and the like or a mixed solvent thereof and the like are preferable. When an acidic substance is released by the reaction, the reaction can be performed in the presence of a deacidifying agent to remove the acidic substance from the reaction system. Examples of the deacidifying agent include basic salts such as sodium carbonate, potassium carbonate, cesium carbonate, calcium carbonate, sodium hydrogen carbonate and the like, organic bases such as triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2] octane, 1,8-diazabicyclo[5.4.0]-7-undecene etc., and the like. While the reaction time varies depending on the reagent and solvent to be used, it is generally 10 min to 24 hr, preferably 30 min to 4 hr. The reaction temperature is generally 0° C. to 100° C., preferably 0° C. to 70° C.

Compound (I) can be produced by reacting compound (XXXVII) with a carbonating agent. The carbonation reaction can be performed according to, for example, the method described in Shin Jikken Kagaku Koza (New Experimental Chemistry Course), vols. 14 and 15, pages 230-239 (The Chemical Society of Japan Ed.) and the like, or a method analogous thereto.

A carboxylic acid represented by the formula $R^1$—COOH, a salt thereof or a reactive derivative thereof, or an isocyanate represented by the formula $R^1$—NCO may be a commercially available product, or can also be produced by a method known per se, or a method analogous thereto.

Of compound (I) or compound (XXXVII), a compound wherein $R^2$ is a hydrocarbon group optionally having substituent(s) can be produced by subjecting compound (I) or compound (XXXVII) wherein $R^2$ is a hydrogen atom to an alkylation reaction using the corresponding alkylating agent (e.g., alkyl halide, sulfonic acid ester of alcohol and the like) in the presence of a base. The alkylating agent is used in a proportion of about 1.0 to 50 mol, preferably about 1.0 to 3.0 mol, per 1 mol of compound (XXXVII). Examples of the base include inorganic bases, basic salts, organic bases, metal alkoxides, alkali metal hydrides, metal amides and the like. The base is used in a proportion of about 1.0 to 5.0 mol, preferably about 1.0 to 2.0 mol, per 1 mol of compound (I) or compound (XXXVII). This reaction is advantageously performed using a solvent inert to the reaction. While such solvent is not particularly limited as long as the reaction proceeds, for example, a solvent such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 30 min to 48 hr, preferably 30 min to 6 hr. The reaction temperature is generally −20° C. to 200° C., preferably −10° C. to 150° C.

Compounds (I), (XXVIII-a), (XXVIII-b), (XXVIII-c), (XXX), (XXXII), (XXXIII-a), (XXXIII-b), (XXXIII-c), (XXXIV), (XXXV), (XXXVI) and (XXXVII) can be produced as a single configuration isomer or stereoisomer, or a mixture thereof. These isomers can be each obtained as a single product by a synthesis method, a separation method (e.g., concentration, solvent extraction, column chromatography, recrystallization and the like), an optical resolution method (e.g., fractional recrystallization, chiral column method, diastereomer method and the like), each known per se, and the like. In addition, they can be converted to desired isomers by using heating, acid catalyst, transition metal complex, metal catalyst, radical species catalyst, photoirradiation, strong base catalyst and the like according to the methods described in Shin Jikken Kagaku Koza (New Experimental Chemistry Course), vol. 14, pages 251-253 (The Chemical Society of Japan Ed.), 4th Ed. Jikken Kagaku Koza (Courses in Experimental Chemistry), vol. 19, pages 273-274 (The Chemical Society of Japan Ed.) and the like or a method analogous thereto.

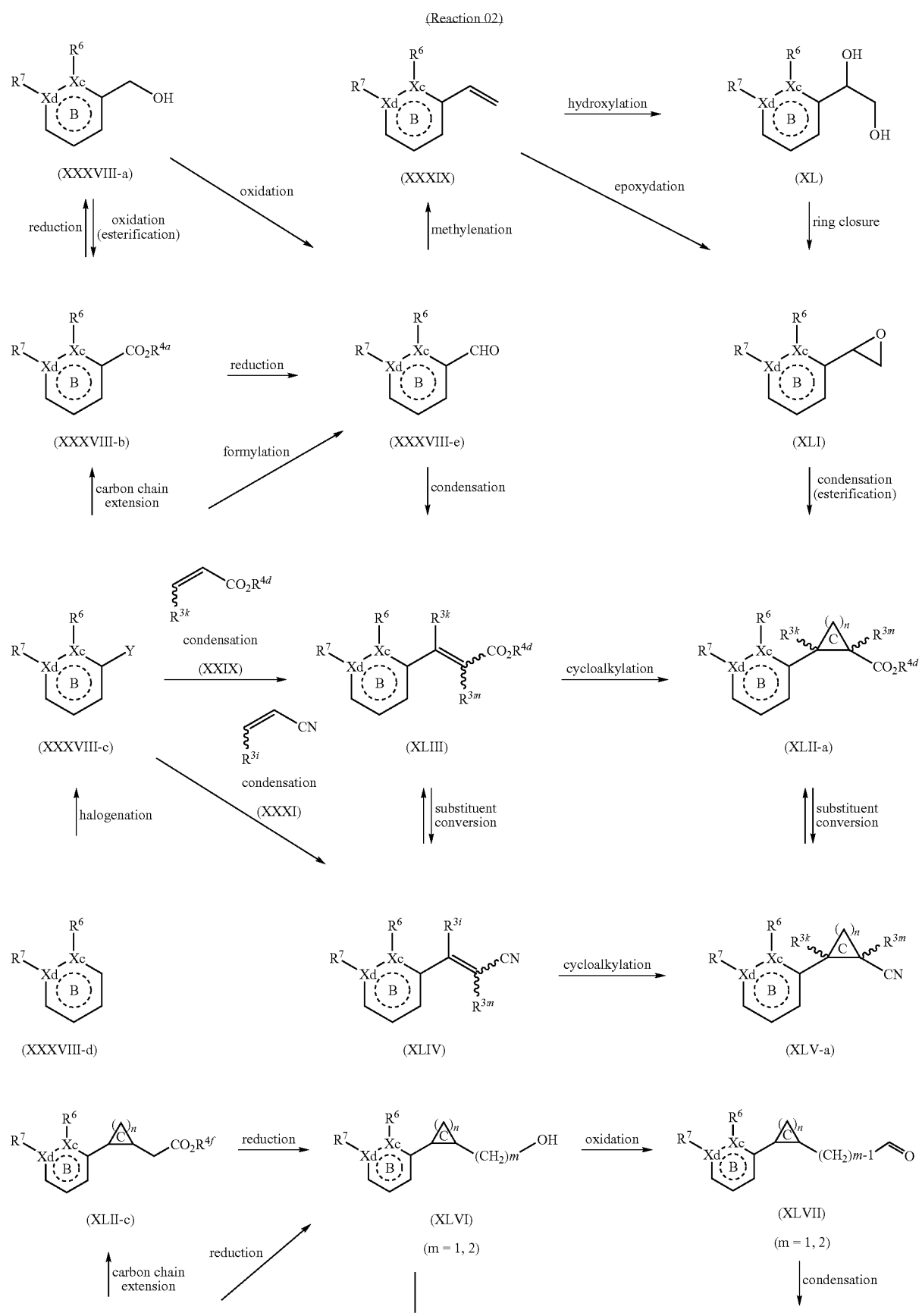

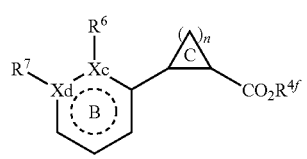
(XLII-b)
⇅ substituent conversion (alkylation)
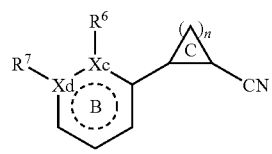
(XLV-b)
↓ carbon chain extension
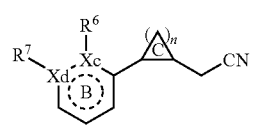
(XLV-c)
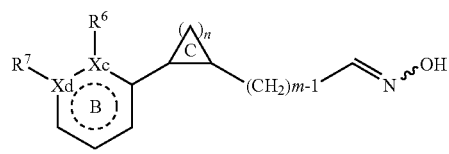
(XLVIII) (m = 1, 2)
↓ reduction (alkylation)
substituent conversion (alkylation) ↓
reduction (alkylation) ↗
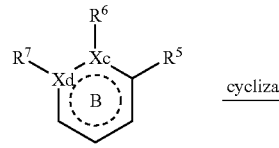 →reduction (alkylation)→ 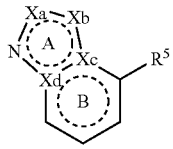 →acylation ureation carbonation (alkylation)→ 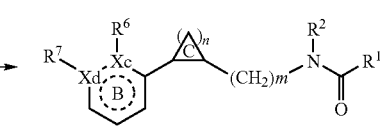
(XLIX)     (L)
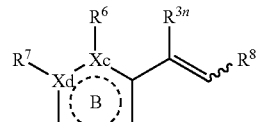 →cyclization→ 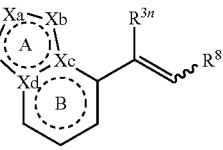
(LI)     (III)
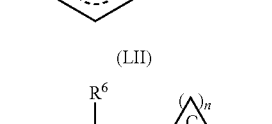 →cyclization→ 
(LII)     (LIII)
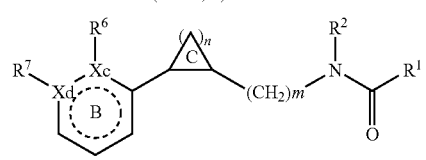 →cyclization→ 
(LIV) (m = 1, 2)     (LV) (m = 1, 2)
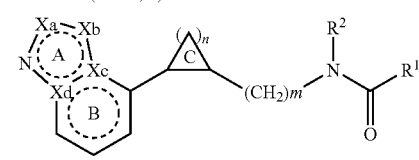
(L) →cyclization→ (I)

Compound (XXXVIII-a) whose formula collectively shows combinations of Xc, Xd, $R^6$ and $R^7$ [Xc:C, Xd:C, $R^6$:—$CH_2$—$R^{3a}$, $R^7$:—$NP^1P^2$], [Xc:C, Xd:C, $R^6$:H, $R^7$:—NH—CO—$R^{3c}$], [Xc:C, Xd:C, $R^6$:$NO_2$, $R^7$:—NH—CO—$R^{3c}$], [Xc:C, Xd:C, $R^6$:—$NP^3P^4$, $R^7$:—NH—CO—$R^{3c}$], [Xc:N, Xd:C, $R^6$:H, $R^7$:—$NP^5P^6$], [Xc:N, Xd:C, $R^6$:H, $R^7$:—N=C($R^{3f}$)N($CH_3$)$_2$], [Xc:N, Xd:C, $R^6$:H, $R^7$:—NH—C($R^{3f}$)=N—OH], [Xc:N, Xd:C, $R^6$:H, $R^7$:Y], [Xc:N, Xd:C, $R^6$:H, $R^7$:—NH—$NH_2$], [Xc:C, Xd:N, $R^6$:H, $R^7$:H], [Xc:C, Xd:N, $R^6$:—CO—$R^{3i}$, $R^7$:H], [Xc:C, Xd:N, $R^6$:—C($R^{3i}$)=N—OH, $R^7$:H], [Xc:C, Xd:C, $R^6$:H, $R^7$:—$NP^7P^8$] and [Xc:C, Xd:C, $R^6$:Y, $R^7$:—$NP^7P^8$], wherein each symbol is as defined above, can be produced by a method similar to the method of producing compound (III-l).

Compound (XXXVIII-b) can be produced by a method similar to the method of producing compound (III-m), compound (XXXVIII-c) can be produced by a method similar to the method of producing compound (III-n), compound (XXXVIII-d) can be produced by a method similar to the method of producing compound (III-o), compound (XXXVIII-e) can be produced by a method similar to the method of producing compound (III-p), compound (XXXIX) can be produced by a method similar to the method of producing compound (XXV), compound (XL) can be produced by a method similar to the method of producing compound (XXVI), compound (XLI) can be produced by a method similar to the method of producing compound (XXVII), compound (XLII-a) can be produced by a method similar to the method of producing compound (XXVIII-a), compound (XLIII) can be produced by a method similar to the method of producing compound (XXX), compound (XLIV) can be produced by a method similar to the method of producing compound (XXXII), compound (XLV-a) can be produced by a method similar to the method of producing compound (XXXIII-a), compound (XLII-c) can be produced by a method similar to the method of producing compound (XXVIII-c), compound (XLII-b) can be produced by a method similar to the method of producing compound (XXVIII-b), compound (XLV-b) can be produced by a method similar to the method of producing compound (XXXIII-b), compound (XLV-c) can be produced by a method similar to the method of producing compound (XXXIII-c), compound (XLVI) can be produced by a method similar to the method of producing compound (XXXIV), compound (XLVII) can be produced by a method similar to the method of producing compound (XXXV), compound (XLVIII) can be produced by a method similar to the method of producing compound (XXXVI), compound (XLIX) can be produced by a method similar to the method of producing compound (XXXVII), and compound (L) can be produced by a method similar to the method of producing compound (I).

Compound (III) can be produced by subjecting compound (LI) to a series of reaction steps including a cyclization reaction. Examples of the series of reaction steps including a cyclization reaction include a method of producing compound (III-a) or (III-b) from compound (II), a method of producing compound (III-c) from compound (VI), a method of producing compound (III-d) from compound (VII), a method of producing compound (III-f) from compound (XIV), a method of producing compound (III-e) from compound (X), a method of producing compound (III-g), compound (III-h) or compound (III-i) from compound (XV), a method of producing compound (III-j) from compound (XX), a method of producing compound (III-k) from compound (XXIII) and the like, and the reaction can be performed by a method similar to the methods of producing them.

Compound (LIII) can be produced by subjecting compound (LII) to a series of reaction steps including a cyclization reaction. These reactions can be performed by a method similar to the method of producing compound (III) from compound (LI).

Compound (LV) can be produced by subjecting compound (LIV) to a series of reaction steps including a cyclization reaction. These reactions can be performed by a method similar to the method of producing compound (III) from compound (LI).

Compound (I) can be produced by subjecting compound (L) to a series of reaction steps including a cyclization reaction. These reactions can be performed by a method similar to the method of producing compound (III) from compound (LI).

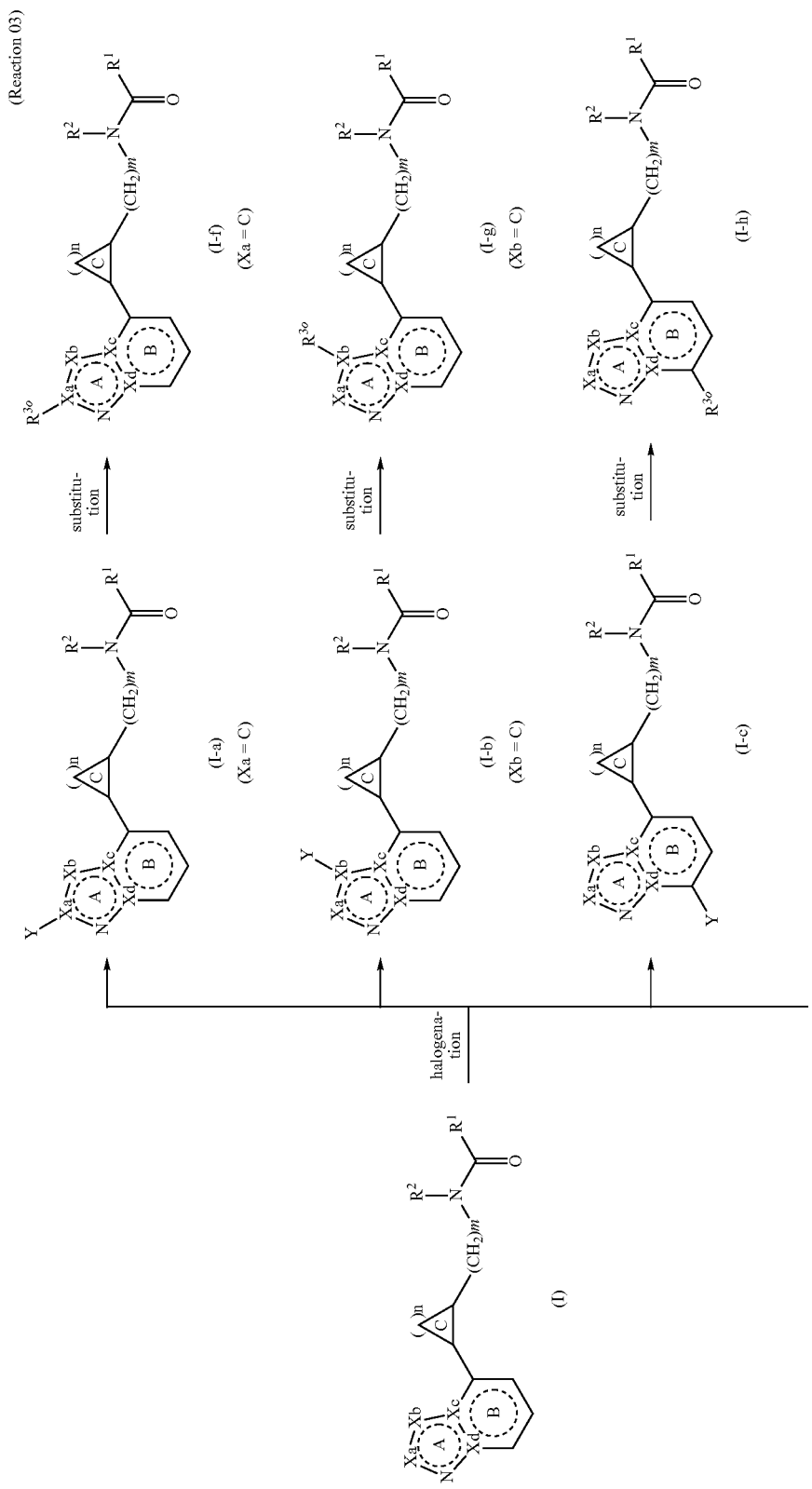

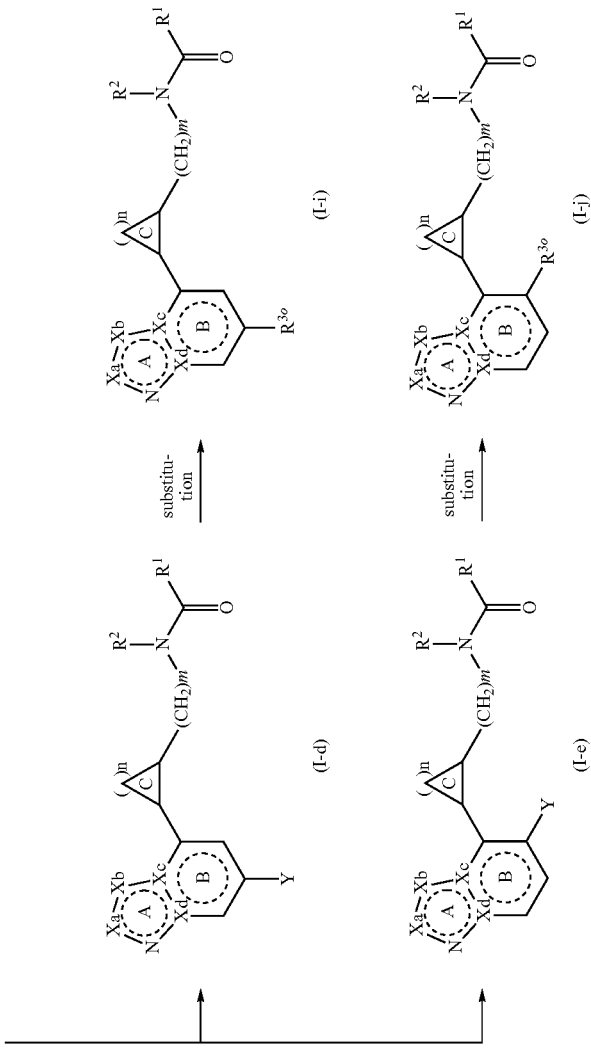

Compound (I-f) can be produced by reacting compound (I) with a halogenating agent to give compound (I-a), then subjecting the compound to a condensation reaction using organic boronic acid or organic boronic acid ester and a metal catalyst. Examples of the halogenating agent include phosphorus halide, succinimides, halogen, thionyl chloride, and mixtures thereof and the like. The halogenating agent is used in a proportion of about 1.0 to 100 mol, preferably about 1.0 to 10 mol, per 1 mol of compound (I). To promote the reaction, the reaction can be performed in the presence of a base. Examples of the base include inorganic bases, basic salts and the like. This reaction is advantageously performed without solvent or in a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, sulfoxides, acid anhydrides, organic acids, inorganic acids, water and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 200° C., preferably 10° C. to 100° C.

The condensation reaction is performed by reacting compound (I-a) with an organic boronic acid or organic boronic acid ester in the presence of a metal catalyst. Examples of the organic boronic acid or organic boronic acid ester include a compound represented by the formula $R^{3o}$-M wherein M is the boron atom part of the organic boronic acid or organic boronic acid ester. Preferable examples of M include dihydroxyboranyl group, 4,4,5,5-tetramethyl-1,3,2-dioxaborolan-2-yl group and the like. As the metal catalyst, a palladium compound is preferable. The reaction is generally performed in the presence of a base. Examples of the base include inorganic bases, basic salts and the like. The organic boronic acid or organic boronic acid ester is used in a proportion of about 0.1 to 10 mol, preferably about 0.8 to 2.0 mol, per 1 mol of compound (I-a). The metal catalyst is used in a proportion of about 0.000001 to 5.0 mol, preferably about 0.0001 to 1.0 mol, per 1 mol of compound (I-a). The base is used in a proportion of about 1.0 to 20 mol, preferably about 1.0 to 5.0 mol, per 1 mol of compound (I-a). When a metal catalyst unstable to oxygen is used for these reactions, the reaction is preferably performed, for example, in an inert gas stream such as argon gas, nitrogen gas and the like. This reaction is advantageously performed using a solvent inert to the reaction. While such solvent is not particularly limited as long as the reaction proceeds, for example, a solvent such as alcohols, ethers, aromatic hydrocarbons, saturated hydrocarbons, amides, halogenated hydrocarbons, nitriles, esters, water and the like or a mixed solvent thereof and the like are preferable. While the reaction time varies depending on the reagent and solvent to be used, it is generally 1 min to 200 hr, preferably 5 min to 100 hr. The reaction temperature is −10° C. to 250° C., preferably 0° C. to 150° C.

As the organic boronic acid or organic boronic acid ester repreented by the formula $R^{3o}$-M, a commercially available product may be used or can also be produced by a method known per se or a method analogous thereto.

Compound (I-f) can also be produced by subjecting compound (I-a) to a desired substituent exchange reaction known per se. The reaction can be carried out, for example, by the method described in Shin Jikken Kagaku Koza (New Experimental Chemistry Course), vols. 14 and 15 (edited by the Chemical Society of Japan) and the like, or a method analogous thereto.

Compounds (I-g), (I-h), (I-i) and (I-j) can be produced by a method similar to the method for producing compound (I-f) from compound (I).

A compound represented by the formula

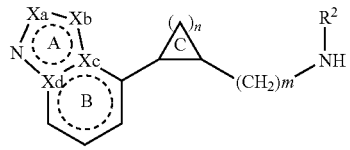

wherein each symbol is as defined above, or a salt thereof, which is obtained in the reaction step to give the aforementioned compound (I), is a novel compound, and can be used as a starting material of the compound of the present invention. Preferable compounds include 1-[2-(2-methyl-2H-indazol-4-yl)cyclopropyl]methanamine,
1-[2-(2-methyl[1,2,4]triazolo[1,5-a]pyridin-8-yl)cyclopropyl]methanamine,
1-[2-(2-methylpyrazolo[1,5-a]pyridin-4-yl)cyclopropyl]methanamine,
1-[2-(2-ethyl-2H-indazol-4-yl)cyclopropyl]methanamine,
1-[2-(5-fluoro-2-methyl-2H-indazol-4-yl)cyclopropyl]methanamine,
1-[2-(5-chloro-2-methyl-2H-indazol-4-yl)cyclopropyl]methanamine,
1-[2-(5-bromo-2-methyl-2H-indazol-4-yl)cyclopropyl]methanamine,
1-[2-(7-fluoro-2-methyl-2H-indazol-4-yl)cyclopropyl]methanamine,
1-[2-(7-chloro-2-methyl-2H-indazol-4-yl)cyclopropyl]methanamine,
1-[2-(2-methylimidazo[1,2-a]pyridin-5-yl)cyclopropyl]methanamine,
1-{2-[2-(trifluoromethyl)imidazo[1,2-a]pyridin-5-yl]cyclopropyl}methanamine,
1-[2-(2-methyl[1,2,4]triazolo[1,5-a]pyridin-5-yl)cyclopropyl]methanamine,
1-[2-(2-methyl-1,3-benzothiazol-7-yl)cyclopropyl]methanamine,
1-[2-(1,2,3-benzothiadiazol-7-yl)cyclopropyl]methanamine,
1-[2-(2,1-benzisothiazol-4-yl)cyclopropyl]methanamine, an optically active form thereof, a salt thereof and the like.

In the aforementioned respective reactions, when the starting compound has amino, carboxy, hydroxy or a heterocyclic group, these groups may be protected by a protecting group generally used in the peptide chemistry and the like. In this case, the object compound can be obtained by removing the protecting group as necessary after the reaction. Introduction and removal of these protecting groups can be performed by a method known per se, for example, the method described in "Protective Groups in Organic Synthesis, 3$^{rd}$ Ed." (Theodora W. Greene, Peter G. M. Wuts, Wiley-Interscience, 1999) and the like.

The configuration isomers of the aforementioned compounds (II)-(LV) can be isolated and purified by, for example, a conventional separation means such as extraction, recrystallization, distillation, chromatography and the like, when isomerization occurs, whereby a pure compound can be produced. In addition, isomerization of double bond may be promoted by heating, acid catalyst, transition metal complex, metal catalyst, radical species catalyst, photoirradiation or strong base catalyst and the like according to the method described in Shin Jikken Kagaku Koza (New Experimental Chemistry Course), vol. 14, pp. 251-253 (edited by the Chemical Society of Japan), Jikken Kagaku Koza (Courses in Experimental Chemistry), 4th Ed., vol. 19, pp. 273-274 (edited by the Chemical Society of Japan) and the like or a method analogous thereto, whereby a corresponding pure isomer can be obtained. While compound (I) has a stereoisomer depending on the kind of the substituent, not only the isomer itself but also a mixture thereof are encompassed in the present invention. In the above-mentioned reaction steps, where desired, compound (I) can be produced by a known hydrolysis, deprotection, acylation reaction, alkylation reaction, hydrogenation reaction, oxidation reaction, reduction reaction, carbon chain extension reaction or substituent exchange reaction, conducted individually or by a combination of two or more thereof. These reactions can be carried out, for example, according to the method described in Shin Jikken Kagaku Koza (New Experimental Chemistry Course), vols. 14 and 15 (edited by the Chemical Society of Japan) and the like.

Compound (I) can be isolated and purified by a known means, for example, phase transfer, concentration, solvent extraction, fractional distillation, liquid conversion, crystallization, recrystallization, chromatography and the like.

When compound (I) is obtained as a free compound, it can be converted into a desired salt by a method known per se or a modification thereof; conversely, when compound (I) is obtained as a salt, it can be converted into a free form or another desired salt by a method known per se or a modification thereof.

Compound (I) may be used as a prodrug. A prodrug of compound (I) means a compound which is converted to compound (I) with a reaction due to an enzyme, gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

A prodrug of compound (I) may be a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting hydroxy in compound (I) to an acylation, alkylation, phosphorylation or boration (e.g., a compound obtained by subjecting hydroxy in compound (I) to an acetylation, palmitoylation, propanoylation, pivaloylation, succinylation, fumarylation, alanylation, dimethylaminomethylcarbonylation, etc.); a compound obtained by subjecting carboxy in compound (I) to an esterification or amidation (e.g., a compound obtained by subjecting carboxy in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7 (Design of Molecules), p. 163-198 (HIROKAWA SHOTEN).

When compound (I) has isomers such as optical isomer, stereoisomer, positional isomer, rotational isomer and the like, any isomers and mixtures are encompassed in compound (I). For example, when compound (I) has an optical isomer, an optical isomer separated from a racemate is also encompassed in compound (I). These isomers can be obtained as independent products by a synthesis means or a separation means (e.g., concentration, solvent extraction, column chromatography, recrystallization and the like), optical resolution methods (e.g., fractional recrystallization, chiral column method, diastereomer method and the like) and the like known per se.

Compound (I) has a stereoisomer due to ring C, with preference given to a trans form.

Compound (I) may be a crystal, and both a single crystal and crystal mixtures are encompassed in compound (I) of the present invention. Crystals can be produced by crystallization according to crystallization methods known per se.

Compound (I) may be a solvate (e.g., hydrate etc.) or a non-solvate (e.g., non-hydrate etc.), both of which are encompassed in compound (I) of the present invention.

A compound labeled with an isotope (e.g., $^2H$, $^3H$, $^{14}C$, $^{35}S$, $^{125}I$ and the like) is also encompassed in compound (I) of the present invention.

Compound (I) of the present invention shows high affinity for melatonin receptors ($MT_1$ receptor, $MT_2$ receptor). Since compound (I) acts as a melatonin agonist, has physiological activities such as melatonin receptor affinity and the like, shows low toxicity (e.g., acute toxicity, chronic toxicity, genetic toxicity, reproductive toxicity, cardiotoxicity, drug interaction, carcinogenicity and the like), and is superior in the stability and in vivo kinetics (absorption, distribution, metabolism, excretion and the like), it is useful as a pharmaceutical product. Compound (I) acts as a melatonin agonist in mammals (e.g., mouse, rat, hamster, rabbit, cat, dog, bovine, sheep, monkey, human and the like), is useful as a composition with a binding affinity for melatonin receptor, particularly, a melatonin receptor agonist, and can be used as a prophylactic or therapeutic drug for a disease possibly influenced by melatonin. As the "disease possibly influenced by melatonin", for example, sleep disorders [e.g., intrinsic sleep disorders (e.g., psychophysiological insomnia and the like), extrinsic sleep disorders, circadian rhythm disorders (e.g., time-zone change syndrome (jet lag), shift work sleep disorder, irregular sleep-wake pattern, delayed sleep phase syndrome, advanced sleep phase syndrome, non-24 hour sleep-wake syndrome and the like), parasomnias, sleep disorder associated with internal or psychic disorders (e.g., chronic obstructive pulmonary disease, Alzheimer's disease, Parkinson's disease, cerebrovascular dementia, schizophrenia, depression, anxiety neurosis), insomnia and the like], neurodegenerative diseases (e.g., senile dementia, Alzheimer's disease, Parkinson's disease, Creutzfeldt-Jakob disease, amyotrophic lateral sclerosis (ALS), Huntington's disease, spinocerebellar degeneration, multiple sclerosis (MS) and the like), psychoneurotic diseases (e.g., depression, anxiety, bipolar disorder, posttraumatic stress disorder (PTSD), seasonal melancholia, schizophrenia and the like), memory disorders (e.g., senile dementia, mild cognitive impairment (MCI), amnesia and the like), ischemic central nervous disorders (e.g., cerebral infarction, cerebral hemorrhage, brain edema and the like), central nervous system injury (e.g., head trauma, spinal cord injury, whiplash injury and the like), vascular dementia (e.g., multi-infarct dementia, Binswanger's disease and the like), cancer (e.g., brain tumor, pituitary adenoma, glioma, acoustic schwannoma, retinoblastoma, thyroid cancer, pharyngeal cancer, laryngeal cancer, cancer of the tongue, thymoma, mesothelial tumor, breast cancer, lung cancer, non-small cell lung cancer, small cell lung cancer, gastric cancer, esophageal cancer, duodenal cancer, colorectal cancer, colon cancer, rectal cancer, liver cancer, hepatocellular carcinoma, pancreatic cancer, pancreatic endocrine tumor, biliary tract cancer, gallbladder cancer, penile cancer, kidney cancer, renal pelvic cancer, ureteral cancer, renal cell cancer, testis tumor, prostate cancer, urinary bladder cancer, vulvar cancer, uterine cancer, cancer of uterine cervix, cancer of uterine body, uterine sarcoma, chorionic disease, vaginal cancer, ovary cancer, ovarian germ cell tumor, skin cancer, malignant melanoma, mycosis fungoides, basal cell tumor, soft tissue sarcoma, malignant lymphoma, Hodgkin's disease, osteomyelodysplasia syndrome, multiple myeloma, leukemia, acute myelocytic leukemia, chronic myelocytic leukemia, acute lymphatic leukemia, chronic lymphatic leukemia, adult T cell leukemia, chronic myeloproliferative disease, pancreatic endocrine tumor, fibrous histiocytoma, leiomyosarcoma, rhabdomyosarcoma, unknown primary cancer and the like), hyperinsulinemia, metabolic syndrome, obesity, diabetes, diabetic complications (e.g., diabetic retinopathy, diabetic neuropathy, diabetic nephropathy and the like), hypertriglyceridemia (hyperlipidemia), hypertension, circulatory disease [e.g., ischemic cardiac diseases (e.g., myocardial infarction, angina pectoris and the like), cerebral apoplexy, arteriosclerosis, arterial restenosis after PTCA and the like], lower urinary tract disease or disorder (e.g., dysuria, incontinence and the like), osteoporosis, reproductive and neuroendocrine diseases, convulsion, glaucoma, headache, irritable bowel syndrome and the like can be mentioned. In addition, it is effective for immunoregulation, cognitive enhancement, tranquilization, stress or regulation of ovulation (e.g., contraception and the like).

Compound (I) [sometimes to be abbreviated as "the compound of the present invention"] can be safely administered orally or parenterally (e.g., subcutaneous, topical, rectal, intravenous administrations etc.) by itself, or in the form of a pharmaceutical composition containing a pharmacologically acceptable carrier according to a conventional method (e.g., the method described in the Japanese Pharmacopoeia etc.), such as tablet (including sugar-coated tablet, film-coated tablet and the like), powder, granule, capsule, liquid, emulsion, suspension, injection, suppository, sustained-release preparation (e.g., sublingual tablet, microcapsule etc.), plaster, orally disintegrating tablet, orally disintegrating film and the like.

As pharmacologically acceptable carriers, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidizing agent, colorant, sweetening agent, adsorbent, wetting agent and the like can be used appropriately.

As the excipient, for example, lactose, sucrose, D-mannitol, starch, cornstarch, crystalline cellulose, light anhydrous silicic acid and the like can be mentioned. As the lubricant, for example, magnesium stearate, calcium stearate, talc, colloidal silica and the like can be mentioned. As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like can be mentioned. As the disintegrant, for example, starch, carboxymethylcellulose, calcium carboxymethylcellulose, croscarmellose sodium, sodium carboxymethyl starch, L-hydroxypropylcellulose and the like can be mentioned. As the solvent, for example, water for injection, alcohol, propylene glycol, macrogol, sesame oil, corn oil, olive oil and the like can be mentioned. As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned. As the suspending agent, for example, surfactants such as stearyltriethanolamine, sodium lauryl sulfate, lauryl aminopropionate, lecithin, benzalkonium chloride, benzethonium chloride, glyceryl monostearate, and the like; for example, hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose etc., and the like can be mentioned. As the isotonicity agent, for example, glucose, D-sorbitol, sodium chloride, glycerol, D-mannitol and the like can be mentioned. As the buffer, for example, buffer such as phosphate, acetate, carbonate, citrate etc., and the like can be mentioned. As the soothing agent, for example, benzyl alcohol and the like can be mentioned. As the preservative, for example, p-hydroxybenzoates, chlorobutanol, benzyl alcohol, phenethyl alcohol, dehydroacetic acid, sorbic acid and the like can be mentioned. As the antioxidizing agent, for example, sulfite, ascorbic acid, $\alpha$-tocopherol and the like can be mentioned.

While the dose of the compound of the present invention varies depending on the subject of administration, administration route and symptom and is not particularly limited, for example, for oral administration to adult patients for the treatment of insomnia, it is about 0.001 to about 3 mg/kg body weight, preferably about 0.005 to about 2 mg/kg body weight, more preferably about 0.01 to about 1 mg/kg body weight, as the compound of the present invention, which is the active ingredient. The dose is desirably administered about 1 to 3 times a day according to the symptom.

The content of the compound of the present invention in the above-mentioned "agent (pharmaceutical composition)" is about 0.01 to 100 wt % of the whole composition.

When the compound of the present invention is applied to each of the above-mentioned diseases, it can be used in appropriate combination with a pharmaceutical agent or a treatment method generally employed for the disease.

In the following, a combined use of the compound of the present invention with a concomitant drug is referred to as "the combination agent of the present invention".

As such concomitant drug, for example, sleep inducing agents (e.g., GABA system sleep inducing agent such as brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol etc.; non-GABA system sleep inducing agent such as eplivaserin, pruvanserin, diphenhydramine, trazodone, doxepin etc., and the like), antidepressants (e.g., fluoxetine, sertraline, paroxetine, venlafaxine, nefazodone, reboxetine, mirtazapine, imipramine hydrochloride, duloxetine, escitalopram, mifepristone, doxepin, etc.), antianxiety agents (e.g., alprazolam, bromazepam, chlordiazepoxide, diazepam, etizolam, flutoprazepam, lorazepam, etc.), therapeutic agents for Alzheimer's disease (e.g., cholinesterase inhibitors such as donepezil, rivastigmine, galanthamine, zanapezil etc.; cerebral function activators such as idebenone, memantine, vinpocetine etc.; agents for suppressing progression such as Alzhemed etc., and the like), antiparkinson agents (e.g., L-DOPA, deprenyl, carbidopa+levodopa, pergolide, ropinirole, cabergoline, pramipexole, entacaprone, lazabemide etc.), therapeutic agents for amyotrophic lateral sclerosis (e.g., riluzole, mecasermin, gabapentin, etc.), neurotrophic factors, therapeutic agents for schizophrenia (e.g., olanzapine, risperidone, quetiapine, iloperidone, etc.), hypolipidemic agents (e.g., simvastatin, fluvastatin, pravastatin, atorvastatin, etc.), antihypertensive agents (e.g., captopril, delapril, enalapril, nifedipine, nicardipine, amlodipine, alprenolol, propranolol, metoprolol, losartan, valsartan, candesartan, etc.), therapeutic agents for diabetes (e.g., pioglitazone, rosiglitazone, metformin, glibenclamide, nateglinide, voglibose, etc.), antiplatelet agents (e.g., ticlopidine, heparin, urokinase, alteplase, tisokinase, nasaruplase, cilostazol, etc.), antioxidizing agents (e.g., linolenic acid, ascorbic acid, icosapentaenoic acid, docosahexaenoic acid, tocopherol, etc.), vitamins (e.g., tocopherol, ascorbic acid, etc.), sex hormones (e.g., estrogen, estrone, estradiol, etc.), antiinflammatory agents (e.g., prednisolone, betamethasone, dexamethasone, etc.), nonsteroidal antiinflammatory agents (e.g., indomethacin, ibuprofen, acetylsalicylic acid, diclofenac, naproxen, piroxicam, etc.), COX-2 inhibitors (e.g., celecoxib, rofecoxib, etc.), cerebral circulation metabolism improving agents (e.g., nicergoline, ibudilast, ifenprodil, etc.), anticonvulsants (e.g., carbamazepine, valproic acid, clonazepam, vigabatrin, lamotrigine, gabapentin, etc.) and pharmacologically acceptable salts thereof and the like can be mentioned.

By combining the compound of the present invention and a concomitant drug, a superior effect such as (1) the dose can be reduced as compared to single administration of the compound of the present invention or a concomitant drug,
(2) the concomitant drug can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

A combination agent of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules, solutions, emulsions, suspensions, injections, suppositories, sustained release preparations (e.g., sublingual tablet, microcapsule etc.), plasters, orally disintegrating tablets, orally disintegrating films and the like, which can be safely administered orally or parenterally (e.g., subcutaneous, topical, rectal, intravenous administrations etc.).

As pharmacologically acceptable carriers usable for the production of the combination agent of the present invention, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidizing agent, colorant, sweetening agent, adsorbent, wetting agent and the like can be used appropriately.

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the compound of the present invention and the concomitant drug is not particularly restricted, and it is sufficient that the compound of the present invention and the concomitant drug are combined in administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention and the concomitant drug.

The SEQ ID NOs in the sequence listing in the present specification shows the following sequences.

SEQ ID NO: 1 shows the base sequence of cDNA fragment encoding the full-length human melatonin 1 receptor (human $MT_1$ receptor). (see Gen Bank ACCESSION No. NM_005958)

SEQ ID NO: 2 shows the base sequence of cDNA fragment encoding the full-length human melatonin 2 receptor (human $MT_2$ receptor). (see Gen Bank ACCESSION No. NM_005959)

EXAMPLES

The present invention is explained in detail in the following by referring to Reference Examples, Examples, Formulation Examples and Experimental Examples. However, the examples are mere exemplifications and do not limit the present invention. The present invention may be modified without departing from the scope of the invention. In the following Reference Examples and Examples, the "room temperature" means generally about 10° C. to about 35° C., % means mol/mol % for the yield, % by volume for the solvent used for chromatography, and wt % for others. M means mol/L.

Other abbreviations used in the text mean the following.
s: singlet
d: doublet
t: triplet
q: quartet
m: multiplet
br: broad
J: coupling constant
Hz: Hertz
CDCl$_3$: deuteriochloroform
DMSO-d$_6$: deuteriodimethyl sulfoxide
METHANOL-d$_4$: deuteriomethanol
$^1$H-NMR: proton nuclear magnetic resonance The elution for the column chromatography in the Examples was performed under observation by TLC (Thin Layer Chromatography). In the TLC observation, 60F254 manufactured by Merck or NH (DM1020) manufactured by Fuji Silysia Chemical Ltd. was used as a TLC plate.

Unless otherwise specified, the silica gel packed in the column was silica gel 60 (70-230 mesh or 230-400 mesh) (manufactured by Merck) or PURIF-pack (SI 60 μm) (manufactured by Moritex Corporation). When described as silica gel chromatography (NH), CHROMATOREX-NH DM1020 (100-200 mesh) (manufactured by Fuji Silysia Chemical Ltd.) or PURIF-pack (NH 60 μm) (manufactured by Moritex Corporation) was used. Unless otherwise specified, moreover, the elution solvent for silica gel column chromatography is in volume ratio.

For preparative purification by TLC, unless otherwise specified, 60F254 manufactured by Merck was used. When indicated as TLC (NH), NH (DM1020) manufactured by Fuji Silysia Chemical Ltd. was used. The elution solvent is, unless otherwise specified, in a volume mixing ratio.

Preparative separation and purification by HPLC (High performance liquid chromatography) was performed using the following apparatus and conditions (condition A and condition B).
Condition A
Apparatus: Gilson high throughput purification system
Column: YMC CombiPrep ODS-A S-5 μm, 50×20 mm
Solvent: A; 0.1% trifluoroacetic acid aqueous solution, B; 0.1% trifluoroacetic acid acetonitrile solution
Gradient: A/B=100/0 to A/B=0/100
Detection: UV 220 nm
Condition B
Apparatus: Waters Preparative HPLC system
Column: Develosil ODS-UG-10 column, 50×100 mm or YMC CombiPrep ODS-A S-5 μm, 50×20 mm
Solvent: A; 0.1% trifluoroacetic acid aqueous solution, B; 0.1% trifluoroacetic acid acetonitrile solution
Gradient: A/B=100/0 to A/B=0/100
Detection: UV 220 nm In Reference Examples and Examples, $^1$H-NMR spectrum was measured using tetramethylsilane as the internal standard and the chemical shift is expressed in δ value and the coupling constant is expressed in Hz.

In the following Reference Examples and Examples, melting point, mass spectrum (MS) and nuclear magnetic resonance spectrum (NMR) were measured under the following conditions. Melting point apparatus: Yanagimoto micromelting point apparatus, or Buchi B-545 melting point apparatus MS measurement instrument: Waters ZMD, Waters ZQ, or Thermo Fisher Scientific Inc. Finnigan LCQ Advantage MAX, ionization method: Electron Spray Ionization (ESI) NMR measurement instrument: Varian, Inc., Varian Mercury 300 (300 MHz), Varian, Inc., Varian VNMRS-400 (400 MHz) or Bruker BioSpin AVANCE 300 (300 MHz)

Reference Example 1 methyl 1H-indazole-4-carboxylate

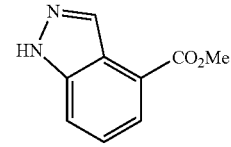

A mixture of methyl 3-amino-o-toluate (100 g, 605 mmol), a solution of ammonium tetrafluoroborate (83.0 g, 787 mmol) in water (600 mL) and concentrated hydrochloric acid (121 mL, 3.93 mmol) was cooled to 0° C., and a solution of sodium nitrite (41.8 g, 605 mmol) in water (88 mL) was added dropwise to the mixture over 25 min. This mixture was stirred for 35 min, and the resulting solid was collected by filtration. This solid was washed with water, methanol and diethyl ether, dried under nitrogen atmosphere, and added to a solution of potassium acetate (65.4 g, 666 mmol) and 18-crown-6 (4.50 g, 17.0 mmol) in chloroform (1.37 L). The resulting mixture was stirred at room temperature for 2 hr, and water (700 mL) was added. The partitioned organic layer was washed with water, and dried over anhydrous magnesium sulfate, and the solvent was evaporated under reduced pressure. The residue was triturated with hexane, and collected by filtration to give the title compound (63.0 g, yield 59%).

$^1$H-NMR (CDCl$_3$) δ: 4.03 (3H, s), 7.47 (1H, dd, 8.4, 7.2 Hz), 7.73 (1H, d, J=8.4 Hz), 7.96 (1H, d, J=7.2 Hz), 8.61 (1H, s),

MS (ESI+): 177 (M+H).

Reference Example 2 methyl 2-methyl-2H-indazole-4-carboxylate

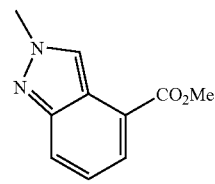

To a solution of methyl 1H-indazole-4-carboxylate (63.0 g, 358 mmol) in ethyl acetate (1.19 L) was added trimethyloxonium tetrafluoroborate (68.8 g, 465 mmol), and the mixture was stirred under nitrogen atmosphere at room temperature for 12 hr. The reaction solution was diluted with ethyl acetate, saturated aqueous sodium hydrogen carbonate solution was added, and the mixture was extracted with ethyl acetate. The extract was dried over anhydrous magnesium sulfate and the solvent was evaporated under reduced pressure. The residue was purified by recrystallization (ethyl acetate/hexane) to give the title compound (57.0 g, yield 84%).

$^1$H-NMR (CDCl$_3$) δ: 3.98 (3H, s), 4.27 (3H, s), 7.34 (1H, dd, J=8.4, 7.2 Hz), 7.91 (1H, d, J=6.4 Hz), 7.93 (1H, d, J=8.4 Hz), 8.42 (1H, s),

MS (ESI+): 191 (M+H).

Reference Example 3

(2-methyl-2H-indazol-4-yl)methanol

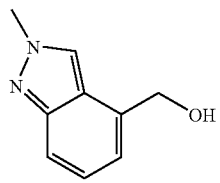

To a suspension of lithium aluminum hydride (14.27 g, 421 mmol) in tetrahydrofuran (315 mL) was added a solution of methyl 2-methyl-2H-indazole-4-carboxylate (40.0 g, 210 mmol) in tetrahydrofuran (106 mL) under nitrogen atmosphere at 0° C., and the mixture was stirred at room temperature for 1 hr. The reaction solution was diluted with diethyl ether at 0° C., water (15 mL), 10% aqueous sodium hydroxide solution (15 mL) and water (30 mL) were added and the mixture was stirred until gas generation stopped. The resulting precipitate was collected by filtration, and washed with ethyl acetate. The filtrate was concentrated under reduced pressure and the residue was triturated with ethyl acetate and hexane to give the title compound (30.7 g, yield 90%).

$^1$H-NMR (CDCl$_3$) δ: 1.79 (1H, t, J=6.0 Hz), 4.23 (3H, s), 4.93 (2H, d, J=6.0 Hz), 7.01 (1H, d, J=6.4 Hz), 7.24 (1H, dd, J=8.8, 6.4 Hz), 7.63 (1H, d, J=8.8 Hz), 8.07 (1H, s).

Reference Example 4

2-methyl-2H-indazole-4-carbaldehyde

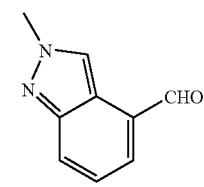

Under nitrogen atmosphere, dimethyl sulfoxide (70.0 mL, 987 mmol) was added to a solution of oxalyl chloride (43.2 mL, 493 mmol) in dichloromethane (2.47 L) at −78° C., and the mixture was stirred for 2 hr. To the reaction mixture was added (2-methyl-2H-indazol-4-yl)methanol (40.0 g, 247 mmol), and the mixture was stirred for 1 hr. To the reaction mixture was added triethylamine (139 mL, 987 mmol) at −78° C., and the mixture was stirred for 1 hr and warmed to room temperature over 4 hr. To the reaction mixture was added aqueous ammonium is chloride solution, and the mixture was extracted with dichloromethane. The extract was washed with saturated brine, and dried over anhydrous magnesium sulfate, and the solvent was evaporated under reduced pressure. The residue was purified by recrystallization (dichloromethane/hexane) to give the title compound (36.3 g, yield 92%).

$^1$H-NMR (CDCl$_3$) δ: 4.29 (3H, s), 7.46 (1H, dd, J=8.8, 6.8 Hz), 7.67 (1H, d, J=6.8 Hz), 8.01 (1H, dd, J=8.8, 0.8 Hz), 8.61 (1H, s), 10.1 (1H, s),

MS (ESI+): 161 (M+H).

Reference Example 5

1-amino-3-(hydroxymethyl)pyridinium 2,4-dinitrobenzenolate

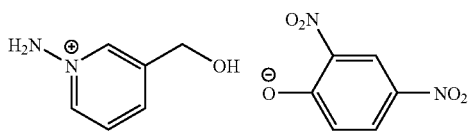

To a solution of 1-(aminooxy)-2,4-dinitrobenzene (117 g, 0.590 mol) in acetonitrile (1.18 L) was added 3-pyridinemethanol (64.1 g, 0.590 mol) at 40° C., and the mixture was stirred for 24 hr. The solvent was evaporated under reduced pressure, and the residue was washed with dichloromethane (1 L×2) to give the title compound (150 g, yield 83%).

$^1$H-NMR (DMSO-d$_6$) δ: 4.70 (2H, s), 5.87 (1H, br s), 6.32 (1H, d, J=10.0 Hz), 7.78 (1H, dd, J=9.6, 3.2 Hz), 7.97 (1H, dd, J=8.0, 6.4 Hz), 8.15 (1H, d, J=8.0 Hz), 8.49 (2H, s), 8.59 (1H, d, J=3.2 Hz), 8.66 (1H, d, J=6.4 Hz), 8.71 (1H, s).

Reference Example 6

(2-methyl[1,2,4]triazolo[1,5-a]pyridin-8-yl)methanol

To a solution of 1-amino-3-(hydroxymethyl)pyridinium 2,4-dinitrobenzenolate (100 g, 323 mmol) in acetonitrile (1.08 L), was added 2 N sodium hydroxide (485 mL) at room temperature, and the mixture was stirred for 12 hr. Acetonitrile was evaporated under reduced pressure, and the residual aqueous solution was extracted with 3 times with chloroform. The extract was dried over anhydrous sodium sulfate and the solvent was evaporated under reduced pressure. The residue was purified by recrystallization (ethyl acetate/hexane) to give the title compound (14.0 g, yield 29%).

$^1$H-NMR (CDCl$_3$) δ: 2.59 (3H, s), 4.05 (1H, br s), 5.04 (2H, d, J=4.4 Hz), 6.95 (1H, t, J=6.8 Hz), 7.45 (1H, d, J=6.8 Hz), 8.42 (1H, d, J=6.8 Hz),

MS (ESI+): 164 (M+H).

Reference Example 7

2-methyl[1,2,4]triazolo[1,5-a]pyridine-8-carbaldehyde

Under nitrogen atmosphere, to a solution of oxalyl chloride (16.0 mL, 180 mmol) in dichloromethane (200 mL) was added dimethyl sulfoxide (30.0 mL, 0.420 mol) at −78° C., and the mixture was stirred for 30 min. To the reaction mixture was added a solution of (2-methyl[1,2,4]triazolo[1,5-a]pyridin-8-yl)methanol (23.0 g, 0.141 mmol) in dichloromethane (82 mL), and the mixture was stirred for 2 hr. To the reaction mixture was added triethylamine (99.0 mL, 0.710 mol) at −78° C., and the mixture was stirred for 1 hr and warmed to room temperature. After concentration under reduced pressure, the residue was purified by silica gel column chromatography (methanol/ethyl acetate=1/10) to give the title compound (19.0 g, yield 84%).

$^1$H-NMR (CDCl$_3$) δ: 2.68 (3H, s), 7.15 (1H, t, J=6.8 Hz), 8.10 (1H, dd, J=7.2, 1.2 Hz), 8.73 (1H, dd, J=6.8, 1.2 Hz), 10.62 (1H, s),

MS (ESI+): 162 (M+H).

Reference Example 8 ethyl 4-(hydroxymethyl)-2-methylpyrazolo[1,5-a]pyridine-3-carboxylate

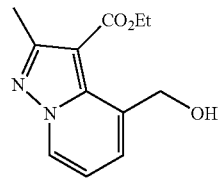

To a solution of 1-amino-3-(hydroxymethyl)pyridinium 2,4-dinitrobenzenolate (200 g, 0.650 mol) in dimethylformamide (1.3 L) was added potassium carbonate (224 g, 1.62 mol). To the mixture was added ethyl 2-butynoate (72.8 g, 0.650 mol) at room temperature, and the mixture was stirred for 12 hr. Water was added to the reaction mixture, and the mixture was extracted with ethyl acetate. The extract was dried over anhydrous sodium sulfate and the solvent was evaporated under reduced pressure. The residue was purified by silica gel column chromatography (ethyl acetate/hexane=1/3) to give the title compound (41.0 g, yield 27%).

$^1$H-NMR (CDCl$_3$) δ: 1.44 (3H, t, J=7.2 Hz), 2.65 (3H, s), 4.41 (2H, q, J=7.2 Hz), 4.86 (2H, d, J=8.0 Hz), 5.03 (1H, t, J=7.6 Hz), 6.87 (1H, t, J=6.8 Hz), 7.30 (1H, dd, J=7.2, 1.2 Hz), 8.37 (1H, dd, J=6.8, 1.2 Hz).

Reference Example 9

(2-methylpyrazolo[1,5-a]pyridin-4-yl)methanol

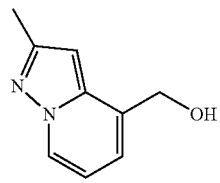

A mixture of ethyl 4-(hydroxymethyl)-2-methylpyrazolo[1,5-a]pyridine-3-carboxylate (41.0 g, 0.180 mol) and 40% aqueous sulfuric acid solution (350 mL) was stirred at 100° C. for 2 hr. The reaction mixture was basified with 10% aqueous sodium hydroxide solution, and extracted with dichloromethane. The extract was dried over anhydrous sodium sulfate and the solvent was evaporated under reduced pressure to give the title compound (28.0 g, yield 99%).

$^1$H-NMR (CDCl$_3$) δ: 2.13 (1H, br s), 2.48 (3H, s), 4.84 (2H, s), 6.34 (1H, s), 6.65 (1H, t, J=6.8 Hz), 7.09 (1H, dd, J=6.8, 1.2 Hz), 8.28 (1H, d, J=6.8 Hz),

MS (ESI+): 163 (M+H).

Reference Example 10

2-methylpyrazolo[1,5-a]pyridine-4-carbaldehyde

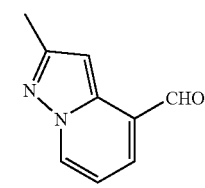

Under nitrogen atmosphere, to a solution of oxalyl chloride (18.9 mL, 216 mmol) in dichloromethane (200 mL) was added dimethyl sulfoxide (35.4 mL, 499 mmol) at −78° C., and the mixture was stirred for 30 min. To the reaction mixture was added a solution of (2-methylpyrazolo[1,5-a]pyridin-4-yl)methanol (27.0 g, 166 mmol) in dichloromethane (133 mL), and the mixture was stirred for 2 hr. To the reaction mixture was added triethylamine (117 mL, 831 mmol) at −78° C., and the mixture was stirred for 1 hr and warmed to room temperature. After concentration under reduced pressure, the residue was purified by silica gel column chromatography (ethyl acetate/hexane=1/1) to give the title compound (7.00 g, yield 26%).

$^1$H-NMR (CDCl$_3$) δ: 2.55 (3H, s), 6.85 (1H, t, J=6.8 Hz), 7.10 (1H, s), 7.67 (1H, d, J=6.8 Hz), 8.58 (1H, dd, J=6.8, 0.8 Hz), 10.05 (1H, d, J=0.8 Hz),

MS (ESI+): 161 (M+H).

Reference Example 11 ethyl (2E)-3-(2-methyl-2H-indazol-4-yl)acrylate

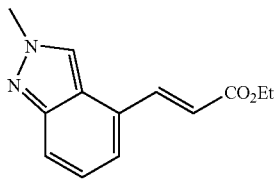

Under nitrogen atmosphere, to a suspension of sodium hydride (1.26 g, 31.5 mmol) in tetrahydrofuran (50 mL) was added a solution of ethyl diethylphosphonoacetate (7.06 g, 31.5 mmol) in tetrahydrofuran (50 mL) at 0° C., and the mixture is was stirred for 20 min. To the reaction mixture was added a solution of 2-methyl-2H-indazole-4-carbaldehyde (4.60 g, 28.7 mmol) in tetrahydrofuran (100 mL), and the mixture was warmed to room temperature over 2 hr. Water was added and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane=1/1) to give the title compound (6.50 g, yield 98%).

$^1$H-NMR (CDCl$_3$) δ: 1.37 (3H, t, J=7.2 Hz), 4.27 (2H, s), 4.30 (2H, q, J=7.2 Hz), 6.49 (1H, d, J=16 Hz), 7.26-7.33 (2H, m), 7.77 (1H, dd, J=6.8, 2.2 Hz), 7.90 (1H, d, J=16 Hz), 8.20 (1H, s).

Reference Example 12 ethyl (2E)-3-(2-methyl[1,2,4]triazolo[1,5-a]pyridin-8-yl)acrylate

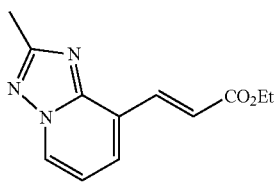

Under nitrogen atmosphere, to a suspension of sodium hydride (1.42 g, 35.5 mmol) in tetrahydrofuran (35 mL) was added a solution of ethyl diethylphosphonoacetate (7.10 mL, 35.5 mmol) in tetrahydrofuran (5.0 mL) at 0° C., and the mixture was stirred for 20 min. To the reaction mixture was added a solution of 2-methyl[1,2,4]triazolo[1,5-a]pyridine-8-carbaldehyde (5.20 g, 32.3 mmol) in tetrahydrofuran (60 mL), and the mixture was warmed to room temperature over 4 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/1) to give the title compound (6.30 g, yield 84%).

$^1$H-NMR (CDCl$_3$) δ: 1.36 (3H, t, J=7.6 Hz), 2.64 (3H, s), 4.30 (2H, q, J=7.6 Hz), 6.99 (1H, t, J=6.8 Hz), 7.56 (1H, d, J=5.6 Hz), 7.58 (1H, d, J=16.0 Hz), 7.81 (1H, d, J=16.0 Hz), 8.48 (1H, dd, J=6.8, 0.8 Hz).

Reference Example 13 ethyl (2E)-3-(2-methylpyrazolo[1,5-a]pyridin-4-yl)acrylate

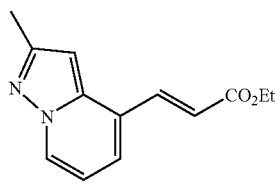

Under nitrogen atmosphere, to a suspension of sodium hydride (2.70 g, 61.8 mmol) in tetrahydrofuran (42 mL) was added a solution of ethyl diethylphosphonoacetate (13.8 g, 61.8 mmol) in tetrahydrofuran (20 mL) at 0° C., and the mixture was stirred for 20 min. To the reaction mixture was added a solution of 2-methylpyrazolo[1,5-a]pyridine-4-carbaldehyde (9.00 g, 56.2 mmol) in tetrahydrofuran (50 mL), and the mixture was warmed to room temperature over 4 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=3/1) to give the title compound (11.8 g, yield 91%).

$^1$H-NMR (CDCl$_3$) δ: 1.36 (3H, t, J=6.8 Hz), 2.52 (3H, s), 4.30 (2H, q, J=7.2 Hz), 6.56 (1H, d, J=16 Hz), 6.58 (1H, s), 6.71 (1H, t, J=7.2 Hz), 7.27 (1H, d, J=6.8 Hz), 7.78 (1H, d, J=16 Hz), 8.38 (1H, d, J=6.8 Hz),
MS (ESI+): 231 (M+H).

Reference Example 14 trans-ethyl 2-(2-methyl-2H-indazol-4-yl)cyclopropanecarboxylate

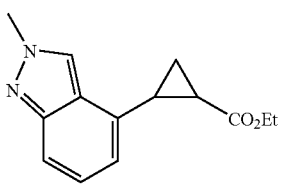

Under nitrogen atmosphere, to a suspension of sodium hydride (0.650 g, 15.6 mmol) in dimethyl sulfoxide (5.0 mL) was added a solution of trimethylsulfoxonium iodide (3.34 g, 15.6 mmol) in dimethyl sulfoxide (35 mL) at 0° C., and the mixture was stirred at room temperature for 1 hr. To the reaction mixture was added a solution of ethyl (2E)-3-(2-methyl-2H-indazol-4-yl)acrylate (3.00 g, 13.0 mmol) in dimethyl sulfoxide (30 mL) at 0° C., and the mixture was stirred at room temperature for 12 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/1) to give the title compound (1.10 g, yield 35%).

$^1$H-NMR (CDCl$_3$) δ: 1.34 (3H, t, J=7.2 Hz), 1.41-1.46 (1H, m), 1.61-2.04 (1H, m), 2.01-2.05 (1H, m), 2.71-2.76 (1H, m), 4.21 (2H, q, J=7.2 Hz), 4.22 (3H, s), 6.73 (1H, d, J=6.8 Hz), 7.18 (1H, dd, J=8.8, 6.8 Hz), 7.55 (1H, d, J=8.8 Hz), 7.97 (1H, s).

Reference Example 15 ethyl 2-(2-methyl[1,2,4]triazolo[1,5-a]pyridin-8-yl)cyclopropanecarboxylate

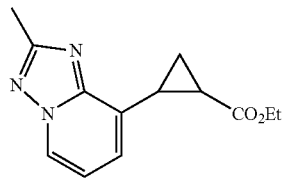

Under nitrogen atmosphere, to a suspension of sodium hydride (0.830 g, 20.8 mmol) in dimethyl sulfoxide (10 mL) was added a solution of trimethylsulfoxonium iodide (4.57 g, 20.8 mmol) in dimethyl sulfoxide (35 mL) at 0° C., and the mixture was stirred at room temperature for 1 hr. To the reaction mixture was added a solution of ethyl (2E)-3-(2-methyl[1,2,4]triazolo[1,5-a]pyridin-8-yl)acrylate (4.00 g, 17.3 mmol) in dimethyl sulfoxide (30 mL) at 0° C., and the mixture was stirred at room temperature for 14 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/2) to give the title compound (1.84 g, yield 43%).

$^1$H-NMR (CDCl$_3$) δ: 1.34 (3H, t, J=7.2 Hz), 1.69-1.81 (2H, m), 2.47-2.52 (1H, m), 2.60 (3H, s), 2.88-2.96 (1H, m), 4.22 (2H, q, J=7.2 Hz), 6.85 (1H, t, J=6.8 Hz), 7.13 (1H, d, J=6.8 Hz), 8.32 (1H, d, J=6.8 Hz).

Reference Example 16 trans-ethyl 2-(2-methylpyrazolo[1,5-a]pyridin-4-yl)cyclopropanecarboxylate

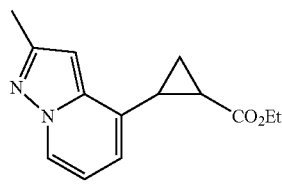

Under nitrogen atmosphere, to a suspension of sodium hydride (1.64 g, 41.0 mmol) in dimethyl sulfoxide (30 mi.') was added trimethylsulfoxonium iodide (9.01 g, 41.0 mmol) at 0° C., and the mixture was stirred at room temperature for 1 hr. To the reaction mixture was added a solution of ethyl (2E)-3-(2-methylpyrazolo[1,5-a]pyridin-4-yl)acrylate (7.86 g, 34.1 mmol) in dimethyl sulfoxide (120 mL) at 0° C., and the mixture was stirred at room temperature for 14 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/2) to give the title compound (5.10 g, yield 61%).

$^1$H-NMR (CDCl$_3$) δ: 1.31 (3H, t, J=7.2 Hz), 1.36-1.41 (1H, m), 1.59-1.65 (1H, m), 1.94-1.98 (1H, m), 2.49 (3H, s), 2.62-2.67 (1H, m), 4.22 (2H, q, J=7.2 Hz), 6.37 (1H, s), 6.58 (1H, t, J=7.2 Hz), 6.72 (1H, d, J=7.2 Hz), 8.24 (1H, d, J=7.2 Hz).

Reference Example 17 trans-[2-(2-methyl-2H-indazol-4-yl)cyclopropyl]methanol

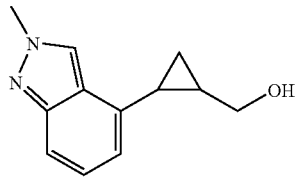

Under nitrogen atmosphere, to a solution of trans-ethyl 2-(2-methyl-2H-indazol-4-yl)cyclopropanecarboxylate (3.89 g, 15.9 mmol) in tetrahydrofuran (100 mL) was added lithium aluminum hydride (0.540 g, 15.9 mmol) at 0° C., and the mixture was stirred for 10 min. To the reaction mixture were added ethyl acetate, water and 10% aqueous sodium hydroxide solution, and the mixture was extracted with ethyl acetate. The extract was washed with 2 N hydrochloric acid and saturated brine, and dried over anhydrous sodium sulfate, and the solvent was evaporated under reduced pressure. The residue was purified by recrystallization (ethyl acetate) to give the title compound (3.00 g, yield 93%).

$^1$H-NMR (CDCl$_3$) δ: 0.93-0.97 (1H, m), 1.13-1.17 (1H, m), 1.46 (1H, t, J=5.6 Hz), 2.05-2.08 (1H, m), 3.59-3.65 (1H, m), 3.76-3.80 (1H, m), 4.23 (3H, s), 6.72 (1H, d, J=6.8 Hz), 7.18 (1H, dd, J=8.8, 6.8 Hz), 7.52 (1H, d, J=8.8 Hz), 8.07 (1H, s),

MS (ESI+): 203 (M+H).

Reference Example 18

[2-(2-methyl[1,2,4]triazolo[1,5-a]pyridin-8-yl)cyclopropyl]methanol

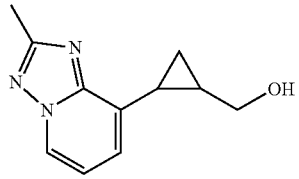

Under nitrogen atmosphere, to a solution of ethyl 2-(2-methyl[1,2,4]triazolo[1,5-a]pyridin-8-yl)cyclopropanecarboxylate (1.80 g, 7.37 mmol) obtained in Reference Example 15 in tetrahydrofuran (100 mL) was added lithium aluminum hydride (0.250 g, 7.37 mmol) at 0° C., and the mixture was stirred for 10 min. To the reaction mixture were added ethyl acetate, water and 10% aqueous sodium hydroxide solution, and the mixture was extracted with ethyl acetate. The extract was washed with 2 N hydrochloric acid and saturated brine, and dried over anhydrous sodium sulfate, and the solvent was evaporated under reduced pressure. The residue was purified by recrystallization (ethyl acetate/hexane) to give the title compound (1.30 g, yield 87%).

$^1$H-NMR (CDCl$_3$) δ: 1.06-1.11 (1H, m), 1.24-1.29 (1H, m), 1.34-1.42 (1H, m), 2.18-2.19 (1H, m), 2.60 (3H, s), 3.32 (1H, dd, J=10.8, 9.2 Hz), 4.02 (1H, dd, J=10.8, 4.8 Hz), 6.86 (1H, t, J=6.8 Hz), 7.09 (1H, d, J=7.2 Hz), 8.33 (1H, d, J=6.8 Hz),

MS (ESI+): 204 (M+H).

Reference Example 19 trans-[2-(2-methylpyrazolo[1,5-a]pyridin-4-yl)cyclopropyl]methanol

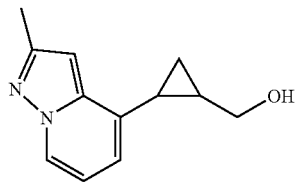

Under nitrogen atmosphere, to a solution of trans-ethyl 2-(2-methylpyrazolo[1,5-a]pyridin-4-yl)cyclopropanecarboxylate (5.40 g, 22.1 mmol) in tetrahydrofuran (150 mL) was added lithium aluminum hydride (0.750 g, 22.1 mmol) at 0° C., and the mixture was stirred for 30 min. To the reaction mixture were added ethyl acetate, water and 10% aqueous sodium hydroxide solution, and the mixture was extracted with ethyl acetate. The extract was washed with 2 N hydrochloric acid and saturated brine, and dried over anhydrous sodium sulfate, and the solvent was evaporated under reduced pressure. The residue was purified by recrystallization (ethyl acetate/hexane) to give the title compound (4.30 g, yield 96%).

$^1$H-NMR (CDCl$_3$) δ: 0.94-1.10 (2H, m), 1.44-1.52 (1H, m), 1.72 (1H, t, J=4.8 Hz), 1.93-1.98 (1H, m), 2.49 (3H, s), 3.62-3.78 (2H, m), 6.43 (1H, s), 6.56 (1H, t, J=6.8 Hz), 6.67 (1H, d, J=7.2 Hz), 8.21 (1H, d, J=6.8 Hz),

MS (ESI+): 203 (M+H).

Reference Example 20 trans-2-(2-methyl-2H-indazol-4-yl)cyclopropanecarbaldehyde

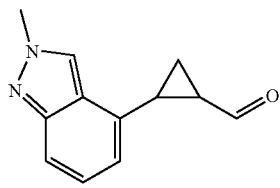

Trans-[2-(2-methyl-2H-indazol-4-yl)cyclopropyl]methanol (500 mg, 2.47 mmol), 4 Å molecular sieves (200 mg), 4-methylmorpholine N-oxide (724 mg, 6.18 mmol) and tetra-n-propylammonium perruthenate(VII) (43.6 mg, 0.124 mmol) were dissolved in acetonitrile (25 mL), and the mixture was stirred at room temperature for 2 hr. 2-Propanol was added, and the mixture was stirred for 30 min. The solvent was evaporated under reduced pressure, and the residue was purified by silica gel column chromatography (ethyl acetate) to give the title compound (382 mg, yield 77%).

$^1$H-NMR (CDCl$_3$) δ: 1.63-1.84 (2H, m), 2.19-2.33 (1H, m), 2.80-2.91 (1H, m), 4.23 (3H, s), 6.77 (1H, d, J=6.9 Hz), 7.19 (1H, dd, J=8.5, 6.9 Hz), 7.58 (1H, d, J=8.5 Hz), 7.93 (1H, s), 9.42 (1H, d, J=4.7 Hz),

MS (ESI+): 201 (M+H).

Reference Example 21

2-(2-methyl[1,2,4]triazolo[1,5-a]pyridin-8-yl)cyclopropanecarbaldehyde

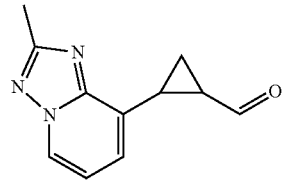

[2-(2-Methyl[1,2,4]triazolo[1,5-a]pyridin-8-yl)cyclopropyl]methanol (900 mg, 4.43 mmol) obtained in Reference Example 18, 4 Å molecular sieves (400 mg), 4-methylmorpholine N-oxide (1.30 g, 11.1 mmol) and tetra-n-propylammonium perruthenate(VII) (77.8 mg, 0.221 mmol) were dissolved in acetonitrile (45 mL), and the mixture was stirred at room temperature for 2 hr. 2-Propanol was added, and the mixture was stirred for 30 min, and filtered. The solvent was evaporated under reduced pressure. The residue was purified by silica gel column chromatography (ethyl acetate/hexane=50/50→80/20) to give the title compound (564 g, yield 63%).

$^1$H-NMR (CDCl$_3$) δ: 1.78-1.87 (1H, m), 1.94-2.05 (1H, m), 2.60 (3H, s), 2.62-2.73 (1H, m), 2.99-3.07 (1H, m), 6.84-6.90 (1H, m), 7.11-7.15 (1H, m), 8.36 (1H, dd, J=6.9, 1.1 Hz), 9.35 (1H, d, J=4.7 Hz),

MS (ESI+): 202 (M+H).

Reference Example 22 trans-2-(2-methylpyrazolo[1,5-a]pyridin-4-yl)cyclopropanecarbaldehyde

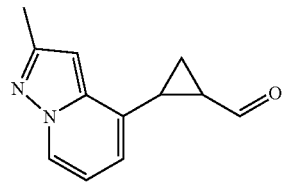

Trans-[2-(2-methylpyrazolo[1,5-a]pyridin-4-yl)cyclopropyl]methanol (2000 mg, 9.89 mmol), 4 Å molecular sieves (800 mg), 4-methylmorpholine N-oxide (1.74 g, 14.8 mmol) and tetra-n-propylammonium perruthenate(VII) (174 mg, 0.494 mmol) were dissolved in acetonitrile (100 mL), and the mixture was stirred at room temperature for 2 hr. 2-Propanol was added and the mixture was stirred for 30 min, diluted with ethyl acetate, and washed with water and saturated brine. The organic layer was dried over anhydrous sodium sulfate and the solvent was evaporated under reduced pressure. The residue was purified by silica gel column chromatography (ethyl acetate) to give the title compound (1.62 g, yield 82%).

¹H-NMR (CDCl₃) δ: 1.58-1.68 (1H, m), 1.72-1.82 (1H, m), 2.15-2.28 (1H, m), 2.50 (3H, s), 2.68-2.82 (1H, m), 6.32 (1H, s), 6.60 (1H, t, J=7.2 Hz), 6.76 (1H, d, J=7.2 Hz), 8.27 (1H, d, J=7.1 Hz), 9.47 (1H, d, J=4.4 Hz),

MS (ESI+): 201 (M+H).

Reference Example 23 trans-2-(2-methyl-2H-indazol-4-yl)cyclopropanecarbaldehyde oxime

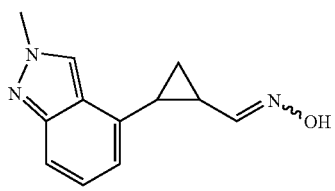

Trans-2-(2-methyl-2H-indazol-4-yl)cyclopropanecarbaldehyde (330 mg, 1.65 mmol), 8 M aqueous sodium hydroxide solution (824 μL, 6.59 mmol) and hydroxylamine hydrochloride (378 mg, 5.44 mmol) were dissolved in ethanol/water (15 mL/3 mL), and the mixture was stirred at 60° C. for 3 hr. The reaction solution was concentrated, extracted with ethyl acetate, washed with saturated brine, and dried over anhydrous sodium sulfate, and the solvent was evaporated under reduced pressure to give the title compound (349 mg, yield 98%).

MS (ESI+): 216 (M+H).

Reference Example 24

2-(2-methyl[1,2,4]triazolo[1,5-a]pyridin-8-yl)cyclopropanecarbaldehyde oxime

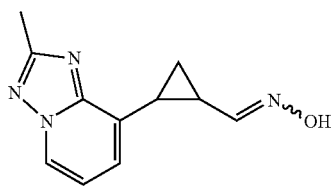

2-(2-Methyl[1,2,4]triazolo[1,5-a]pyridin-8-yl)cyclopropanecarbaldehyde (560 mg, 2.78 mmol) obtained in Reference Example 21, 8 M aqueous sodium hydroxide solution (1.39 mL, 11.1 mmol) and hydroxylamine hydrochloride (592 mg, 9.18 mmol) were dissolved in ethanol/water (22 mL/6 mL), and the mixture was stirred at 70° C. for 16 hr. The reaction solution was concentrated, water was added, and the mixture was extracted with ethyl acetate. The extract was washed with saturated brine, and dried over anhydrous sodium sulfate, and the solvent was evaporated under reduced pressure. The residue was washed with diisopropyl ether to give the title compound (196 mg, yield 33%).

¹H-NMR (CDCl₃) δ: 1.37-1.70 (2H, m), 2.03-2.17 (0.6 Hz, m), 2.61 (1.8H, s), 2.62 (1.2H, s), 2.69-2.78 (1H, m), 2.81-2.91 (0.4H, m), 6.33 (0.4H, d, J=8.2 Hz), 6.83-6.90 (1H, m), 6.99-7.03 (0.6H, m), 7.05-7.09 (0.4H, m), 7.29 (0.6H, d, J=7.4 Hz), 8.30-8.35 (1H, m), 8.63 (0.4H, br s), 9.38 (0.6H, br s).

Reference Example 25 trans-2-(2-methylpyrazolo[1,5-a]pyridin-4-yl)cyclopropanecarbaldehyde oxime

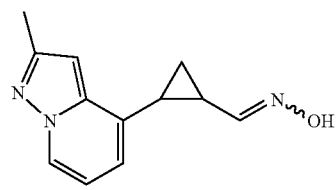

Trans-2-(2-methylpyrazolo[1,5-a]pyridin-4-yl)cyclopropanecarbaldehyde (1.62 g, 8.08 mmol), 8 M aqueous sodium hydroxide solution (4.04 mL, 32.3 mmol) and hydroxylamine hydrochloride (1.85 g, 26.7 mmol) was dissolved in ethanol/water (65 mL/13 mL), and the mixture was stirred at 60° C. for 3 hr. The reaction solution was concentrated, extracted with ethyl acetate, washed with saturated brine, and dried over anhydrous sodium sulfate, and the solvent was evaporated under reduced pressure to give the title compound (1.67 g, yield 96%).

MS (ESI+): 216 (M+H).

Reference Example 26 trans-1-[2-(2-methyl-2H-indazol-4-yl)cyclopropyl]methanamine

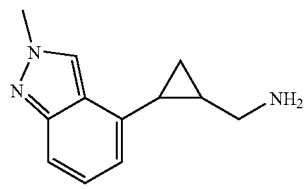

To a suspension of lithium aluminum hydride (319 mg, 8.61 mmol) in tetrahydrofuran (17 mL) was added a solution of trans-2-(2-methyl-2H-indazol-4-yl)cyclopropanecarbaldehyde oxime (349 mg, 1.62 mmol) in tetrahydrofuran (17 mL) at room temperature, and the mixture was stirred at 60° C. for 1 hr. Sodium sulfate decahydrate (3.5 g) was added under ice-cooling, and the mixture was filtered through celite. The filtrate was concentrated under reduced pressure to give the title compound (325 mg, yield 99%).

¹H-NMR (CDCl₃) δ: 0.85-0.94 (1H, m), 1.05-1.14 (1H, m), 1.39-1.51 (1H, m), 1.91-2.02 (1H, m), 2.80 (2H, dd, J=6.7, 2.1 Hz), 4.23 (3H, s), 6.70 (1H, d, J=7.0 Hz), 7.18 (1H, dd, J=8.8, 7.0 Hz), 7.51 (1H, d, J=8.8 Hz), 8.02 (1H, s), hidden (2H),

MS (ESI+): 202 (M+H).

Reference Example 27

1-[2-(2-methyl[1,2,4]triazolo[1,5-a]pyridin-8-yl)cyclopropyl]methanamine

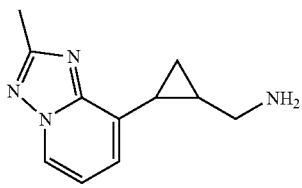

To a suspension of lithium aluminum hydride (150 mg, 3.24 mmol) in tetrahydrofuran (8 mL) was added a solution of 2-(2-methyl[1,2,4]triazolo[1,5-a]pyridin-8-yl)cyclopropanecarbaldehyde oxime (175 mg, 0.809 mmol) obtained in Reference Example 24 in tetrahydrofuran (8 mL) at room temperature, and the mixture was stirred at room temperature for 30 min. Sodium sulfate decahydrate (1.8 g) was added under ice-cooling, and the mixture was filtered through celite. The filtrate was concentrated under reduced pressure. The residue was dissolved in tetrahydrofuran (8 mL), the solution was added to a suspension of lithium aluminum hydride (150 mg, 3.24 mmol) in tetrahydrofuran (8 mL) at 0° C., and the mixture was stirred at room temperature for 3 hr. Sodium sulfate decahydrate (1.8 g) was added under ice-cooling, and the mixture was filtered through celite to give the title compound (98.9 mg, yield 60%).

$^1$H-NMR (CDCl$_3$) δ: 1.01-1.09 (1H, m), 1.12-1.20 (1H, m), 1.45-1.58 (1H, m), 2.26-2.35 (1H, m), 2.61 (3H, s), 2.68-2.77 (1H, m), 2.83-2.91 (1H, m), 6.80-6.86 (1H, m), 6.91-6.95 (1H, m), 8.29 (1H, dd, J=6.7, 1.2 Hz), hidden (2H),
MS (ESI+): 203 (M+H).

Reference Example 28 trans-1-[2-(2-methylpyrazolo[1,5-a]pyridin-4-yl)cyclopropyl]methanamine

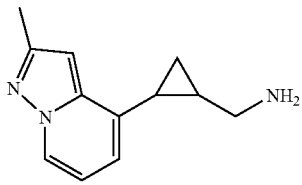

To a suspension of lithium aluminum hydride (1.18 g, 31.0 mmol) in tetrahydrofuran (70 mL) was added a solution of trans-2-(2-methylpyrazolo[1,5-a]pyridin-4-yl)cyclopropanecarbaldehyde oxime (1.67 g, 7.76 mmol) in tetrahydrofuran (8 mL) at room temperature, and the mixture was stirred at room temperature for 1.5 hr. Sodium sulfate decahydrate (17 g) was added under ice-cooling, and the mixture was filtered through celite. The filtrate was concentrated under reduced pressure to give the title compound (1.39 g, yield 89%).

$^1$H-NMR (CDCl$_3$) δ: 0.82-0.97 (1H, m), 0.99-1.11 (1H, m), 1.30-1.40 (1H, m), 1.80-1.91 (1H, m), 2.50 (3H, s), 2.71-2.89 (2H, m), 6.40 (1H, s), 6.56 (1H, t, J=6.9 Hz), 6.65 (1H, d, J=6.9 Hz), 8.20 (1H, d, J=6.9 Hz), hidden (2H),
MS (ESI+): 202 (M+H).

Reference Example 29

1-[(1S,2S)-2-(2-methyl-2H-indazol-4-yl)cyclopropyl]methanamine dihydrochloride

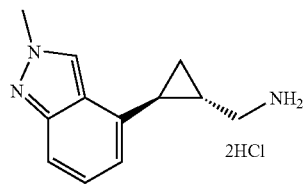

To a solution of tert-butyl {[(1S,2S)-2-(2-methyl-2H-indazol-4-yl)cyclopropyl]methyl}carbamate (2.68 g, 8.89 mmol) in ethyl acetate (50 mL) was added 4 M hydrochloric acid/ethyl acetate (50 mL) solution, and the mixture was stirred at room temperature for 3 hr. The solvent was concentrated under reduced pressure, and the obtained crystals were washed with ethyl acetate to give the title compound (2.40 g, yield 98%).

$^1$H-NMR (DMSO-d$_6$) δ: 0.94-1.28 (2H, m), 1.43-1.50 (1H, m), 2.29-2.35 (1H, m), 2.73-3.06 (2H, m), 4.18 (3H, s), 6.69 (1H, d, J=6.9 Hz), 7.17 (1H, dd, J=8.5, 6.9 Hz), 7.38 (1H, d, J=8.5 Hz), 8.37 (3H, br s), 8.78 (1H, s), 11.58 (1H, br s),
melting point: 211-212° C.,
$[α]_D^{20}$: +27.5° (c 0.50, methanol),
elemental analysis: for C$_{12}$H$_{17}$N$_3$Cl$_2$
Calculated (%): C, 52.57; H, 6.25; N, 15.33; Cl, 25.86
Found (%): C, 52.20; H, 6.27; N, 15.25; Cl, 25.53.

Reference Example 30

1-[(1R,2R)-2-(2-methyl-2H-indazol-4-yl)cyclopropyl]methanamine dihydrochloride

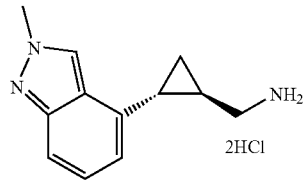

To a solution of tert-butyl {[(1R,2R)-2-(2-methyl-2H-indazol-4-yl)cyclopropyl]methyl}carbamate (2.68 g, 8.89 mmol) in ethyl acetate (50 mL) was added 4 M hydrochloric acid/ethyl acetate (50 mL) solution, and the mixture was stirred at room temperature for 2 hr. The solvent was concentrated under reduced pressure, and the obtained crystals were washed with ethyl acetate to give the title compound (2.38 g, yield 98%).

$^1$H-NMR (DMSO-d$_6$) δ: 1.01-1.26 (2H, m), 1.40-1.57 (1H, m), 2.24-2.40 (1H, m), 2.77-3.03 (2H, m), 4.20 (3H, s), 6.70 (1H, d, J=6.8 Hz), 7.18 (1H, dd, J=8.7, 6.8 Hz), 7.40 (1H, d, J=8.7 Hz), 8.29 (3H, br s), 8.75 (1H, s), 9.39 (1H, br s),
melting point: 210-212° C.,
$[α]_D^{20}$: -27.6° (c 0.52, methanol),
elemental analysis: for C$_{12}$H$_{17}$N$_3$Cl$_2$
Calculated (%): C, 52.57; H, 6.25; N, 15.33; Cl, 25.86
Found (%): C, 52.17; H, 6.38; N, 15.16; Cl, 25.65.

Reference Example 31

1-acetyl-4-bromo-1H-indazole

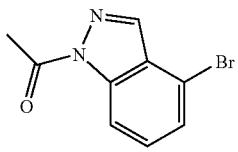

To a mixture of 3-bromo-2-methylaniline (2.00 mL, 16.0 mmol) and potassium acetate (1.60 g, 16.3 mmol) in toluene (160 mL) was added acetic anhydride (4.54 mL, 48.0 mmol) at room temperature, and the mixture was stirred at 60° C. for 30 min. Isoamyl nitrite (3.22 mL, 24.0 mmol) was added, and the mixture was stirred at 60° C. for 18 hr. The reaction mixture was diluted with water, and the mixture was extracted with ethyl acetate. The extract was washed with saturated brine, and dried over anhydrous sodium sulfate, and the solvent was evaporated under reduced pressure to give the title compound as a crudely purified product.

$^1$H-NMR (CDCl$_3$) δ: 2.79 (3H, s), 7.36-7.42 (1H, m), 7.46-7.50 (1H, m), 8.13 (1H, s), 8.35-8.40 (1H, m).

Reference Example 32

4-bromo-1H-indazole

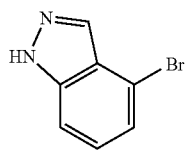

A crudely purified product of 1-acetyl-4-bromo-1H-indazole obtained in Reference Example 31 was suspended in 6 M hydrochloric acid (32 mL), and the mixture was stirred at 60° C. for 2 hr, and basified with 8 M aqueous sodium hydroxide solution. The resulting precipitate was collected by filtration, and dissolved in ethyl acetate. This solution was dried over anhydrous sodium sulfate and the solvent was evaporated under reduced pressure to give the title compound (2.24 g, total yield from Reference Example 31, 71%).

$^1$H-NMR (CDCl$_3$) δ: 7.24 (1H, dd, J=8.3, 7.4 Hz), 7.33 (1H, dd, J=7.4, 0.8 Hz), 7.43-7.47 (1H, m), 8.11 (1H, d, J=0.8 Hz), 10.59 (1H, br s),

MS (ESI+): 197 (M+H).

Reference Example 33

4-bromo-2-methyl-2H-indazole

To a solution of 4-bromo-1H-indazole (2.24 g, 11.4 mmol) in ethyl acetate (110 mL) was added trimethyloxonium tetrafluoroborate (2.19 g, 14.8 mmol) at room temperature, and the mixture was stirred for 3 hr. The reaction solution was diluted with ethyl acetate, washed with aqueous sodium hydrogen carbonate solution and dried over anhydrous sodium sulfate, and the solvent was evaporated under reduced pressure. The residue was purified by silica gel column chromatography (ethyl acetate/hexane=10/90→40/60) to give the title compound (2.29 g, yield 95%).

$^1$H-NMR (CDCl$_3$) δ: 4.23 (3H, s), 7.13 (1H, dd, J=8.5, 7.2 Hz), 7.23 (1H, dd, J=7.2, 0.8 Hz), 7.60-7.64 (1H, m), 7.91 (1H, m),

MS (ESI+): 211 (M+H).

Reference Example 34

3-(2-methyl-2H-indazol-4-yl)prop-2-yn-1-ol

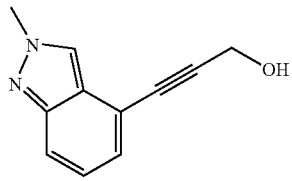

Under argon gas atmosphere, a mixture of 4-bromo-2-methyl-2H-indazole (1.00 g, 4.74 mmol), propargyl alcohol (1.10 mL, 18.9 mmol) and bis(triphenylphosphine)palladium (II) dichloride (665 mg, 0.947 mmol) in triethylamine (47 mL) was stirred at 70° C. for 14 hr, and concentrated under reduced pressure. The residue was dissolved in ethyl acetate, and insoluble material was filtered off. The filtrate was washed with water and saturated brine, and dried over anhydrous sodium sulfate, and the solvent was evaporated under reduced pressure. The residue was purified by silica gel column chromatography (NH, ethyl acetate/hexane=70/30→100/0) and the obtained crudely purified product was washed with ethyl acetate to give the title compound (403 mg, yield 46%).

$^1$H-NMR (CDCl$_3$) δ: 2.35 (1H, t, J=6.3 Hz), 4.20 (3H, s), 4.57 (2H, d, J=6.3 Hz), 7.18-7.24 (1H, m), 7.65-7.71 (1H, m), 7.93 (1H, s), melting point: 139-140° C. (recrystallized from ethyl acetate/hexane),

MS (ESI+): 187 (M+H), elemental analysis: for $C_{11}H_{10}N_2O$

Calculated (%): C, 70.95; H, 5.41; N, 15.04

Found (%): C, 70.98; H, 5.50; N, 15.05.

Reference Example 35

(2Z)-3-(2-methyl-2H-indazol-4-yl)prop-2-en-1-ol

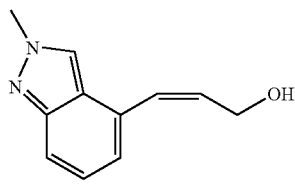

Under hydrogen gas atmosphere, a mixture of 3-(2-methyl-2H-indazol-4-yl)prop-2-yn-1-ol (50.0 mg, 0.269 mmol) and 5% palladium-calcium carbonate (lead poisoned, Lindlar catalyst, 5 mg) in methanol (3 mL) was stirred at −10° C. for 90 min, and filtered. The solvent was evaporated under reduced pressure. The residue was washed with diisopropyl ether to give the title compound (41.6 mg, yield 82%).

$^1$H-NMR (METHANOL-$d_4$) δ: 4.20 (3H, s), 4.34 (2H, dd, J=6.3, 1.9 Hz), 5.98 (1H, dt, J=11.8, 6.3 Hz), 6.79 (1H, d, J=11.8 Hz), 6.86 (1H, d, J=7.0 Hz), 7.27 (1H, dd, J=8.8, 7.0 Hz), 7.49 (1H, d, J=8.0 Hz), 8.22 (1H, s), hidden (1H),

MS (ESI+): 189 (M+H).

Reference Example 36 cis-[2-(2-methyl-2H-indazol-4-yl)cyclopropyl]methanol

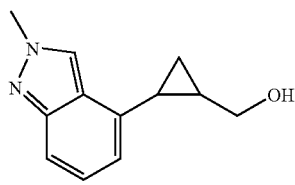

Under argon gas atmosphere, to a suspension of (2Z)-3-(2-methyl-2H-indazol-4-yl)prop-2-en-1-ol (60.0 mg, 0.319 mmol) in methylene chloride (3 mL) was added 1 M diethylzinc hexane solution (1.60 mL, 1.60 mmol) under ice-cooling and the mixture was stirred for 10 min. Diiodomethane (128 μL, 1.59 mmol) was added, and the mixture was stirred at room temperature for 2 hr. The reaction solution was diluted with saturated aqueous ammonium chloride solution and water, and the mixture was extracted with ethyl acetate. The extract was washed with saturated aqueous sodium hydrogen carbonate solution and saturated brine, and dried over anhydrous sodium sulfate, and the solvent was evaporated under reduced pressure. The residue was purified by silica gel column chromatography (methanol/ethyl acetate=0/100→5/95) to give the title compound (40.5 mg, yield 63%).

$^1$H-NMR (CDCl$_3$) δ: 0.92-1.00 (1H, m), 1.04-1.15 (1H, m), 1.55-1.71 (1H, m), 2.33-2.44 (1H, m), 3.16 (1H, dd, J=11.8, 8.5 Hz), 3.40-3.49 (1H, m), 4.15 (3H, d, J=2.7 Hz), 6.79 (1H, d, J=6.9 Hz), 7.14-7.22 (1H, m), 7.52 (1H, d, J=8.5 Hz), 8.02 (1H, s), hidden (1H),

MS (ESI+): 203 (M+H).

Reference Example 37 cis-2-{[2-(2-methyl-2H-indazol-4-yl)cyclopropyl]methyl}-1H-isoindole-1,3(2H)-dione

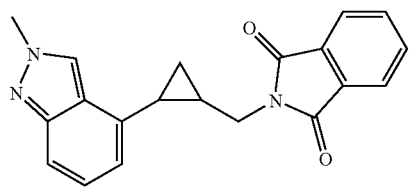

Under argon gas atmosphere, to a solution of cis-[2-(2-methyl-2H-indazol-4-yl)cyclopropyl]methanol (130 mg, 0.643 mmol) in tetrahydrofuran (6.5 mL) were added a solution (40%, 0.351 mL, 0.771 mmol) of diethyl azodicarboxylate in toluene, triphenylphosphine (219 mg, 0.835 mmol) and phthalimide (123 mg, 0.836 mmol), and the mixture was stirred at room temperature for 5 hr. To the reaction mixture was added a solution (40%, 0.176 mL, 0.386 mmol) of diethyl azodicarboxylate in toluene, triphenylphosphine (110 mg, 0.419 mmol) and phthalimide (61.5 mg, 0.418 mmol) were added, and the mixture was stirred at room temperature for 30 min. The solvent was evaporated under reduced pressure. The residue was purified by silica gel column chromatography (ethyl acetate/hexane=20/80→50/50) to give the title compound as a crudely purified product.

MS (ESI+): 322 (M+H).

Reference Example 38 cis-1-[2-(2-methyl-2H-indazol-4-yl)cyclopropyl]methanamine

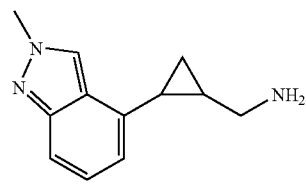

A crudely purified product of cis-2-{[2-(2-methyl-2H-indazol-4-yl)cyclopropyl]methyl}-1H-isoindole-1,3(2H)-dione was dissolved in ethanol (6.5 mL), and hydrazine monohydrate (3 mL) was added. The mixture was heated under reflux for 20 min. The solvent was evaporated under reduced pressure. Saturated aqueous sodium hydrogen carbonate solution was added to the residue, and the mixture was extracted with ethyl acetate. The extract was dried over anhydrous sodium sulfate and the solvent was evaporated under reduced pressure to give the title compound as a crudely purified product.

MS (ESI+): 202 (M+H).

Reference Example 39 methyl 5-bromo-2-ethyl-2H-indazole-4-carboxylate

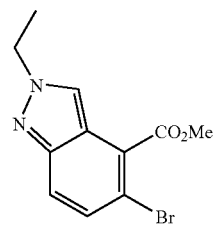

To a solution of methyl 5-bromo-1H-indazole-4-carboxylate (2.00 g, 7.84 mmol) in ethyl acetate (80 mL) was added triethyloxonium hexafluorophosphate (2.92 g, 11.8 mmol), and the mixture was stirred under nitrogen atmosphere at room temperature for 15 hr. The reaction solution was diluted with ethyl acetate, saturated aqueous sodium hydrogen carbonate solution was added, and the mixture was extracted with ethyl acetate. The extract was dried over anhydrous sodium sulfate and the solvent was evaporated under reduced pressure. The residue was purified by silica gel column chromatography (NH, ethyl acetate/hexane=5/95→50/50) to give the title compound (2.03 g, yield 91%).

$^1$H-NMR (CDCl$_3$) δ: 1.65 (3H, t, J=7.3 Hz), 4.02 (3H, s), 4.48 (2H, q, J=7.4 Hz), 7.49 (1H, d, J=9.1 Hz), 7.65-7.71 (1H, m), 8.18 (1H, s),

MS (ESI+): 283 (M+H).

Reference Example 40

(2-ethyl-2H-indazol-4-yl)methanol

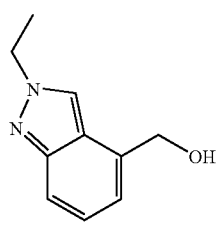

To a suspension of lithium aluminum hydride (1.09 g, 28.7 mmol) in tetrahydrofuran (60 mL) was added a solution of methyl 5-bromo-2-ethyl-2H-indazole-4-carboxylate (2.03 g, 7.17 mmol) in tetrahydrofuran (15 mL) under nitrogen atmosphere at 0° C., and the mixture was stirred at room temperature for 50 hr. Sodium sulfate decahydrate (10 g) was added under ice-cooling, and the mixture was filtered through celite. The filtrate was concentrated under reduced pressure and purified by silica gel column chromatography (ethyl acetate/hexane=25/75→60/40) to give the title compound (1.14 g, yield 90%).

$^1$H-NMR (CDCl$_3$) δ: 1.57-1.70 (3H, m), 1.88 (1H, br s), 4.47 (2H, q, J=7.1 HZ), 4.93 (2H, d, J=4.1 Hz), 6.99 (1H, d, J=6.9 Hz), 7.18-7.27 (1H, m), 7.64 (1H, d, J=8.8 Hz), 8.09 (1H, s),

MS (ESI+): 177 (M+H).

Reference Example 41

2-ethyl-2H-indazole-4-carbaldehyde

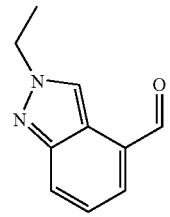

(2-Ethyl-2H-indazol-4-yl)methanol (1.14 g, 6.47 mmol), 4 Å molecular sieves (550 mg), 4-methylmorpholine N-oxide (1.89 g, 16.2 mmol) and tetra-n-propylammonium perruthenate(VII) (114 mg, 0.323 mmol) were added to acetonitrile (70 mL) under ice-cooling, and the mixture was stirred at room temperature for 2 hr. 2-Propanol was added, and the mixture was stirred for 30 min. The mixture was filtered by silica gel column chromatography (ethyl acetate). The solvent was evaporated under reduced pressure. The residue was purified by silica gel column chromatography (ethyl acetate/hexane=10/90→50/50) to give the title compound (820 mg, yield 73%).

$^1$H-NMR (CDCl$_3$) δ: 1.67 (3H, t, J=7.3 Hz), 4.53 (2H, q, J=7.4 Hz), 7.44 (1H, dd, J=8.5, 6.9 Hz), 7.66 (1H, d, J=6.9 Hz), 8.02 (1H, d, J=8.5 Hz), 8.63 (1H, s), 10.08 (1H, s),

MS (ESI+): 175 (M+H).

Reference Example 42

(2E)-3-(2-ethyl-2H-indazol-4-yl)acrylonitrile

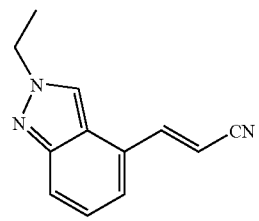

To a solution of diethyl cyanomethylphosphonate (254 μL, 1.57 mmol) in tetrahydrofuran (6 mL) was added 60% sodium hydride (57.9 mg, 1.45 mmol) under ice-cooling, and the mixture was stirred at 0° C. for 15 min. To the mixture was added a solution of 2-ethyl-2H-indazole-4-carbaldehyde (210 mg, 1.20 mmol) in tetrahydrofuran (6 mL) under ice-cooling, and the mixture was stirred under ice-cooling for 15 min. The reaction solution was diluted with saturated aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=15/85→50/50) to give the title compound (222 mg, yield 93%).

$^1$H-NMR (CDCl$_3$) δ: 1.68 (3H, t, J=7.3 Hz), 4.53 (2H, q, J=7.2 Hz), 5.93 (1H, d, J=16.5 Hz), 7.21-7.25 (1H, m), 7.27-7.35 (1H, m), 7.61 (1H, d, J=16.5 Hz), 7.79-7.86 (1H, m), 8.10 (1H, d, J=0.8 Hz),

MS (ESI+): 198 (M+H).

Reference Example 43

2-(2-ethyl-2H-indazol-4-yl)cyclopropanecarbonitrile

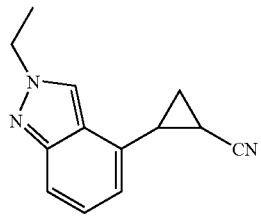

To a suspension of sodium hydride (122 mg, 3.04 mmol) in dimethyl sulfoxide (15 mL) was added trimethylsulfoxonium iodide (725 mg, 3.30 mmol) at room temperature, and the mixture was stirred under nitrogen atmosphere at room temperature for 1 hr. To the reaction mixture was added a solution of (2E)-3-(2-ethyl-2H-indazol-4-yflacrylonitrile (500 mg, 2.56 mmol) in dimethyl sulfoxide (10 mL) at 0° C., and the mixture was stirred at 70° C. for 24 hr. To the reaction mixture was added saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=10/90→50/50) to give the title compound (304 mg, yield 57%).

$^1$H-NMR (CDCl$_3$) δ: 1.58-1.72 (6H, m), 2.80-2.92 (1H, m), 4.51 (2H, q, J=7.4 Hz), 6.69-6.74 (1H, m), 7.18 (1H, dd, J=8.8, 6.9 Hz), 7.62 (1H, d, J=8.8 Hz), 8.06 (1H, s),
MS (ESI+): 212 (M+H).

Reference Example 44

1-[2-(2-ethyl-2H-indazol-4-yl)cyclopropyl]methanamine

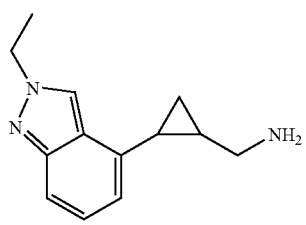

To a solution of 2-(2-ethyl-2H-indazol-4-yl)cyclopropanecarbonitrile (304 mg, 1.44 mmol) obtained in Reference Example 43 in ethanol (7.5 mL) were added Raney cobalt (1.5 g) and 2 M ammonia/ethanol solution (7.5 mL), and the mixture was stirred under hydrogen atmosphere at room temperature for 8 hr. The catalyst was filtered off through celite, and the filtrate was concentrated under reduced pressure. The obtained residue was dissolved in ethanol (7.5 mL) solution, Raney cobalt (3.0 g) and 2 M ammonia/ethanol solution (7.5 mL) were added, and the mixture was stirred under hydrogen atmosphere at room temperature for 3 hr. The catalyst was filtered off through celite, and the filtrate was concentrated under reduced pressure to give the title compound (303 mg, yield 98%).

$^1$H-NMR (CDCl$_3$) δ: 0.83-0.95 (1H, m), 1.03-1.14 (1H, m), 1.37-1.52 (1H, m), 1.64 (3H, t, J=7.4 Hz), 1.89-2.01 (1H, m), 2.71-2.89 (2H, m), 4.47 (2H, q, J=7.2 Hz), 6.68 (1H, d, J=6.9 Hz), 7.16 (1H, dd, J=8.5, 6.9 Hz), 7.51 (1H, d, J=8.5 Hz), 8.04 (1H, s), hidden (2H).

Reference Example 45

6-fluoro-2-methyl-3-nitrobenzoic acid

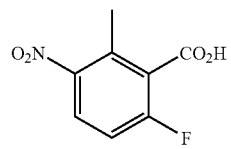

To a solution of nitric acid (6.96 mL, 156 mmol) in sulfuric acid (44 mL) was added a solution of 2-fluoro-6-methylbenzoic acid (16 g, 104 mmol) in concentrated sulfuric acid (150 mL) at −15° C., and the mixture was stirred at 0° C. for 30 min. The reaction solution was poured into ice water (500 mL), and the mixture was extracted with ethyl acetate. The extract was dried over anhydrous sodium sulfate and the solvent was evaporated under reduced pressure to give the title compound as a crudely purified product (20.7 g, yield 100%).

$^1$H-NMR (CDCl$_3$) δ: 2.64 (3H, s), 7.17 (1H, t, J=8.6 Hz), 8.04 (1H, dd, J=9.2, 5.2 Hz), hidden (1H).

Reference Example 46 methyl 6-fluoro-2-methyl-3-nitrobenzoate

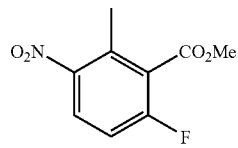

A crudely purified product (20.7 g) of 6-fluoro-2-methyl-3-nitrobenzoic acid was dissolved in N,N-dimethylformamide (208 mL), and potassium carbonate (28.7 g, 208 mmol) and iodomethane (8.45 mL, 135 mmol) were added at room temperature. The reaction solution was stirred at room temperature for 12 hr, and poured into water, and the mixture was extracted with ethyl acetate. The extract was dried over anhydrous sodium sulfate and the solvent was evaporated under reduced pressure to give the title compound as a crudely purified product (21.0 g, yield 95%).

¹H-NMR (CDCl₃) δ: 2.53 (3H, s), 3.99 (3H, s), 7.11 (1H, t, J=8.6 Hz), 8.01 (1H, dd, J=9.0, 5.0 Hz).

Reference Example 47 methyl 3-amino-6-fluoro-2-methylbenzoate

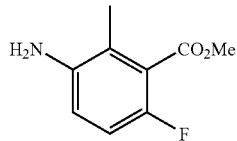

To a solution of a crudely purified product (27.7 g, 130 mmol) of methyl 6-fluoro-2-methyl-3-nitrobenzoate in methanol (260 mL) was added palladium carbon (6.00 g, 10 wt %) and the mixture was stirred under hydrogen atmosphere for 12 hr. The catalyst was filtered off through celite, the filtrate was concentrated under reduced pressure, and the residue was purified by flash silica gel column chromatography (ethyl acetate/hexane=1/1) to give the title compound (15.0 g, yield 63%).

¹H-NMR (CDCl₃) δ: 2.13 (3H, s), 3.56 (2H, br s), 3.93 (3H, s), 6.67 (1H, d, J=8.8, 4.8 Hz), 6.80 (1H, t, J=8.8 Hz).

Reference Example 48 methyl 3-[(tert-butylthio)diazenyl]-6-fluoro-2-methylbenzoate

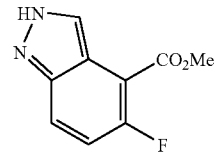

To a solution of methyl 3-amino-6-fluoro-2-methylbenzoate (12.0 g, 65.5 mmol) in hydrochloric acid (6 N, 200 mL) was added a solution of sodium nitrite (4.97 g, 72.1 mmol) in water (10 mL) at 0° C., and the mixture was stirred for 2 hr. An aqueous potassium acetate solution (30%) was added to the reaction solution at 0° C. to adjust the reaction solution to pH 4, and a solution of 2-methylpropane-2-thiol (8.12 mL, 72.1 mmol) in ethanol (10 mL) was added. The reaction solution was stirred at room temperature for 12 hr, and the mixture was extracted with ethyl acetate. The extract was dried over anhydrous sodium sulfate and the solvent was evaporated under reduced pressure to give the title compound (18.5 g, yield 99%) as a crudely purified product.

¹H-NMR (CDCl₃) δ: 1.60 (9H, s), 2.12 (3H, s), 3.96 (3H, s), 6.86 (1H, dd, J=8.4, 5.2 Hz), 7.03 (1H, t, J=8.8 Hz).

Reference Example 49 methyl 5-fluoro-2H-indazole-4-carboxylate

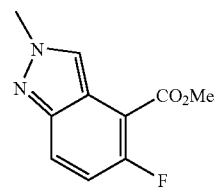

To a solution of a crudely purified product (18.5 g, 65.1 mmol) of methyl 3-[(tert-butylthio)diazenyl]-6-fluoro-2-methylbenzoate in dimethyl sulfoxide (200 mL) was added a solution of potassium tert-butoxide (10.6 g, 98.0 mmol) in dimethyl sulfoxide (125 mL) at room temperature, and the mixture was stirred for 12 hr. The reaction solution was diluted with water, and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/2) to give the title compound (3.20 g, yield 25%).

¹H-NMR (CDCl₃) δ: 4.05 (3H, s), 7.29 (1H, dd, J=10.6, 9.0 Hz), 7.68 (1H, dd, J=9.0, 3.8 Hz), 8.54 (1H, s), hidden (1H).

Reference Example 50 methyl 5-fluoro-2-methyl-2H-indazole-4-carboxylate

To a solution of methyl 5-fluoro-2H-indazole-4-carboxylate (4.50 g, 23.2 mmol) in ethyl acetate (93 mL) was added trimethyloxonium tetrafluoroborate (4.46 g, 30.1 mmol) at room temperature, and the mixture was stirred for 5 hr. The reaction solution was diluted with water, and the mixture was extracted with ethyl acetate. The extract was dried over anhydrous sodium sulfate and the solvent was evaporated under reduced pressure. The residue was purified by flash silica gel column chromatography (ethyl acetate/hexane=1/2) to give the title compound (4.10 g, yield 85%).

¹H-NMR (CDCl₃) δ: 4.00 (3H, s), 4.25 (3H, s), 7.14 (1H, dd, J=11.2, 9.2 Hz), 7.88 (1H, dd, J=9.2, 4.0 Hz), 8.39 (1H, s).

Reference Example 51

(5-fluoro-2-methyl-2H-indazol-4-yl)methanol

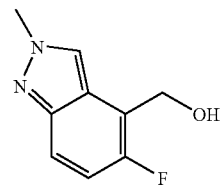

To a solution of methyl 5-fluoro-2-methyl-2H-indazole-4-carboxylate (4.10 g, 19.7 mmol) in tetrahydrofuran (197 mL) was slowly added a solution (1 M, 59.1 mL, 59.1 mmol) of diisobutylaluminum hydride in hexane at −78° C., and the mixture was stirred at room temperature for 3 hr. Water was added to the reaction mixture at 0° C., and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/1) to give the title compound (3.30 g, yield 93%).

¹H-NMR (CDCl₃) δ: 1.98 (1H, br s), 4.20 (2H, s), 4.98 (2H, s), 7.05 (1H, t, J=9.8 Hz), 7.59 (1H, dd, J=9.2, 4.4 Hz), 8.09 (1H, s).

Reference Example 52

5-fluoro-2-methyl-2H-indazole-4-carbaldehyde

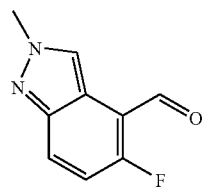

To a solution of dimethyl sulfoxide (7.56 mL, 107 mmol) in dichloromethane (100 mL) was added oxalyl chloride (4.86 mL, 53.3 mmol) at −78° C., and the mixture was stirred for 30 min. To the reaction mixture was added a solution of (5-fluoro-2-methyl-2H-indazol-4-yl)methanol (3.20 g, 17.8 mmol) in dichloromethane (78.0 mL), and the mixture was stirred for 2 hr. To the reaction mixture was added triethylamine (22.5 mL, 160 mmol) at −78° C., and the mixture was stirred for 1 hr. The reaction mixture was concentrated under reduced pressure, and the residue was purified by flash silica gel column chromatography (ethyl acetate/hexane=1/3) to give the title compound (3.00 g, yield 95%).

¹H-NMR (CDCl₃) δ: 4.26 (3H, s), 7.12-7.18 (1H, m), 7.97-8.01 (1H, m), 8.58 (1H, s), 10.52 (1H, s).

Reference Example 53 ethyl (2E)-3-(5-fluoro-2-methyl-2H-indazol-4-yl)acrylate

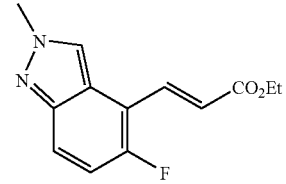

To a suspension of sodium hydride (0.88 g, 21.9 mmol) in tetrahydrofuran (20 mL) was added a solution of ethyl diethylphosphonoacetate (4.38 mL, 21.9 mmol) in tetrahydrofuran (5 mL) at 0° C., and the mixture was stirred for 20 min. To the reaction mixture was added a solution of 5-fluoro-2-methyl-2H-indazole-4-carbaldehyde (3.0 g, 16.8 mmol) in tetrahydrofuran (8.7 mL), and the mixture was warmed to room temperature over 4 hr. Water was added and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/3) to give the title compound (4.10 g, yield 98%)

¹H-NMR (CDCl₃) δ: 1.37 (3H, t, J=7.2 Hz), 4.25 (3H, s), 4.31 (2H, q, J=7.2 Hz), 6.54 (1H, d, J=16.0 Hz), 7.11 (1H, dd, J=10.8, 9.2 Hz), 7.72 (1H, dd, J=9.2, 4.8 Hz), 8.08 (1H, d, J=16.0 Hz), 8.16 (1H, s).

Reference Example 54 trans-ethyl 2-(5-fluoro-2-methyl-2H-indazol-4-yl)cyclopropanecarboxylate

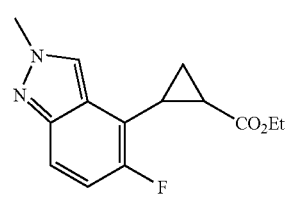

To a suspension of sodium hydride (0.793 g, 18.2 mmol) in dimethyl sulfoxide (100 mL) was added a solution of trimethylsulfoxonium iodide (4.00 g, 18.2 mmol) in dimethyl sulfoxide (100 mL) at 0° C., and the mixture was stirred at room temperature for 1 hr. To the reaction mixture was added a solution of ethyl (2E)-3-(5-fluoro-2-methyl-2H-indazol-4-yl)acrylate (4.10 g, 16.5 mmol) in dimethyl sulfoxide (130 mL) at 0° C., and the mixture was stirred at room temperature for 14 hr. Water was added, and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/3) to give the title compound (2.00 g, yield 46%).

¹H-NMR (CDCl₃) δ: 1.32 (3H, t, J=7.2 Hz), 1.53-1.58 (1H, m), 1.64-1.69 (1H, m), 2.17-2.22 (1H, m), 2.62-2.67 (1H, m), 4.21 (3H, s), 4.22 (2H, q, J=7.2 Hz), 7.01 (1H, dd, J=10.4, 9.2 Hz), 7.52 (1H, dd, J=9.2, 4.2 Hz), 7.91 (1H, s).

Reference Example 55 trans-[2-(5-fluoro-2-methyl-2H-indazol-4-yl)cyclopropyl]methanol

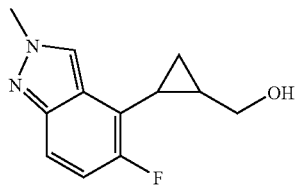

To a solution of trans-ethyl 2-(5-fluoro-2-methyl-2H-indazol-4-yl)cyclopropanecarboxylate (2.00 g, 7.63 mmol) in tetrahydrofuran (76 mL) was slowly added a solution (1 M, 22.9 ml, 22.9 mmol) of diisobutylaluminum hydride in hexane at −78° C., and the mixture was stirred at room temperature for 3 hr. Water was added to the reaction mixture at 0° C., and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/3) to give the title compound (1.51 g, yield 90%

¹H-NMR (CDCl₃) δ: 0.95-0.99 (1H, m), 1.19-1.23 (1H, m), 1.63-1.71 (1H, m), 1.95-2.00 (2H, m), 3.57 (1H, dd, J=11.2, 7.6 Hz), 3.85 (1H, dd, J=11.2, 6.0 Hz), 4.18 (3H, s), 7.01 (1H, dd, J=10.6, 9.4 Hz), 7.48 (1H, dd, J=9.2, 4.4 Hz), 8.00 (1H, s),

MS (ESI+): 221 (M+H).

Reference Example 56 trans-1-[2-(5-fluoro-2-methyl-2H-indazol-4-yl)cyclopropyl]methanamine

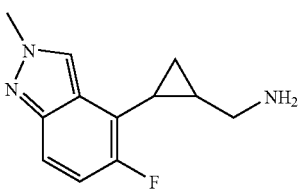

To a solution of trans-[2-(5-fluoro-2-methyl-2H-indazol-4-yl)cyclopropyl]methanol (500 mg, 2.27 mmol) in tetrahydrofuran (22 mL) were added a solution (40%, 1.24 mL, 2.72 mmol) of diethyl azodicarboxylate in toluene, triphenylphosphine (774 mg, 2.95 mmol) and phthalimide (434 mg, 2.95 mmol), and the mixture was stirred under nitrogen atmosphere at room temperature for 1.5 hr. The solvent was evaporated under reduced pressure. The residue was purified by silica gel column chromatography (NH, ethyl acetate/hexane=10/90→40/60) to give trans-2-{[2-(5-fluoro-2-methyl-2H-indazol-4-yl)cyclopropyl]methyl}-1H-isoindole-1,3(2H)-dione as a crudely purified product (893 mg).

780 mg from the obtained crudely purified product (893 mg) of trans-2-{[2-(5-fluoro-2-methyl-2H-indazol-4-yl)cyclopropyl]methyl}-1H-isoindole-1,3(2H)-dione was dissolved in ethanol (20 mL), hydrazine monohydrate (8 mL) was added, and the mixture was heated under reflux for 5 min. The solvent was evaporated under reduced pressure. The residue was diluted with diethyl ether, and saturated aqueous sodium hydrogen carbonate solution was added. The aqueous layer was extracted with diethyl ether. The extract was dried over anhydrous sodium sulfate, and the solvent was evaporated under reduced pressure. The residue was purified by silica gel column chromatography (NH, ethyl acetate/hexane=50/50→70/30, then methanol/ethyl acetate=0/100→5/95) to give the title compound (231 mg).

¹H-NMR (CDCl₃) δ: 0.84-0.94 (1H, m), 1.12-1.22 (1H, m), 1.41-1.63 (3H, m), 1.86-1.95 (1H, m), 2.71-2.89 (2H, m), 4.19 (3H, s), 7.01 (1H, dd, J=10.7, 9.3 Hz), 7.42-7.50 (1H, m), 7.95 (1H, s).

Reference Example 57

1-[(1S,2S)-2-(5-fluoro-2-methyl-2H-indazol-4-yl)cyclopropyl]methanamine dihydrochloride

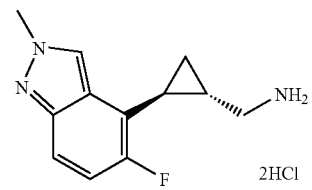

To a solution of tert-butyl {[(1S,2S)-2-(5-fluoro-2-methyl-2H-indazol-4-yl)cyclopropyl]methyl}carbamate (315 mg, 0.986 mmol) in methanol (1 mL) was added hydrochloric acid-methanol reagent (manufactured by TCI, 3 mL) solution, and the mixture was stirred at room temperature for 14 hr. The solvent was concentrated under reduced pressure and the obtained crystals were washed with ethyl acetate to give the title compound (297 mg, yield 100%).

¹H-NMR (DMSO-d₆) δ: 1.01-1.32 (2H, m), 1.69-1.74 (1H, m), 2.15-2.20 (1H, m), 2.85-3.04 (2H, m), 4.15 (3H, s), 5.28 (3H, br s), 7.07 (1H, dd, J=11.1, 9.2 Hz), 7.46 (1H, dd, J=9.2, 4.1 Hz), 8.20 (1H, br s), 8.51 (1H, s).

Reference Example 58

1-[(1R,2R)-2-(5-fluoro-2-methyl-2H-indazol-4-yl)cyclopropyl]methanamine dihydrochloride

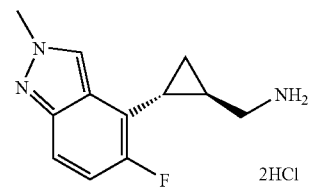

To a solution of tert-butyl {[(1R,2R)-2-(5-fluoro-2-methyl-2H-indazol-4-yl)cyclopropyl]methyl}carbamate (343 mg, 1.07 mmol) in methanol (1 mL) was added hydrochloric acid-methanol reagent (manufactured by TCI, 3 mL) solution, and the mixture was stirred at room temperature for 14 hr. The solvent was concentrated under reduced pressure and the obtained crystals were washed with ethyl acetate to give the title compound (246 mg, yield 79%).

$^1$H-NMR (DMSO-d$_6$) δ: 1.02-1.31 (2H, m), 1.61-1.84 (1H, m), 2.11-2.27 (1H, m), 2.78-3.14 (2H, m), 4.15 (3H, s), 5.68 (3H, br s), 7.07 (1H, dd, J=10.9, 9.2 Hz), 7.46 (1H, dd, J=9.2, 4.1 Hz), 8.20 (1H, br s), 8.51 (1H, s).

Reference Example 59 methyl 3-amino-6-chloro-2-methylbenzoate

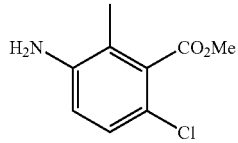

To a solution of methyl 3-amino-2-methylbenzoate (25.0 g, 151 mmol) in N,N-dimethylformamide (757 mL) was added N-chlorosuccinimide (20.2 g, 151 mmol) at room temperature, and the mixture was stirred for 3 days. The reaction mixture was concentrated under reduced pressure to a half volume, and the mixture was extracted with dichloromethane. The extract was dried over anhydrous sodium sulfate and the solvent was evaporated under reduced pressure. The residue was purified by flash silica gel column chromatography (ethyl acetate/hexane=1/5) to give the title compound (13.5 g, yield 45%).

$^1$H-NMR (CDCl$_3$) δ: 2.08 (3H, s), 3.71 (2H, br s), 3.93 (3H, s), 6.64 (1H, d, J=8.8 Hz), 7.04 (1H, d, J=8.8 Hz).

Reference Example 60 methyl 5-chloro-2H-indazole-4-carboxylate

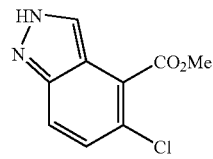

To a solution of methyl 3-amino-6-chloro-2-methylbenzoate (25.0 g, 125 mmol) in water (139 mL) were added concentrated hydrochloric acid (26.1 mL, 313 mmol), ammonium tetrafluoroborate (17.1 g, 163 mmol) and sodium nitrite (8.64 g, 125 mmol) at 0° C., and the mixture was stirred for 30 min. The reaction solution was diluted with water, and washed with ethyl acetate. The water of the obtained aqueous layer was evaporated under reduced pressure, and the residue was dissolved in chloroform (287 mL). 18-Crown-6 (993 mg, 3.76 mmol) and potassium acetate (13.5 g, 138 mmol) were added. The reaction mixture was stirred at room temperature for 2 hr. Water was added to the reaction mixture, and the mixture was extracted with ethyl acetate. The extract was dried over anhydrous sodium sulfate and the solvent was evaporated under reduced pressure. The residue was purified by flash silica gel column chromatography (ethyl acetate/hexane=1/3) to give the title compound (4.10 g, yield 20%).

$^1$H-NMR (CDCl$_3$) δ: 4.07 (3H, s), 7.46 (1H, d, J=8.8 Hz), 7.57 (1H, d, J=8.8, 0.8 Hz), 8.32 (1H, d, J=0.8 Hz), hidden (1H).

Reference Example 61 methyl 5-chloro-2-methyl-2H-indazole-4-carboxylate

To a solution of methyl 5-chloro-2H-indazole-4-carboxylate (3.80 g, 18.0 mmol) in ethyl acetate (72 mL) was added trimethyloxonium tetrafluoroborate (3.47 g, 23.5 mmol) at room temperature, and the mixture was stirred for 5 hr. The reaction solution was diluted with water, and the mixture was extracted with ethyl acetate. The extract was dried over anhydrous sodium sulfate and the solvent was evaporated under reduced pressure. The residue was purified by flash silica gel column chromatography (ethyl acetate/hexane=1/3) to give the title compound (3.20 g, yield 79%).

$^1$H-NMR (CDCl$_3$) δ: 4.02 (3H, s), 4.23 (3H, s), 7.32 (1H, d, J=9.2 Hz), 7.76 (1H, d, J=9.2 Hz), 8.20 (1H, s).

Reference Example 62

(5-chloro-2-methyl-2H-indazol-4-yl)methanol

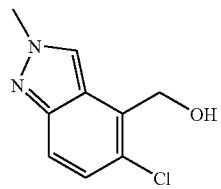

To a solution of methyl 5-chloro-2-methyl-2H-indazole-4-carboxylate (3.00 g, 13.4 mmol) in tetrahydrofuran (129 mL) was slowly added a solution (1 M, 40.1 mL, 40.1 mmol) of diisobutylaluminum hydride in hexane at −78° C., and the mixture was stirred at room temperature for 3 hr. Water was added to the reaction mixture at 0° C., and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/2) to give the title compound (2.63 g, yield 99%).

¹H-NMR (CDCl₃) δ: 2.12 (1H, t, J=5.6 Hz), 4.20 (3H, s), 5.05 (2H, d, J=4.8 Hz), 7.21 (1H, d, J=9.2 Hz), 7.55 (1H, d, J=9.2 Hz), 8.15 (1H, s).

Reference Example 63

5-chloro-2-methyl-2H-indazole-4-carbaldehyde

To a solution of dimethyl sulfoxide (5.70 mL, 80.0 mmol) in dichloromethane (100 mL) was added oxalyl chloride (3.51 mL, 40.1 mmol) at −78° C., and the mixture was stirred for 30 min. To the reaction mixture was added a solution of (5-chloro-2-methyl-2H-indazol-4-yl)methanol (2.63 g, 13.4 mmol) in dichloromethane (34 mL), and the mixture was stirred for 2 hr. To the reaction mixture was added triethylamine (16.9 mL, 120 mmol) at −78° C., and the mixture was stirred for 1 hr. The reaction mixture was concentrated under reduced pressure, and the residue was purified by flash silica gel column chromatography (ethyl acetate/hexane=1/4) to give the title compound (2.20 g, yield 85%).

¹H-NMR (CDCl₃) δ: 4.26 (3H, s), 7.31 (1H, d, J=9.2 Hz), 7.91 (1H, dd, J=9.2, 0.8 Hz), 8.64 (1H, s), 10.62 (1H, s).

Reference Example 64 ethyl (2E)-3-(5-chloro-2-methyl-2H-indazol-4-yl)acrylate

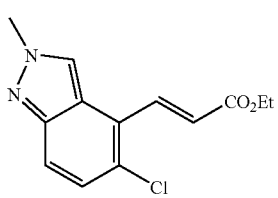

To a suspension of sodium hydride (0.488 g, 12.2 mmol) in tetrahydrofuran (10 mL) was added a solution of ethyl diethylphosphonoacetate (2.44 mL, 12.2 mmol) in tetrahydrofuran (5 mL) at 0° C., and the mixture was stirred for 20 min. To the reaction mixture was added a solution of 5-chloro-2-methyl-2H-indazole-4-carbaldehyde (2.16 g, 11.1 mmol) in tetrahydrofuran (10.0 mL), and the mixture was warmed to room temperature over 4 hr. Water was added and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/3) to give the title compound (2.54 g, yield 86%).

¹H-NMR (CDCl₃) δ: 1.38 (3H, t, J=7.0 Hz), 4.25 (3H, s), 4.32 (2H, q, J=7.0 Hz), 6.54 (1H, d, J=16.4 Hz), 7.30 (1H, d, J=9.2 Hz), 7.67 (1H, d, J=9.2 Hz), 8.14 (1H, s), 8.25 (1H, d, J=16.4 Hz).

Reference Example 65 ethyl 2-(5-chloro-2-methyl-2H-indazol-4-yl)cyclopropanecarboxylate

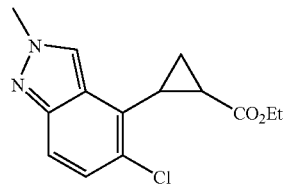

To a suspension of sodium hydride (0.453 g, 10.4 mmol) in dimethyl sulfoxide (50.0 mL) was added a solution of trimethylsulfoxonium iodide (2.29 g, 10.4 mmol) in dimethyl sulfoxide (89 mL) at 0° C., and the mixture was stirred at room temperature for 1 hr. To the reaction mixture was added a solution of ethyl (2E)-3-(5-chloro-2-methyl-2H-indazol-4-yl)acrylate (4.20 g, 18.2 mmol) in dimethyl sulfoxide (50.0 mL) at 0° C., and the mixture was stirred at room temperature for 14 hr. Water was added, and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/3) to give the title compound (2.10 g, yield 80%).

¹H-NMR (CDCl₃) δ: 1.34 (3H, t, J=7.2 Hz), 1.44-1.49 (1H, m), 1.73-1.78 (1H, m), 2.05-2.09 (1H, m), 2.71-2.76 (1H, m), 4.22 (3H, s), 4.22-4.29 (2H, m), 7.22 (1H, d, J=9.2 Hz), 7.52 (1H, d, J=9.2 Hz), 7.91 (1H, s).

Reference Example 66

[2-(5-chloro-2-methyl-2H-indazol-4-yl)cyclopropyl]methanol

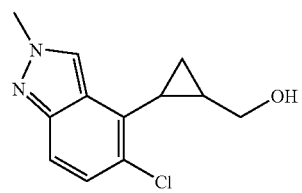

To a solution of ethyl 2-(5-chloro-2-methyl-2H-indazol-4-yl)cyclopropanecarboxylate (2.66 g, 9.54 mmol) obtained in Reference Example 65 in tetrahydrofuran (95.0 mL) was slowly added a solution (1 M, 28.6 mL, 28.6 mmol) of diisobutylaluminum hydride in hexane at −78° C., and the mixture was stirred at room temperature for 3 hr. Water was added to the reaction mixture at 0° C., and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/3) to give the title compound (1.77 g, yield 78%).

$^1$H-NMR (CDCl$_3$) δ: 1.03-1.08 (1H, m), 1.13-1.18 (1H, m), 1.58-1.66 (1H, m), 1.89 (1H, t, J=5.6 Hz), 2.04-2.09 (1H, m), 3.64-3.70 (1H, m), 3.83-3.89 (1H, m), 4.20 (3H, s), 7.21 (1H, d, J=9.2 Hz), 7.49 (1H, d, J=9.2 Hz), 8.11 (1H, s),

MS (ESI+): 237 (M+H).

Reference Example 67 methyl 3-amino-6-bromo-2-methylbenzoate

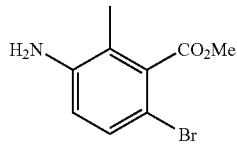

To a mixture of methyl 3-amino-2-methylbenzoate (5.00 mL, 34.7 mmol) in acetic acid (100 mL)-methanol (200 mL) was added bromine (5.55 g, 34.7 mmol) under ice-cooling, and the mixture was stirred for 5 min. The reaction solution was diluted with saturated aqueous sodium thiosulfate solution, and the organic solvent was evaporated under reduced pressure. The residual aqueous solution was diluted with saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=5/95→20/80) to give the title compound (4.66 g, yield 55%).

$^1$H-NMR (CDCl$_3$) δ: 2.08 (3H, s), 3.70 (2H, br s), 3.94 (3H, s), 6.58 (1H, d, J=8.5 Hz), 7.18 (1H, d, J=8.5 Hz).

Reference Example 68 methyl 5-bromo-1H-indazole-4-carboxylate

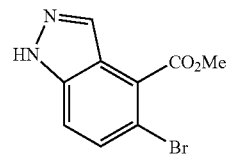

To a solution of methyl 3-amino-6-bromo-2-methylbenzoate (5.44 g, 22.3 mmol) in acetic acid (110 mL) was added a solution of sodium nitrite (1.69 g, 24.5 mmol) in water (11 mL) at room temperature, and the mixture was stirred for 20 hr. The organic solvent was evaporated under reduced pressure. The residual aqueous solution was diluted with saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane=10/90→30/70) to give the title compound (4.86 g, yield 86%).

$^1$H-NMR (CDCl$_3$) δ: 4.06 (3H, s), 7.48 (1H, dd, J=8.8, 1.1 Hz), 7.63 (1H, d, J=8.8 Hz), 8.26 (1H, d, J=1.1 Hz), 10.59 (1H, br s), melting point: 164-165° C. (recrystallized from ethyl acetate), elemental analysis: for C$_9$H$_7$N$_2$O$_2$Br.0.1H$_2$O
Calculated (%): C, 42.08; H, 2.83; N, 10.91
Found (%): C, 41.97; H, 2.93; N, 10.97.

Reference Example 69 methyl 5-bromo-2-methyl-2H-indazole-4-carboxylate

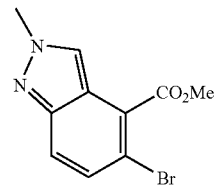

To a solution of methyl 5-bromo-1H-indazole-4-carboxylate (4.50 g, 17.6 mmol) in ethyl acetate (176 mL) was added trimethyloxonium tetrafluoroborate (3.38 g, 22.9 mmol) at room temperature, and the mixture was stirred for 2.5 hr. The reaction solution was diluted with saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=5/95→30/70) to give the title compound (3.42 g, yield 73%).

$^1$H-NMR (CDCl$_3$) δ: 4.01 (3H, s), 4.22 (3H, s), 7.49 (1H, d, J=9.1 Hz), 7.66 (1H, dd, J=9.1, 0.8 Hz), 8.15 (1H, s), melting point: 103-104° C. (recrystallized from ethyl acetate/hexane), elemental analysis: for C$_{10}$H$_9$N$_2$O$_2$Br
Calculated (%): C, 44.63; H, 3.37; N, 10.41
Found (%): C, 44.69; H, 3.30; N, 10.50.

Reference Example 70

(5-bromo-2-methyl-2H-indazol-4-yl)methanol

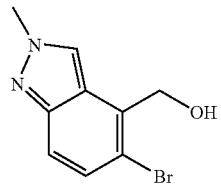

To a suspension of lithium aluminum hydride (152 mg, 4.00 mmol) in tetrahydrofuran (15 mL) was added a solution of methyl 5-bromo-2-methyl-2H-indazole-4-carboxylate (534 mg, 2.00 mmol) in tetrahydrofuran (5 mL) at 0° C., and the mixture was stirred at room temperature for 15 min. To the reaction solution was added sodium sulfate decahydrate (1.5 g), and the mixture was stirred for 15 min and filtered through celite. The filtrate was concentrated under reduced pressure and the residue was purified by silica gel column chromatography (ethyl acetate/hexane=40/60→80/20) to give the title compound (351 mg, yield 73%).

$^1$H-NMR (CDCl$_3$) δ: 2.26 (1H, t, J=6.3 Hz), 4.18 (3H, s), 5.02 (2H, d, J=6.3 Hz), 7.35 (1H, d, J=9.1 Hz), 7.47 (1H, d, J=9.1 Hz), 8.15 (1H, s), melting point: 123-125° C. (recrystallized from ethyl acetate/hexane),

MS (ESI+): 161 (M+H), elemental analysis: for C$_9$H$_9$N$_2$OBr

Calculated (%): C, 44.84; H, 3.76; N, 11.62

Found (%): C, 44.56; H, 3.77; N, 11.58.

Reference Example 71

5-bromo-2-methyl-2H-indazole-4-carbaldehyde

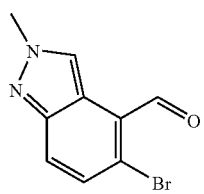

(5-Bromo-2-methyl-2H-indazol-4-yl)methanol (324 mg, 1.34 mmol) and o-iodoxybenzoic acid (414 mg, 1.48 mmol) were dissolved in dimethyl sulfoxide (6.7 mL), and the mixture was stirred at room temperature for 1 hr. The reaction solution was diluted with diethyl ether, washed with saturated aqueous sodium hydrogen carbonate solution and saturated brine, and dried over anhydrous sodium sulfate. The solvent was evaporated under reduced pressure. The residue was purified by silica gel column chromatography (ethyl acetate) to give the title compound (311 mg, yield 97%).

$^1$H-NMR (CDCl$_3$) δ: 4.25 (3H, s), 7.48 (1H, d, J=9.1 Hz), 7.82 (1H, d, J=9.1 Hz), 8.64 (1H, s), 10.46 (1H, s), melting point: 137-140° C. (recrystallized from ethyl acetate/hexane),

MS (ESI+): 239 (M+H), elemental analysis: for C$_9$H$_7$N$_2$OBr

Calculated (%): C, 45.22; H, 2.95; N, 11.72

Found (%): C, 45.14; H, 2.86; N, 11.72.

Reference Example 72

(2E)-3-(5-bromo-2-methyl-2H-indazol-4-yl)acrylonitrile

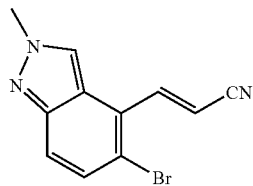

To a solution of diethyl cyanomethylphosphonate (88.0 μL, 0.544 mmol) in tetrahydrofuran (2 mL) was added 60% sodium hydride (20.1 mg, 0.502 mmol) under ice-cooling, and the mixture was stirred at 0° C. for 15 min. To the mixture was added a solution of 5-bromo-2-methyl-2H-indazole-4-carbaldehyde (100 mg, 0.418 mmol) in tetrahydrofuran (2 mL) under ice-cooling, and the mixture was stirred for 15 min. The reaction solution was diluted with saturated aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=40/60→80/20) to give the title compound (108 m yield 98%).

$^1$H-NMR (CDCl$_3$) δ: 4.26 (3H, s), 6.00 (1H, d, J=16.8 Hz), 7.47 (1H, d, J=9.1 Hz), 7.63 (1H, d, J=9.1 Hz), 7.94 (1H, d, J=16.8 Hz), 8.04 (1H, s),

MS (ESI+): 262 (M+H).

Reference Example 73

2-(5-bromo-2-methyl-2H-indazol-4-yl)cyclopropanecarbonitrile

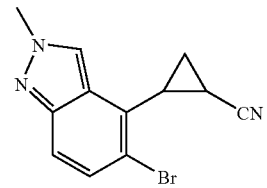

To a suspension of sodium hydride (19.6 mg, 0.490 mmol) in dimethyl sulfoxide (2 mL) was added trimethylsulfoxonium iodide (117 mg, 0.531 mmol) at room temperature, and the mixture was stirred at room temperature for 1 hr. Thereto was added a solution of (2E)-3-(5-bromo-2-methyl-2H-indazol-4-yl)acrylonitrile (107 mg, 0.408 mmol) in dimethyl sulfoxide (2 mL), and the mixture was stirred for 48 hr. The reaction mixture was diluted with ethyl acetate, washed with saturated aqueous sodium hydrogen carbonate solution and saturated brine, and dried over anhydrous sodium sulfate. The solvent was evaporated under reduced pressure. The residue was purified by silica gel column chromatography (ethyl acetate/hexane=30/70→100/0) to give the title compound (50.0 mg, yield 44%).

$^1$H-NMR (CDCl$_3$) δ: 1.52-1.62 (1H, m), 1.68-1.78 (1H, m), 1.80-1.90 (1H, m), 2.69-2.84 (1H, m), 4.23 (3H, s), 7.38 (1H, q, J=9.1 Hz), 7.50 (1H, d, J=9.1 Hz), 7.96 (1H, s), melting point: 154-156° C. (recrystallized from ethyl acetate/hexane), MS (ESI+): 276 (M+H), elemental analysis: for C$_{12}$H$_{10}$N$_3$Br Calculated (%): C, 52.20; H, 3.65; N, 15.22

Found (%): C, 52.35; H, 3.57; N, 15.49.

Reference Example 74

1-[2-(5-bromo-2-methyl-2H-indazol-4-yl)cyclopropyl]methanamine

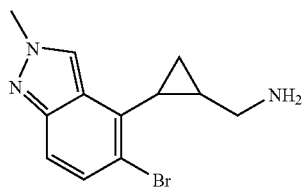

To a solution of 2-(5-bromo-2-methyl-2H-indazol-4-yl)cyclopropanecarbonitrile (300 mg, 1.09 mmol) obtained in Reference Example 73 in ethanol (5.5 mL) were added Raney cobalt (3.0 g) and 2 M ammonia/ethanol solution (5.5 mL), and the mixture was stirred under hydrogen atmosphere at room temperature for 2.5 hr. The catalyst was filtered off through celite, and the filtrate was concentrated under reduced pressure to give the title compound (287 mg, yield 94%).

$^1$H-NMR (CDCl$_3$) δ: 0.96-1.06 (1H, m), 1.05-1.15 (1H, m), 1.44-1.57 (1H, m), 1.95-2.04 (1H, m), 2.79 (1H, dd, J=12.9, 6.9 Hz), 2.99 (1H, dd, J=12.9, 6.3 Hz), 4.20 (3H, s), 7.32-7.43 (2H, m), 8.07 (1H, s), hidden (2H).

Reference Example 75 methyl 3-amino-4-fluoro-2-methylbenzoate

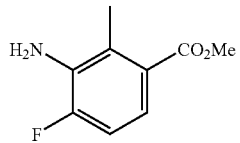

To fuming nitric acid (20.3 mL, 409 mmol) was slowly added dropwise 4-fluoro-2-methylbenzoic acid (4.50 g, 29.2 mmol) while maintaining the temperature of the reaction mixture at 5-10° C. The reaction solution was stirred at 0-5° C. for 1 hr, and poured into ice. The precipitated solid was recovered, washed with water, and dried under reduced pressure to give 4-fluoro-2-methyl-3-nitrobenzoic acid (5.70 g, purity 25%) as a crudely purified product.

$^1$H-NMR (CDCl$_3$) δ: 2.63 (3H, s), 7.22 (1H, m), 8.23 (1H, dd, J=8.8, 5.2 Hz), hidden (1H).

A solution of the obtained crudely purified product (5.70 g, purity 25%) of 4-fluoro-2-methyl-3-nitrobenzoic acid and sulfuric acid (1.00 mL, 18.8 mmol) in methanol (100 mL) was heated under reflux for 12 hr. The solvent was evaporated under reduced pressure. The residue was diluted with ethyl acetate, washed with aqueous sodium hydroxide solution (10%), water and saturated brine, and dried over anhydrous sodium sulfate, and the solvent was evaporated under reduced pressure to give methyl 4-fluoro-2-methyl-3-nitrobenzoate (6.01 g, purity 25%) as a crudely purified product. Recrystallization from ether gave methyl 4-fluoro-2-methyl-3-nitrobenzoate (3.01 g, purity 50%) as a crudely purified product.

$^1$H-NMR (CDCl$_3$) δ: 2.57 (3H, s), 3.88 (3H, s) 7.04 (1H, d, J=8.0 Hz), 8.06 (1H, dd, J=8.4, 3.2 Hz).

A mixture of a crudely purified product (6.00 g, purity 50%) of methyl 4-fluoro-2-methyl-3-nitrobenzoate and wet palladium carbon (10 wt %, 300 mg, 2.81 mmol) in methanol (100 mL) was stirred under hydrogen atmosphere for 4 hr. The catalyst was filtered off through celite, the filtrate was concentrated under reduced pressure, and the residue was purified by flash silica gel column chromatography (ethyl acetate/hexane=1/20→1/10) to give the title compound (2.13 g, yield 42%).

$^1$H-NMR (CDCl$_3$) δ: 2.40 (3H, s), 3.79 (2H, br s), 3.87 (3H, s), 6.89 (1H, t, J=9.2 Hz), 7.25 (1H, dd, J=8.8, 5.6 Hz).

Reference Example 76 methyl 7-fluoro-1H-indazole-4-carboxylate

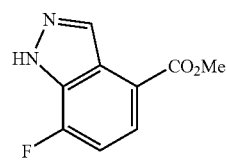

To a solution of methyl 3-amino-4-fluoro-2-methylbenzoate (3.00 g, 16.4 mmol) in hydrochloric acid (6 N, 54.6 mL) was added a solution of sodium nitrite (1.24 g, 18.0 mmol) in water (3 mL) at 0° C., and the mixture was stirred for 2 hr. To the reaction solution was added aqueous potassium acetate solution (30%) at 0° C. to adjust the reaction solution to pH 4, and a solution of 2-methylpropane-2-thiol (2.03 mL, 18.0 mmol) in ethanol (3 mL) was added. The reaction solution was stirred at room temperature for 12 hr, and the mixture was extracted with ethyl acetate. The extract was dried over anhydrous sodium sulfate and the solvent was evaporated under reduced pressure to give methyl 3-[(tert-butylthio)diazenyl]-4-fluoro-2-methylbenzoate (2.90 g, yield 62%) as a crudely purified product.

$^1$H-NMR (CDCl$_3$) δ: 1.62 (9H, s), 2.10 (3H, s), 3.90 (3H, s), 7.04 (1H, t, J=8.8 Hz). 7.88 (1H, dd, J=5.4, 3.4 Hz).

To a solution of the obtained crudely purified product (2.90 g, 10.2 mmol) of methyl 3-[(tert-butylthio)diazenyl]-4-fluoro-2-methylbenzoate in dimethyl sulfoxide (20 mL) was added a solution of potassium tert-butoxide (2.29 g, 20.4 mmol) in dimethyl sulfoxide (41 mL) at room temperature, and the mixture was stirred for 12 hr. The reaction solution was diluted with water, and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/2) to give the title compound (1.23 g, yield 62%).

¹H-NMR (CDCl₃) δ: 4.03 (3H, s), 7.15 (1H, dd, J=10.0, 8.0 Hz). 7.95 (1H, dd, J=8.0, 4.4 Hz), 8.65 (1H, d, J=3.6 Hz), hidden (1H).

Reference Example 77 methyl 7-fluoro-2-methyl-2H-indazole-4-carboxylate

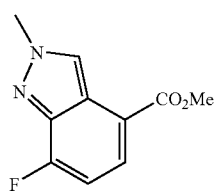

To a solution of methyl 7-fluoro-1H-indazole-4-carboxylate (2.93 g, 15.1 mmol) in ethyl acetate (60 mL) was added trimethyloxonium tetrafluoroborate (2.90 g, 19.6 mmol) at room temperature, and the mixture was stirred for 5 hr. The reaction solution was diluted with water, and the mixture was extracted with ethyl acetate. The extract was dried over anhydrous sodium sulfate and the solvent was evaporated under reduced pressure. The residue was purified by flash silica gel column chromatography (ethyl acetate/hexane=1/2) to give the title compound (2.10 g, yield 67%).

¹H-NMR (CDCl₃) δ: 3.97 (3H, s), 4.30 (3H, s), 6.98 (1H, dd, J=10.6, 7.8 Hz). 7.88 (1H, dd, J=8.0, 4.4 Hz), 8.46 (1H, d, J=2.8 Hz).

Reference Example 78

(7-fluoro-2-methyl-2H-indazol-4-yl)methanol

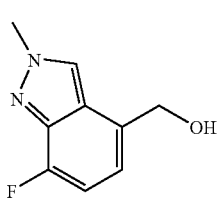

To a solution of methyl 7-fluoro-2-methyl-2H-indazole-4-carboxylate (2.10 g, 10.1 mmol) in tetrahydrofuran (101 mL) was slowly added a solution (1 M, 30.3 mL, 30.3 mmol) of diisobutylaluminum hydride in hexane at −78° C., and the mixture was stirred at room temperature for 3 hr. Water was added to the reaction mixture at 0° C., and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/1) to give the title compound (1.80 g, yield 99%).

¹H NMR (CDCl₃) δ: 4.23 (3H, s), 4.95 (2H, s), 6.83-6.91 (2H, m), 8.10 (1H, d, J=2.8 Hz), hidden (1H).

Reference Example 79

7-fluoro-2-methyl-2H-indazole-4-carbaldehyde

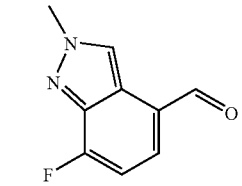

To a solution of dimethyl sulfoxide (4.30 mL, 60.5 mmol) in dichloromethane (50 mL) was added oxalyl chloride (2.65 mL, 30.3 mmol) at −78° C., and the mixture was stirred for 30 min. To the reaction mixture was added a solution of (7-fluoro-2-methyl-2H-indazol-4-yl)methanol (1.82 g, 10.1 mmol) in dichloromethane (51 mL), and the mixture was stirred for 2 hr. To the reaction mixture was added triethylamine (12.8 mL, 91.0 mmol) at −78° C., and the mixture was stirred for 1 hr. The reaction mixture was concentrated under reduced pressure, and the residue was purified by silica gel column chromatography (ethyl acetate/hexane=1/3) to give the title compound (1.60 g, yield 89%).

¹H-NMR (CDCl₃) δ: 4.31 (3H, s), 7.08 (1H, dd, J=10.6, 7.8 Hz), 7.64 (1H, dd, J=7.8, 4.2 Hz), 8.67 (1H, d, J=2.8 Hz), 10.01 (1H, s).

Reference Example 80 ethyl (2E)-3-(7-fluoro-2-methyl-2H-indazol-4-yl)acrylate

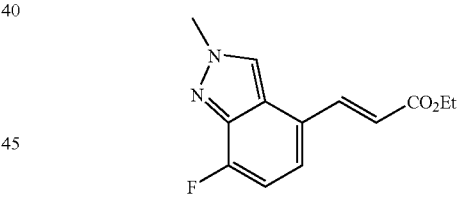

To a suspension of sodium hydride (0.467 g, 11.7 mmol) in tetrahydrofuran (10 mL) was added a solution of ethyl diethylphosphonoacetate (2.34 mL, 11.7 mmol) in tetrahydrofuran (3 mL) at 0° C., and the mixture was stirred for 20 min. To the reaction mixture was added a solution of 7-fluoro-2-methyl-2H-indazole-4-carbaldehyde (1.60 g, 8.98 mmol) in tetrahydrofuran (5 mL), and the mixture was warmed to room temperature over 4 hr. Water was added and the mixture was extracted with ethyl acetate. The extract was washed with saturated brine, and dried over anhydrous sodium sulfate, and the solvent was evaporated under reduced pressure. The residue is was purified by silica gel column chromatography (ethyl acetate/hexane=1/3) to give the title compound (1.85 g, yield 83%).

¹H-NMR (CDCl₃) δ: 1.36 (3H, t, J=7.2 Hz), 4.27-4.30 (2H, q, J=7.2 Hz), 4.29 (3H, s), 6.40 (1H, d, J=16.0 Hz), 6.94 (1H, dd, J=7.8, 10.6 Hz), 7.21 (1H, dd, J=7.8, 4.2 Hz), 7.83 (1H, d, J=16.0 Hz), 8.23 (1H, d, J=2.8 Hz),

MS (ESI+): 249 (M+H).

Reference Example 81 ethyl 2-(7-fluoro-2-methyl-2H-indazol-4-yl)cyclo-propanecarboxylate

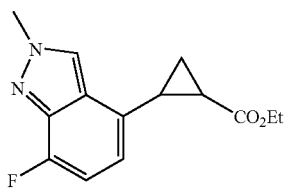

Under nitrogen atmosphere, to a suspension of sodium hydride (290 mg, 7.25 mmol) in dimethyl sulfoxide (45 mL) was added trimethylsulfoxonium iodide (1.73 g, 7.86 mmol) at 0° C., and the mixture was stirred at room temperature for 1 hr. To the reaction mixture was added a solution of ethyl (2E)-3-(7-fluoro-2-methyl-2H-indazol-4-yl)acrylate (1.50 g, 6.04 mmol) in dimethyl sulfoxide (15 mL) at 0° C., and the mixture was stirred at 70° C. for 27 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=15/85→50/50) to give the title compound (1.20 g, yield 76%).

$^1$H-NMR (CDCl$_3$) δ: 1.31 (3H, t, J=7.2 Hz), 1.35-1.44 (1H, m), 1.56-1.66 (1H, m), 1.92-2.02 (1H, m), 2.63-2.75 (1H, m), 4.15-4.32 (5H, m), 6.37 (1H, s), 6.63 (1H, dd, J=7.6, 4.0 Hz), 6.81 (1H, dd, J=11.0, 7.7 Hz), 8.00 (1H, d, J=2.7 Hz),

MS (ESI+): 263 (M+H).

Reference Example 82

[2-(7-fluoro-2-methyl-2H-indazol-4-yl)cyclopropyl]methanol

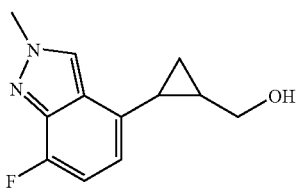

To a suspension of lithium aluminum hydride (695 mg, 18.3 mmol) in tetrahydrofuran (30 mL) was added a solution of ethyl 2-(7-fluoro-2-methyl-2H-indazol-4-yl)cyclopropanecarboxylate (1.20 g, 4.58 mmol) obtained in Reference Example 81 in tetrahydrofuran (15 mL) under nitrogen atmosphere at 0° C., and the mixture was stirred at 0° C. for 15 min. Sodium sulfate decahydrate (7.0 g) was added under ice-cooling, and the mixture was filtered through celite. The filtrate was concentrated under reduced pressure and purified by silica gel column chromatography (ethyl acetate/hexane=15/85→100/0) to give the title compound (961 mg, yield 95%).

$^1$H-NMR (CDCl$_3$) δ: 0.84-0.97 (1H, m), 1.03-1.14 (1H, m), 1.39-1.52 (1H, m), 1.95-2.07 (1H, m), 3.49-3.64 (1H, m), 3.77-3.88 (1H, m), 4.24 (3H, s), 6.61 (1H, dd, J=7.6, 4.0 Hz), 6.80 (1H, dd, J=11.3, 7.7 Hz), 8.12 (1H, d, J=2.5 Hz),

MS (ESI+): 221 (M+H).

Reference Example 83

1-[2-(7-fluoro-2-methyl-2H-indazol-4-yl)cyclopropyl]methanamine

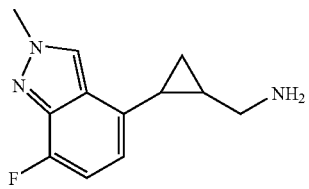

To a solution of [2-(7-fluoro-2-methyl-2H-indazol-4-yl)cyclopropyl]methanol (942 mg, 4.28 mmol) obtained in Reference Example 82 in tetrahydrofuran (43 mL) were added a solution (40%, 2.34 mL, 5.13 mmol) of diethyl azodicarboxylate in toluene, triphenylphosphine (1.46 g, 5.56 mmol) and phthalimide (818 mg, 5.56 mmol), and the mixture was stirred under nitrogen atmosphere at room temperature for 1.5 hr. The solvent was evaporated under reduced pressure to give 2-{[2-(7-fluoro-2-methyl-2H-indazol-4-yl)cyclopropyl]methyl}-1H-isoindole-1,3(2H)-dione as a crudely purified product. The obtained crudely purified product of 2-{[2-(7-fluoro-2-methyl-2H-indazol-4-yl)cyclopropyl]methyl}-1H-isoindole-1,3(2H)-dione was dissolved in ethanol (42 mL), hydrazine monohydrate (17 mL) was added, and the mixture was heated under reflux for 10 min. The solvent was evaporated under reduced pressure, the residue was diluted with tetrahydrofuran, and saturated aqueous sodium hydrogen carbonate solution was added. The aqueous layer was extracted with tetrahydrofuran, and the extract was dried over sodium sulfate. The solvent was evaporated under reduced pressure. The residue was purified by silica gel column chromatography (NH, hexane/ethyl acetate=55/45→45/55, then ethyl acetate/methanol=100/0→90/10) to give the title compound (721 mg, yield 77%).

$^1$H-NMR (CDCl$_3$) δ: 0.80-0.93 (1H, m), 0.96-1.08 (1H, m), 1.29-1.43 (1H, m), 1.84-1.95 (1H, m), 4.24 (3H, s), 6.58 (1H, dd, J=7.3, 4.3 Hz), 6.79 (1H, dd, J=11.3, 7.7 Hz), 8.06 (1H, d, J=2.5 Hz), hidden (2H).

Reference Example 84 methyl 3-amino-4-chloro-2-methylbenzoate

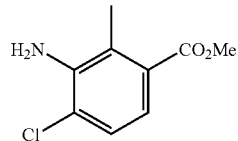

To fuming nitric acid (20.4 mL, 410 mmol) was slowly added dropwise 4-chloro-2-methylbenzoic acid (5.0 g, 29.3 mmol) while maintaining the temperature of the reaction mixture at 5-10° C. The reaction solution was stirred at 0-5° C. for 1 hr, and poured into ice. The precipitated solid was recovered, washed with water, and dried under reduced pressure to give 4-chloro-2-methyl-3-nitrobenzoic acid (6.14 g, purity 33%) as a crudely purified product.

$^1$H-NMR (CDCl$_3$) δ: 2.60 (3H, s), 7.48 (1H, d, J=8.4 Hz), 8.12 (1H, d, J=8.4 Hz), hidden (1H).

A solution of the obtained crudely purified product of 4-chloro-2-methyl-3-nitrobenzoic acid (6.14 g, purity 33%) and sulfuric acid (1.00 mL, 18.8 mmol) in methanol (100 mL) was heated under reflux for 12 hr, and the solvent was evaporated under reduced pressure. The residue was diluted with ethyl acetate, washed with aqueous sodium hydroxide solution (10%), water and saturated brine, and dried over anhydrous sodium sulfate. The solvent was evaporated under reduced pressure to give methyl 4-chloro-2-methyl-3-nitrobenzoate (6.50 g, purity 33%) as a crudely purified product.

$^1$H-NMR (CDCl$_3$) δ: 2.53 (3H, s), 3.93 (3H, s) 7.41 (1H, d, J=8.4 Hz), 7.95 (1H, d, J=8.4 Hz).

The obtained crudely purified product of methyl 4-chloro-2-methyl-3-nitrobenzoate (14.6 g, purity 33%) was dissolved in ethyl acetate (500 mL) and methanol (50 mL), tin(IV) chloride (2.30 g, 382 mmol) was added, and the mixture was heated under reflux for 3 days. The reaction solution was cooled to room temperature, ethyl acetate (500 mL) and saturated aqueous sodium hydrogen carbonate solution were added, and the mixture was filtered through celite. The filtrate was extracted with ethyl acetate, the extract was washed with saturated brine, and dried over anhydrous sodium sulfate, and the solvent was evaporated under reduced pressure. The residue was purified by silica gel column chromatography (ethyl acetate/hexane=1/20) to give the title compound (5.60 g, 44%).

$^1$H-NMR (DMSO-d$_6$) δ: 2.24, (3H, s), 3.77 (3H, s), 5.28 (2H, br s), 6.89 (1H, d, J=8.4 Hz), 7.16 (1H, d, J=8.4 Hz).

Reference Example 85 methyl 7-chloro-1H-indazole-4-carboxylate

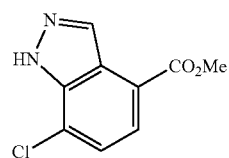

To a solution of methyl 3-amino-4-chloro-2-methylbenzoate (6.50 g, 32.6 mmol) and ammonium tetrafluoroborate (4.44 g, 42.3 mmol) in water (2.0 mL) and concentrated hydrochloric acid (17.6 mL, 212 mmol) was added a solution of sodium nitrite (2.25 g, 32.6 mmol) in water (8 mL) at 0° C. for 25 min, and the mixture was stirred for 35 min. The precipitated solid was collected by filtration, washed with ether, and dried under reduced pressure. The obtained solid was dissolved in chloroform (100 mL), and 18-crown-6 (258 mg, 0.98 mmol) and potassium acetate (3.52 g, 35.8 mmol) were added. The reaction mixture was stirred at room temperature for 2 hr, water was added to the reaction mixture, and the mixture was extracted with ethyl acetate. The extract was washed with water, and dried over anhydrous sodium sulfate, and the solvent was evaporated under reduced pressure. The residue was triturated with hexane, and collected by filtration to give the title compound (16.1 g, yield 50%). $^1$H-NMR (CDCl$_3$) δ: 4.03 (3H, s), 7.45 (1H, d, J=7.6 Hz), 7.90 (1H, d, J=7.6 Hz), 8.64 (1H, s), 10.71 (1H, br s).

Reference Example 86 methyl 7-chloro-2-methyl-2H-indazole-4-carboxylate

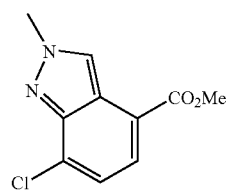

To a solution of methyl 7-chloro-1H-indazole-4-carboxylate (5.40 g, 25.6 mmol) in ethyl acetate (150 mL) was added trimethyloxonium tetrafluoroborate (5.69 g, 38.5 mmol) at room temperature, and the mixture was stirred for 5 hr. The is reaction solution was diluted with water, and the mixture was extracted with ethyl acetate. The extract was dried over anhydrous sodium sulfate and the solvent was evaporated under reduced pressure. The residue was purified by flash silica gel column chromatography (ethyl acetate/hexane=1/2) to give the title compound (4.10 g, yield 71%).

$^1$H-NMR (CDCl$_3$) δ: 3.97 (3H, s), 4.29 (3H, s), 7.35 (1H, d, J=7.4 Hz), 7.79 (1H, d, J=7.6 Hz), 8.43 (1H, s).

Reference Example 87

(7-chloro-2-methyl-2H-indazol-4-yl)methanol

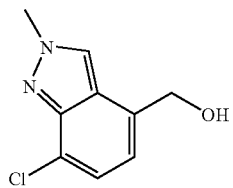

To a solution of methyl 7-chloro-2-methyl-2H-indazole-4-carboxylate (4.10 g, 18.3 mmol) in tetrahydrofuran (100 mL) was added a solution (1 M, 54.8 mL, 54.8 mmol) of diisobutylaluminum hydride in hexane at −78° C., and the mixture was stirred for 20 min. The reaction mixture was warmed to room temperature, and the mixture was stirred at room temperature for 1 hr. Water was added to the reaction mixture at 0° C. An aqueous sodium hydroxide solution (1 N, 20 mL) was added, and the mixture was stirred at 0° C. for 10 min. The reaction mixture was acidified with 6 M hydrochloric acid (10 mL), and the mixture was extracted with ethyl acetate. The extract was washed with saturated brine, and dried over anhydrous sodium sulfate, and the solvent was evaporated under reduced pressure. The residue was purified by flash silica gel column chromatography (ethyl acetate/hexane=1/1) to give the title compound (3.40 g, yield 95%).

¹H-NMR (CDCl₃) δ: 1.74 (1H, t, J=6.0 Hz), 4.27 (3H, s), 4.90 (2H, d, J=6.0 Hz), 6.93 (1H, d, J=7.6 Hz), 7.26 (1H, d, J=7.2 Hz), 8.14 (1H, s).

Reference Example 88

7-chloro-2-methyl-2H-indazole-4-carbaldehyde

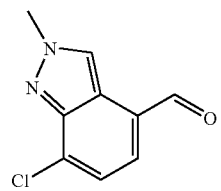

To a solution of oxalyl chloride (2.93 mL, 34.6 mmol) in dichloromethane (50 mL) was added dimethyl sulfoxide (3.68 mL, 51.9 mmol) at −78° C. To the reaction mixture was added a solution of (7-chloro-2-methyl-2H-indazol-4-yl)methanol (3.40 g, 17.3 mmol) in dichloromethane (10 mL), and the mixture was stirred for 2 hr. To the reaction mixture was added triethylamine (14.6 mL, 104 mmol) at −78° C., and the mixture was stirred for 30 min. The reaction mixture was warmed to room temperature, and the mixture was stirred at room temperature for 4 hr. To the reaction mixture was added saturated aqueous ammonium chloride solution, and the aqueous layer was extracted with dichloromethane. The combined extract was washed with saturated brine, and dried over anhydrous sodium sulfate, and the solvent was evaporated under reduced pressure. The obtained crude product was purified by recrystallization (hexane/dichloromethane) to give the title compound (3.07 g, yield 91%).

¹H-NMR (CDCl₃) δ: 4.32 (3H, s), 7.47 (1H, d, J=7.2 Hz), 7.58 (1H, d, J=7.2 Hz), 8.66 (1H, s), 10.05 (1H, s),
MS (ESI+): 195 (M+H).

Reference Example 89

(2E)-3-(7-chloro-2-methyl-2H-indazol-4-yl)acrylonitrile

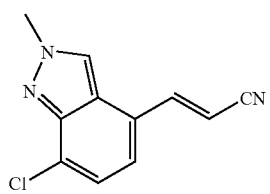

To a solution of diethyl cyanomethylphosphonate (1.62 mL, 10.02 mmol) in tetrahydrofuran (70 mL) was added 60% sodium hydride (370 mg, 9.25 mmol) under ice-cooling, and the mixture was stirred at 0° C. for 30 min. To the mixture was added a solution of 7-chloro-2-methyl-2H-indazole-4-carbaldehyde (1.50 g, 7.71 mmol) in tetrahydrofuran (30 mL) under ice-cooling, and the mixture was stirred at room temperature for 1 hr. The reaction solution was diluted with saturated aqueous ammonium chloride solution, and the mixture was extracted with ethyl acetate. The extract was washed with saturated brine, and dried over anhydrous sodium sulfate, and the solvent was evaporated under reduced pressure.

The residue was purified by silica gel column chromatography (ethyl acetate/hexane=15/85→40/60) to give the title compound (1.45 g, yield 86%).

¹H-NMR (CDCl₃) δ: 4.32 (3H, s), 5.91 (1H, d, J=16.7 Hz), 7.16 (1H, d, J=7.4 Hz), 7.34 (1H, d, J=7.4 Hz), 7.55 (1H, d, J=16.7 Hz), 8.13 (1H, s),
MS (ESI+): 218 (M+H).

Reference Example 90

[2-(7-chloro-2-methyl-2H-indazol-4-yl)cyclopropyl]acetonitrile

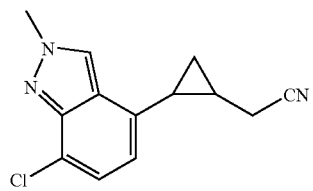

Under nitrogen atmosphere, to a suspension of sodium hydride (320 mg, 7.99 mmol) in dimethyl sulfoxide (50 mL) was added trimethylsulfoxonium iodide (1.91 g, 8.866 mmol) at 0° C., and the mixture was stirred at room temperature for 1 hr. To the reaction mixture was added a solution of (2E)-3-(7-chloro-2-methyl-2H-indazol-4-yl)acrylonitrile (1.45 g, 6.66 mmol) in dimethyl sulfoxide (16 mL) at 0° C., and the mixture was stirred at 70° C. for 23 hr. Water was added to the reaction mixture, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=15/85→40/60) to give the title compound (832 mg, yield 54%).

¹H-NMR (CDCl₃) δ: 1.52-1.63 (2H, m), 1.69 (1H, d, J=8.8 Hz), 2.74-2.87 (1H, m), 4.30 (3H, m), 6.65 (1H, d, J=7.7 Hz), 7.21 (1H, d, J=7.4 Hz), 8.10 (1H, s),
MS (ESI+): 232 (M+H).

Reference Example 91

1-[2-(7-chloro-2-methyl-2H-indazol-4-yl)cyclopropyl]methanamine

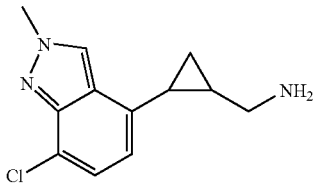

To a solution of [2-(7-chloro-2-methyl-2H-indazol-4-yl)cyclopropyl]acetonitrile (837 mg, 3.61 mmol) obtained in Reference Example 90 in ethanol (25 mL) were added Raney cobalt (8.3 g) and 2 M ammonia/ethanol solution (18 mL) and the mixture was stirred under hydrogen atmosphere at room temperature for 2 hr. The catalyst was filtered off through celite, and the filtrate was concentrated under reduced pressure to give the title compound (827 mg, yield 97%).

¹H-NMR (CDCl₃) δ: 0.84-0.96 (1H, m), 0.99-1.10 (1H, m), 1.30-1.48 (1H, m), 1.85-1.98 (1H, m), 2.78 (2H, d, J=6.6 Hz), 4.26 (3H, s), 6.60 (1H, d, J=7.7 Hz), 7.17 (1H, d, J=7.4 Hz), 8.08 (1H, s), hidden (2H).

Reference Example 92

1-[(1S,2S)-2-(2-methylpyrazolo[1,5-a]pyridin-4-yl)cyclopropyl]methanamine dihydrochloride

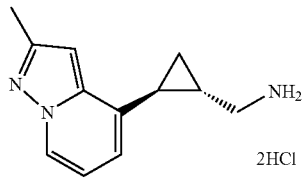

To a solution of tert-butyl {[(1S,2S)-2-(2-methylpyrazolo[1,5-a]pyridin-4-yl)cyclopropyl]methyl}carbamate (1.84 g, 6.11 mmol) in methanol (6 mL) was added hydrochloric acid-methanol reagent (manufactured by TCI, 18 mL) solution, and the mixture was stirred at room temperature for 15 hr. The solvent was concentrated under reduced pressure to give the title compound (1.69 g, yield 100%).

¹H-NMR (DMSO-d₆) δ: 1.11 (2H, t, J=7.2 Hz), 1.40-1.60 (1H, m), 2.13-2.28 (1H, m), 2.41 (3H, s), 2.91 (2H, t, J=5.7 Hz), 6.59-6.89 (3H, m), 7.91 (1H, br s), 8.23-8.54 (4H, m).

Reference Example 93

1-[(1R,2R)-2-(2-methylpyrazolo[1,5-a]pyridin-4-yl)cyclopropyl]methanamine dihydrochloride

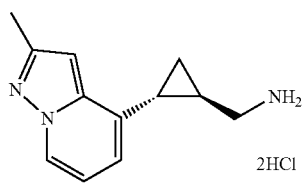

To a solution of tert-butyl {[(1R,2R)-2-(2-methylpyrazolo[1,5-a]pyridin-4-yl)cyclopropyl]methyl}carbamate (1.71 g, 5.67 mmol) in methanol (6 mL) was added hydrochloric acid-methanol reagent (manufactured by TCI, 18 mL) solution and the mixture was stirred at room temperature for 15 hr. The solvent was concentrated under reduced pressure to give the title compound (1.61 g, yield 100%).

¹H-NMR (DMSO-d₆) δ: 1.06-1.19 (2H, m), 1.39-1.57 (1H, m), 2.13-2.29 (1H, m), 2.40 (3H, s), 2.92 (2H, t, J=5.7 Hz), 6.63 (1H, s), 6.71 (1H, t, J=6.8 Hz), 6.81 (1H, d, J=6.8 Hz), 7.01 (1H, br s), 8.30 (3H, br s), 8.40 (1H, d, J=6.8 Hz).

Reference Example 94

5-bromo-2-methylimidazo[1,2-a]pyridine

6-Bromopyridin-2-amine (25.0 g, 144 mmol) and 1-chloroacetone (20.0 mL, 251 mmol) were dissolved in ethanol (300 mL) and the mixture was heated under reflux for 3 days. The precipitated solid was collected by filtration and dissolved in dichloromethane. The solution was washed with saturated aqueous sodium hydrogen carbonate solution, and dried over anhydrous sodium sulfate, and the solvent was evaporated under reduced pressure to give the title compound (25.0 g, yield 75%).

¹H-NMR (CDCl₃) δ: 2.50 (3H, s), 7.75-7.83 (2H, m), 7.92 (1H, d, J=8.8 Hz), 8.24 (1H, s).

Reference Example 95 ethyl (2E)-3-(2-methylimidazo[1,2-a]pyridin-5-yl)acrylate

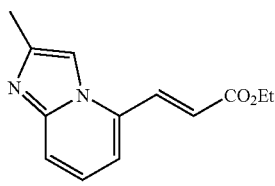

To a solution of 5-bromo-2-methylimidazo[1,2-a]pyridine (5.00 g, 23.7 mmol) in N,N-dimethylacetamide (60 mL) were added sodium acetate trihydrate (3.89 g, 47.4 mmol), ethyl acrylate (3.10 mL, 28.4 mmol) and [1,1'bis(diphenylphosphino)ferrocene]dichloropalladium(II)-dichloromethane complex (1.73 g, 2.37 mmol) at room temperature, and the mixture was stirred under nitrogen stream at 100° C. for 24 hr. Water was added to the reaction solution, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane=20/80) to give the title compound (3.00 g, yield 55%).

¹H-NMR (CDCl₃) δ: 1.38 (3H, t, J=7.6 Hz), 2.50 (3H, s), 4.32 (2H, q, J=7.2 Hz), 6.62 (1H, d, J=16.0 Hz), 7.08 (1H, d,

J=7.2 Hz), 7.18 (1H, t, J=7.2 Hz), 7.58 (1H, d, J=7.2 Hz), 7.61 (1H, s), 7.84 (1H, d, J=16.0 Hz).

Reference Example 96 ethyl 2-(2-methylimidazo[1,2-a]pyridin-5-yl)cyclopropanecarboxylate

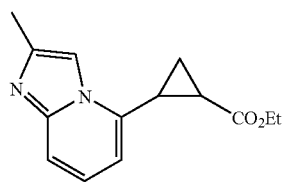

To a suspension of 60% sodium hydride (1.10 g, 25.3 mmol) in dimethyl sulfoxide (50 mL) was added trimethylsulfoxonium iodide (5.56 g, 25.3 mmol) at 0° C., and the mixture was stirred at room temperature for 1 hr. To the reaction mixture was added a solution of ethyl (2E)-3-(2-methylimidazo[1,2-a]pyridin-5-yl)acrylate (4.85 g, 21.1 mmol) in dimethyl sulfoxide (100 mL) at 0° C., and the mixture was stirred at room temperature for 4 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=33/67) to give the title compound (3.40 g, yield 66%).

$^1$H-NMR (CDCl$_3$) δ: 1.34 (3H, t, J=7.6 Hz), 1.40-1.45 (1H, m), 1.68-1.73 (1H, m), 1.94-1.99 (1H, m), 2.50 (3H, s), 2.62-2.67 (1H, m), 4.24-4.30 (2H, m), 6.54 (1H, d, J=7.2 Hz), 7.09 (1H, dd, J=8.8, 6.8 Hz), 7.42 (1H, s), 7.46 (1H, d, J=8.8 Hz).

Reference Example 97

[2-(2-methylimidazo[1,2-a]pyridin-5-yl)cyclopropyl]methanol

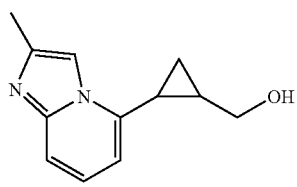

To a solution of ethyl 2-(2-methylimidazo[1,2-a]pyridin-5-yl)cyclopropanecarboxylate (1.60 g, 6.55 mmol) obtained in Reference Example 96 in tetrahydrofuran (10 mL) was added a solution (1 M, 19.7 mL, 19.7 mmol) of diisobutylaluminum hydride in hexane at −78° C., and the mixture was stirred for 20 min. The mixture was warmed to room temperature and further stirred for 1 hr. Water was added to the reaction solution, and the mixture was warmed to 0° C. 1 M aqueous sodium hydroxide solution was added and the mixture was stirred for 10 min. The mixture was acidified with 6 M hydrochloric acid, and the mixture was extracted with ethyl acetate. The extract was washed with saturated brine, and dried over anhydrous sodium sulfate, and the solvent was evaporated under reduced pressure. The obtained crystals were purified by recrystallization (ethyl acetate/hexane) to give the title compound (1.24 g, yield 94%).

$^1$H-NMR (CDCl$_3$) δ: 1.04-1.15 (2H, m), 1.44-1.51 (1H, m), 1.95-2.00 (1H, m), 2.50 (3H, s), 3.62 (1H, dd, J=11.2, 7.6 Hz), 3.97 (1H, dd, J=11.2, 5.6 Hz), 6.52 (1H, t, J=7.2 Hz), 7.08 (1H, dd, J=8.8, 7.2 Hz), 7.42 (1H, d, J=8.8 Hz), 7.72 (1H, s),

MS (ESI+): 203 (M+H).

Reference Example 98

2-{[2-(2-methylimidazo[1,2-a]pyridin-5-yl)cyclopropyl]methyl}-1H-isoindole-1,3(2H)-dione

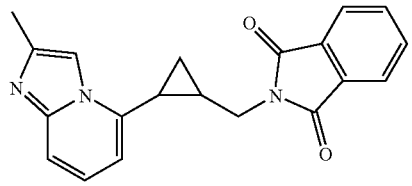

To a solution of [2-(2-methylimidazo[1,2-a]pyridin-5-yl) cyclopropyl]methanol (303 mg, 1.50 mmol) obtained in Reference Example 97, triphenylphosphine (826 mg, 3.15 mmol) and phthalimide (463 mg, 3.15 mmol) in tetrahydrofuran (15 mL) was added a solution (40%, 1.37 mL, 3.00 mmol) of diethyl azodicarboxylate in toluene, and the mixture was stirred at room temperature for 30 min. The solvent was evaporated under reduced pressure. The residue was purified by silica gel column chromatography (ethyl acetate/hexane=50/50→100/0) to give the title compound (461 mg, yield 93%).

$^1$H-NMR (CDCl$_3$) δ: 1.10-1.23 (2H, m), 1.57-1.71 (1H, m), 2.07-2.16 (1H, m), 2.33 (3H, s), 3.80 (1H, dd, J=14.0, 7.7 Hz), 3.94 (1H, dd, J=14.0, 6.0 Hz), 6.42 (1H, d, J=7.0 Hz), 7.03 (1H, dd, J=8.9, 7.0 Hz), 7.37 (1H, d, J=8.9 Hz), 7.42 (1H, s), 7.71-7.80 (2H, m), 7.82-7.95 (2H, m),

MS (ESI+): 332 (M+H).

Reference Example 99

1-[2-(2-methylimidazo[1,2-a]pyridin-5-yl)cyclopropyl]methanamine

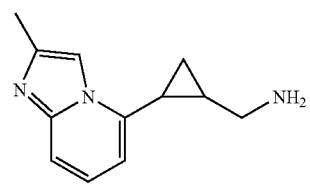

2-{[2-(2-Methylimidazo[1,2-a]pyridin-5-yl)cyclopropyl] methyl}-1H-isoindole-1,3(2H)-dione (230 mg, 0.694 mmol) obtained in Reference Example 98 was dissolved in ethanol (7.0 mL), hydrazine monohydrate (2.0 mL) was added, and the mixture was heated under reflux for 30 min. The solvent was evaporated under reduced pressure. The residue was diluted with ethyl acetate, washed with saturated aqueous sodium hydrogen carbonate solution and saturated brine, and dried over anhydrous sodium sulfate. The solvent was evaporated under reduced pressure to give the title compound (94.2 mg, yield 67%).

$^1$H-NMR (CDCl$_3$) δ: 0.91-1.08 (2H, m), 1.31-1.45 (1H, m), 1.81-1.92 (1H, m), 2.50 (3H, s), 2.78-2.99 (2H, m), 6.51 (1H, d, J=7.0 Hz), 7.08 (1H, dd, J=9.1, 7.0 Hz), 7.41 (1H, d, J=9.1 Hz), 7.60 (1H, s), hidden (2H),

MS (ESI+): 202 (M+H).

Reference Example 100

5-bromo-2-(trifluoromethyl)imidazo[1,2-a]pyridine

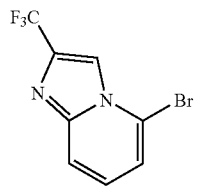

6-Bromopyridin-2-amine (20.0 g, 116 mmol) and 3-bromo-1,1,1-trifluoroacetone (24.0 mL, 231 mmol) were dissolved in ethanol (200 mL), and the mixture was heated under reflux for 4 days. The precipitated solid was collected by filtration and dissolved in dichloromethane. The solution was washed with saturated aqueous sodium hydrogen carbonate solution, and dried over anhydrous sodium sulfate, and the solvent was evaporated under reduced pressure to give the title compound (26.0 g, yield 85%).

$^1$H-NMR (CDCl$_3$) δ: 7.18 (1H, dd, J=7.2, 0.8 Hz), 7.25 (1H, dd, J=8.8, 7.2 Hz), 7.70 (1H, d, J=9.2 Hz), 8.12 (1H, s).

Reference Example 101 ethyl (2E)-3-[2-(trifluoromethyl)imidazo[1,2-a]pyridin-5-yl]acrylate

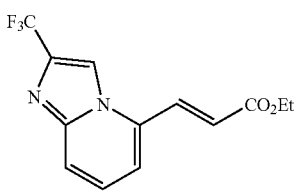

To a solution of 5-bromo-2-(trifluoromethyl)imidazo[1,2-a]pyridine (10.0 g, 37.7 mmol) in N,N-dimethylacetamide (60 mL) were added sodium acetate trihydrate (6.19 g, 75.0 mmol), ethyl acrylate (4.94 mL, 45.3 mmol) and [1,1'bis(diphenylphosphino)ferrocene]dichloropalladium(II)-dichloromethane complex (2.76 g, 3.77 mmol) at room temperature, and the mixture was stirred under nitrogen stream at 110° C. for 24 hr. Water was added to the reaction solution, and the mixture was extracted with ethyl acetate, washed with saturated brine, and dried over anhydrous sodium sulfate. The solvent was evaporated under reduced pressure. The residue was purified by silica gel column chromatography (ethyl acetate/hexane=20/80) to give the title compound (6.74 g, yield 63%).

$^1$H-NMR (CDCl$_3$) δ: 1.39 (3H, t, J=7.2 Hz), 4.34 (2H, q, J=7.2 Hz), 6.68 (1H, d, J=16.0 Hz), 7.24 (1H, d, J=6.8 Hz), 7.37 (1H, dd, J=9.2, 7.2 Hz), 7.76 (1H, d, J=9.2 Hz), 7.84 (1H, d, J=16.0 Hz), 8.13 (1H, s).

Reference Example 102 ethyl 2-[2-(trifluoromethyl)imidazo[1,2-a]pyridin-5-yl]cyclopropanecarboxylate

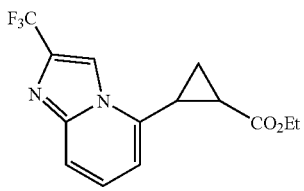

To a suspension of 60% sodium hydride (1.24, 28.5 mmol) in dimethyl sulfoxide (50 mL) was added trimethylsulfoxonium iodide (6.26 g, 28.5 mmol) at 0° C., and the mixture was stirred at room temperature for 1 hr. To the reaction mixture was added a solution of ethyl (2E)-3-[2-(trifluoromethyl)imidazo[1,2-a]pyridin-5-yl]acrylate (6.74 g, 23.7 mmol) in dimethyl sulfoxide (100 mL) at 0° C., and the mixture was stirred at room temperature for 4 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=33/67) to give the title compound (3.40 g, yield 48%).

$^1$H-NMR (CDCl$_3$) δ: 1.35 (3H, t, J=7.2 Hz), 1.42-1.47 (1H, m), 1.76-1.81 (1H, m), 2.01-2.05 (1H, m), 2.66-2.71 (1H, m), 4.26-4.34 (2H, m), 6.73 (1H, d, J=6.8 Hz), 7.28 (1H, dd, J=9.2, 6.8 Hz), 7.63 (1H, d, J=9.2 Hz), 7.99 (1H, s).

Reference Example 103

{2-[2-(trifluoromethyl)imidazo[1,2-a]pyridin-5-yl]cyclopropyl}methanol

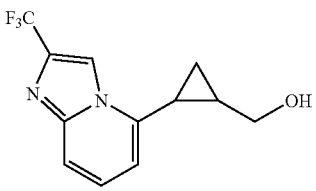

To a solution of ethyl 2-[2-(trifluoromethyl)imidazo[1,2-a]pyridin-5-yl]cyclopropanecarboxylate (2.89 g, 9.69 mmol) obtained in Reference Example 102 in tetrahydrofuran (50 mL) was added a solution (1 M, 29.1 mL, 29.1 mmol) of diisobutylaluminum hydride in hexane at −78° C., and the mixture was stirred for 20 min. The mixture was warmed to room temperature and further stirred for 1 hr. Water was added to the reaction solution, and the mixture was warmed to 0° C. 1 M aqueous sodium hydroxide solution was added and the mixture was stirred for 10 min. The mixture was acidified with 6 M hydrochloric acid, and the mixture was extracted with ethyl acetate. The extract was washed with saturated brine, and dried over anhydrous sodium sulfate, and the solvent was evaporated under reduced pressure. The obtained crystals were purified by recrystallization (ethyl acetate/hexane) to give the title compound (2.40 g, yield 97%).

$^1$H-NMR (CDCl$_3$) δ: 1.11-1.22 (2H, m), 1.44-1.52 (1H, m), 2.02-2.12 (2H, m), 3.47-3.53 (1H, m), 4.08-4.14 (1H, m), 6.70 (1H, d, J=6.8 Hz), 7.26 (1H, dd, J=9.2, 7.2 Hz), 7.58 (1H, d, J=9.2 Hz), 8.49 (1H, s).

Reference Example 104

2-methyl[1,2,4]triazolo[1,5-a]pyridine

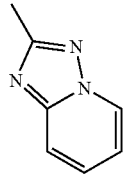

To a solution of 1-aminopyridinium iodide (139 g, 626 mmol) in acetonitrile (1.25 L) was added 10% aqueous sodium hydroxide solution (751 mL, 1.88 mmol), and the mixture was stirred at room temperature for 12 hr. Half of the reaction mixture was evaporated under reduced pressure, and the residue was extracted with dichloromethane. The extract was dried over anhydrous sodium sulfate and the solvent was evaporated under reduced pressure to give the title compound (47.0 g, yield 56%)

$^1$H-NMR (CDCl$_3$) δ: 2.61 (3H, s), 6.89-6.94 (1H, m), 7.49-7.45 (1H, m), 7.64 (1H, dd, J=8.8, 1.2 Hz), 8.51-8.49 (1H, m).

Reference Example 105

5-iodo-2-methyl[1,2,4]triazolo[1,5-a]pyridine

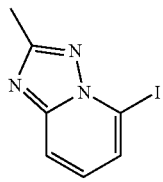

To a solution of 2-methyl[1,2,4]triazolo[1,5-a]pyridine (63.2 g, 475 mmol) in tetrahydrofuran (1.37 L) was added dropwise 2.5 M n-butyllithium/hexane solution (5.62 mL, 8.99 mmol) at −78° C. and the mixture was stirred at −78° C. for 30 min. A solution of iodine (181 g, 712 mmol) in tetrahydrofuran (1.00 L) was added, and the mixture was stirred at −78° C. for 30 min, and at room temperature for 1 hr. Water (500 mL) was added to the reaction solution, and the mixture was extracted with ethyl acetate. The extract was dried over anhydrous sodium sulfate and the solvent was evaporated under reduced pressure. The residue was purified by silica gel column chromatography (ethyl acetate/hexane=1/2) to give the title compound (45.0 g, yield 37%).

$^1$H-NMR (CDCl$_3$) δ: 2.65 (3H, s), 7.21 (1H, dd, J=8.8, 7.2 Hz), 7.45 (1H, dd, J=7.2, 0.8 Hz), 7.61 (1H, dd, J=8.8, 0.8 Hz).

Reference Example 106

(2-methyl[1,2,4]triazolo[1,5-a]pyridin-5-yl)methanol

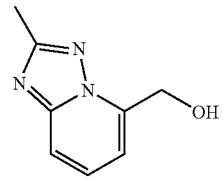

To a solution of 5-iodo-2-methyl[1,2,4]triazolo[1,5-a]pyridine (13.5 g, 52.1 mmol) in methanol (521 mL) were added palladium acetate (1.17 g, 5.21 mmol), potassium carbonate (21.6 g, 156 mmol) and 1,1'-bis(diphenylphosphino)ferrocene (2.15 g, 5.21 mmol), and the mixture was stirred under carbon monoxide atmosphere at 2 atm at room temperature for 1 hr. The mixture was warmed to 50° C. and stirred for 12 hr. The reaction mixture was filtered through celite. The solvent was evaporated under reduced pressure. The residue was dissolved in water (300 mL), washed with chloroform, and 2 M hydrochloric acid was added to adjust the solution to pH 2. The aqueous layer was evaporated under reduced pressure, the residue was dissolved in methanol, and insoluble material was filtered off. The solvent was evaporated under reduced pressure to give 2-methyl[1,2,4]triazolo[1,5-a]pyridine-5-carboxylic acid as a crudely purified product.

$^1$H-NMR (DMSO-d$_6$) δ: 2.46 (3H, s), 7.08 (1H, dd, J=6.8, 1.6 Hz), 7.51-7.59 (2H, m), hidden (1H).

The obtained crudely purified product of 2-methyl[1,2,4]triazolo[1,5-a]pyridine-5-carboxylic acid was dissolved in methanol (353 mL), and thionyl chloride (10.3 mL, 141 mmol) was added at 0° C. The reaction mixture was heated under reflux for 12 hr. The solvent was evaporated under reduced pressure to give methyl 2-methyl[1,2,4]triazolo[1,5-a]pyridine-5-carboxylate as a crudely purified product.

$^1$H-NMR (CDCl$_3$) δ: 2.53 (3H, s), 3.98 (3H, s), 7.72-7.76 (2H, m), 7.98-8.02 (1H, m).

The obtained crudely purified product of methyl 2-methyl[1,2,4]triazolo[1,5-a]pyridine-5-carboxylate was dissolved in ethanol (157 mL), sodium borohydride (5.34 g, 141 mmol) was added at 0° C., and the mixture was stirred at room temperature for 12 hr. Water (200 mL) was added to the reaction solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=5/1) to give the title compound (3.00 g, yield 39%).

$^1$H-NMR (CDCl$_3$) δ: 2.62 (3H, s), 5.50 (2H, d, J=6.0 Hz), 6.96 (1H, d, J=6.8 Hz), 7.48 (1H, dd, J=8.8, 6.8 Hz), 7.60 (1H, dd, J=8.8, 1.2 Hz), hidden (1H).

Reference Example 107

2-methyl[1,2,4]triazolo[1,5-a]pyridine-5-carbaldehyde

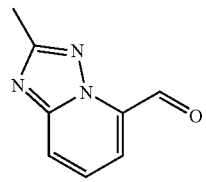

To a solution of dimethyl sulfoxide (7.83 mL, 110 mmol) in dichloromethane (100 mL) was added oxalyl chloride (4.83 mL, 55.2 mmol) at −78° C., and the mixture was stirred for 30 min. To the reaction mixture was added a solution of (2-methyl[1,2,4]triazolo[1,5-a]pyridin-5-yl)methanol (3.00 g, 18.4 mmol) in dichloromethane (84.0 mL), and the mixture was stirred for 2 hr. To the reaction mixture was added triethylamine (22.3 mL, 165 mmol) at −78° C., and the mixture was stirred for 1 hr. The reaction mixture was concentrated under reduced pressure, and the residue was purified by silica gel column chromatography (ethyl acetate/hexane=1/3) to give the title compound (2.80 g, yield 95%).

$^1$H-NMR (CDCl$_3$) δ: 2.68 (3H, s), 7.58-7.65 (2H, m), 7.91 (1H, dd, J=8.2, 1.8 Hz), 10.78 (1H, s).

Reference Example 108 ethyl (2E)-3-(2-methyl[1,2,4]triazolo[1,5-a]pyridin-5-yl)acrylate

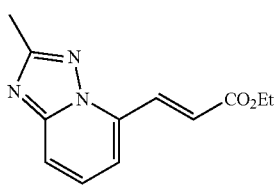

To a suspension of sodium hydride (0.570 g, 13.0 mmol) in tetrahydrofuran (50 mL) was added a solution of ethyl diethylphosphonoacetate (2.36 mL, 11.8 mmol) in tetrahydrofuran (10 mL) at 0° C., and the mixture was stirred for 20 min. To the reaction mixture was added a solution of 2-methyl[1,2,4]triazolo[1,5-a]pyridine-5-carbaldehyde (1.90 g, 11.8 mmol) in tetrahydrofuran (58 mL), and the mixture was warmed to room temperature over 4 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/2) to give the title compound (2.50 g, yield 92%).

$^1$H-NMR (CDCl$_3$) δ: 1.38 (3H, t, J=7.2 Hz), 2.66 (3H, s), 4.33 (2H, q, J=7.2 Hz), 7.19 (1H, d, J=7.6 Hz), 7.51 (1H, dd, J=8.8, 7.6 Hz), 7.54 (1H, d, J=16.0 Hz), 7.69 (1H, d, J=8.8 Hz), 7.95 (1H, d, J=16.0 Hz).

Reference Example 109 ethyl 2-(2-methyl[1,2,4]triazolo[1,5-a]pyridin-5-yl)cyclopropanecarboxylate

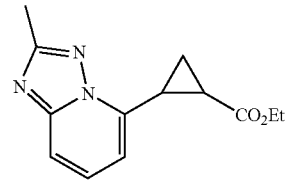

To a suspension of sodium hydride (0.950 g, 24.8 mmol) in dimethyl sulfoxide (82 mL) was added a solution of trimethylsulfoxonium iodide (4.77 g, 21.8 mmol) in dimethyl sulfoxide (35 mL) at 0° C., and the mixture was stirred at room temperature for 1 hr. To the reaction mixture was added a solution of ethyl (2E)-3-(2-methyl[1,2,4]triazolo[1,5-a]pyridin-5-yl)acrylate (4.20 g, 18.2 mmol) in dimethyl sulfoxide (100 mL) at 0° C., and the mixture was stirred at room temperature for 14 hr. Water was added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/2) to give the title compound (1.80 g, yield 40%).

$^1$H-NMR (CDCl$_3$) δ: 1.31 (3H, t, J=6.8 Hz), 1.59-1.64 (1H, m), 1.77-1.82 (1H, m), 2.26-2.34 (1H, m), 2.62 (3H, s), 3.16-3.21 (1H, m), 4.20-4.26 (2H, m), 6.61 (1H, d, J=7.6 Hz), 7.38 (1H, dd, J=8.8, 7.6 Hz), 7.52 (1H, d, J=8.8 Hz).

Reference Example 110

[2-(2-methyl[1,2,4]triazolo[1,5-a]pyridin-5-yl)cyclopropyl]methanol

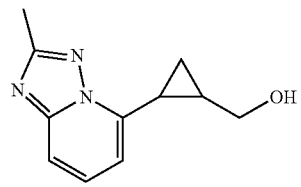

To a solution of ethyl 2-(2-methyl[1,2,4]triazolo[1,5-a]pyridin-5-yl)cyclopropanecarboxylate (4.40 g, 17.9 mmol) obtained in Reference Example 109 in tetrahydrofuran (179 mL) was added lithium aluminum hydride (0.61 g, 17.9 mmol) at 0° C., and the mixture was stirred for 1 hr. To the reaction mixture were added water and 10% aqueous sodium hydroxide solution, and the mixture was extracted with ethyl acetate. The extract was washed with saturated brine, and dried over anhydrous sodium sulfate, and the solvent was evaporated under reduced pressure. The residue was purified by recrystallization (ethyl acetate/hexane) to give the title compound (2.60 g, yield 71%).

¹H-NMR (CDCl₃) δ: 1.17-1.21 (1H, m), 1.31-1.42 (2H, m), 2.20-2.24 (1H, m), 2.63 (3H, s), 3.23 (1H, t, J=10.0 Hz), 4.10-4.16 (1H, m), 4.22 (1H, d, J=8.8 Hz), 6.61 (1H, d, J=7.2 Hz), 7.43 (1H, dd, J=9.2, 7.2 Hz), 7.55 (1H, d, J=9.2 Hz),

MS (ESI+): 204 (M+H).

Reference Example 111

2-(2-methyl[1,2,4]triazolo[1,5-a]pyridin-5-yl)cyclopropanecarbaldehyde

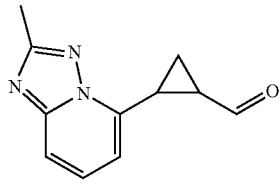

[2-(2-Methyl[1,2,4]triazolo[1,5-a]pyridin-5-yl)cyclopropyl]methanol (500 mg, 2.47 mmol) obtained in Reference Example 110, 4 Å molecular sieves (200 mg), 4-methylmorpholine N-oxide (721 mg, 6.15 mmol) and tetra-n-propylammonium perruthenate(VII) (43.2 mg, 0.123 mmol) were dissolved in acetonitrile (25 mL), and the mixture was stirred at room temperature for 1 hr. 2-Propanol was added, and the mixture was stirred for 10 min. The solvent was evaporated under reduced pressure, and the residue was purified by silica gel column chromatography (methanol/ethyl acetate=0/100→10/90) to give the title compound (257 mg, yield 52%).

¹H-NMR (CDCl₃) δ: 1.76-1.95 (2H, m), 2.39-2.52 (1H, m), 2.61 (3H, s), 3.21-3.33 (1H, m), 6.64 (1H, d, J=7.1 Hz), 7.35-7.44 (1H, m), 7.55 (1H, dd, J=8.9, 1.2 Hz), 7.93 (1H, s), 9.44 (1H, d, J=4.4 Hz).

Reference Example 112

2-(2-methyl[1,2,4]triazolo[1,5-a]pyridin-5-yl)cyclopropanecarbaldehyde oxime

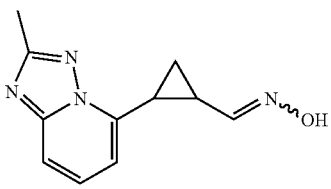

2-(2-Methyl[1,2,4]triazolo[1,5-a]pyridin-5-yl)cyclopropanecarbaldehyde (236 mg, 1.17 mmol) obtained in Reference Example 111, 8 M aqueous sodium hydroxide solution (590 μL, 4.69 mmol) and hydroxylamine hydrochloride (269 mg, 3.87 mmol) were dissolved in ethanol/water (10 mL/2 mL), and the mixture was stirred at 60° C. for 18 hr. The reaction solution was concentrated, and the mixture was extracted with ethyl acetate. The extract was washed with saturated brine, dried over anhydrous magnesium sulfate and the solvent was evaporated under reduced pressure to give the title compound (210 mg, yield 83%).

MS (ESI+): 217 (M+H).

Reference Example 113

1-[2-(2-methyl[1,2,4]triazolo[1,5-a]pyridin-5-yl)cyclopropyl]methanamine

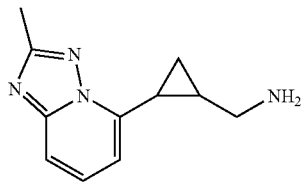

To a solution of [2-(2-methyl[1,2,4]triazolo[1,5-a]pyridin-5-yl)cyclopropyl]methanol (500 mg, 2.46 mmol) obtained in Reference Example 110 in tetrahydrofuran (25 mL) were added diethyl azodicarboxylate (40%, 1.34 mL, 2.95 mmol), triphenylphosphine (840 mg, 3.20 mmol) and phthalimide (471 mg, 3.20 mmol), and the mixture was stirred under nitrogen atmosphere at room temperature for 18 hr. The solvent was evaporated under reduced pressure, and the residue was purified by silica gel column chromatography (ethyl acetate/hexane=50/50→90/10) to give 2-{[2-(2-methyl[1,2,4]triazolo[1,5-a]pyridin-5-yl)cyclopropyl]methyl}-1H-isoindole-1,3(2H)-dione as a crudely purified product. The obtained crudely purified product of 2-{[2-(2-methyl[1,2,4]triazolo[1,5-a]pyridin-5-yl)cyclopropyl]methyl}-1H-isoindole-1,3(2H)-dione was dissolved in ethanol (4 mL), hydrazine monohydrate (1.6 mL) was added, and the mixture was heated under reflux for 20 min. The solvent was evaporated under reduced pressure, and saturated aqueous sodium hydrogen carbonate solution was added. The aqueous layer was extracted with ethyl acetate, the organic layer was dried over anhydrous sodium sulfate, and the solvent was evaporated under reduced pressure. The residue was purified by silica gel column chromatography (NH, methanol/ethyl acetate=0/100→10/90) to give the title compound (135 mg, yield 27%).

¹H-NMR (CDCl₃) δ: 1.10-1.30 (1H, m), 1.18-1.29 (1H, m), 1.33-1.40 (1H, m), 2.11 (2H, br s), 2.41-2.50 (1H, m), 2.60-2.67 (4H, m), 3.02 (1H, dd, J=12.9, 5.2 Hz), 6.52 (1H, d, J=7.1 Hz), 7.32-7.42 (1H, m), 7.43-7.53 (1H, m).

Reference Example 114 methyl 2-(acetylamino)-3-nitrobenzoate

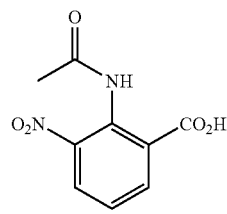

A solution of methyl anthranilate (21.0 mL, 162 mmol) in acetic anhydride (170 mL) was stirred at room temperature for 1 hr. To the reaction mixture was added dropwise a mixture of acetic anhydride (35 mL), acetic acid (30 mL) and 60% nitric acid (50 ml, 162 mmol) at 10-15° C. over 2 hr. The reaction mixture was stirred at 10-15° C. for 2.5 hr, and poured into ice-cold water. The resulting solid was collected by filtration, washed with water, and after recrystallization (chloroform/methanol), the crystals were collected by filtration. The filtrate was extracted with methylene chloride, and dried over anhydrous sodium sulfate, and the solvent was evaporated under reduced pressure. The residue was crystallized from ether to give the title compound (20.0 g, yield 52%).

$^1$H-NMR (CDCl$_3$) δ: 2.24 (3H, s), 3.97 (3H, s), 7.31 (1H, t, J=8.0 Hz), 8.90 (1H, d, J=8.4 Hz), 8.21 (1H, d, J=8.0 Hz), 10.34 (1H, br s).

Reference Example 115

2-iodo-3-nitrobenzoic acid

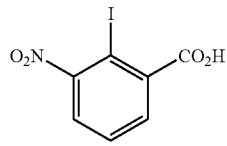

A mixture of methyl 2-(acetylamino)-3-nitrobenzoate (4.19 g, 17.6 mmol) and potassium hydroxide (4.93 g, 88.0 mmol) in water (20 mL) was stirred at 60° C. overnight. The resulting solid was collected by filtration, washed with methanol, and is suspended in water (14 mL). Concentrated hydrochloric acid (7.3 mL, 88 mmol) was added to the suspension, and a solution of sodium nitrite (1.88 g, 27.3 mmol) in water (10 mL) was added at 0° C. over 1.5 hr. The reaction mixture was added to a solution of potassium iodide (4.53 g, 27.3 mmol) and iodine (3.73 g, 14.7 mmol) in dimethyl sulfoxide (130 mL) at 5° C. over 20 min. The resulting reaction mixture was stirred at 50° C. for 20 min, and extracted with ethyl acetate. The extract was washed with water, and dried over anhydrous sodium sulfate, and the solvent was evaporated under reduced pressure. The residue was washed with hexane to give the title compound (3.71 g, yield 72%).

$^1$H-NMR (CDCl$_3$) δ: 7.56 (1H, t, J=8.0 Hz), 7.69 (1H, dd, J=8.0, 1.2 Hz), 7.93 (1H, dd, J=8.0, 1.2 Hz).

Reference Example 116 methyl 2-iodo-3-nitrobenzoate

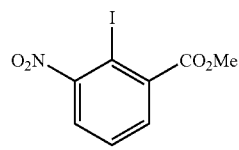

A mixture of 2-iodo-3-nitrobenzoic acid (31.0 g, 106 mmol) and concentrated sulfuric acid (24.9 mL, 317 mmol) in methanol (600 mL) was heated under reflux for 12 hr. The solvent was evaporated under reduced pressure and the residue was extracted with methylene chloride. The extract was washed with saturated aqueous sodium hydrogen carbonate solution and water, and dried over anhydrous sodium sulfate, and the solvent was evaporated under reduced pressure. The residue was purified by recrystallization (chloroform/hexane) to give the title compound (31.0 g, yield 95%).

$^1$H-NMR (DMSO-d$_6$) δ: 3.90 (3H, s), 7.70 (1H, t, J=7.6 Hz), 7.82 (1H, dd, J=7.6, 1.2 Hz), 7.98 (1H, dd, J=7.6, 1.2 Hz).

Reference Example 117 methyl 3-amino-2-iodobenzoate

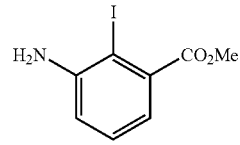

A mixture of methyl 2-iodo-3-nitrobenzoate (77.0 g, 251 mmol) and a catalytic amount of Raney nickel in ethyl acetate (100 mL) was stirred under hydrogen atmosphere at room temperature for 2 days, and filtered through celite. The solvent was evaporated under reduced pressure. The residue was purified by silica gel column chromatography (ethyl acetate/hexane=1/10) to give the title compound (60.0 g, yield 86%).

$^1$H-NMR (DMSO-d$_6$) δ: 3.81 (3H, s), 5.52 (2H, br s), 6.71 (1H, dd, J=7.2, 1.6 Hz), 6.87 (1H, dd, J=8.0, 1.6 Hz), 7.13 (1H, t, J=8.0 Hz).

Reference Example 118 methyl 3-(acetylamino)-2-iodobenzoate

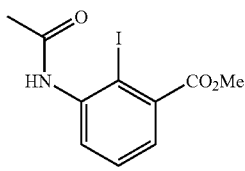

To a solution of methyl 3-amino-2-iodobenzoate (70.0 g, 253 mmol) in methylene chloride (1000 mL) was added triethylamine (52.8 mL, 379 mmol) and the mixture was stirred at 0° C. for 30 min. To the reaction mixture was added acetyl chloride (35.9 mL, 505 mmol) at 0° C. and the mixture was stirred at room temperature for 4 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/10) to give the title compound (76.6 g, yield 95%).

$^1$H-NMR (CDCl$_3$) δ: 2.27 (3H, s), 3.94 (3H, s), 7.38 (1H, t, J=8.0 Hz), 7.46 (1H, dd, J=8.0, 1.2 Hz), 7.79 (1H, br s), 8.33 (1H, d, J=6.8 Hz).

Reference Example 119 methyl 3-(ethanethioylamino)-2-iodobenzoate

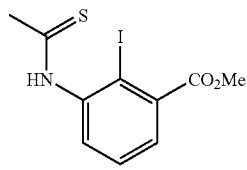

To a solution of methyl 3-(acetylamino)-2-iodobenzoate (77.0 g, 240 mmol) in tetrahydrofuran (500 mL) was added Lawesson's reagent (90.0 g, 223 mmol) at room temperature, and the mixture was heated under reflux for 4 hr and filtered through celite. The solvent was evaporated under reduced pressure. The residue was purified by silica gel column chromatography (ethyl acetate/hexane=1/2) to give the title compound (60.0 g, purity 65%) as a crude product.

$^1$H-NMR (CDCl$_3$) δ: 2.82 (3H, s), 3.95 (3H, s), 7.45 (1H, t, J=7.6 Hz), 7.66 (1H, d, J=6.4 Hz), 8.22 (1H, d, J=7.6 Hz), 8.67 (1H, br s).

Reference Example 120 methyl 2-methyl-1,3-benzothiazole-7-carboxylate

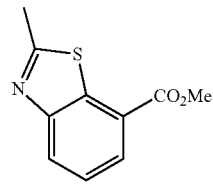

Under nitrogen atmosphere, a mixture of methyl 3-(ethanethioylamino)-2-iodobenzoate (6.00 g, 11.6 mmol) obtained in Reference Example 119, copper(I) iodide (0.110 g, 0.580 mmol), 1,10-phenanthroline (0.210 g, 1.16 mmol) and potassium t-butoxide (1.96 g, 17.5 mmol) in 1,2-dimethoxyethane (50 mL) was heated under reflux for 24 hr, and filtered through celite. The solvent was evaporated under reduced pressure. The residue was purified by silica gel column chromatography (ethyl acetate/hexane=1/2) to give the title compound (1.80 g, yield 75%).

$^1$H-NMR (CDCl$_3$) δ: 2.87 (3H, s), 4.02 (3H, s), 7.54 (1H, t, J=7.6 Hz), 8.09 (1H, dd, J=7.6, 1.2 Hz), 8.14 (1H, dd, J=8.0, 1.2 Hz).

Reference Example 121

(2-methyl-1,3-benzothiazol-7-yl)methanol

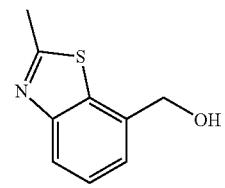

Under nitrogen atmosphere, to a solution of methyl 2-methyl-1,3-benzothiazole-7-carboxylate (6.00 g, 29.0 mmol) in tetrahydrofuran (150 mL) was added lithium aluminum hydride (1.18 g, 34.7 mmol) at 0° C., and the mixture was stirred at room temperature for 1 hr. The reaction mixture was diluted with ethyl acetate and water, 1 M aqueous sodium hydroxide solution (10 mL) and 2 M hydrochloric acid (10 mL) were added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/1) to give the title compound (4.78 g, yield 92%).

$^1$H-NMR (CDCl$_3$) δ: 2.86 (3H, s), 4.92 (2H, s), 7.33 (1H, d, J=7.2 Hz), 7.45 (1H, t, J=8.0 Hz), 7.90 (1H, d, J=8.4 Hz).

Reference Example 122

2-methyl-1,3-benzothiazole-7-carbaldehyde

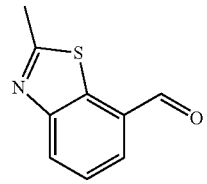

Under nitrogen atmosphere, to a solution of oxalyl chloride (3.78 mL, 44.6 mmol) in dichloromethane (20 mL) was added dimethyl sulfoxide (4.75 mL, 66.9 mmol) at −78° C. and the mixture was stirred for 30 min. To the reaction mixture was added (2-methyl-1,3-benzothiazol-7-yl)methanol (4.00 g, 22.3 mmol) at −78° C. and the mixture was stirred for 2 hr. To the reaction mixture was added triethylamine (18.8 mL, 134 mmol) at −78° C. and the mixture was stirred for 30 min. The reaction mixture was warmed to room temperature, and the mixture was further stirred at room temperature for 4 hr. Saturated aqueous ammonium chloride solution was added and the mixture was extracted with dichloromethane. The extract was washed with saturated brine, and dried over anhydrous sodium sulfate, and the solvent was evaporated under reduced pressure. The residue was purified by recrystallization (dichloromethane/hexane) to give the title compound (3.54 g, yield 90%).

$^1$H-NMR (CDCl$_3$) δ: 2.91 (3H, s), 7.67 (1H, t, J=8.0 Hz), 7.90 (1H, d, J=7.6 Hz), 8.23 (1H, d, J=8.0 Hz), 10.20 (1H, s).

Reference Example 123 ethyl(2E)-3-(2-methyl-1,3-benzothiazol-7-yl)acrylate

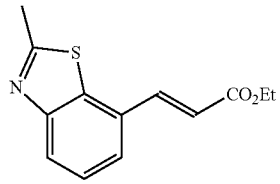

Under nitrogen atmosphere, to a suspension of 60% sodium hydride (1.26 g, 31.5 mmol) in tetrahydrofuran (50 mL) was added a solution of ethyl diethylphosphonoacetate (7.06 g, 31.5 mmol) in tetrahydrofuran (50 mL) at 0° C. and the mixture was stirred for 20 min. To the reaction mixture was added a solution of 2-methyl-1,3-benzothiazole-7-carbaldehyde (4.60 g, 26.0 mmol) in tetrahydrofuran (100 mL), and the mixture was warmed to room temperature over 2 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/1) to give the title compound (6.50 g, yield 98%).

$^1$H-NMR (CDCl$_3$) δ: 1.37 (3H, t, J=6.8 Hz), 2.89 (3H, s), 4.31 (2H, q, J=6.8 Hz), 6.55 (1H, d, J=16.4 Hz), 7.50 (1H, t, J=7.6 Hz), 7.54 (1H, d, J=6.4 Hz), 7.86 (1H, d, J=16.4 Hz), 7.99 (1H, d, J=7.6 Hz).

Reference Example 124 ethyl 2-(2-methyl-1,3-benzothiazol-7-yl)cyclopropanecarboxylate

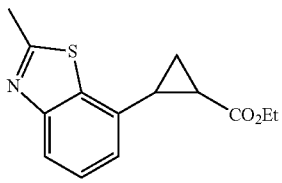

To a suspension of 60% sodium hydride (0.600 g, 15.6 mmol) in dimethyl sulfoxide (10 mL) was added a solution of trimethylsulfoxonium iodide (3.44 g, 15.6 mmol) in dimethyl sulfoxide (35 mL) at 0° C., and the mixture was stirred at room temperature for 1 hr. To the reaction mixture was added a solution of ethyl (2E)-3-(2-methyl-1,3-benzothiazol-7-yl)acrylate (1.60 g, 6.47 mmol) in dimethyl sulfoxide (30 mL) at 0° C., and the mixture was stirred at room temperature for 6 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/2) to give the title compound (3.62 g, yield 69%).

$^1$H-NMR (CDCl$_3$) δ: 1.32 (3H, t, J=7.2 Hz), 1.41-1.46 (1H, m), 1.64-1.69 (1H, m), 1.99-2.03 (1H, m), 2.64-2.71 (1H, m), 2.85 (3H, s), 4.23 (2H, q, J=7.2 Hz), 7.03 (1H, d, J=7.6 Hz), 7.38 (1H, t, J=7.6 Hz), 7.82 (1H, d, J=8.0 Hz).

Reference Example 125

[2-(2-methyl-1,3-benzothiazol-7-yl)cyclopropyl]methanol

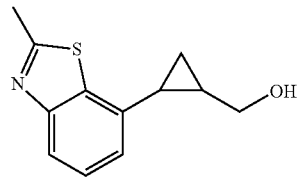

Under nitrogen atmosphere, to a solution of ethyl 2-(2-methyl-1,3-benzothiazol-7-yl)cyclopropanecarboxylate (3.60 g, 13.8 mmol) obtained in Reference Example 124 in tetrahydrofuran (100 mL) was added lithium aluminum hydride (0.56 g, 16.5 mmol) at 0° C., and the mixture was stirred at room temperature for 1 hr. The reaction mixture was diluted with ethyl acetate and water, 1 M aqueous sodium hydroxide solution (5 mL) and 2 M hydrochloric acid (10 mL) were added, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/1) to give the title compound (2.65 g, yield 88%).

$^1$H-NMR (CDCl$_3$) δ: 0.99-1.04 (1H, m), 1.12-1.17 (1H, m), 1.50-1.58 (2H, m), 1.96-2.01 (1H, m), 2.85 (3H, s), 3.66-3.77 (2H, m), 7.01 (1H, d, J=7.6 Hz), 7.37 (1H, t, J=7.6 Hz), 7.79 (1H, d, J=8.4 Hz).

MS (ESI+): 220 (M+H).

Reference Example 126

2-(2-methyl-1,3-benzothiazol-7-yl)cyclopropanecarbaldehyde

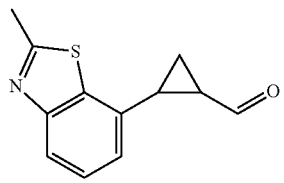

[2-(2-Methyl-1,3-benzothiazol-7-yl)cyclopropyl]methanol (1000 mg, 4.56 mmol) obtained in Reference Example 125, 4 Å molecular sieves (400 mg), 4-methylmorpholine N-oxide (1340 mg, 11.4 mmol) and tetra-n-propylammonium perruthenate(VII) (80.1 mg, 0.228 mmol) were dissolved in acetonitrile (45 mL), and the mixture was stirred at room temperature for 40 min. 2-Propanol was added, and the mixture was stirred for 30 min and filtered by silica gel column chromatography (ethyl acetate). The solvent was evaporated under reduced pressure. The residue was purified by silica gel column chromatography (ethyl acetate/hexane=20/80→50/50) to give the title compound (620 mg, yield 63%).

$^1$H-NMR (CDCl$_3$) δ: 1.62-1.72 (1H, m), 1.75-1.86 (1H, m), 2.20-2.32 (1H, m), 2.72-2.84 (1H, m), 2.85 (3H, s), 7.06 (1H, d, J=8.0 Hz), 7.39 (1H, t, J=8.0 Hz), 7.84 (1H, d, J=8.0 Hz), 9.46 (1H, d, J=4.4 Hz),

MS (ESI+): 218 (M+H).

Reference Example 127

2-{[2-(2-methyl-1,3-benzothiazol-7-yl)cyclopropyl]methyl}-1H-isoindole-1,3(2H)-dione

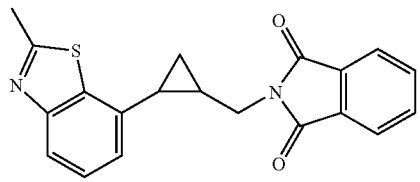

To a solution of [2-(2-methyl-1,3-benzothiazol-7-yl)cyclopropyl]methanol (800 mg, 3.65 mmol) obtained in Reference Example 125 in tetrahydrofuran (40 mL) were added a solution (40%, 1.97 mL, 4.38 mmol) of diethyl azodicarboxylate in toluene, triphenylphosphine (1240 mg, 4.74 mmol) and phthalimide (697 mg, 4.74 mmol), and the mixture was stirred under nitrogen atmosphere at room temperature for 23 hr. The solvent was evaporated under reduced pressure, and the residue was purified by silica gel column chromatography (NH, ethyl acetate/hexane=10/90→45/55) to give the title compound (948 mg, yield 75%).

$^1$H-NMR (CDCl$_3$) δ: 1.08-1.21 (2H, m), 1.60-1.73 (1H, m), 2.11-2.25 (1H, m), 2.71 (3H, s), 3.63-3.77 (2H, m), 3.82-3.94 (1H, m), 6.93 (1H, d, J=7.2 Hz), 7.31 (1H, t, J=7.2 Hz), 7.66-7.80 (3H, m), 7.82-7.94 (2H, m), melting point: 151-153° C. (recrystallized from ethyl acetate/hexane),

MS (ESI+): 349 (M+H), elemental analysis: for C$_{20}$H$_{16}$N$_2$O$_2$S

Calculated (%): C, 68.95; H, 4.63; N, 8.04

Found (%): C, 68.80; H, 4.61; N, 7.98.

Reference Example 128

1-[2-(2-methyl-1,3-benzothiazol-7-yl)cyclopropyl]methanamine

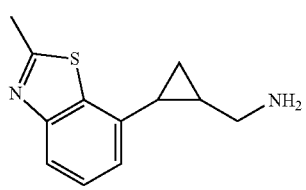

To a solution of 2-{[2-(2-methyl-1,3-benzothiazol-7-yl)cyclopropyl]methyl}-1H-isoindole-1,3(2H)-dione (333 mg, 0.96 mmol) obtained in Reference Example 127 in ethanol (10 mL) was added hydrazine monohydrate (4 mL), and the mixture was heated under reflux for 20 min. The solvent was evaporated under reduced pressure. The residue was diluted with ethyl acetate, and saturated aqueous sodium hydrogen carbonate solution was added. The aqueous layer was extracted with ethyl acetate, and dried over anhydrous sodium sulfate, and the solvent was evaporated under reduced pressure. The residue was purified by silica gel column chromatography (NH, methanol/ethyl acetate=0/100→10/90) to give the title compound (142 mg, yield 68%).

$^1$H-NMR (CDCl$_3$) δ: 0.87-0.99 (1H, m), 1.03-1.16 (1H, m), 1.29-1.57 (3H, m), 1.81-1.93 (1H, m), 2.80 (2H, d, J=6.4 Hz), 2.85 (3H, s), 6.99 (1H, d, J=7.2 Hz), 7.36 (1H, t, J=7.8 Hz), 7.78 (1H, d, J=8.0 Hz).

Reference Example 129 methyl 2-chloro-3-nitrobenzoate

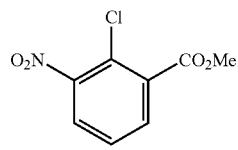

A mixture of 2-chloro-3-nitrobenzoic acid (24.8 g, 123 mmol) and sulfuric acid (3.00 mL, 38.2 mmol) in methanol (400 mL) was stirred at. 80° C. for 12 hr. The solvent was evaporated under reduced pressure, and the residue was diluted with ethyl acetate. This mixture was washed with 10% aqueous sodium hydroxide solution, water and saturated brine and dried over anhydrous sodium sulfate, and the solvent was evaporated under reduced pressure to give the title compound (26.5 g, yield 99%).

$^1$H-NMR (CDCl$_3$) δ: 3.98 (3H, s), 7.48 (1H, t, J=8.0 Hz), 7.84 (1H, dd, J=1.6, 8.0 Hz), 7.95 (1H, dd, J=1.6, 8.0 Hz).

Reference Example 130 methyl 2-(benzylthio)-3-nitrobenzoate

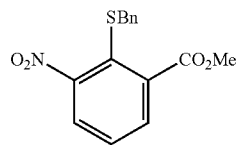

Under nitrogen atmosphere, to a mixture of methyl 2-chloro-3-nitrobenzoate (20.8 g, 96.5 mmol) and potassium carbonate (40.0 g, 289 mmol) in N,N-dimethylformamide (300 mL) was added benzyl mercaptan (11.5 mL, 98.0 mmol) at 0° C., and the mixture was stirred at 90° C. for 6 hr, diluted with water and extracted with ethyl acetate. The extract was washed with saturated brine and water and dried over anhydrous sodium sulfate, and the solvent was evaporated under reduced pressure. The residue was purified by silica gel column chromatography (ethyl acetate/hexane=1/1→1/2) to give the title compound (28.5 g, yield 97%).

¹H-NMR (CDCl₃) δ: 3.95 (3H, s), 4.15 (2H, s) 7.19-7.28 (5H, m), 7.50 (1H, t, J=8.0 Hz), 7.69 (1H, dd, J=8.0, 1.2 Hz), 7.74 (1H, dd, J=7.6, 1.6 Hz).

Reference Example 131 methyl 3-amino-2-(benzylthio)benzoate

Under hydrogen atmosphere, a mixture of methyl 2-(benzylthio)-3-nitrobenzoate (28.5 g, 94.0 mmol) and a catalytic amount of Raney nickel in ethyl acetate (500 mL) was stirred at room temperature for 12 hr, and filtered through celite. The solvent was evaporated under reduced pressure to give the title compound (25.7 g, yield 96%).

¹H-NMR (CDCl₃) δ: 3.86 (3H, s), 3.96 (2H, s), 4.43 (2H, br s), 6.77 (1H, dd, J=1.2, 8.0 Hz), 6.89 (1H, dd, J=1.2, 7.6 Hz), 7.17-7.15 (3H, m), 7.24-7.21 (3H, m).

Reference Example 132 methyl 1,2,3-benzothiadiazole-7-carboxylate

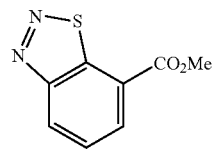

A mixture of methyl 3-amino-2-(benzylthio)benzoate (26.9 g, 98.4 mmol), acetic acid (1.00 L, 1.75 mol), water (200 mL) and concentrated hydrochloric acid (172 mL, 2.06 mol) was stirred at room temperature for 30 min. To the reaction mixture was added a solution of sodium nitrite (7.59 g, 110 mmol) in water (200 mL) at 0° C. and the mixture was stirred at 0-5° C. for 2 hr. The precipitate was collected by filtration, washed with water, and dried under reduced pressure to give the title compound (12.5 g, yield 65%).

¹H-NMR (CDCl₃) δ: 4.08 (3H, s), 7.76 (1H, dd, J=8.4, 7.6 Hz), 8.40 (1H, dd, J=7.2, 0.8 Hz), 8.85 (1H, dd, J=8.4, 0.8 Hz).

Reference Example 133

1,2,3-benzothiadiazol-7-ylmethanol

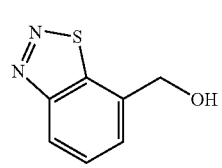

To a solution of methyl 1,2,3-benzothiadiazole-7-carboxylate (10.0 g, 51.5 mmol) in tetrahydrofuran (200 mL) was added a solution (1 M, 154 mL, 154 mmol) of diisobutylaluminum hydride in hexane at −78° C. and the mixture was stirred for 20 min. The mixture was stirred at room temperature for 1 hr, water and 1 M aqueous sodium hydroxide solution (20 mL) were added at 0° C., and the mixture was stirred at 0° C. for 10 min. To the reaction mixture was added 6 M hydrochloric acid (10 mL) and the mixture was extracted with ethyl acetate. The extract was washed with saturated brine, and dried over anhydrous sodium sulfate, and the solvent was evaporated under reduced pressure. The residue was purified by recrystallization (ethyl acetate/methanol) to give the title compound (8.25 g, yield 96%).

¹H-NMR (CDCl₃) δ: 2.27 (1H, br s), 5.05 (2H, s). 7.54 (1H, d, J=8.4 Hz), 7.62 (1H, t, J=7.6 Hz), 8.55 (1H, d, J=8.4 Hz).

Reference Example 134

1,2,3-benzothiadiazole-7-carbaldehyde

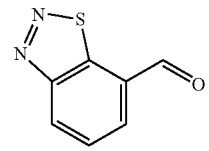

Under nitrogen atmosphere, to a solution of oxalyl chloride (7.03 mL, 83.0 mmol) in methylene chloride (50 mL) was added dimethyl sulfoxide (8.84 mL, 125 mmol) and the mixture was stirred at −78° C. for 30 min. To the reaction mixture was added 1,2,3-benzothiadiazol-7-ylmethanol (6.90 g, 41.5 mmol) at −78° C. and the mixture was stirred for 2 hr. To the reaction mixture was added triethylamine (35.0 mL, 249 mmol) at −78° C. and the mixture was stirred for 30 min. The reaction mixture was warmed to room temperature, and stirred at room temperature for 4 hr. Saturated aqueous ammonium chloride solution was added to the reaction mixture, and the mixture was extracted with methylene chloride. The extract was washed with saturated brine, and dried over anhydrous sodium sulfate, and the solvent was evaporated under reduced pressure. The residue was purified by recrystallization (methylene chloride/hexane) to give the title compound (6.20 g, yield 91%).

¹H-NMR (CDCl₃) δ: 7.90 (1H, dd, J=8.4, 7.2 Hz), 8.25 (1H, dd, J=7.2, 1.2 Hz), 8.94 (1H, dd, J=8.4, 0.8 Hz), 10.30 (1H, s).

Reference Example 135 ethyl(2E)-3-(1,2,3-benzothiadiazol-7-yl)acrylate

To a suspension of 55% sodium hydride (1.81 g, 41.5 mmol) in tetrahydrofuran (30 mL) was added a solution of ethyl diethylphosphonoacetate (8.31 mL, 41.5 mmol) in tetrahydrofuran (10 mL) at 0° C. and the mixture was stirred for 20 min. To the reaction mixture was added a solution of 1,2,3-benzothiadiazole-7-carbaldehyde (6.20 g, 37.8 mmol) in tetrahydrofuran (60 mL) at 0° C. and the mixture was stirred at room temperature for 4 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/1) and recrystallization (ethyl acetate/hexane) to give the title compound (8.70 g, yield 98%).

$^1$H-NMR (CDCl$_3$) δ: 1.39 (3H, t, J=7.2 Hz), 4.33 (2H, q, J=7.2 Hz), 6.46 (1H, d, J=16 Hz), 7.72 (1H, t, J=7.2 Hz), 7.83 (1H, d, J=7.2 Hz), 7.94 (1H, d, J=16 Hz), 8.69 (1H, d, J=7.2 Hz).

Reference Example 136 ethyl 2-(1,2,3-benzothiadiazol-7-yl)cyclopropanecarboxylate

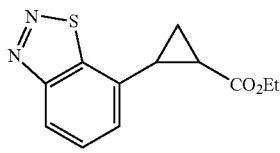

To a suspension of 60% sodium hydride (1.34 g, 30.7 mmol) in dimethyl sulfoxide (20 mL) was added a solution of trimethylsulfoxonium iodide (6.76 g, 30.7 mmol) in dimethyl sulfoxide (50 mL) at 0° C., and the mixture was stirred at room temperature for 1 hr. To the reaction mixture was added a solution of ethyl(2E)-3-(1,2,3-benzothiadiazol-7-yl)acrylate (6.00 g, 25.6 mmol) in dimethyl sulfoxide (130 mL) at 0° C., and the mixture was stirred at room temperature for 6 hr. Water was added and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/2) to give the title compound (3.00 g, yield 47%).

$^1$H-NMR (CDCl$_3$) δ: 1.33 (3H, t, J=6.8 Hz), 1.45-1.50 (1H, m), 1.71-1.75 (1H, m), 2.04-2.10 (1H, m), 2.75-2.80 (1H, m), 4.18-4.30 (m, 2H), 7.38 (1H, d, J=6.8 Hz), 7.59 (1H, t, J=7.6 Hz), 8.51 (1H, d, J=8.4 Hz).

Reference Example 137

[2-(1,2,3-benzothiadiazol-7-yl)cyclopropyl]methanol

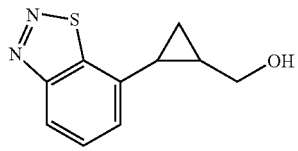

To a solution of ethyl 2-(1,2,3-benzothiadiazol-7-yl)cyclopropanecarboxylate (800 mg, 3.22 mmol) obtained in Reference Example 136 in tetrahydrofuran (20 mL) was added a solution (1 M, 9.67 mL, 9.67 mmol) of diisobutylaluminum hydride in hexane at −78° C. and the mixture was warmed to room temperature over 1 hr. To the reaction mixture were added water and 1 M aqueous sodium hydroxide solution (10 mL) at 0° C. and the mixture was stirred at 0° C. for 10 min. To the reaction mixture was added 2 M hydrochloric acid (20 mL) and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=1/3) to give the title compound (660 mg, yield 99%).

$^1$H-NMR (CDCl$_3$) δ: 1.08-1.12 (1H, m), 1.17-1.21 (1H, m), 1.50-1.57 (1H, m), 1.59-1.66 (1H, m), 2.09-2.13 (1H, m), 3.66-3.82 (2H, m), 7.34 (1H, dd, J=7.2, 0.8 Hz), 7.57 (1H, t, J=7.6 Hz), 8.46 (1H, d, J=8.4 Hz),

MS (ESI+): 207 (M+H).

Reference Example 138

2-{[2-(1,2,3-benzothiadiazol-7-yl)cyclopropyl]methyl}-1H-isoindole-1,3(2H)-dione

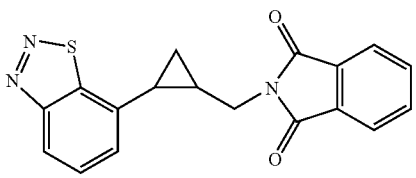

To a solution of [2-(1,2,3-benzothiadiazol-7-yl)cyclopropyl]methanol (1.00 g, 3.65 mmol) obtained in Reference Example 137 in tetrahydrofuran (50 mL) were added a solution (40%, 2.65 mL, 5.81 mmol) of diethyl azodicarboxylate in toluene, triphenylphosphine (1.65 g, 6.30 mmol) and phthalimide (927 mg, 6.30 mmol), and the mixture was stirred under nitrogen atmosphere at room temperature for 20 hr. To the reaction mixture were added diethyl azodicarboxylate (1.32 mL, 2.90 mmol), triphenylphosphine (825 mg, 3.15 mmol) and phthalimide (463 mg, 3.15 mmol), and the mixture was further stirred under nitrogen atmosphere at room temperature for 20 hr. The solvent was evaporated under reduced pressure, and the residue was purified by silica gel column chromatography (NH, ethyl acetate/hexane=10/90→45/55) to give the title compound (1.32 g, yield 82%).

$^1$H-NMR (CDCl$_3$) δ: 1.13-1.32 (2H, m), 1.63-1.79 (1H, m), 2.24-2.39 (1H, m), 3.66 (1H, dd, J=14.2, 8.1 Hz), 3.95 (1H, dd, J=14.0, 6.1 Hz), 7.25 (1H, d, J=7.2 Hz), 7.52 (1H, dd, J=8.3, 7.2 Hz), 7.70-7.81 (2H, m), 7.84-7.95 (2H, m), 8.42 (1H, d, J=8.3 Hz), melting point: 123-125° C. (recrystallized from ethyl acetate/hexane),

MS (ESI+): 336 (M+H).

Reference Example 139

1-[2-(1,2,3-benzothiadiazol-7-yl)cyclopropyl]methanamine

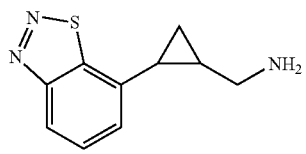

To a solution of 2-{[2-(1,2,3-benzothiadiazol-7-yl)cyclopropyl]methyl}-1H-isoindole-1,3(2H)-dione (1.00 g, 2.98 mmol) obtained in Reference Example 138 in ethanol (30 mL) was added hydrazine monohydrate (12 mL), and the mixture was heated under reflux for 15 min. The solvent was evaporated under reduced pressure. The residue was diluted with ethyl acetate, and saturated aqueous sodium hydrogen carbonate solution was added. The aqueous layer was extracted with ethyl acetate, and dried over anhydrous sodium sulfate, and the solvent was evaporated under reduced pressure. The residue was purified by silica gel column chromatography (NH, methanol/ethyl acetate=0/100→10/90) to give the title compound (507 mg, yield 83%).

$^1$H-NMR (CDCl$_3$) δ: 0.95-1.07 (1H, m), 1.09-1.20 (1H, m), 1.28-1.57 (3H, m), 1.93-2.03 (1H, m), 2.83 (2H, d, J=6.8 Hz), 7.32 (1H, d, J=7.2 Hz), 7.52-7.60 (1H, m), 8.45 (1H, d, J=8.3 Hz).

Reference Example 140 methyl 2-methyl-3-(sulfinylamino)benzoate

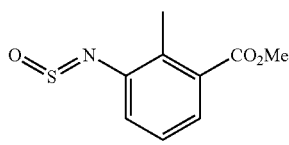

To a solution of thionyl chloride (6.63 mL, 91.0 mmol) in benzene (60 mL) was added a solution of methyl 3-amino-2-methylbenzoate (13.1 g, 91.0 mmol) in benzene (31 mL) at room temperature, and the mixture was heated under reflux for 18 hr. Water was added, and the mixture was extracted with dichloromethane, washed with saturated brine, and dried over anhydrous sodium sulfate. The solvent was evaporated under reduced pressure to give the title compound (17.3 g, yield 90%).

$^1$H-NMR (CDCl$_3$) δ: 2.57 (3H, s), 3.86 (3H, s), 7.21 (1H, t, J=8.0 Hz), 7.78 (1H, d, J=8.0 Hz), 8.41 (1H, d, J=8.0 Hz).

Reference Example 141 methyl 2,1-benzisothiazole-4-carboxylate

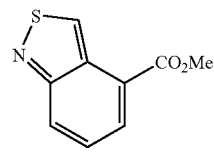

To a solution of methyl 2-methyl-3-(sulfinylamino)benzoate (15.0 g, 71.0 mmol) in benzene (200 mL) was added a solution of N-sulfinylmethanesulfonamide (10.0 g, 71.0 mmol) and pyridine (9.19 mL, 114 mmol) in benzene (80 mL) at 0° C. The reaction mixture was heated under reflux for 18 hr, water was added, and the mixture was extracted with dichloromethane. The extract was washed with saturated brine, and dried over anhydrous sodium sulfate, and the solvent was evaporated under reduced pressure. The residue was purified by silica gel column chromatography (ethyl acetate/hexane=20/80) to give the title compound (5.0 g, yield 36%).

$^1$H-NMR (CDCl$_3$) δ: 4.01 (3H, s), 7.52 (1H, dd, J=8.8, 6.8 Hz), 7.09 (1H, d, J=8.8 Hz), 8.11 (1H, d, J=6.8 Hz), 10.04 (1H, s).

Reference Example 142

2,1-benzisothiazol-4-ylmethanol

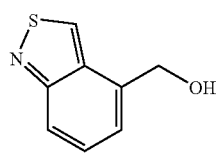

To a solution of methyl 2,1-benzisothiazole-4-carboxylate (5.00 g, 25.9 mmol) in tetrahydrofuran (129 mL) was added diisobutylaluminum hydride (1 M hexane solution, 78.0 mL, 78.0 mmol) at −78° C., and the mixture was stirred at room temperature for 3 hr. The reaction solution was cooled to 0° C., and water was added. The mixture was extracted with ethyl acetate, washed with saturated brine, and dried over anhydrous sodium sulfate, and the solvent was evaporated under reduced pressure. The residue was purified by silica gel column chromatography (ethyl acetate/hexane=20/80) to give the title compound (4.2 g, yield 98%).

$^1$H-NMR (CDCl$_3$) δ: 2.01 (1H, t, J=6.0 Hz), 5.01 (2H, d, J=6.0 Hz), 7.20 (1H, d, J=6.8 Hz), 7.41 (1H, dd, J=8.8, 6.8 Hz), 7.79 (1H, d, J=8.8 Hz), 9.39 (1H, s).

Reference Example 143

2,1-benzisothiazole-4-carbaldehyde

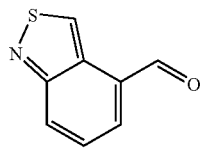

Under nitrogen atmosphere, dimethyl sulfoxide (10.8 mL, 153 mmol) was added to a solution of oxalyl chloride (6.68 mL, 76.0 mmol) in dichloromethane (200 mL) at −78° C., and the mixture was stirred for 30 min. To the reaction mixture was added a solution of 2,1-benzisothiazol-4-ylmethanol (4.20 g, 25.4 mmol) in dichloromethane (54 mL), and the mixture was stirred for 2 hr. To the reaction mixture was added triethylamine (32.2 mL, 229 mmol) at −78° C., and the mixture was stirred for 1 hr. The solvent was evaporated under reduced pressure. The residue was purified by silica gel column chromatography (ethyl acetate/hexane=20/80) to give the title compound (3.94 g, yield 95%).

$^1$H-NMR (CDCl$_3$) δ: 7.65 (1H, dd, J=8.0, 6.8 Hz), 7.83 (1H, d, J=6.8 Hz), 8.16 (1H, d, J=8.8 Hz), 10.16 (1H, s), 10.22 (1H, s).

Reference Example 144 ethyl(2E)-3-(2,1-benzisothiazol-4-yl)acrylate

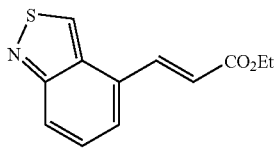

Under nitrogen atmosphere, to a suspension of sodium hydride (60%, 1.16 g, 26.6 mmol) in tetrahydrofuran (30 mL) was added a solution of ethyl diethylphosphonoacetate (4.83 mL, 5.41 mmol) in tetrahydrofuran (10 mL) at 0° C., and the mixture was stirred for 20 min. To the reaction mixture was added a solution of 2,1-benzisothiazole-4-carbaldehyde (3.94 g, 24.1 mmol) in tetrahydrofuran (8.3 mL), and the mixture was warmed to room temperature over 4 hr. Water was added and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane=20/80) to give the title compound (4.80 g, yield 85%).

$^1$H-NMR (CDCl$_3$) δ: 1.38 (3H, t, J=7.2 Hz), 4.32 (2H, q, J=7.2 Hz), 6.62 (1H, d, J=16.0 Hz), 7.46-7.52 (2H, m), 7.91 (1H, d, J=8.0 Hz), 8.06 (1H, d, J=16.0 Hz), 9.49 (1H, s).

Reference Example 145 ethyl 2-(2,1-benzisothiazol-4-yl)cyclopropanecarboxylate

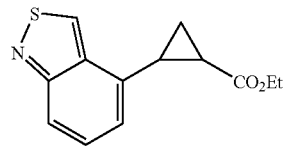

Under nitrogen atmosphere, to a suspension of sodium hydride (60%, 1.08 g, 24.7 mmol) in dimethyl sulfoxide (100 mL) was added a solution of trimethylsulfoxonium iodide (5.43 g, 24.7 mmol) in dimethyl sulfoxide (100 mL) at 0° C., and the mixture was stirred at room temperature for 1 hr. To the reaction mixture was added a solution of ethyl(2E)-3-(2,1-benzisothiazol-4-yl)acrylate (4.80 g, 20.6 mmol) in dimethyl sulfoxide (200 mL) at 0° C., and the mixture was stirred at room temperature for 12 hr. Water was added to the reaction mixture, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane=20/80) to give the title compound (2.70 g, yield 53%).

$^1$H-NMR (CDCl$_3$) δ: 1.33 (3H, t, J=7.2 Hz), 1.40-1.45 (1H, m), 1.67-1.72 (1H, m), 1.98-2.02 (1H, m), 2.83-2.88 (1H, m), 4.24 (2H, q, J=7.2 Hz), 6.90 (1H, d, J=6.4 Hz), 7.36 (1H, dd, J=8.8, 6.4 Hz), 7.74 (1H, d, J=8.8 Hz), 9.34 (1H, s).

Reference Example 146

[2-(2,1-benzisothiazol-4-yl)cyclopropyl]methanol

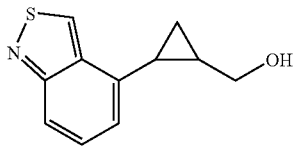

To a solution of ethyl 2-(2,1-benzisothiazol-4-yl)cyclopropanecarboxylate (2.70 g, 10.9 mmol) obtained in Reference Example 145 in tetrahydrofuran (54.6 mL) was added diisobutylaluminum hydride (1 M hexane solution, 32.8 mL, 32.8 mmol) at −78° C., and the mixture was stirred at room temperature for 3 hr. The reaction solution was cooled to 0° C., and water was added. The mixture was extracted with ethyl acetate, washed with saturated brine, and dried over anhydrous sodium sulfate. The solvent was evaporated under reduced pressure. The residue was purified by silica gel column chromatography (ethyl acetate/hexane=33/67) to give the title compound (1.48 g, yield 66%).

$^1$H-NMR (CDCl$_3$) δ: 0.96-1.01 (1H, m), 1.11-1.15 (1H, m), 1.42-1.50 (1H, m), 1.91 (1H, br s), 2.15-2.20 (1H, m), 3.55-3.61 (1H, m), 3.91-3.96 (1H, m), 6.87 (1H, d, J=6.8 Hz), 7.34 (1H, dd, J=8.8, 6.8 Hz), 7.69 (1H, d, J=8.8 Hz), 9.58 (1H, s),

MS (ESI+): 206 (M+H).

Reference Example 147

2-{[2-(2,1-benzisothiazol-4-yl)cyclopropyl]methyl}-1H-isoindole-1,3(2H)-dione

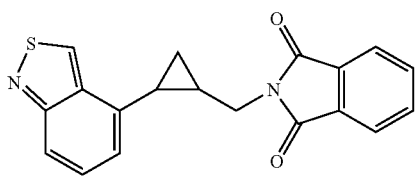

To a solution of [2-(2,1-benzisothiazol-4-yl)cyclopropyl]methanol (700 mg, 3.41 mmol) obtained in Reference Example 146 in tetrahydrofuran (30 mL) were added a solution (40%, 745 mg, 4.09 mmol) of diethyl azodicarboxylate in toluene, triphenylphosphine (1.16 g, 4.43 mmol) and phthalimide (652 mg, 4.43 mmol), and the mixture was stirred under nitrogen atmosphere at room temperature for 26 hr. To the reaction mixture were added diethyl azodicarboxylate (745 mg, 4.09 mmol), triphenylphosphine (1.16 g, 4.43 mmol) and phthalimide (652 mg, 4.43 mmol), and the mixture was further stirred under nitrogen atmosphere at room temperature for 2 hr. The solvent was evaporated under reduced pressure, and ethyl acetate was added. Insoluble material was filtered off and the solvent was evaporated under reduced pressure. The residue was recrystallized from methanol to give the title compound (690 mg, yield 61%).

$^1$H-NMR (CDCl$_3$) δ: 1.13-1.21 (2H, m), 1.51-1.69 (1H, m), 2.33-2.49 (1H, m), 3.72 (1H, dd, J=14.0, 7.7 Hz), 3.99 (1H, dd, J=14.0, 5.8 Hz), 6.71 (1H, d, J=6.9 Hz), 7.29 (1H, dd, J=9.1, 6.9 Hz), 7.64 (1H, d, J=9.1 Hz), 7.71 (2H, dd, J=5.2, 3.0 Hz), 7.86 (2H, dd, J=5.2, 3.0 Hz), 9.42 (1H, d, J=1.1 Hz),
melting point: 148-151° C. (recrystallized from methanol),
MS (ESI+): 335 (M+H),
elemental analysis: for C$_{14}$H$_{19}$N$_2$O$_2$S
Calculated (%): C, 68.24; H, 4.22; N, 8.38
Found (%): C, 68.09; H, 4.20; N, 8.49.

Reference Example 148

1-[2-(2,1-benzisothiazol-4-yl)cyclopropyl]methanamine

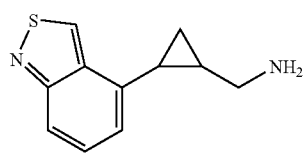

To a solution of 2-{[2-(2,1-benzisothiazol-4-yl)cyclopropyl]methyl}-1H-isoindole-1,3(2H)-dione (500 mg, 1.50 mmol) obtained in Reference Example 147 in ethanol (15 mL) was added hydrazine monohydrate (6 mL), and the mixture was heated under reflux for 20 min. The solvent was evaporated under reduced pressure, the residue was diluted with ethyl acetate, and saturated aqueous sodium hydrogen carbonate solution was added. The aqueous layer was extracted with ethyl acetate, and dried over anhydrous sodium sulfate, and the solvent was evaporated under reduced pressure. The residue was purified by silica gel column chromatography (NH, methanol/ethyl acetate=0/100→10/90) to give the title compound (263 mg, yield 86%).

$^1$H-NMR (CDCl$_3$) δ: 0.93-0.98 (1H, m), 1.04-1.07 (1H, m), 1.34-1.39 (1H, m), 2.02-2.13 (1H, m), 2.85 (2H, d, J=6.6 Hz), 6.83 (1H, d, J=6.9 Hz), 7.33 (1H, dd, J=9.1, 6.9 Hz), 7.67 (1H, d, J=9.1 Hz), 9.47 (1H, s), hidden (2H).

Example 1 trans-N-{[2-(2-methyl-2H-indazol-4-yl)cyclopropyl]methyl}acetamide

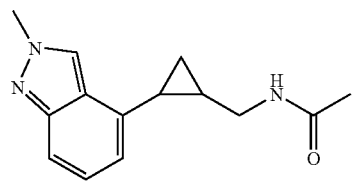

To a solution of trans-1-[2-(2-methyl-2H-indazol-4-yl)cyclopropyl]methanamine (100 mg, 0.497 mmol) and triethylamine (104 μL, 0.746 mmol) in tetrahydrofuran (5 mL) was added acetic anhydride (70.5 μL, 0.746 mmol) under ice-cooling, and the mixture was stirred at room temperature for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) and recrystallization (ethyl acetate/hexane) to give the title compound (63.2 mg, yield 52%).

$^1$H-NMR (CDCl$_3$) δ: 0.90-0.98 (1H, m), 1.09-1.17 (1H, m), 1.32-1.46 (1H, m), 2.00 (3H, s), 2.04-2.11 (1H, m), 3.33-3.40 (2H, m), 4.22 (3H, s), 5.73 (1H, br s), 6.63 (1H, d, J=6.9 Hz), 7.16 (1H, dd, J=8.8, 6.9 Hz), 7.50 (1H, d, J=8.8 Hz), 7.99 (1H, s),
melting point: 153-154° C. (recrystallized from ethyl acetate/hexane),
MS (ESI+): 244 (M+H),
elemental analysis: for C$_{14}$H$_{17}$N$_3$O
Calculated (%): C, 69.11; H, 7.04; N, 17.27
Found (%): C, 68.96; H, 7.09; N, 17.24.

Example 2 trans-N-{[2-(2-methyl-2H-indazol-4-yl)cyclopropyl]methyl}propanamide

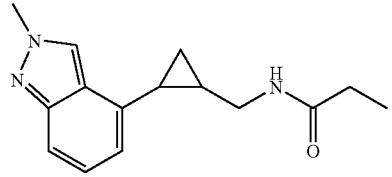

To a solution of trans-1-[2-(2-methyl-2H-indazol-4-yl)cyclopropyl]methanamine (64.0 mg, 0.318 mmol) and triethylamine (88.7 μL, 0.636 mmol) in tetrahydrofuran (3 mL) was added propionic anhydride (49.0 μL, 0.382 mmol) under ice-cooling, and the mixture was stirred at room temperature for 10 min. The reaction solution was diluted with saturated aqueous sodium hydrogen carbonate solution. The solvent was evaporated under reduced pressure and the residue was purified by silica gel column chromatography (methanol/ethyl acetate=0/100→15/85) to give the title compound (68.0 mg, yield 83%).

$^1$H-NMR (CDCl$_3$) δ: 0.87-1.00 (1H, m), 1.08-1.15 (1H, m), 1.17 (3H, t, J=7.6 Hz), 1.29-1.45 (1H, m), 2.06-2.10 (1H, m), 2.22 (2H, q, J=7.6 Hz), 3.28-3.44 (2H, m), 4.22 (3H, s), 5.65 (1H, br s), 6.63 (1H, d, J=6.9 Hz), 7.15 (1H, dd, J=8.5, 6.9 Hz), 7.50 (1H, d, J=8.5 Hz), 8.01 (1H, s), melting point: 104-106° C. (recrystallized from ethyl acetate/hexane),

MS (ESI+): 258 (M+H), elemental analysis: for C$_{15}$H$_{19}$N$_3$O

Calculated (%): C, 70.01; H, 7.44; N, 16.33

Found (%): C, 69.78; H, 7.36; N, 16.37.

Example 3

N-{[2-(2-methyl[1,2,4]triazolo[1,5-a]pyridin-8-yl)cyclopropyl]methyl}acetamide

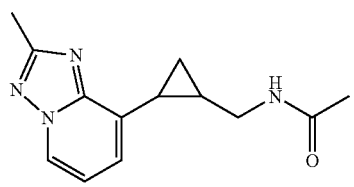

To a solution of 1-[2-(2-methyl[1,2,4]triazolo[1,5-a]pyridin-8-yl)cyclopropyl]methanamine (49.5 mg, 0.245 mmol) obtained in Reference Example 27 and triethylamine (51.2 μL, 0.367 mmol) in tetrahydrofuran (3 mL) was added acetic anhydride (34.7 μL, 0.367 mmol) under ice-cooling, and the mixture was stirred at room temperature for 30 min. The reaction solution was diluted with saturated aqueous sodium hydrogen carbonate solution. The solvent was evaporated under reduced pressure and the residue was purified by silica gel column chromatography (methanol/ethyl acetate=0/100→20/80) and recrystallization (ethyl acetate/diisopropyl ether) to give the title compound (23.5 mg, yield 39%).

$^1$H-NMR (CDCl$_3$) δ: 1.02-1.16 (2H, m), 1.22-1.35 (1H, m), 1.97-2.08 (1H, m), 2.13 (3H, s), 2.54-2.67 (4H, m), 3.96-4.10 (1H, m), 6.84-6.92 (1H, m), 7.12-7.16 (1H, m), 8.11 (1H, br s), 8.33-8.38 (1H, m), melting point: 116-118° C. (recrystallized from ethyl acetate/diisopropyl ether),

MS (ESI+): 245 (M+H), elemental analysis: for C$_{13}$H$_{16}$N$_4$O

Calculated (%): C, 63.91; H, 6.60; N, 22.93

Found (%): C, 63.81; H, 6.54; N, 22.53.

Example 4

N-{[2-(2-methyl[1,2,4]triazolo[1,5-a]pyridin-8-yl)cyclopropyl]methyl}propanamide

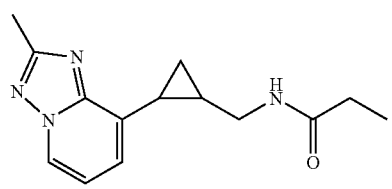

To a solution of 1-[2-(2-methyl[1,2,4]triazolo[1,5-a]pyridin-8-yl)cyclopropyl]methanamine (49.5 mg, 0.245 mmol) obtained in Reference Example 27 and triethylamine (51.2 μL, 0.367 mmol) in tetrahydrofuran (3 mL) was added propionic anhydride (47.1 μL, 0.367 mmol) under ice-cooling, and the mixture was stirred at room temperature for 30 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (16.1 mg, yield 25%).

$^1$H-NMR (CDCl$_3$) δ: 0.99-1.14 (2H, m), 1.20-1.34 (4H, m), 2.00-2.11 (1H, m), 2.30-2.41 (2H, m), 2.54-2.67 (4H, m), 3.93-4.08 (1H, m), 6.83-6.90 (1H, m), 7.12 (1H, d, J=7.1 Hz), 7.89 (1H, br s), 8.31-8.38 (1H, m),

MS (ESI+): 259 (M+H).

Example 5 trans-N-{[2-(2-methylpyrazolo[1,5-a]pyridin-4-yl)cyclopropyl]methyl}acetamide

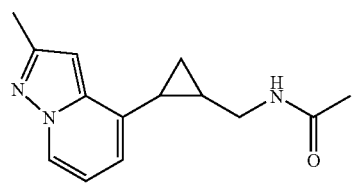

To a solution of trans-1-[2-(2-methylpyrazolo[1,5-a]pyridin-4-yl)cyclopropyl]methanamine (200 mg, 0.994 mmol) and triethylamine (208 μL, 1.49 mmol) in tetrahydrofuran (10 mL) was added acetic anhydride (113 μL, 1.20 mmol) under ice-cooling, and the mixture was stirred at room temperature for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) and recrystallization (ethyl acetate/hexane) to give the title compound (131 mg, yield 54%).

$^1$H-NMR (CDCl$_3$) δ: 0.91-1.00 (1H, m), 1.04-1.13 (1H, m), 1.25-1.39 (1H, m), 1.90-2.00 (1H, m), 2.01 (3H, s), 2.48 (3H, s), 3.31-3.40 (2H, m), 5.69 (1H, br s), 6.36 (1H, s), 6.50-6.63 (2H, m), 8.19 (1H, d, J=6.6 Hz),

Example 6 trans-N-{[2-(2-methylpyrazolo[1,5-a]pyridin-4-yl)cyclopropyl]methyl}propanamide

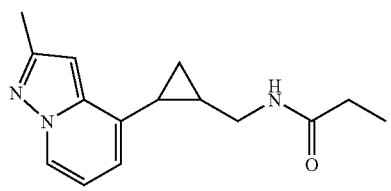

To a solution of trans-1-[2-(2-methylpyrazolo[1,5-a]pyridin-4-yl)cyclopropyl]methanamine (600 mg, 2.98 mmol) and triethylamine (499 µL, 3.58 mmol) in tetrahydrofuran (15 mL) was added propionic anhydride (420 µL, 3.28 mmol) under ice-cooling, and the mixture was stirred at room temperature for 5 min. The reaction solution was diluted with saturated aqueous sodium hydrogen carbonate solution. The solvent was evaporated under reduced pressure and the residue was purified by silica gel column chromatography (methanol/ethyl acetate=0/100→5/95) to give the title compound (521 mg, yield 68%).

$^1$H-NMR (CDCl$_3$) δ: 0.89-1.01 (1H, m), 1.04-1.14 (1H, m), 1.19 (3H, t, J=7.5 Hz), 1.24-1.39 (1H, m), 1.91-2.03 (1H, m), 2.24 (2H, q, J=7.5 Hz), 2.49 (3H, s), 3.37 (2H, dd, J=6.7, 5.9 Hz), 5.67 (1H, br s), 6.38 (1H, s), 6.51-6.65 (2H, m), 8.20 (1H, d, J=6.6 Hz), melting point: 95-98° C. (recrystallized from ethyl acetate/hexane),

MS (ESI+): 258 (M+H), elemental analysis: for C$_{15}$H$_{19}$N$_3$O

Calculated (%): C, 70.01; H, 7.44; N, 16.33

Found (%): C, 70.01; H, 7.41; N, 16.40.

Example 7 trans-tert-butyl{[2-(2-methyl-2H-indazol-4-yl)cyclopropyl]methyl}carbamate

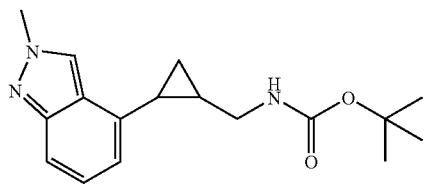

To a solution of trans-1-[2-(2-methyl-2H-indazol-4-yl)cyclopropyl]methanamine (5.75 g, 28.6 mmol) in tetrahydrofuran (150 mL) were added triethylamine (7.96 mL, 57.1 mmol) and di-t-butyl dicarbonate (9.36 g, 42.9 mmol), and the mixture was stirred at room temperature for 2 hr. The solvent was evaporated under reduced pressure. The residue was purified by silica gel column chromatography (ethyl acetate/hexane=50/50→100/0) to give the title compound (7.69 g, yield 89%).

$^1$H-NMR (CDCl$_3$) δ: 0.84-0.97 (1H, m), 1.07-1.18 (1H, m), 1.31-1.42 (1H, m), 1.46 (9H, s), 1.99-2.14 (1H, m), 3.12-3.36 (2H, m), 4.22 (3H, s), 4.73 (1H, br s), 6.65 (1H, d, J=6.9 Hz), 7.16 (1H, dd, J=8.8, 6.9 Hz), 7.50 (1H, d, J=8.8 Hz), 8.02 (1H, s), melting point: 120-121° C. (recrystallized from ethyl acetate/hexane),

MS (ESI+): 302 (M+H), elemental analysis: for C$_{17}$H$_{23}$N$_3$O$_2$

Calculated (%): C, 67.75; H, 7.69; N, 13.94

Found (%): C, 67.81; H, 7.73; N, 14.01.

Example 8 tert-butyl{[(1S,2S)-2-(2-methyl-2H-indazol-4-yl)cyclopropyl]methyl}carbamate

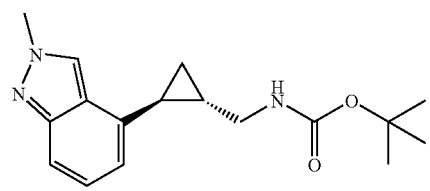

Trans-tert-butyl{[2-(2-methyl-2H-indazol-4-yl)cyclopropyl]methyl}carbamate (5.90 g) was fractionated by high performance liquid chromatography (instrument: Prep LC 2000 (manufactured by Nihon Waters K.K.), column: CHIRALPAK AD (50 mm ID×500 mm L, manufactured by Dicel Chemical Industries, Ltd.), mobile phase: A) hexane 100%, B) ethanol 100%, mixing ratio: A/B=900/100, flow rate: 80 mL/min, column temperature: 30° C., sample injection amount: 200 mg (dissolved in 100 mL of mobile phase). A fraction solution containing an optically active compound having a shorter retention time under the above-mentioned high performance liquid chromatography conditions was concentrated to give the title compound (2.92 g, 99.6% ee). Enantiomer excess (ee) was measured by high performance liquid chromatography (column: CHIRALPAK AD (4.6 mm ID×250 mm L, manufactured by Dicel Chemical Industries, Ltd.), mobile phase: hexane/ethanol=900/100, flow rate: 1.0 mL/min, column temperature: 30° C., sample concentration: 0.5 mg/mL (mobile phase), injection volume: 10 µL).

$^1$H-NMR (CDCl$_3$) δ: 0.89-0.92 (1H, m), 1.11-1.15 (1H, m), 1.26-1.42 (1H, m), 1.46 (9H, s), 1.97-2.14 (1H, m), 3.07-3.39 (2H, m), 4.21 (3H, s), 4.78 (1H, br s), 6.65 (1H, d, J=6.8 Hz), 7.16 (1H, dd, J=8.8, 6.8 Hz), 7.51 (1H, d, J=8.7 Hz), 8.03 (1H, s), melting point: 141-142° C. (recrystallized from ethyl acetate/hexane),

[α]$_D^{20}$: −16.7° (c 0.53, methanol),

MS (ESI+): 302 (M+H), elemental analysis: for C$_{17}$H$_{23}$N$_3$O$_2$

Calculated (%): C, 67.75; H, 7.69; N, 13.94

Found (%): C, 67.76; H, 7.65; N, 14.16.

---

(Preceding melting point 114-115° C. entry:)

melting point: 114-115° C. (recrystallized from ethyl acetate/hexane),

MS (ESI+): 244 (M+H), elemental analysis: for C$_{14}$H$_{17}$N$_3$O

Calculated (%): C, 69.11; H, 7.04; N, 17.27

Found (%): C, 69.06; H, 7.00; N, 17.35.

Example 9 tert-butyl{[(1R,2R)-2-(2-methyl-2H-indazol-4-yl)cyclopropyl]methyl}carbamate

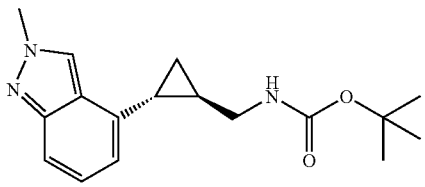

Trans-tert-butyl{[2-(2-methyl-2H-indazol-4-yl)cyclopropyl]methyl}carbamate (5.90 g) was fractionated by high performance liquid chromatography (instrument: Prep LC 2000 (manufactured by Nihon Waters K.K.), column: CHIRALPAK AD (50 mm ID×500 mm L, manufactured by Dicel Chemical Industries, Ltd.), mobile phase: A) hexane 100%, B) ethanol 100%, mixing ratio: A/B=900/100, flow rate: 80 mL/min, column temperature: 30° C., sample injection amount: 200 mg (dissolved in 100 mL of mobile phase). A fraction solution containing an optically active compound having a longer retention time under the above-mentioned high performance liquid chromatography conditions was concentrated to give the title compound (2.88 g, 99.0% ee). Enantiomer excess (ee) was measured by high performance liquid chromatography (column: CHIRALPAK AD (4.6 mm ID×250 mm L, manufactured by Dicel Chemical Industries, Ltd.), mobile phase: hexane/ethanol=900/100, flow rate: 1.0 mL/min, column temperature: 30° C., sample concentration: 0.5 mg/mL (mobile phase), injection volume: 10 μL).

$^{1}$H-NMR (CDCl$_3$) δ: 0.83-0.97 (1H, m), 1.08-1.18 (1H, m), 1.30-1.42 (1H, m), 1.46 (9H, s), 1.97-2.16 (1H, m), 3.08-3.36 (2H, m), 4.22 (3H, s), 4.75 (1H, br s), 6.66 (1H, d, J=6.8 Hz), 7.17 (1H, dd, J=8.7, 6.8 Hz), 7.51 (1H, d, J=8.7 Hz), 8.03 (1H, s), melting point: 140-142° C. (recrystallized from ethyl acetate/hexane), $[\alpha]_D^{20}$: +15.5° (c 0.53, methanol),

MS (ESI+): 302 (M+H), elemental analysis: for C$_{17}$H$_{23}$N$_3$O$_2$

Calculated (%): C, 67.75; H, 7.69; N, 13.94

Found (%): C, 67.71; H, 7.66; N, 14.10.

Example 10

N-{[(1S,2S)-2-(2-methyl-2H-indazol-4-yl)cyclopropyl]methyl}acetamide

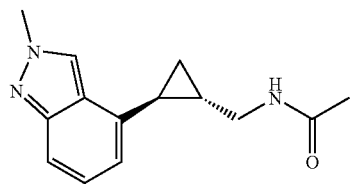

To a solution of 1-[(1S,2S)-2-(2-methyl-2H-indazol-4-yl)cyclopropyl]methanamine dihydrochloride (300 mg, 1.09 mmol) and triethylamine (305 μL, 2.19 mmol) in tetrahydrofuran (10 mL) was added acetic anhydride (124 μL, 1.31 mmol), and the mixture was stirred at room temperature for 1 hr. The reaction solution was concentrated under reduced pressure and the residue was purified by silica gel column chromatography (methanol/ethyl acetate=5/95→20/80) to give the title compound (242 mg, yield 99%).

$^{1}$H-NMR (CDCl$_3$) δ: 0.86-1.01 (1H, m), 1.06-1.19 (1H, m), 1.32-1.45 (1H, m), 2.00 (3H, s), 2.02-2.13 (1H, m), 3.36 (2H, t, J=6.2 Hz), 4.21 (3H, s), 5.82 (1H, br s), 6.63 (1H, d, J=7.0 Hz), 7.16 (1H, dd, J=8.7, 7.0 Hz), 7.50 (1H, d, J=8.7 Hz), 7.99 (1H, s), melting point: 145-147° C. (recrystallized from ethyl acetate/hexane), $[\alpha]_D^{20}$: +7.7° (c 0.51, methanol),

MS (ESI+): 244 (M+H), elemental analysis: for C$_{14}$H$_{17}$N$_3$O

Calculated (%): C, 69.11; H, 7.04; N, 17.27

Found (%): C, 68.99; H, 6.96; N, 17.21.

Example 11

N-{[(1R,2R)-2-(2-methyl-2H-indazol-4-yl)cyclopropyl]methyl}acetamide

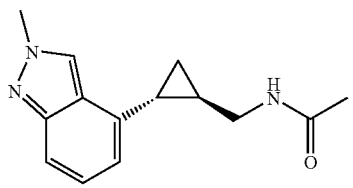

To a solution of 1-[(1R,2R)-2-(2-methyl-2H-indazol-4-yl)cyclopropyl]methanamine dihydrochloride (2.00 g, 7.29 mmol) and triethylamine (4.07 mL, 29.2 mmol) in tetrahydrofuran (70 mL) was added acetic anhydride (828 μL, 8.75 mmol), and the mixture was stirred at room temperature for 1 hr. The reaction solution was concentrated under reduced pressure and the residue was purified by silica gel column chromatography (methanol/ethyl acetate=5/95→20/80) to give the title compound (1.65 g, yield 93%).

$^{1}$H-NMR (CDCl$_3$) δ: 0.86-1.00 (1H, m), 1.07-1.18 (1H, m), 1.32-1.47 (1H, m), 2.00 (3H, s), 2.05-2.10 (1H, m), 3.36 (2H, t, J=6.4 Hz), 4.22 (3H, s), 5.77 (1H, br s), 6.63 (1H, d, J=7.0 Hz), 7.16 (1H, dd, J=8.7, 7.0 Hz), 7.50 (1H, d, J=8.7 Hz), 8.00 (1H, s), melting point: 145-147° C. (recrystallized from ethyl acetate), $[\alpha]_D^{20}$: −6.9° (c 0.52, methanol),

MS (ESI+): 244 (M+H), elemental analysis: for C$_{14}$H$_{17}$N$_3$O

Calculated (%): C, 69.11; H, 7.04; N, 17.27

Found (%): C, 69.31; H, 7.11; N, 17.41.

Example 12

N-{[(1S,2S)-2-(2-methyl-2H-indazol-4-yl)cyclopropyl]methyl}propanamide

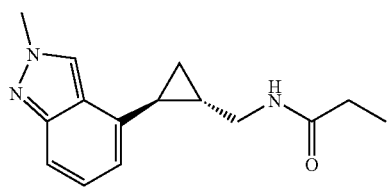

To a solution of 1-[(1S,2S)-2-(2-methyl-2H-indazol-4-yl)cyclopropyl]methanamine dihydrochloride (500 mg, 1.82 mmol) and triethylamine (1.02 mL, 7.29 mmol) in tetrahydrofuran (20 mL) was added propionic anhydride (281 μL, 2.19 mmol), and the mixture was stirred at room temperature for 2 hr. The reaction solution was concentrated under reduced pressure and the residue was purified by silica gel column chromatography (methanol/ethyl acetate=0/100→15/85) to give the title compound (477 mg, yield 100%).

$^1$H-NMR (CDCl$_3$) δ: 0.85-1.03 (1H, m), 1.13-1.18 (1H, m), 1.18 (3H, t, J=7.6 Hz), 1.31-1.47 (1H, m), 2.00-2.15 (1H, m), 2.22 (2H, q, J=7.5 Hz), 3.27-3.47 (2H, m), 4.23 (3H, s), 5.64 (1H, br s), 6.64 (1H, d, J=7.0 Hz), 7.17 (1H, dd, J=8.7, 7.0 Hz), 7.51 (1H, d, J=8.7 Hz), 8.02 (1H, s), melting point: 79-80° C. (recrystallized from ethyl acetate/hexane),

[α]$_D^{20}$: +4.4° (c 0.52, methanol),

MS (ESI+): 258 (M+H), elemental analysis: for C$_{15}$H$_{19}$N$_3$O

Calculated (%): C, 70.01; H, 7.44; N, 16.33

Found (%): C, 69.89; H, 7.39; N, 16.42.

Example 13

N-{[(1R,2R)-2-(2-methyl-2H-indazol-4-yl)cyclopropyl]methyl}propanamide

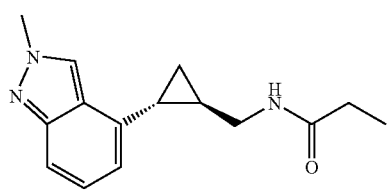

To a solution of 1-[(1R,2R)-2-(2-methyl-2H-indazol-4-yl)cyclopropyl]methanamine dihydrochloride (2.00 g, 7.29 mmol) and triethylamine (4.00 mL, 28.7 mmol) in tetrahydrofuran (80 mL) was added propionic anhydride (1.38 mL, 10.8 mmol), and the mixture was stirred at room temperature for 12 hr. The reaction solution was concentrated under reduced pressure and the residue was purified by silica gel column chromatography (methanol/ethyl acetate=0/100→15/85) to give the title compound (1.79 g, yield 95%).

$^1$H-NMR (CDCl$_3$) δ: 0.87-0.99 (1H, m), 1.08-1.15 (1H, m), 1.17 (3H, t, J=7.6 Hz), 1.30-1.44 (1H, m), 2.06-2.10 (1H, m), 2.22 (2H, q, J=7.6 Hz), 3.32-3.39 (2H, m), 4.21 (3H, s), 5.69 (1H, br s), 6.62 (1H, d, J=7.1 Hz), 7.15 (1H, dd, J=8.8, 7.1 Hz), 7.49 (1H, d, J=8.8 Hz), 8.00 (1H, s), melting point: 78-80° C. (recrystallized from ethyl acetate/hexane),

[α]$_D^{20}$: -4.3° (c 0.51, methanol),

MS (ESI+): 258 (M+H), elemental analysis: for C$_{15}$H$_{19}$N$_3$O

Calculated (%): C, 70.01; H, 7.44; N, 16.33

Found (%): C, 70.01; H, 7.36; N, 16.43.

Example 14 cis-N-{[2-(2-methyl-2H-indazol-4-yl)cyclopropyl]methyl}propanamide

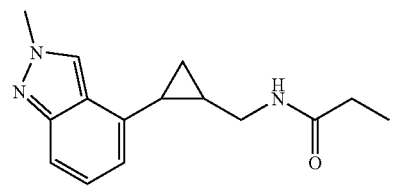

To a mixture of a crudely purified product of cis-1-[2-(2-methyl-2H-indazol-4-yl)cyclopropyl]methanamine and triethylamine (134 μL, 0.961 mmol) in tetrahydrofuran (6.5 mL) was added propionic anhydride (124 μL, 0.967 mL) at room temperature, and the mixture was stirred for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) and recrystallization (ethyl acetate/hexane) to give the title compound (55.6 mg, total yield from Reference Example 38, 34%).

$^1$H-NMR (CDCl$_3$) δ: 0.93-1.01 (4H, m), 1.06-1.16 (1H, m), 1.50-1.64 (1H, m), 1.98 (2H, q, J=7.4 Hz), 2.31-2.41 (1H, m), 2.78-2.88 (1H, m), 3.05-3.16 (1H, m), 4.24 (3H, s), 5.04 (1H, br s), 6.79 (1H, d, J=6.9 Hz), 7.20 (1H, dd, J=8.5, 6.9 Hz), 7.56 (1H, d, J=8.5 Hz), 8.04 (1H, s), melting point: 155-156° C. (recrystallized from ethyl acetate/hexane),

MS (ESI+): 258 (M+H), elemental analysis: for C$_{15}$H$_{19}$N$_3$O

Calculated (%): C, 70.01; H, 7.44; N, 16.33

Found (%): C, 70.00; H, 7.50; N, 16.37.

Example 15

4-bromo-N-{[(1R,2R)-2-(2-methyl-2H-indazol-4-yl)cyclopropyl]methyl}benzamide

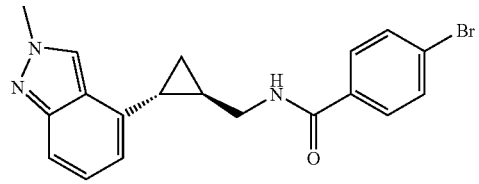

To a solution of 1-[(1R,2R)-2-(2-methyl-2H-indazol-4-yl)cyclopropyl]methanamine dihydrochloride (200 mg, 0.729 mmol) and triethylamine (407 µL, 2.92 mmol) in tetrahydrofuran (7 mL) was added 4-bromobenzoyl chloride (192 mg, 0.875 mmol), and the mixture was stirred at room temperature for 1 hr. The reaction solution was concentrated under reduced pressure and the residue was purified by silica gel column chromatography (ethyl acetate/hexane=40/60→90/10) to give the title compound (247 mg, yield 88%).

$^1$H-NMR (CDCl$_3$) δ: 0.89-1.06 (1H, m), 1.13-1.27 (1H, m), 1.42-1.47 (1H, m), 2.13-2.17 (1H, m), 3.44-3.67 (2H, m), 4.14 (3H, s), 6.38 (1H, br s), 6.64 (1H, dd, J=6.9, 1.9 Hz), 7.08-7.20 (1H, m), 7.42-7.71 (5H, m), 7.95 (1H, d, J=3.6 Hz), melting point: 140-142° C. (recrystallized from ethyl acetate/hexane), $[α]_D^{20}$: −3.5° (c 0.50, methanol),

MS (ESI+): 385 (M+H), elemental analysis: for C$_{15}$H$_{19}$N$_3$O

Calculated (%): C, 59.39; H, 4.72; N, 10.94; Br, 20.79

Found (%): C, 59.47; H, 4.75; N, 10.89; Br, 20.82.

Example 16

N-{[2-(2-ethyl-2H-indazol-4-yl)cyclopropyl]methyl}acetamide

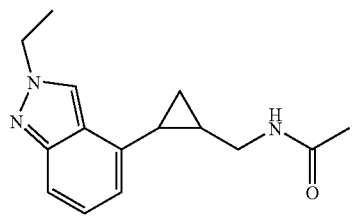

To a solution of 1-[2-(2-ethyl-2H-indazol-4-yl)cyclopropyl]methanamine (100 mg, 0.464 mmol) obtained in Reference Example 44 and triethylamine (77.7 µL, 0.557 mmol) in tetrahydrofuran (5 mL) was added acetic anhydride (48.3 µL, 0.511 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (108 mg, yield 90%).

$^1$H-NMR (CDCl$_3$) δ: 0.90-1.00 (1H, m), 1.09-1.19 (1H, m), 1.33-1.47 (1H, m), 1.60-1.72 (3H, m), 2.00 (3H, s), 2.03-2.14 (1H, m), 3.30-3.42 (2H, m), 4.48 (2H, q, J=7.2 Hz), 5.70 (1H, br s), 6.62 (1H, d, J=6.9 Hz), 7.16 (1H, dd, J=8.5, 6.9 Hz), 7.52 (1H, d, J=8.5 Hz), 8.03 (1H, s), melting point: 155-159° C. (recrystallized from ethyl acetate/hexane),

MS (ESI+): 258 (M+H), elemental analysis: for C$_{15}$H$_{19}$N$_3$O

Calculated (%): C, 70.01; H, 7.44; N, 16.33

Found (%): C, 69.92; H, 7.45; N, 16.30.

Example 17

N-{[2-(2-ethyl-2H-indazol-4-yl)cyclopropyl]methyl}propanamide

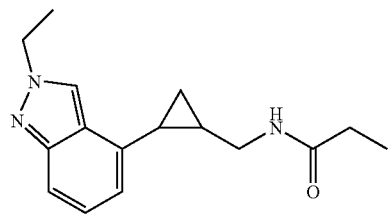

To a solution of 1-[2-(2-ethyl-2H-indazol-4-yl)cyclopropyl]methanamine (100 mg, 0.464 mmol) obtained in Reference Example 44 and triethylamine (77.7 µL, 0.557 mmol) in tetrahydrofuran (5 mL) was added propionic anhydride (65.6 µL, 0.511 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (119 mg, yield 94%).

$^1$H-NMR (CDCl$_3$) δ: 0.90-1.00 (1H, m), 1.11-1.22 (4H, m), 1.32-1.45 (1H, m), 1.60-1.70 (3H, m), 2.05-2.15 (1H, m), 2.17-2.28 (2H, m), 3.29-3.47 (2H, m), 4.47 (2H, q, J=7.2 Hz), 5.65 (1H, br s), 6.62 (1H, d, J=6.9 Hz), 7.16 (1H, dd, J=8.5, 6.9 Hz), 7.51 (1H, d, J=8.5 Hz), 8.05 (1H, s), melting point: 114-115° C. (recrystallized from ethyl acetate/hexane),

MS (ESI+): 272 (M+H), elemental analysis: for C$_{16}$H$_{21}$N$_3$O

Calculated (%): C, 70.82; H, 7.80; N, 15.49

Found (%): C, 70.85; H, 7.75; N, 15.55.

Example 18 trans-N-{[2-(3-fluoro-2-methyl-2H-indazol-4-yl)cyclopropyl]methyl}acetamide

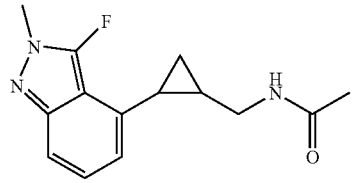

To a solution of trans-N-{[2-(2-methyl-2H-indazol-4-yl)cyclopropyl]methyl}acetamide (400 mg, 1.644 mmol) in acetonitrile (16 mL) was added xenon difluoride (306 mg, 1.808 mmol), and the mixture was stirred under nitrogen atmosphere at room temperature for 4.5 hr. The reaction mixture was diluted with saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane=50/50→100/0), HPLC and TLC to give the title compound (24 mg, yield 6%).

¹H-NMR (CDCl₃) δ: 0.90-1.02 (1H, m), 1.06-1.18 (1H, m), 1.30-1.44 (1H, m), 1.98-2.05 (3H, m), 2.11-2.20 (1H, m), 3.32-3.41 (2H, m), 4.01-4.10 (3H, m), 5.66 (1H, br s), 6.54 (1H, d, J=6.9 Hz), 7.11 (1H, dd, J=8.8, 6.9 Hz), 7.30 (1H, dd, J=8.8, 2.2 Hz), melting point: 109-111° C. (recrystallized from ethyl acetate/hexane),

MS (ESI+): 262 (M+H), elemental analysis: for C₁₄H₁₆FN₃O

Calculated (%): C, 64.35; H, 6.17; N, 16.08

Found (%): C, 64.13; H, 6.29; N, 16.03.

Example 19

N-{[(1R,2R)-2-(3-fluoro-2-methyl-2H-indazol-4-yl)cyclopropyl]methyl}acetamide

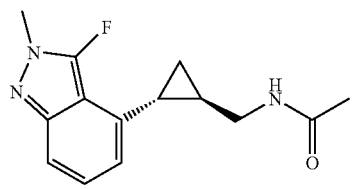

To a solution of N-{[(1R,2R)-2-(2-methyl-2H-indazol-4-yl)cyclopropyl]methyl}acetamide (100 mg, 0.411 mmol) in acetonitrile (4.1 mL) was added xenon difluoride (76.5 mg, 0.452 mmol), and the mixture was stirred at room temperature for 4 hr. The reaction solution was diluted with ethyl acetate, washed with saturated aqueous sodium hydrogen carbonate is solution and saturated brine, and dried over anhydrous sodium sulfate. The solvent was evaporated under reduced pressure. The residue was purified by silica gel column chromatography (NH, ethyl acetate/hexane=50/50→100/0) and preparative TLC (methanol/ethyl acetate=10/90) to give the title compound (13.9 mg, yield 11%).

¹H-NMR (CDCl₃) δ: 0.90-1.01 (1H, m), 1.05-1.17 (1H, m), 1.28-1.45 (1H, m), 2.01 (3H, s), 2.08-2.20 (1H, m), 3.36 (2H, t, J=6.2 Hz), 4.05 (3H, d, J=1.6 Hz), 5.67 (1H, br s), 6.54 (1H, d, J=6.6 Hz), 7.11 (1H, dd, J=8.6, 6.6 Hz), 7.30 (1H, dd, J=8.6, 2.1 Hz), melting point: 138-139° C. (recrystallized from ethyl acetate/hexane),

MS (ESI+): 262 (M+H), elemental analysis: for C₁₄H₁₆N₃FO

Calculated (%): C, 64.35; H, 6.17; N, 16.08

Found (%): C, 64.03; H, 6.18; N, 16.09.

Example 20 trans-tert-butyl{[2-(5-fluoro-2-methyl-2H-indazol-4-yl)cyclopropyl]methyl}carbamate

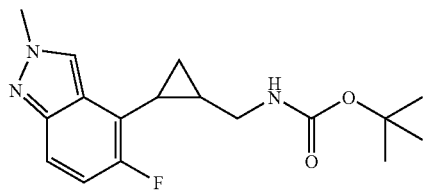

To a solution of trans-1-[2-(5-fluoro-2-methyl-2H-indazol-4-yl)cyclopropyl]methanamine (514 mg, 2.34 mmol) in tetrahydrofuran (20 mL) were added triethylamine (654 μL, 4.69 mmol) and di-t-butyl dicarbonate (613 mg, 2.81 mmol), and the mixture was stirred at room temperature for 2 hr. The solvent was evaporated under reduced pressure. The residue was purified by silica gel column chromatography (ethyl acetate/hexane=50/50→100/0) to give the title compound (741 mg, yield 99%).

¹H-NMR (CDCl₃) δ: 0.86-1.02 (1H, m), 1.11-1.25 (1H, m), 1.46 (9H, s), 1.50-1.60 (1H, m), 1.85-2.02 (1H, m), 2.98-3.22 (1H, m), 3.32-3.37 (1H, m), 4.19 (3H, s), 4.83 (1H, br s), 7.00 (1H, dd, J=10.6, 9.2 Hz), 7.47 (1H, dd, J=9.2, 4.3 Hz), 7.92 (1H, s),

MS (ESI+): 320 (M+H).

Example 21 tert-butyl{[(1S,2S)-2-(5-fluoro-2-methyl-2H-indazol-4-yl)cyclopropyl]methyl}carbamate Trans-tert-butyl{[2-(5-fluoro-2-methyl-2H-indazol-4-yl)cyclopropyl]methyl}carbamate (735 mg) was fractionated by high performance liquid chromatography (instrument: K-Prep (manufactured by YMC), column: CHIRALPAK AS (50 mm ID×500 mm L, manufactured by Dicel Chemical Industries, Ltd.), mobile phase: A) hexane 100%, B) 2-propanol 100%, mixing ratio: A/B=900/100, flow rate: 80 mL/min, column temperature: 25° C., sample concentration: 21 mg/mL (hexane/2-propanol=900/100), injection amount: 735 mg). A fraction solution containing an optically active compound having a longer retention time under the above-mentioned high performance liquid chromatography conditions was concentrated to give the title compound (353 mg, 99.9% ee). Enantiomer excess (ee) was measured by high performance liquid chromatography (column: CHIRALPAK AS (4.6 mm ID×250 mm L, manufactured by Dicel Chemical Industries, Ltd.), mobile phase: hexane/2-propanol=90/10, flow rate: 1.0 mL/min, column temperature: 30° C., sample concentration: 0.5 mg/mL (hexane/2-propanol=90/10), injection volume: 10 µL).

$^1$H-NMR (CDCl$_3$) δ: 0.82-0.98 (1H, m), 1.09-1.32 (1H, m), 1.38-1.64 (10H, m), 1.80-2.01 (1H, m), 2.98-3.18 (1H, m), 3.24-3.45 (1H, m), 4.17 (3H, s), 4.92 (1H, br s), 6.96 (1H, m), 7.45 (1H, dd, J=8.9, 4.0 Hz), 7.91 (1H, s),

MS (ESI+): 320 (M+H).

Example 22 tert-butyl{[(1R,2R)-2-(5-fluoro-2-methyl-2H-indazol-4-yl)cyclopropyl]methyl}carbamate

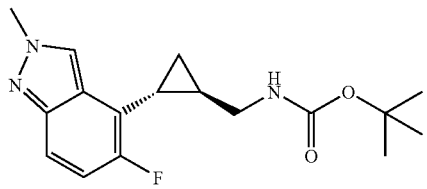

Trans-tert-butyl{[2-(5-fluoro-2-methyl-2H-indazol-4-yl)cyclopropyl]methyl}carbamate (735 mg) was fractionated by high performance liquid chromatography (instrument: K-Prep (manufactured by YMC), column: CHIRALPAK AS (50 mm ID×500 mm L, manufactured by Dicel Chemical Industries, Ltd.), mobile phase: A) hexane 100%, B) 2-propanol 100%, mixing ratio: A/B=900/100, flow rate: 80 mL/min, column temperature: 25° C., sample concentration: 21 mg/mL (hexane/2-propanol=900/100), injection amount: 735 mg). A fraction solution containing an optically active compound having a shorter retention time under the above-mentioned high performance liquid chromatography conditions was concentrated to give the title compound (323 mg, 99.9% ee). Enantiomer excess (ee) was measured by high performance liquid chromatography (column: CHIRALPAK AS (4.6 mm ID×250 mm L, manufactured by Dicel Chemical Industries, Ltd.), mobile phase: hexane/2-propanol=90/10, flow rate: 1.0 mL/min, column temperature: 30° C., sample concentration: 0.5 mg/mL (hexane/2-propanol=90/10), injection volume: 10 µL).

$^1$H-NMR (CDCl$_3$) δ: 0.83-1.02 (1H, m), 1.09-1.29 (1H, m), 1.38-1.64 (10H, m), 1.85-2.09 (1H, m), 3.03-3.23 (1H, m), 3.27-3.45 (1H, m), 4.17 (3H, s), 4.91 (1H, br s), 6.98 (1H, dd, J=10.7, 9.2 Hz), 7.45 (1H, dd, J=9.2, 4.0 Hz), 7.91 (1H, s),

MS (ESI+): 320 (M+H).

Example 23 trans-N-{[2-(5-fluoro-2-methyl-2H-indazol-4-yl)cyclopropyl]methyl}acetamide

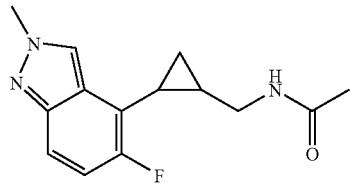

To a solution of trans-1-[2-(5-fluoro-2-methyl-2H-indazol-4-yl)cyclopropyl]methanamine (95.0 mg, 0.433 mmol) and triethylamine (72.4 µL, 0.520 mmol) in tetrahydrofuran (5 mL) was added acetic anhydride (45.1 µL, 0.477 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (NH, methanol/ethyl acetate=0/100→5/95) to give the title compound (97 mg, yield 86%).

$^1$H-NMR (CDCl$_3$) δ: 0.92-1.06 (1H, m), 1.16-1.30 (1H, m), 1.48-1.58 (1H, m), 1.91-2.00 (1H, m), 2.03 (3H, s), 3.09-3.26 (1H, m), 3.48-3.64 (1H, m), 4.20 (3H, s), 5.86 (1H, br s), 7.01 (1H, dd, J=10.8, 9.2 Hz), 7.49 (1H, dd, J=9.2, 4.3 Hz), 7.92 (1H, s), melting point: 157-159° C. (recrystallized from ethyl acetate/hexane),

MS (ESI+): 262 (M+H), elemental analysis: for C$_{14}$H$_{16}$FN$_3$O

Calculated (%): C, 64.35; H, 6.17; N, 16.08

Found (%): C, 64.00; H, 6.16; N, 16.05.

Example 24

N-{[(1S,2S)-2-(5-fluoro-2-methyl-2H-indazol-4-yl)cyclopropyl]methyl}acetamide

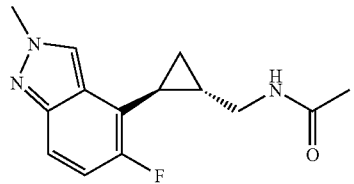

A solution of 1-[(1S,2S)-2-(5-fluoro-2-methyl-2H-indazol-4-yl)cyclopropyl]methanamine dihydrochloride (230 mg, 0.787 mmol) and triethylamine (549 µL, 3.936 mmol) in tetrahydrofuran (8 mL) was stirred at room temperature for 20 min. To the reaction solution was added acetic anhydride (112 µL, 1.181 mmol) under ice-cooling, and the mixture was stirred under ice-cooling for 15 min. The reaction solution was diluted with saturated aqueous sodium hydrogen carbonate solution. The solvent was evaporated under reduced pressure and the residue was purified by silica gel column chromatography (NH, methanol/ethyl acetate=0/100→5/95) to give the title compound (213 mg, yield 99%).

$^1$H-NMR (CDCl$_3$) δ: 0.92-1.02 (1H, m), 1.15-1.28 (1H, m), 1.49-1.61 (1H, m), 1.89-2.00 (1H, m), 2.03 (3H, s), 3.09-3.22 (1H, m), 3.49-3.63 (1H, m), 4.19 (3H, s), 5.86 (1H, br s), 7.00 (1H, dd, J=10.7, 9.3 Hz), 7.48 (1H, dd, J=9.3, 4.4 Hz), 7.91 (1H, s), melting point: 120° C. (recrystallized from ethyl acetate/hexane), $[α]_D^{20}$: +84.6° (c 0.54, methanol),

MS (ESI+): 262 (M+H), elemental analysis: for C$_{14}$H$_{16}$FN$_3$O

Calculated (%): C, 64.35; H, 6.17; N, 16.08

Found (%): C, 64.35; H, 6.17; N, 16.17.

Example 25

N-{[(1R,2R)-2-(5-fluoro-2-methyl-2H-indazol-4-yl)cyclopropyl]methyl}acetamide

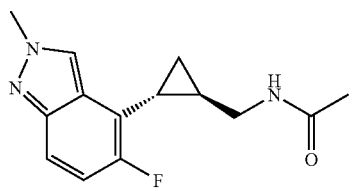

A solution of 1-[(1R,2R)-2-(5-fluoro-2-methyl-2H-indazol-4-yl) cyclopropyl]methanamine dihydrochloride (258 mg, 0.883 mmol) and triethylamine (615 μL, 4.415 mmol) in tetrahydrofuran (9 mL) was stirred at room temperature for 20 min. To the reaction solution was added acetic anhydride (125 μL, 1.325 mmol) under ice-cooling, and the mixture was stirred under ice-cooling for 15 min. The reaction solution was diluted with saturated aqueous sodium hydrogen carbonate solution. The solvent was evaporated under reduced pressure and the residue was purified by silica gel column chromatography (NH, methanol/ethyl acetate=0/100→5/95) to give the title compound (227 mg, yield 98%).

$^1$H-NMR (CDCl$_3$) δ: 0.92-1.02 (1H, m), 1.16-1.26 (1H, m), 1.49-1.59 (1H, m), 1.89-2.00 (1H, m), 2.03 (3H, s), 3.09-3.23 (1H, m), 3.49-3.64 (1H, m), 4.20 (3H, s), 5.85 (1H, br s), 7.00 (1H, dd, J=10.7, 9.1 Hz), 7.43-7.57 (1H, m), 7.92 (1H, s), melting point: 120° C. (recrystallized from ethyl acetate/hexane),

MS (ESI+): 262 (M+H), $[α]_D^{20}$: −83.7° (c 0.47, methanol), elemental analysis: for C$_{14}$H$_{16}$FN$_3$O Calculated (%): C, 64.35; H, 6.17; N, 16.08

Found (%): C, 64.36; H, 6.15; N, 16.16.

Example 26 trans-N-{[2-(5-fluoro-2-methyl-2H-indazol-4-yl)cyclopropyl]methyl}propanamide

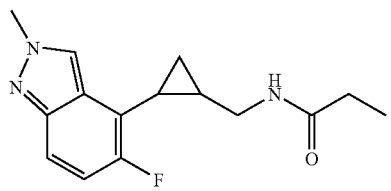

To a solution of trans-1-[2-(5-fluoro-2-methyl-2H-indazol-4-yl)cyclopropyl]methanamine (45.0 mg, 0.205 mmol) and triethylamine (34.3 μL, 0.246 mmol) in tetrahydrofuran (2 mL) was added propionic anhydride (28.9 μL, 0.226 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→8/92) to give the title compound (53.2 mg, yield 94%).

$^1$H-NMR (CDCl$_3$) δ: 0.89-1.05 (1H, m), 1.13-1.31 (4H, m), 1.45-1.58 (1H, m), 1.88-2.00 (1H, m), 2.26 (2H, q, J=7.4 Hz), 3.06-3.24 (1H, m), 3.50-3.66 (1H, m), 4.19 (3H, s), 5.84 (1H, br s), 6.94-7.07 (1H, m), 7.48 (1H, dd, J=9.2, 4.0 Hz), 7.92 (1H, s), melting point: 158-159° C. (recrystallized from ethyl acetate/hexane),

MS (ESI+): 276 (M+H), elemental analysis: for C$_{15}$H$_{18}$FN$_3$O

Calculated (%): C, 65.44; H, 6.59; N, 15.26

Found (%): C, 65.13; H, 6.57; N, 15.25.

Example 27

N-{[2-(5-chloro-2-methyl-2H-indazol-4-yl)cyclopropyl]methyl}acetamide

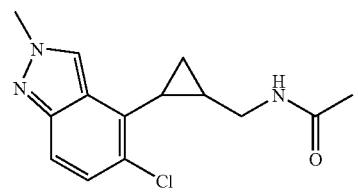

To a solution of [2-(5-chloro-2-methyl-2H-indazol-4-yl)cyclopropyl]methanol (750 mg, 3.17 mmol) obtained in Reference Example 66 in tetrahydrofuran (35 mL) were added a solution (40%, 1.72 mL, 3.80 mmol) of diethyl azodicarboxylate in toluene, triphenylphosphine (1.08 g, 4.12 mmol) and phthalimide (606 mg, 4.12 mmol), and the mixture was stirred under nitrogen atmosphere at room temperature for 16 hr. The solvent was evaporated under reduced pressure. The residue was purified by silica gel column chromatography (NH, ethyl acetate/hexane=10/90→40/60) to give 2-{[2-(5-chloro-2-methyl-2H-indazol-4-yl)cyclopropyl]methyl}-1H-isoindole-1,3(2H)-dione as a crudely purified product. The obtained crudely purified product of 2-{[2-(5-chloro-2-methyl-2H-indazol-4-yl)cyclopropyl]methyl}-1H-isoindole-1,3(2H)-dione was dissolved in ethanol (50 mL), hydrazine monohydrate (15 mL) was added, and the mixture was heated under reflux for 15 min. The solvent was evaporated under reduced pressure. The residue was diluted with diethyl ether, and saturated aqueous sodium hydrogen carbonate solution was added. The aqueous layer was extracted with ethyl acetate, and the extract was dried over anhydrous sodium sulfate. The solvent was evaporated under reduced pressure. The residue was purified by silica gel column chromatography (NH, methanol/ethyl acetate=0/100→8/92) to give 1-[2-(5-chloro-2-methyl-2H-indazol-4-yl)cyclopropyl]methanamine as a crudely purified product (1.84 g). 1.23 g from the obtained crudely purified product (1.84 g) of 1-[2-(5-chloro-2-methyl-2H-indazol-4-yl)cyclopropyl]methanamine was dissolved in tetrahydrofuran (20 mL), triethylamine (353 μL, 2.534 mmol) and acetic anhydride (220 μL, 2.323 mmol) were added under ice-cooling, and the mixture was stirred under ice-cooling for 10 min. The reaction solution was diluted with saturated aqueous sodium hydrogen carbonate solution. The solvent was evaporated under reduced pressure and the residue was purified by silica gel column chromatography (methanol/ethyl acetate=0/100→5/95, then NH, ethyl acetate/hexane=35/65→100/0) and recrystallization (ethyl acetate/hexane) to give the title compound (409 mg, yield 70%).

¹H-NMR (CDCl₃) δ: 0.99-1.10 (1H, m), 1.12-1.22 (1H, m), 1.45-1.59 (1H, m), 2.00-2.12 (4H, m), 3.27-3.40 (1H, m), 3.43-3.55 (1H, m), 4.20 (3H, s), 5.92 (1H, br s), 7.19 (1H, d, J=9.1 Hz), 7.48 (1H, d, J=9.1 Hz), 7.96 (1H, s), melting point: 149-150° C. (recrystallized from ethyl acetate/hexane),

MS (ESI+): 278 (M+H), elemental analysis: for C₁₄H₁₆ClN₃O

Calculated (%): C, 60.54; H, 5.81; N, 15.13

Found (%): C, 60.54; H, 5.78; N, 15.18.

Example 28

N-{[2-(5-chloro-2-methyl-2H-indazol-4-yl)cyclopropyl]methyl}propanamide

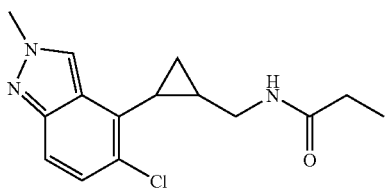

To a solution of [2-(5-chloro-2-methyl-2H-indazol-4-yl)cyclopropyl]methanol (750 mg, 3.17 mmol) obtained in Reference Example 66 in tetrahydrofuran (35 mL) were added a solution (40%, 1.72 mL, 3.80 mmol) of diethyl azodicarboxylate in toluene, triphenylphosphine (1.08 g, 4.12 mmol) and phthalimide (606 mg, 4.12 mmol), and the mixture was stirred under nitrogen atmosphere at room temperature for 16 hr. The solvent was evaporated under reduced pressure. The residue was purified by silica gel column chromatography (NH, ethyl acetate/hexane=10/90→40/60) to give 2-{[2-(5-chloro-2-methyl-2H-indazol-4-yl)cyclopropyl]methyl}-1H-isoindole-1,3(2H)-dione as a crudely purified product. The obtained crudely purified product of 2-{[2-(5-chloro-2-methyl-2H-indazol-4-yl)cyclopropyl]methyl}-1H-isoindole-1,3(2H)-dione was dissolved in ethanol (50 mL), hydrazine monohydrate (15 mL) was added, and the mixture was heated under reflux for 15 min. The solvent was evaporated under reduced pressure. The residue was diluted with diethyl ether, and saturated aqueous sodium hydrogen carbonate solution was added. The aqueous layer was extracted with ethyl acetate, and the extract was dried over anhydrous sodium sulfate. The solvent was evaporated under reduced pressure. The residue was purified by silica gel column chromatography (NH, methanol/ethyl acetate=0/100→8/92) to give 1-[2-(5-chloro-2-methyl-2H-indazol-4-yl)cyclopropyl]methanamine as a crudely purified product (1.84 g). 613 mg from the obtained crudely purified product (1.84 g) of 1-[2-(5-chloro-2-methyl-2H-indazol-4-yl)cyclopropyl]methanamine was dissolved in tetrahydrofuran (10 mL), triethylamine (177 μL, 1.267 mmol) and propionic anhydride (149 μL, 1.162 mmol) were added under ice-cooling, and the mixture was stirred under ice-cooling for 10 min. The reaction solution was diluted with saturated aqueous sodium hydrogen carbonate solution. The solvent was evaporated under reduced pressure and the residue was purified by silica gel column chromatography (methanol/ethyl acetate=0/100→5/95) and recrystallization (ethyl acetate/hexane) to give the title compound (216 mg, yield 70%).

¹H-NMR (CDCl₃) δ: 0.98-1.09 (1H, m), 1.10-1.25 (4H, m), 1.46-1.57 (1H, m), 2.01-2.11 (1H, m), 2.26 (2H, q, J=7.6 Hz), 3.25-3.37 (1H, m), 3.48-3.60 (1H, m), 4.20 (3H, s), 5.89 (1H, br s), 7.19 (1H, d, J=9.1 Hz), 7.48 (1H, d, J=9.1 Hz), 7.96 (1H, s), melting point: 152-153° C. (recrystallized from ethyl acetate/hexane),

MS (ESI+): 292 (M+H), elemental analysis: for C₁₅H₁₈ClN₃O

Calculated (%): C, 61.75; H, 6.22; N, 14.40

Found (%): C, 61.60; H, 6.21; N, 14.63.

Example 29

N-{[2-(5-bromo-2-methyl-2H-indazol-4-yl)cyclopropyl]methyl}acetamide

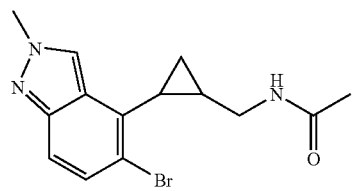

To a solution of 1-[2-(5-bromo-2-methyl-2H-indazol-4-yl)cyclopropyl]methanamine (232 mg, 0.829 mmol) obtained in Reference Example 74 and triethylamine (139 μL, 0.995 mmol) in tetrahydrofuran (8.3 mL) was added acetic anhydride (86.2 μL, 0.912 mmol) under ice-cooling, and the mixture was stirred for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (250 mg, yield 94%).

¹H-NMR (CDCl₃) δ: 1.00-1.11 (1H, m), 1.11-1.19 (1H, m), 1.46-1.58 (1H, m), 1.98-2.10 (1H, m), 2.03 (3H, s), 3.34-3.52 (2H, m), 4.20 (3H, s), 5.94 (1H, br s), 7.35 (1H, d, J=9.1 Hz), 7.41 (1H, d, J=9.1 Hz), 7.97 (1H, s), melting point: 135-137° C. (recrystallized from ethyl acetate/hexane),

MS (ESI+): 322 (M+H), elemental analysis: for C₁₄H₁₆N₃BrO

Calculated (%): C, 52.19; H, 5.01; N, 13.04

Found (%): C, 52.25; H, 4.96; N, 13.20.

Example 30

N-{[2-(5-bromo-2-methyl-2H-indazol-4-yl)cyclopropyl]methyl}propanamide

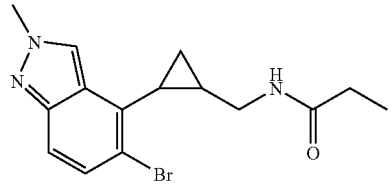

To a solution of 1-[2-(5-bromo-2-methyl-2H-indazol-4-yl)cyclopropyl]methanamine (54.8 mg, 0.195 mmol) obtained in Reference Example 74 and triethylamine (32.6 μL, 0.234 mmol) in tetrahydrofuran (2.0 mL) was added propionic anhydride (27.6 μL, 0.215 mmol) under ice-cooling, and the mixture was stirred for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (64.8 mg, yield 99%).

$^1$H-NMR (CDCl$_3$) δ: 1.02-1.11 (1H, m), 1.12-1.24 (4H, m), 1.49-1.56 (1H, m), 2.00-2.09 (1H, m), 2.27 (2H, q, J=7.4 Hz), 3.45 (2H, t, J=6.7 Hz), 4.21 (3H, s), 5.87 (1H, br s), 7.36 (1H, d, J=9.1 Hz), 7.42 (1H, d, J=9.1 Hz), 7.99 (1H, s), melting point: 119-121° C. (recrystallized from ethyl acetate/hexane),

MS (ESI+): 336 (M+H), elemental analysis: for C$_{15}$H$_{18}$N$_3$BrO

Calculated (%): C, 53.58; H, 5.40; N, 12.50

Found (%): C, 53.61; H, 5.42; N, 12.42.

Example 31

N-{[2-(2,5-dimethyl-2H-indazol-4-yl)cyclopropyl]methyl}acetamide

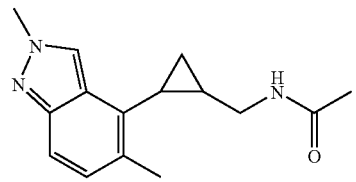

N-{[2-(5-Bromo-2-methyl-2H-indazol-4-yl)cyclopropyl]methyl}acetamide (200 mg, 0.621 mmol) obtained in Example 29, methylboronic acid (74.5 mg, 1.241 mmol), dicyclohexyl(2',4',6'-triisopropylbiphenyl-2-yl)phosphine (17.8 mg, 0.0372 mmol), potassium carbonate (206 mg, 1.49 mmol) and tris(dibenzylideneacetone)dipalladium(0) (22.7 mg, 0.0248 mmol) were added to N,N-dimethylformamide (3.1 mL), and the mixture was stirred under nitrogen atmosphere at 100° C. for 2 days, then stirred under heating at 120° C. for 2 days. The reaction solution was diluted with ethyl acetate, and filtered through celite. The obtained filtrate was washed with water and saturated brine, and dried over anhydrous sodium sulfate, and the solvent was evaporated under reduced pressure. The residue was purified by silica gel column chromatography (NH, methanol/ethyl acetate=0/100→5/95) and HPLC to give the title compound (53.4 mg, yield 33%).

$^1$H-NMR (CDCl$_3$) δ: 0.91-1.03 (2H, m), 1.37-1.51 (1H, m), 1.87-1.98 (1H, m), 2.03 (3H, s), 2.43 (3H, s), 3.10-3.23 (1H, m), 3.64-3.77 (1H, m), 4.18 (3H, s), 5.77 (1H, br s), 7.06 (1H, d, J=8.8 Hz), 7.45 (1H, d, J=8.5 Hz), 7.91 (1H, s), melting point: 139-140° C. (recrystallized from ethyl acetate/hexane),

MS (ESI+): 258 (M+H), elemental analysis: for C$_{15}$H$_{19}$N$_3$O

Calculated (%): C, 70.01; H, 7.44; N, 16.33

Found (%): C, 69.86; H, 7.38; N, 16.45.

Example 32

N-{[2-(5-ethyl-2-methyl-2H-indazol-4-yl)cyclopropyl]methyl}acetamide

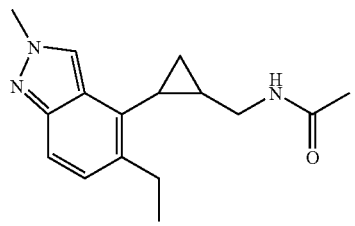

N-{[2-(5-Bromo-2-methyl-2H-indazol-4-yl)cyclopropyl]methyl}acetamide (200 mg, 0.621 mmol) obtained in Example 29, ethylboronic acid (229 mg, 3.105 mmol), dicyclohexyl(2',4',6'-triisopropylbiphenyl-2-yl)phosphine (30.0 mg, 0.0621 mmol), potassium carbonate (206 mg, 1.49 mmol) and tris(dibenzylideneacetone)dipalladium(0) (29.3 mg, 0.0311 mmol) were added to N,N-dimethylformamide (3.1 mL), and the mixture was stirred under nitrogen atmosphere with heating at 120° C. for 1 day. The reaction solution was diluted with ethyl acetate, and filtered through celite. The obtained filtrate was washed with water and saturated brine, and dried over anhydrous sodium sulfate, and the solvent was evaporated under reduced pressure. The residue was purified by silica gel column chromatography (NH, methanol/ethyl acetate=0/100→5/95), silica gel column chromatography (NH, methanol/ethyl acetate=0/100→20/80) and HPLC to give the title compound (31 mg, yield 18%).

$^1$H-NMR (CDCl$_3$) δ: 0.92-1.08 (2H, m), 1.24 (3H, t, J=7.6 Hz), 1.43-1.54 (1H, m), 1.93-2.02 (1H, m), 2.04 (3H, s), 2.85 (2H, q, J=7.4 Hz), 3.12-3.25 (1H, m), 3.63-3.76 (1H, m), 4.19 (3H, s), 5.71 (1H, br s), 7.10 (1H, d, J=8.8 Hz), 7.50 (1H, d, J=8.8 Hz), 7.92 (1H, s),

MS (ESI+): 272 (M+H).

Example 33

N-{[2-(5-cyclopropyl-2-methyl-2H-indazol-4-yl)cyclopropyl]methyl}acetamide

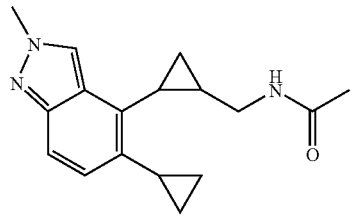

N-{[2-(5-bromo-2-methyl-2H-indazol-4-yl)cyclopropyl]methyl}acetamide (200 mg, 0.621 mmol) obtained in Example 29, cyclopropylboronic acid (80 mg, 0.931 mmol), potassium carbonate (85.8 mg, 0.621 mmol) and tetrakis(triphenylphosphine)palladium(0) (71.8 mg, 0.062 mmol) were added to a mixed solution of water (0.25 mL) and 1,2-dimethoxyethane (2.75 mL), and the mixture was stirred at 120° C. for 20 min using microwave, thereafter at 130° C.

for 40 min. The reaction solution was diluted with ethyl acetate and water, and the aqueous layer was extracted with ethyl acetate. The combined organic layers were dried over anhydrous sodium sulfate and the solvent was evaporated under reduced pressure. The residue was purified by silica gel column chromatography (methanol/ethyl acetate=0/100→10/90) and HPLC to give the title compound (68 mg, yield 39%).

$^1$H-NMR (CDCl$_3$) δ: 0.64-0.78 (2H, m), 0.94-1.03 (3H, m), 1.05-1.13 (1H, m), 1.47-1.57 (1H, m), 2.03 (3H, s), 2.09-2.19 (1H, m), 2.21-2.35 (1H, m), 3.09-3.23 (1H, m), 3.67-3.82 (1H, m), 4.18 (3H, s), 5.70 (1H, br s), 6.84 (1H, d, J=8.8 Hz), 7.45 (1H, d, J=9.1 Hz), 7.90 (1H, s), melting point: 102-103° C. (recrystallized from ethyl acetate/hexane),

MS (ESI+): 284 (M+H), elemental analysis: for C$_{17}$H$_{21}$N$_3$O.0.1H$_2$O

Calculated (%): C, 71.60; H, 7.48; N, 14.73

Found (%): C, 71.39; H, 7.32; N, 14.65.

Example 34

N-{[2-(2-methyl-5-phenyl-2H-indazol-4-yl)cyclopropyl]methyl}acetamide

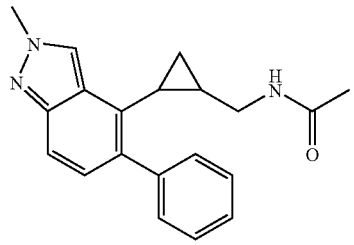

N-{[2-(5-Bromo-2-methyl-2H-indazol-4-yl)cyclopropyl]methyl}acetamide (100 mg, 0.310 mmol) obtained in Example 29, phenylboronic acid (94.6 mg, 0.776 mmol), 2 M aqueous sodium carbonate solution (3 mL) and tetrakis(triphenylphosphine)palladium(0) (35.8 mg, 0.031 mmol) were added to a mixed solution of ethanol (1.5 mL) and toluene (1.5 mL), and the mixture was stirred under nitrogen atmosphere with heating at 80° C. for 15 hr. The reaction solution was diluted with ethyl acetate, washed with water and saturated brine, and dried over anhydrous sodium sulfate, and the solvent was evaporated under reduced pressure. The residue was purified by silica gel column chromatography (methanol/ethyl acetate=0/100→10/90) to give the title compound (98.9 mg, yield 99%).

$^1$H-NMR (CDCl$_3$) δ: 0.71-0.88 (2H, m), 0.88-1.03 (1H, m), 1.89 (3H, s), 2.04-2.16 (1H, m), 2.79-2.93 (1H, m), 3.17-3.29 (1H, m), 4.24 (3H, s), 4.98 (1H, br s), 7.16 (1H, d, J=8.8 Hz), 7.34-7.53 (5H, m), 7.58 (1H, d, J=8.8 Hz), 8.02 (1H, s), melting point: 156-158° C. (recrystallized from ethyl acetate),

MS (ESI+): 320 (M+H), elemental analysis: for C$_{20}$H$_{21}$N$_3$O.0.1H$_2$O

Calculated (%): C, 74.79; H, 6.64; N, 13.08

Found (%): C, 74.75; H, 6.61; N, 13.12.

Example 35

N-{[2-(2-methyl-5-pyridin-3-yl-2H-indazol-4-yl)cyclopropyl]methyl}acetamide

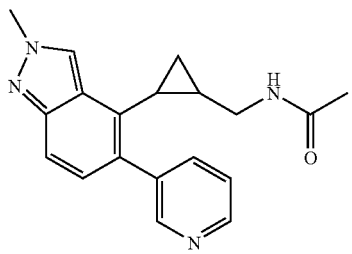

N-{[2-(5-Bromo-2-methyl-2H-indazol-4-yl)cyclopropyl]methyl}acetamide (200 mg, 0.621 mmol) obtained in Example 29, pyridin-3-ylboronic acid (191 mg, 1.552 mmol), 2 M aqueous sodium carbonate solution (6 mL) and tetrakis(triphenylphosphine)palladium(0) (71.8 mg, 0.062 mmol) were added to a mixed solution of ethanol (3 mL) and toluene (3 mL), and the mixture was stirred under nitrogen atmosphere with heating at 80° C. for 16 hr. The reaction solution was diluted with ethyl acetate, washed with water and saturated brine, and dried over anhydrous sodium sulfate, and the solvent was evaporated under reduced pressure. The residue was is purified by silica gel column chromatography (methanol/ethyl acetate=0/100→20/80) to give the title compound (187 mg, yield 94%)

$^1$H-NMR (CDCl$_3$) δ: 0.68-0.83 (2H, m), 0.99-1.12 (1H, m), 1.96 (3H, s), 2.06-2.15 (1H, m), 3.05-3.23 (2H, m), 4.25 (3H, s), 5.39 (1H, br s), 7.15 (1H, dd, J=8.8, 0.8 Hz), 7.40 (1H, dd, J=8.0, 4.9 Hz), 7.61 (1H, dd, J=8.8, 0.8 Hz), 7.72-7.79 (1H, m), 8.06 (1H, s), 8.57-8.63 (1H, m), 8.71 (1H, d, J=2.2 Hz), melting point: 136-138° C. (recrystallized from ethyl acetate/hexane),

MS (ESI+): 321 (M+H).

Example 36

N-{[2-(5-cyano-2-methyl-2H-indazol-4-yl)cyclopropyl]methyl}acetamide

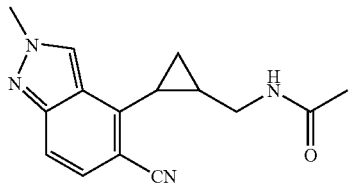

To a solution of N-{[2-(5-bromo-2-methyl-2H-indazol-4-yl)cyclopropyl]methyl}acetamide (200 mg, 0.621 mmol) obtained in Example 29 in N-methylpyrrolidinone (3 mL) were added nickel(II) bromide (136 mg, 0.621 mmol) and sodium cyanide (61 mg, 1.241 mmol), and the mixture was stirred at 180° C. for 40 min using microwave. The reaction solution was diluted with ethyl acetate, washed with water and saturated brine, and dried over anhydrous sodium sulfate, and the solvent was evaporated under reduced pressure. The residue was purified by silica gel column chromatography (methanol/ethyl acetate=0/100→5/95) and recrystallization (ethyl acetate/hexane) to give the title compound (52 mg, yield 31%).

$^1$H-NMR (CDCl$_3$) δ: 1.08-1.20 (1H, m), 1.19-1.31 (1H, m), 1.59-1.73 (1H, m), 2.03 (3H, s), 2.20-2.31 (1H, m), 2.95-3.09 (1H, m), 3.72-3.86 (1H, m), 4.24 (3H, s), 6.47 (1H, br s), 7.33 (1H, d, J=8.8 Hz), 7.59 (1H, d, J=8.8 Hz), 8.15 (1H, s), melting point: 189-192° C. (recrystallized from ethyl acetate/hexane),

MS (ESI+): 269 (M+H), elemental analysis: for C$_{15}$H$_{16}$N$_4$O

Calculated (%): C, 67.15; H, 6.01; N, 20.88

Found (%): C, 66.87; H, 5.99; N, 20.58.

Example 37

N-{[2-(5-methoxy-2-methyl-2H-indazol-4-yl)cyclopropyl]methyl}acetamide

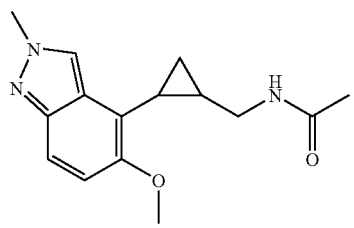

N-{[2-(5-Bromo-2-methyl-2H-indazol-4-yl)cyclopropyl]methyl}acetamide (200 mg, 0.621 mmol) obtained in Example 29, copper(I) bromide (89.0 mg, 0.621 mmol) and methyl acetate (148 μL, 1.863 mmol) were dissolved in 28% sodium methoxide methanol solution (8 mL), and the mixture was heated under reflux for 1.5 hr. The reaction mixture was diluted with aqueous hydrochloric acid solution, and the aqueous layer was extracted with ethyl acetate. The extract was washed with saturated brine, and dried over anhydrous sodium sulfate, and the solvent was evaporated under reduced pressure. The residue was purified by silica gel column chromatography (methanol/ethyl acetate=3/97→10/90), HPLC and recrystallization (ethyl acetate/hexane) to give the title compound (27.1 mg, yield 16%).

$^1$H-NMR (CDCl$_3$) δ: 0.90-0.99 (1H, m), 1.12-1.20 (1H, m), 1.23-1.40 (1H, m), 1.82-1.93 (1H, m), 2.05 (3H, s), 2.80-2.92 (1H, m), 3.70-3.82 (1H, m), 3.94 (3H, s), 4.18 (3H, s), 6.33 (1H, br s), 7.11 (1H, d, J=9.3 Hz), 7.56 (1H, d, J=9.3 Hz), 7.88 (1H, s), melting point: 104-105° C. (recrystallized from ethyl acetate/hexane),

MS (ESI+): 274 (M+H), elemental analysis: for C$_{15}$H$_{19}$N$_3$O$_2$

Calculated (%): C, 65.91; H, 7.01; N, 15.37

Found (%): C, 65.82; H, 7.01; N, 15.50.

Example 38

N-{[2-(7-fluoro-2-methyl-2H-indazol-4-yl)cyclopropyl]methyl}acetamide

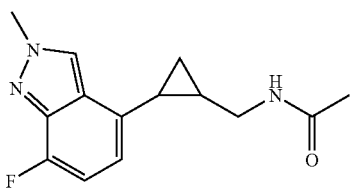

To a solution of 1-[2-(7-fluoro-2-methyl-2H-indazol-4-yl)cyclopropyl]methanamine (200 mg, 0.912 mmol) obtained in Reference Example 83 and triethylamine (153 μL, 1.095 mmol) in tetrahydrofuran (9 mL) was added acetic anhydride (112 μL, 1.186 mmol) under ice-cooling, and the mixture was stirred under ice-cooling for 5 min. The reaction solution was diluted with saturated aqueous sodium hydrogen carbonate solution, and the aqueous layer was extracted with ethyl acetate. The extract was washed with saturated brine, and dried over anhydrous sodium sulfate, and the solvent was evaporated under reduced pressure. The residue was purified by silica gel column chromatography (NH, methanol/ethyl acetate=1/99→5/95) to give the title compound (192 mg, yield 81%).

$^1$H-NMR (CDCl$_3$) δ: 0.87-0.97 (1H, m), 1.04-1.13 (1H, m), 1.25-1.38 (1H, m), 1.98-2.09 (4H, m), 3.25-3.49 (2H, m), 4.25 (3H, s), 5.65 (1H, br s), 6.49-6.55 (1H, m), 6.79 (1H, dd, J=11.1, 7.6 Hz), 8.05 (1H, d, J=2.7 Hz), melting point: 147-148° C. (recrystallized from ethyl acetate/hexane),

MS (ESI+): 262 (M+H), elemental analysis: for C$_{14}$H$_{16}$FN$_3$O

Calculated (%): C, 64.35; H, 6.17; N, 16.08

Found (%): C, 64.29; H, 6.21; N, 16.12.

Example 39

N-{[2-(7-chloro-2-methyl-2H-indazol-4-yl)cyclopropyl]methyl}acetamide

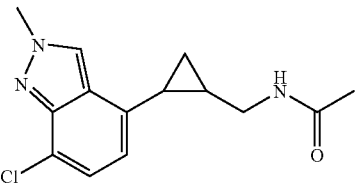

To a solution of 1-[2-(7-chloro-2-methyl-2H-indazol-4-yl)cyclopropyl]methanamine (200 mg, 0.849 mmol) obtained in Reference Example 91 and triethylamine (142 μL, 1.018 mmol) in tetrahydrofuran (8 mL) was added acetic anhydride (104 μL, 1.10 mmol) under ice-cooling, and the mixture was stirred under ice-cooling for 5 min. The reaction solution was diluted with saturated aqueous sodium hydrogen carbonate solution, and the aqueous layer was extracted with ethyl acetate. The extract was washed with saturated brine, and dried over anhydrous sodium sulfate, and the solvent was evaporated under reduced pressure. The residue was purified by silica gel column chromatography (NH, methanol/ethyl acetate=0/100→5/95) to give the title compound (197 mg, yield 84%).

$^1$H-NMR (CDCl$_3$) δ: 0.89-1.01 (1H, m), 1.06-1.18 (1H, m), 1.25-1.41 (1H, m), 1.97-2.11 (4H, m), 3.27-3.48 (2H, m), 4.27 (3H, s), 5.66 (1H, br s), 6.54 (1H, d, J=7.4 Hz), 7.17 (1H, d, J=7.4 Hz), 8.07 (1H, d, J=3.3 Hz), melting point: 153-155° C. (recrystallized from ethyl acetate/hexane),

MS (ESI+): 278 (M+H), elemental analysis: for C$_{14}$H$_{16}$ClN$_3$O

Calculated (%): C, 60.54; H, 5.81; N, 15.13

Found (%): C, 60.54; H, 5.78; N, 15.14.

Example 40 trans-tert-butyl{[2-(2-methylpyrazolo[1,5-a]pyridin-4-yl)cyclopropyl]methyl}carbamate

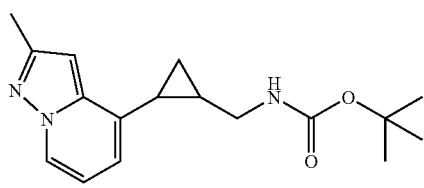

To a solution of trans-1-[2-(2-methylpyrazolo[1,5-a]pyridin-4-yl)cyclopropyl]methanamine (3.60 g, 17.9 mmol) and triethylamine (3.00 mL, 21.5 mmol) in tetrahydrofuran (90 mL) was added di-t-butyl dicarbonate (4.52 mL, 19.7 mmol) under ice-cooling, and the mixture was stirred at room temperature for 2 hr. The reaction solution was diluted with saturated aqueous sodium hydrogen carbonate solution. The solvent was evaporated under reduced pressure. The residue was diluted with ethyl acetate, washed with saturated brine, and dried over anhydrous sodium sulfate. The solvent was evaporated under reduced pressure. The residue was purified by silica gel column chromatography (ethyl acetate/hexane=30/70→50/50) to give the title compound (4.98 g, yield 92%).

$^1$H-NMR (CDCl$_3$) δ: 0.88-0.98 (1H, m), 1.02-1.12 (1H, m), 1.24-1.40 (1H, m), 1.47 (9H, s), 1.90-2.02 (1H, m), 2.49 (3H, s), 3.14-3.35 (2H, m), 4.75 (1H, br s), 6.41 (1H, s), 6.56 (1H, t, J=6.9 Hz), 6.63 (1H, d, J=6.9 Hz), 8.20 (1H, d, J=6.9 Hz), melting point: 105-107° C. (recrystallized from ethyl acetate/hexane),

MS (ESI+): 302 (M+H), elemental analysis: for C$_{17}$H$_{23}$N$_3$O$_2$

Calculated (%): C, 67.75; H, 7.69; N, 13.94

Found (%): C, 67.78; H, 7.74; N, 13.99.

Example 41 tert-butyl{[(1S,2S)-2-(2-methylpyrazolo[1,5-a]pyridin-4-yl)cyclopropyl]methyl}carbamate

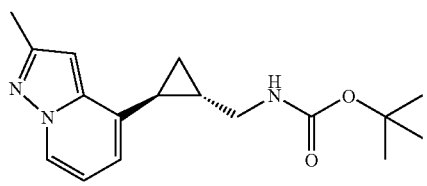

Trans-tert-butyl{[2-(2-methylpyrazolo[1,5-a]pyridin-4-yl)cyclopropyl]methyl}carbamate (4.80 g) was fractionated by supercritical fluid chromatography (instrument: Multigram II (manufactured by Mettler-Toledo), column: CHIRALPAK AD-HKG-010 (20 mm ID×250 mm L, manufactured by Dicel Chemical Industries, Ltd.), mobile phase: A) carbon dioxide 100%, B) methanol 100%, mixing ratio: A/B=900/100, flow rate: 50 mL/min, column temperature: 35° C., sample concentration: 10 mg/mL (methanol), injection volume: 2.5 mL). A fraction solution containing an optically active compound having a shorter retention time under the above-mentioned supercritical fluid chromatography conditions was concentrated to give the title compound (2.21 g, 99.9% ee). Enantiomer excess (ee) was measured using supercritical fluid chromatography (column: CHIRALPAK AD-H LA-145 (4.6 mm ID×250 mm L, manufactured by Dicel Chemical Industries, Ltd.), mobile phase: A) carbon dioxide 100%, B) methanol 100%, mixing ratio: A/B=900/100, flow rate: 2.35 mL/min, column temperature: 35° C., sample concentration: 0.5 mg/mL (methanol), injection volume: 5 μL).

$^1$H-NMR (CDCl$_3$) δ: 0.84-0.99 (1H, m), 1.02-1.14 (1H, m), 1.22-1.38 (1H, m), 1.47 (9H, s), 1.89-2.02 (1H, m), 2.49 (3H, s), 3.09-3.37 (2H, m), 4.76 (1H, br s), 6.41 (1H, s), 6.51-6.68 (2H, m), 8.20 (1H, d, J=6.6 Hz), melting point: 117-118° C. (recrystallized from ethyl acetate/hexane),

MS (ESI+): 302 (M+H), elemental analysis: for C$_{17}$H$_{23}$N$_3$O$_2$

Calculated (%): C, 67.75; H, 7.69; N, 13.94

Found (%): C, 67.72; H, 7.78; N, 14.05.

Example 42 tert-butyl{[(1R,2R)-2-(2-methylpyrazolo[1,5-a]pyridin-4-yl)cyclopropyl]methyl}carbamate

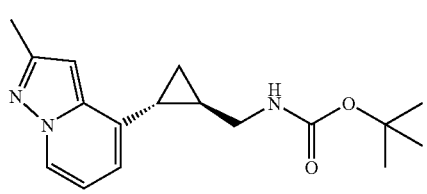

Trans-tert-butyl{[2-(2-methylpyrazolo[1,5-a]pyridin-4-yl)cyclopropyl]methyl}carbamate (4.80 g) was fractionated by supercritical fluid chromatography (instrument: Multigram II (manufactured by Mettler-Toledo), column: CHIRALPAK AD-HKG-010 (20 mm ID×250 mm L, manufactured by Dicel Chemical Industries, Ltd.), mobile phase: A) carbon dioxide 100%, B) methanol 100%, mixing ratio: A/B=900/100, flow rate: 50 mL/min, column temperature: 35° C., sample concentration: 10 mg/mL (methanol), injection volume: 2.5 mL). A fraction solution containing an optically active compound having a longer retention time under the above-mentioned supercritical fluid chromatography conditions was concentrated to give the title compound (2.20 g, 99.9% ee). Enantiomer excess (ee) was measured using supercritical fluid chromatography (column: CHIRALPAK AD-H LA-145 (4.6 mm ID×250 mm L, manufactured by Dicel Chemical Industries, Ltd.), mobile phase: A) carbon dioxide 100%, B) methanol 100%, mixing ratio: A/B=900/100, flow rate: 2.35 mL/min, column temperature: 35° C., sample concentration: 0.5 mg/mL (methanol), injection volume: 5 μL).

$^1$H-NMR (CDCl$_3$) δ: 0.87-0.99 (1H, m), 1.00-1.12 (1H, m), 1.20-1.37 (1H, m), 1.47 (9H, s), 1.87-2.02 (1H, m), 2.49 (3H, s), 3.12-3.34 (2H, m), 4.76 (1H, br s), 6.41 (1H, s), 6.49-6.67 (2H, m), 8.20 (1H, d, J=6.6 Hz), melting point: 118-119° C. (recrystallized from ethyl acetate/hexane),

MS (ESI+): 302 (M+H), elemental analysis: for C$_{17}$H$_{23}$N$_3$O$_2$

Calculated (%): C, 67.75; H, 7.69; N, 13.94

Found (%): C, 67.60; H, 7.66; N, 13.92.

Example 43

N-{[(1S,2S)-2-(2-methylpyrazolo[1,5-a]pyridin-4-yl)cyclopropyl]methyl}acetamide

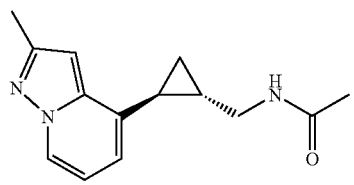

To a suspension of 1-[(1S,2S)-2-(2-methylpyrazolo[1,5-a]pyridin-4-yl)cyclopropyl]methanamine dihydrochloride (750 mg, 2.74 mmol) and triethylamine (1.52 mL, 10.9 mmol) in tetrahydrofuran (27 mL) was added acetic anhydride (388 μL, 4.10 mmol), and the mixture was stirred at room temperature for 14 hr. The reaction solution was concentrated under reduced pressure and the residue was purified by silica gel column chromatography (methanol/ethyl acetate=0/100→10/90) to give the title compound (623 mg, yield 93%).

$^1$H-NMR (CDCl$_3$) δ: 0.93-0.99 (1H, m), 1.06-1.12 (1H, m), 1.25-1.46 (1H, m), 1.87-2.01 (1H, m), 2.02 (3H, s), 2.49 (3H, s), 3.34-3.39 (2H, m), 5.73 (1H, br s), 6.38 (1H, s), 6.51-6.65 (2H, m), 8.21 (1H, d, J=6.6 Hz), melting point: 69-70° C. (recrystallized from ethyl acetate/hexane), $[α]_D^{20}$: −34.9° (c 0.49, methanol),

MS (ESI+): 244 (M+H), elemental analysis: for C$_{15}$H$_{19}$N$_3$O·0.5H$_2$O

Calculated (%): C, 66.64; H, 7.18; N, 16.65

Found (%): C, 66.48; H, 7.18; N, 16.79.

Example 44

N-{[(1R,2R)-2-(2-methylpyrazolo[1,5-a]pyridin-4-yl)cyclopropyl]methyl}acetamide

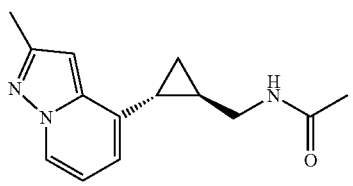

To a suspension of 1-[(1R,2R)-2-(2-methylpyrazolo[1,5-a]pyridin-4-yl)cyclopropyl]methanamine dihydrochloride (750 mg, 2.74 mmol) and triethylamine (1.52 mL, 10.9 mmol) in tetrahydrofuran (27 mL) was added acetic anhydride (388 μL, 4.10 mmol), and the mixture was stirred at room temperature for 14 hr. The reaction solution was concentrated under reduced pressure and the residue was purified by silica gel column chromatography (methanol/ethyl acetate=0/100→10/90) to give the title compound (600 mg, yield 90%).

$^1$H-NMR (CDCl$_3$) δ: 0.89-1.02 (1H, m), 1.02-1.16 (1H, m), 1.21-1.44 (1H, m), 1.90-2.00 (1H, m), 2.02 (3H, s), 2.49 (3H, s), 3.36 (2H, t, J=6.0 Hz), 5.78 (1H, br s), 6.38 (1H, s), 6.47-6.68 (2H, m), 8.21 (1H, d, J=6.6 Hz), melting point: 100-101° C. (recrystallized from ethyl acetate/hexane), $[α]_D^{20}$: +36.5° (c 0.49, methanol),

MS (ESI+): 244 (M+H), elemental analysis: for C$_{15}$H$_{19}$N$_3$O·0.5H$_2$O

Calculated (%): C, 66.64; H, 7.18; N, 16.65

Found (%): C, 66.64; H, 7.14; N, 16.81.

Example 45 trans-N-{[2-(2-methylpyrazolo[1,5-a]pyridin-4-yl)cyclopropyl]methyl}butanamide

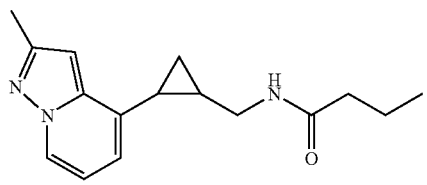

To a solution of trans-1-[2-(2-methylpyrazolo[1,5-a]pyridin-4-yl)cyclopropyl]methanamine (100 mg, 0.497 mmol) and triethylamine (83.2 μL, 0.596 mmol) in tetrahydrofuran (5 mL) was added butanoic anhydride (89.4 μL, 0.547 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→5/95) to give the title compound (97.4 mg, yield 72%).

$^1$H-NMR (CDCl$_3$) δ: 0.90-1.02 (4H, m), 1.04-1.15 (1H, m), 1.22-1.41 (1H, m), 1.63-1.76 (2H, m), 1.92-2.02 (1H, m), 2.18 (2H, t, J=7.4 Hz), 2.49 (3H, s), 3.31-3.42 (2H, m), 5.60 (1H, br s), 6.38 (1H, s), 6.52-6.64 (2H, m), 8.17 (1H, m),
melting point: 82-84° C. (recrystallized from hexane),
MS (ESI+): 272 (M+H),
elemental analysis: for $C_{16}H_{21}N_3O$
Calculated (%): C, 70.82; H, 7.80; N, 15.49
Found (%): C, 70.67; H, 7.86; N, 15.46.

Example 46 trans-2,2,2-trifluoro-N-{[2-(2-methylpyrazolo[1,5-a]pyridin-4-yl)cyclopropyl]methyl}acetamide

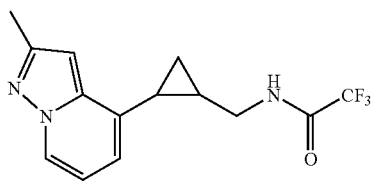

To a solution of trans-1-[2-(2-methylpyrazolo[1,5-a]pyridin-4-yl)cyclopropyl]methanamine (100 mg, 0.497 mmol) and triethylamine (83.2 μL, 0.596 mmol) in tetrahydrofuran (5 mL) was added trifluoroacetic anhydride (76.0 μL, 0.547 mmol) under ice-cooling, and the mixture was stirred under ice-cooling for 20 min. The reaction solution was diluted with saturated aqueous sodium hydrogen carbonate solution. The solvent was evaporated under reduced pressure and the residue was purified by silica gel column chromatography (ethyl acetate/hexane=15/85→55/45) to give the title compound (90.2 mg, yield 61%).

$^1$H-NMR (CDCl$_3$) δ: 0.97-1.07 (1H, m), 1.11-1.25 (1H, m), 1.28-1.44 (1H, m), 1.97-2.11 (1H, m), 2.49 (3H, s), 3.38-3.60 (2H, m), 6.34 (1H, s), 6.44-6.49 (3H, m), 8.23 (1H, d, J=6.8 Hz),
melting point: 136-138° C. (recrystallized from diisopropyl ether/hexane),
MS (ESI+): 298 (M+H),
elemental analysis: for $C_{14}H_{14}F_3N_3O$
Calculated (%): C, 56.56; H, 4.75; N, 14.14
Found (%): C, 56.62; H, 4.66; N, 14.13.

Example 47 trans-N-{[2-(2-methylpyrazolo[1,5-a]pyridin-4-yl)cyclopropyl]methyl}cyclopropanecarboxamide

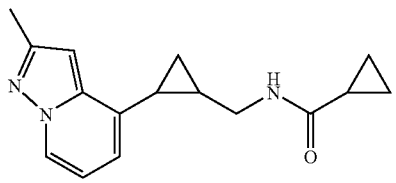

To a solution of trans-1-[2-(2-methylpyrazolo[1,5-a]pyridin-4-yl)cyclopropyl]methanamine (100 mg, 0.497 mmol) and triethylamine (83.2 μL, 0.596 mmol) in tetrahydrofuran (5 mL) was added cyclopropanecarbonyl chloride (49.6 μL, 0.547 mmol) under ice-cooling, and the mixture was stirred under ice-cooling for 10 min. The reaction solution was diluted with saturated aqueous sodium hydrogen carbonate solution. The solvent was evaporated under reduced pressure and the residue was purified by silica gel column chromatography (ethyl acetate/hexane=35/65→90/10) to give the title compound (87.0 mg, yield 65%).

$^1$H-NMR (CDCl$_3$) δ: 0.69-0.83 (2H, m), 0.91-1.17 (4H, m), 1.22-1.44 (2H, m), 1.93-2.03 (1H, m), 2.50 (3H, s), 3.32-3.48 (2H, m), 5.81 (1H, br s), 6.41 (1H, s), 6.52-6.68 (2H, m), 8.21 (1H, d, J=6.8 Hz),
melting point: 133-135° C. (recrystallized from ethyl acetate/hexane),
MS (ESI+): 270 (M+H),
elemental analysis: for $C_{16}H_{19}N_3O$
Calculated (%): C, 71.35; H, 7.11; N, 15.60
Found (%): C, 71.09; H, 7.13; N, 15.42.

Example 48

N-{[(1S,2S)-2-(2-methylpyrazolo[1,5-a]pyridin-4-yl)cyclopropyl]methyl}cyclopropanecarboxamide

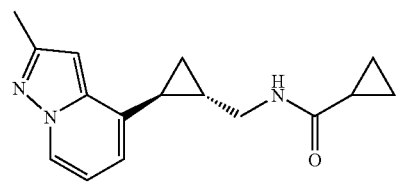

To a suspension of 1-[(1S,2S)-2-(2-methylpyrazolo[1,5-a]pyridin-4-yl)cyclopropyl]methanamine dihydrochloride (750 mg, 2.74 mmol) and triethylamine (1.52 mL, 10.9 mmol) in tetrahydrofuran (27 mL) was added cyclopropanecarbonyl chloride (372 μL, 4.10 mmol) under ice-cooling, and the mixture was stirred at room temperature for 3 hr. Ethanol was added to the reaction solution. The solvent was evaporated under reduced pressure and the residue was purified by silica gel column chromatography (methanol/ethyl acetate=0/100→5/95) to give the title compound (646 mg, yield 88%).

$^1$H-NMR (CDCl$_3$) δ: 0.68-0.83 (2H, m), 0.91-1.05 (3H, m), 1.07-1.16 (1H, m), 1.23-1.42 (2H, m), 1.93-2.03 (1H, m), 2.50 (3H, s), 3.39 (2H, d, J=6.3 Hz), 5.89 (1H, br s), 6.40 (1H, s), 6.50-6.66 (2H, m), 8.20 (1H, d, J=6.9 Hz),
melting point: 124-128° C. (recrystallized from ethyl acetate/hexane),
MS (ESI+): 270 (M+H),
elemental analysis: for $C_{16}H_{19}N_3O$
Calculated (%): C, 71.35; H, 7.11; N, 15.60
Found (%): C, 71.38; H, 7.16; N, 15.68.

Example 49

N-{[(1R,2R)-2-(2-methylpyrazolo[1,5-a]pyridin-4-yl)cyclopropyl]methyl}cyclopropanecarboxamide

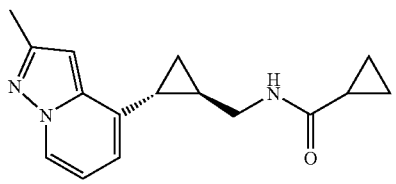

To a suspension of 1-[(1R,2R)-2-(2-methylpyrazolo[1,5-a]pyridin-4-yl)cyclopropyl]methanamine dihydrochloride (750 mg, 2.74 mmol) and triethylamine (1.52 mL, 10.9 mmol) in tetrahydrofuran (27 mL) was added cyclopropanecarbonyl chloride (372 μL, 4.10 mmol) under ice-cooling, and the mixture was stirred at room temperature for 3 hr. Ethanol was added to the reaction solution. The solvent was evaporated under reduced pressure and the residue was purified by silica gel column chromatography (methanol/ethyl acetate=0/100→5/95) to give the title compound (647 mg, yield 88%).

$^1$H-NMR (CDCl$_3$) δ: 0.70-0.82 (2H, m), 0.91-1.06 (3H, m), 1.06-1.16 (1H, m), 1.23-1.42 (2H, m), 1.92-2.04 (1H, m), 2.50 (3H, s), 3.39 (2H, d, J=6.2 Hz), 5.83 (1H, br s), 6.40 (1H, s), 6.50-6.65 (2H, m), 8.20 (1H, d, J=6.6 Hz), melting point: 127-129° C. (recrystallized from ethyl acetate/hexane),

MS (ESI+): 270 (M+H), elemental analysis: for C$_{16}$H$_{19}$N$_3$O

Calculated (%): C, 71.35; H, 7.11; N, 15.60

Found (%): C, 71.35; H, 7.14; N, 15.65.

Example 50 trans-N-{[2-(2-methylpyrazolo[1,5-a]pyridin-4-yl)cyclopropyl]methyl}benzamide

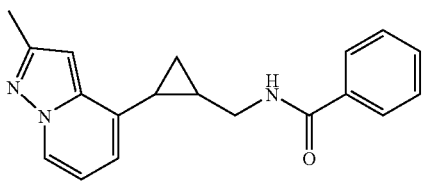

To a solution of trans-1-[2-(2-methylpyrazolo[1,5-a]pyridin-4-yl)cyclopropyl]methanamine (50.0 mg, 0.248 mmol) and triethylamine (41.6 μL, 0.298 mmol) in tetrahydrofuran (2.5 mL) was added benzoyl chloride (31.7 μL, 0.273 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→5/95) 15 and silica gel column chromatography (NH, methanol/ethyl acetate=0/100→5/95) to give the title compound (51.0 mg, yield 67%).

$^1$H-NMR (CDCl$_3$) δ: 0.99-1.10 (1H, m), 1.14-1.23 (1H, m), 1.34-1.46 (1H, m), 2.02-2.11 (1H, m), 2.42 (3H, s), 3.52-3.63 (2H, m), 6.33 (1H, br s), 6.38 (1H, s), 6.56 (1H, t, J=6.9 Hz), 6.61-6.67 (1H, m), 7.39-7.55 (3H, m), 7.77-7.83 (2H, m), 8.20 (1H, d, J=6.6 Hz), melting point: 112-113° C. (recrystallized from ethyl acetate/hexane),

MS (ESI+): 306 (M+H), elemental analysis: for C$_{19}$H$_{19}$N$_3$O

Calculated (%): C, 74.73; H, 6.27; N, 13.76

Found (%): C, 74.58; H, 6.29; N, 13.66.

Example 51 trans-N-ethyl-N'-{[2-(2-methylpyrazolo[1,5-a]pyridin-4-yl)cyclopropyl]methyl}urea

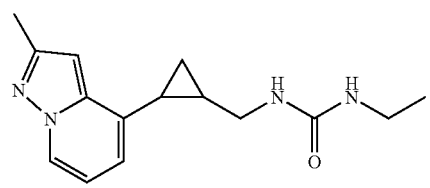

To a solution of trans-1-[2-(2-methylpyrazolo[1,5-a]pyridin-4-yl)cyclopropyl]methanamine (100 mg, 0.497 mmol) in tetrahydrofuran (5 mL) was added isocyanatoethane (43.3 μL, 0.547 mmol) under ice-cooling, and the mixture was stirred under ice-cooling for 10 min. The solvent was evaporated under reduced pressure and the residue was purified by silica gel column chromatography (methanol/ethyl acetate=3/97→15/85) and recrystallization (ethyl acetate/hexane) to give the title compound (52.0 mg, yield 38%).

$^1$H-NMR (CDCl$_3$) δ: 0.86-0.99 (1H, m), 1.00-1.09 (1H, m), 1.14 (3H, t, J=7.2 Hz), 1.27-1.40 (1H, m), 1.86-1.99 (1H, m), 2.48 (3H, s), 3.09-3.43 (4H, m), 4.36 (1H, br s), 4.59 (1H, br s), 6.39 (1H, s), 6.48-6.63 (2H, m), 8.19 (1H, d, J=6.4 Hz), melting point: 108-110° C. (recrystallized from ethyl acetate/hexane),

MS (ESI+): 273 (M+H), elemental analysis: for C$_{15}$H$_{20}$N$_4$O

Calculated (%): C, 66.15; H, 7.40; N, 20.57

Found (%): C, 66.08; H, 7.50; N, 20.22.

Example 52

N-{[2-(2-methylimidazo[1,2-a]pyridin-5-yl)cyclopropyl]methyl}acetamide

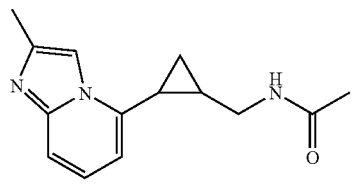

To a solution of 1-[2-(2-methylimidazo[1,2-a]pyridin-5-yl)cyclopropyl]methanamine (47.1 mg, 0.234 mmol) obtained in Reference Example 99 and triethylamine (39.2 μL, 0.281 mmol) in tetrahydrofuran (2.3 mL) was added acetic anhydride (24.3 μL, 0.257 mmol) under ice-cooling, and the mixture was stirred for 5 min. The reaction solution was diluted with saturated aqueous sodium hydrogen carbonate solution. The solvent was evaporated under reduced pressure and the residue was purified by silica gel column chromatography (NH, methanol/ethyl acetate=0/100→10/90) to give the title compound (48.5 mg, yield 85%).

¹H-NMR (CDCl₃) δ: 1.00-1.17 (2H, m), 1.23-1.42 (1H, m), 1.93-2.04 (1H, m), 2.06 (3H, s), 2.50 (3H, s), 3.31-3.59 (2H, m), 5.85 (1H, br s), 6.45 (1H, d, J=7.0 Hz), 7.06 (1H, dd, J=8.8, 7.0 Hz), 7.40 (1H, d, J=8.8 Hz), 7.53 (1H, s), melting point: 170-171° C. (recrystallized from ethanol/ethyl acetate),

MS (ESI+): 244 (M+H), elemental analysis: for $C_{14}H_{17}N_3O$

Calculated (%): C, 69.11; H, 7.04; N, 17.27

Found (%): C, 68.81; H, 6.98; N, 17.14.

Example 53

N-{[2-(2-methylimidazo[1,2-a]pyridin-5-yl)cyclopropyl]methyl}propanamide

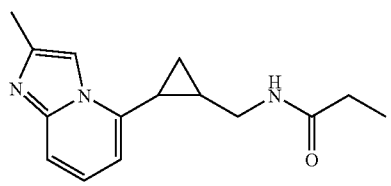

To a solution of 1-[2-(2-methylimidazo[1,2-a]pyridin-5-yl)cyclopropyl]methanamine (47.1 mg, 0.234 mmol) obtained in Reference Example 99 and triethylamine (39.2 μL, 0.281 mmol) in tetrahydrofuran (2.3 mL) was added propionic anhydride (33.0 μL, 0.257 mmol) under ice-cooling, and the mixture was stirred for 5 min. The reaction solution was diluted with saturated aqueous sodium hydrogen carbonate solution. The solvent was evaporated under reduced pressure and the residue was purified by silica gel column chromatography (NH, methanol/ethyl acetate=0/100→10/90) to give the title compound (47.0 mg, yield 78%).

¹H-NMR (CDCl₃) δ: 0.97-1.17 (2H, m), 1.22 (3H, t, J=7.7 Hz), 1.28-1.40 (1H, m), 1.92-2.09 (1H, m), 2.28 (2H, q, J=7.7 Hz), 3.34-3.59 (2H, m), 5.78 (1H, br s), 6.45 (1H, d, J=7.0 Hz), 7.06 (1H, dd, J=8.8, 7.0 Hz), 7.41 (1H, d, J=8.8 Hz), 7.54 (1H, s), melting point: 88-90° C. (recrystallized from ethyl acetate/hexane),

MS (ESI+)': 258 (M+H), elemental analysis: for $C_{15}H_{19}N_3O$

Calculated (%): C, 70.01; H, 7.44; N, 16.33

Found (%): C, 69.71; H, 7.44; N, 16.52.

Example 54

N-({2-[2-(trifluoromethyl)imidazo[1,2-a]pyridin-5-yl]cyclopropyl}methyl)acetamide

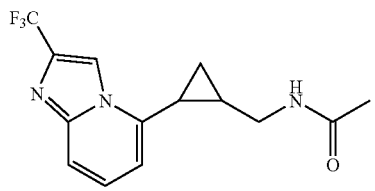

To a solution of {2-[2-(trifluoromethyl)imidazo[1,2-a]pyridin-5-yl]cyclopropyl}methanol (700 mg, 2.73 mmol) obtained in Reference Example 103, triphenylphosphine (1.50 g, 5.73 mmol) and phthalimide (843 mg, 5.73 mmol) in tetrahydrofuran (27 mL) was added a solution (40%, 2.49 mL, 5.46 mmol) of diethyl azodicarboxylate in toluene, and the mixture was stirred at room temperature for 1 hr. The solvent was evaporated under reduced pressure. The residue was purified by silica gel column chromatography (ethyl acetate/hexane=10/90→50/50) to give 2-({2-[2-(trifluoromethyl)imidazo[1,2-a]pyridin-5-yl]cyclopropyl}methyl)-1H-isoindole-1,3(2H)-dione as a crudely purified product.

MS (ESI+): 386 (M+H).

The obtained crudely purified product of 2-({2-[2-(trifluoromethyl)imidazo[1,2-a]pyridin-5-yl]cyclopropyl}methyl)-1H-isoindole-1,3(2H)-dione was dissolved in ethanol (27 mL), hydrazine monohydrate (10 mL) was added, and the mixture was heated under reflux for 30 min. The solvent was evaporated under reduced pressure. The residue was diluted with ethyl acetate, washed with saturated aqueous sodium hydrogen carbonate solution and saturated brine, and dried over anhydrous sodium sulfate. The solvent was evaporated under reduced pressure to give 1-{2-[2-(trifluoromethyl)imidazo[1,2-a]pyridin-5-yl]cyclopropyl}methanamine as a crudely purified product (875 mg).

MS (ESI+): 256 (M+H), 428 mg from the obtained crudely purified product (875 mg) of 1-{2-[2-(trifluoromethyl)imidazo[1,2-a]pyridin-5-yl]cyclopropyl}methanamine and triethylamine (144 μL, 1.03 mmol) were dissolved in tetrahydrofuran (8.6 mL), acetic anhydride (89.4 μL, 0.946 mmol) was added under ice-cooling, and the mixture was stirred for 5 min. The reaction solution was diluted with saturated aqueous sodium hydrogen carbonate solution. The solvent was evaporated under reduced pressure and the residue was purified by silica gel column chromatography (ethyl acetate/hexane=30/70→100/0) to give the title compound (240 mg, yield 59%).

¹H-NMR (CDCl₃) δ: 1.06-1.24 (2H, m), 1.29-1.43 (1H, m), 2.07 (3H, s), 2.07-2.16 (1H, m), 3.34-3.55 (2H, m), 5.87 (1H, br s), 6.61 (1H, d, J=7.1 Hz), 7.19-7.25 (1H, m), 7.56 (1H, d, J=8.8 Hz), 8.19 (1H, s), melting point: 135-137° C. (recrystallized from ethyl acetate/hexane),

MS (ESI+): 298 (M+H), elemental analysis: for $C_{14}H_{14}N_3F_3O$

Calculated (%): C, 56.56; H, 4.75; N, 14.14

Found (%): C, 56.54; H, 4.72; N, 14.24.

Example 55

N-({2-[2-(trifluoromethyl)imidazo[1,2-a]pyridin-5-yl]cyclopropyl}methyl)propanamide

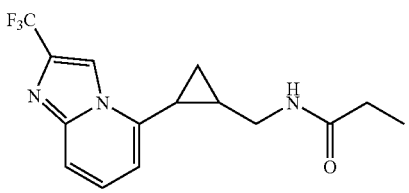

To a solution of {2-[2-(trifluoromethyl)imidazo[1,2-a]pyridin-5-yl]cyclopropyl}methanol (700 mg, 2.73 mmol) obtained in Reference Example 103, triphenylphosphine (1.50 g, 5.73 mmol) and phthalimide (843 mg, 5.73 mmol) in tetrahydrofuran (27 mL) was added a solution (40%, 2.49 mL, 5.46 mmol) of diethyl azodicarboxylate in toluene, and the mixture was stirred at room temperature for 1 hr. The solvent was evaporated under reduced pressure. The residue was purified by silica gel column chromatography (ethyl acetate/hexane=10/90→50/50) to give 2-({2-[2-(trifluoromethyl)imidazo[1,2-a]pyridin-5-yl]cyclopropyl}methyl)-1H-isoindole-1,3(2H)-dione as a crudely purified product.

MS (ESI+): 386 (M+H).

The obtained crudely purified product of 2-({2-[2-(trifluoromethyl)imidazo[1,2-a]pyridin-5-yl]cyclopropyl}methyl)-1H-isoindole-1,3(2H)-dione was dissolved in ethanol (27 mL), hydrazine monohydrate (10 mL) was added, and the mixture was heated under reflux for 30 min. The solvent was evaporated under reduced pressure. The residue was diluted with ethyl acetate, washed with saturated aqueous sodium hydrogen carbonate solution and saturated brine, and dried over anhydrous sodium sulfate. The solvent was evaporated under reduced pressure to give 1-{2-[2-(trifluoromethyl)imidazo[1,2-a]pyridin-5-yl]cyclopropyl}methanamine as a crudely purified product (875 mg).

MS (ESI+): 256 (M+H), 428 mg from the obtained crudely purified product (875 mg) of 1-{2-[2-(trifluoromethyl)imidazo[1,2-a]pyridin-5-yl]cyclopropyl}methanamine and triethylamine (144 µL, 1.03 mmol) were dissolved in tetrahydrofuran (8.6 mL), propionic anhydride (121 µL, 0.946 mmol) was added under ice-cooling, and the mixture was stirred for 5 min. The reaction solution was diluted with saturated aqueous sodium hydrogen carbonate solution. The solvent was evaporated under reduced pressure and the residue was purified by silica gel column chromatography (ethyl acetate/hexane=20/80→100/0) to give the title compound (265 mg, yield 62%).

$^1$H-NMR (CDCl$_3$) δ: 1.07-1.26 (5H, m), 1.30-1.45 (1H, m), 2.03-2.19 (1H, m), 2.29 (2H, q, J=7.7 Hz), 3.30-3.56 (2H, m), 5.85 (1H, br s), 6.61 (1H, d, J=6.9 Hz), 7.18-7.25 (1H, m), 7.56 (1H, d, J=9.3 Hz), 8.18 (1H, s), melting point: 148-151° C. (recrystallized from ethyl acetate/hexane),

MS (ESI+): 312 (M+H), elemental analysis: for C$_{15}$H$_{16}$N$_3$F$_3$O

Calculated (%): C, 57.87; H, 5.18; N, 13.50

Found (%): C, 57.87; H, 5.12; N, 13.60.

Example 56

N-{[2-(2-methyl[1,2,4]triazolo[1,5-a]pyridin-5-yl)cyclopropyl]methyl}acetamide

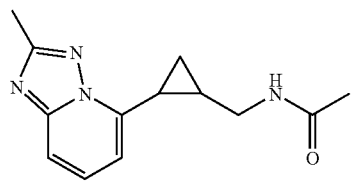

To a solution of 1-[2-(2-methyl[1,2,4]triazolo[1,5-a]pyridin-5-yl)cyclopropyl]methanamine (78 mg, 0.386 mmol) obtained in Reference Example 113 and triethylamine (107 µL, 0.771 mmol) in tetrahydrofuran (4 mL) was added acetic anhydride (43.8 µL, 0.463 mmol), and the mixture was stirred at room temperature for 30 min. The reaction solution was concentrated under reduced pressure, and the residue was purified by recrystallization (ethyl acetate/hexane) to give the title compound (68.4 mg, yield 73%).

$^1$H-NMR (CDCl$_3$) δ: 1.07-1.25 (2H, m), 1.33-1.49 (1H, m), 2.12 (3H, s), 2.13-2.25 (1H, m), 2.57 (1H, t, J=12.1 Hz), 2.68 (3H, s), 4.10-4.18 (1H, m), 6.71 (1H, d, J=7.2 Hz), 7.46 (1H, dd, J=8.7, 7.2 Hz), 7.58 (1H, d, J=8.7 Hz), 7.81 (1H, br s), melting point: 124-126° C. (recrystallized from ethyl acetate/hexane),

MS (ESI+): 245 (M+H).

Example 57

N-{[2-(2-methyl[1,2,4]triazolo[1,5-a]pyridin-5-yl)cyclopropyl]methyl}propanamide

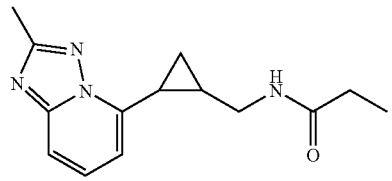

To a suspension of lithium aluminum hydride (141 mg, 3.70 mmol) in tetrahydrofuran (10 mL) was added 2-(2-methyl[1,2,4]triazolo[1,5-a]pyridin-5-yl)cyclopropanecarbaldehyde oxime (200 mg, 0.925 mmol) obtained in Reference Example 112 at room temperature, and the mixture was stirred at room temperature for 2 hr, and at 60° C. for 2 hr. Sodium sulfate decahydrate was added under ice-cooling, and the mixture was filtered through celite. The filtrate was concentrated under reduced pressure to give 1-[2-(2-methyl[1,2,4]triazolo[1,5-a]pyridin-5-yl)cyclopropyl]methanamine as a crudely purified product.

The obtained crudely purified product of 1-[2-(2-methyl[1,2,4]triazolo[1,5-a]pyridin-5-yl)cyclopropyl]methanamine was dissolved in tetrahydrofuran (10 mL), triethylamine (258 µL, 1.85 mmol) and propionic anhydride (143 µL, 1.11 mmol) were added, and the mixture was stirred at room temperature for 1 hr. The reaction solution was concentrated under reduced pressure, and the residue was purified by silica gel column chromatography (methanol/ethyl acetate=0/100→20/80) and silica gel column chromatography (NH, methanol/ethyl acetate=0/100→10/90) to give the title compound (33.0 mg, yield 14%).

$^1$H-NMR (CDCl$_3$) δ: 1.11-1.20 (1H, m), 1.23 (3H, t, J=7.6 Hz), 1.34-1.47 (1H, m), 2.11-2.25 (1H, m), 2.28-2.45 (3H, m), 2.52-2.64 (1H, m), 2.67 (3H, s), 4.06-4.21 (1H, m), 6.70 (1H, d, J=7.1 Hz), 7.44 (1H, dd, J=8.8, 7.1 Hz), 7.59 (1H, d, J=8.8 Hz), 7.64 (1H, br s), melting point: 118-119° C. (recrystallized from ethyl acetate/hexane),

MS (ESI+): 259 (M+H), elemental analysis: for C$_{15}$H$_{19}$N$_3$O

Calculated (%): C, 65.09; H, 7.02; N, 21.69

Found (%): C, 64.94; H, 7.09; N, 21.61.

Example 58

N-{[2-(2-methyl-1,3-benzothiazol-7-yl)cyclopropyl]methyl}acetamide

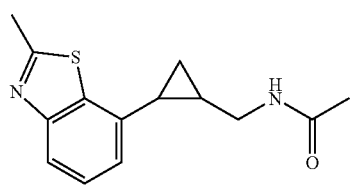

To a solution of 1-[2-(2-methyl-1,3-benzothiazol-7-yl)cyclopropyl]methanamine (58.0 mg, 0.266 mmol) obtained in Reference Example 128 and triethylamine (44.5 μL, 0.319 mmol) in tetrahydrofuran (3 mL) was added acetic anhydride (27.6 μL, 0.292 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→5/95) to give the title compound (62.0 mg, yield 90%).

$^1$H-NMR (CDCl$_3$) δ: 0.95-1.05 (1H, m), 1.10-1.21 (1H, m), 1.34-1.48 (1H, m), 1.92-2.01 (1H, m), 2.03 (3H, s), 2.85 (3H, s), 3.25-3.48 (2H, m), 5.76 (1H, br s), 6.95 (1H, d, J=7.4 Hz), 7.35 (1H, t, J=7.8 Hz), 7.78 (1H, d, J=7.1 Hz), melting point: 96-98° C. (recrystallized from ethyl acetate/hexane),

MS (ESI+): 261 (M+H), elemental analysis: for C$_{14}$H$_{16}$N$_2$OS

Calculated (%): C, 64.58; H, 6.19; N, 10.76

Found (%): C, 64.61; H, 6.28; N, 10.74.

Example 59

N-{[2-(2-methyl-1,3-benzothiazol-7-yl)cyclopropyl]methyl}propanamide

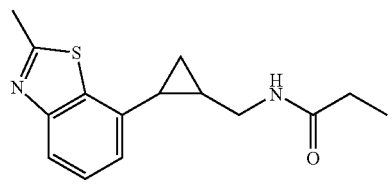

To a solution of 1-[2-(2-methyl-1,3-benzothiazol-7-yl)cyclopropyl]methanamine (58.9 mg, 0.270 mmol) obtained in Reference Example 128 and triethylamine (45.1 μL, 0.323 mmol) in tetrahydrofuran (3 mL) was added propionic anhydride (38.1 μL, 0.297 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→5/95) to give the title compound (67.0 mg, yield 91%).

$^1$H-NMR (CDCl$_3$) δ: 0.95-1.06 (1H, m), 1.09-1.27 (4H, m), 1.32-1.48 (1H, m), 2.26 (2H, q, J=7.6 Hz), 2.85 (3H, s), 3.24-3.50 (2H, m), 5.66 (1H, br s), 6.97 (1H, d, J=7.6 Hz), 7.36 (1H, t, J=7.8 Hz), 7.79 (1H, d, J=8.0 Hz), melting point: 59-61° C. (recrystallized from ethyl acetate/hexane),

MS (ESI+): 275 (M+H), elemental analysis: for C$_{15}$H$_{18}$N$_2$OS

Calculated (%): C, 65.66; H, 6.61; N, 10.21

Found (%): C, 65.32; H, 6.55; N, 10.14.

Example 60

N-{[2-(1,2,3-benzothiadiazol-7-yl)cyclopropyl]methyl}acetamide

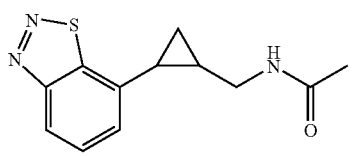

To a solution of 1-[2-(1,2,3-benzothiadiazol-7-yl)cyclopropyl]methanamine (100 mg, 0.487 mmol) obtained in Reference Example 139 and triethylamine (81.4 μL, 0.584 mmol) in tetrahydrofuran (5 mL) was added acetic anhydride (50.7 μL, 0.536 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (108 mg, yield 90%).

$^1$H-NMR (CDCl$_3$) δ: 1.04-1.12 (1H, m), 1.15-1.24 (1H, m), 1.41-1.51 (1H, m), 2.05-2.16 (4H, m), 3.27-3.48 (2H, m), 5.82 (1H, br s), 7.26-7.31 (1H, m), 7.49-7.60 (1H, m), 8.44 (1H, d, J=8.8 Hz), melting point: 81-82° C. (recrystallized from ethyl acetate/hexane),
MS (ESI+): 248 (M+H),
elemental analysis: for $C_{12}H_{13}N_3OS$
Calculated (%): C, 58.28; H, 5.30; N, 16.99
Found (%): C, 58.26; H, 5.30; N, 16.97.

Example 61

N-{[2-(1,2,3-benzothiadiazol-7-yl)cyclopropyl]methyl}propanamide

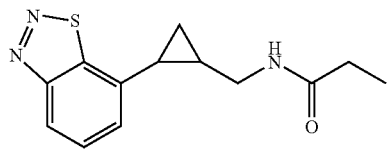

To a solution of 1-[2-(1,2,3-benzothiadiazol-7-yl)cyclopropyl]methanamine (100 mg, 0.487 mmol) obtained in Reference Example 139 and triethylamine (81.4 μL, 0.584 mmol) in tetrahydrofuran (5 mL) was added propionic anhydride (68.8 μL, 0.536 mmol) under ice-cooling, and the mixture was stirred under ice-cooling for 5 min. The reaction solution was diluted with saturated aqueous sodium hydrogen carbonate solution. The solvent was evaporated under reduced pressure and the residue was purified by silica gel column chromatography (methanol/ethyl acetate=0/100→10/90) to give the title compound (121 mg, yield 95%).

$^1$H-NMR (CDCl$_3$) δ: 1.03-1.13 (1H, m), 1.15-1.25 (4H, m), 1.40-1.53 (1H, m), 2.06-2.15 (1H, m), 2.29 (2H, q, J=7.4 Hz), 3.27-3.50 (2H, m), 5.77 (1H, br s), 7.29 (1H, d, J=7.1 Hz), 7.50-7.59 (1H, m), 8.44 (1H, d, J=8.8 Hz),
melting point: 67-69° C. (recrystallized from ethyl acetate/hexane),
MS (ESI+): 262 (M+H),
elemental analysis: for $C_{13}H_{15}N_3OS$
Calculated (%): C, 59.74; H, 5.79; N, 16.08
Found (%): C, 59.85; H, 5.64; N, 16.15.

Example 62

N-{[2-(2,1-benzisothiazol-4-yl)cyclopropyl]methyl}acetamide

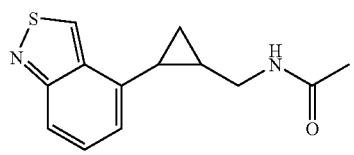

To a solution of 1-[2-(2,1-benzisothiazol-4-yl)cyclopropyl]methanamine (125 mg, 0.612 mmol) obtained in Reference Example 148 and triethylamine (170 μL, 1.22 mmol) in tetrahydrofuran (6 mL) was added acetic anhydride (69.4 μL, 0.734 mmol), and the mixture was stirred at room temperature for 15 min. The reaction solution was concentrated under reduced pressure and the residue was purified by silica gel column chromatography (methanol/ethyl acetate=0/100→5/95) to give the title compound (144 mg, yield 96%).

$^1$H-NMR (CDCl$_3$) δ: 0.93-1.05 (1H, m), 1.07-1.19 (1H, m), 1.22-1.40 (1H, m), 2.02 (3H, s), 2.17-2.30 (1H, m), 3.32-3.53 (2H, m), 5.77 (1H, br s), 6.76 (1H, d, J=6.4 Hz), 7.28-7.37 (1H, m), 7.68 (1H, d, J=9.1 Hz), 9.45 (1H, s),
melting point: 96-97° C. (recrystallized from ethyl acetate/hexane),
MS (ESI+): 247 (M+H),
elemental analysis: for $C_{13}H_{14}N_2OS$
Calculated (%): C, 63.39; H, 5.73; N, 11.37
Found (%): C, 63.37; H, 5.72; N, 11.36.

Example 63

N-{[2-(2,1-benzisothiazol-4-yl)cyclopropyl]methyl}propanamide

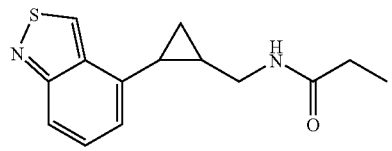

To a solution of 1-[2-(2,1-benzisothiazol-4-yl)cyclopropyl]methanamine (125 mg, 0.612 mmol) obtained in Reference Example 148 and triethylamine (170 μL, 1.22 mmol) in tetrahydrofuran (6 mL) was added propionic anhydride (94 μL, 0.734 mmol), and the mixture was stirred at room temperature for 15 min. The reaction solution was concentrated under reduced pressure and the residue was purified by silica gel column chromatography (ethyl acetate/hexane=80/20→100/0) to give the title compound (127 mg, yield 79%).

$^1$H-NMR (CDCl$_3$) δ: 0.94-1.13 (1H, m), 1.18 (3H, t, J=7.6 Hz), 1.24-1.40 (1H, m), 1.60-1.69 (1H, m), 2.20-2.30 (3H, m), 3.33-3.54 (2H, m), 5.72 (1H, br s), 6.76 (1H, d, J=6.4 Hz), 7.33 (1H, dd, J=8.7, 6.4 Hz), 7.67 (1H, d, J=8.7 Hz), 9.47 (1H, s),
melting point: 84-86° C. (recrystallized from ethyl acetate/hexane),
MS (ESI+): 261 (M+H),
elemental analysis: for $C_{14}H_{16}N_2OS$
Calculated (%): C, 64.58; H, 6.19; N, 10.76
Found (%): C, 64.53; H, 6.12; N, 10.98.

Formulation Example 1

| | |
|---|---|
| (1) Compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is granulated using 10 wt % aqueous gelatin solution (30 mL) (3.0 g as gelatin) by passing a 1 mm mesh sieve, dried at 40° C. and sieved again. The obtained granules are mixed with magnesium stearate (2.0 g) and the mixture is compressed. The obtained core tablets are coated with a sugar coating using an aqueous suspension of saccharose, titanium dioxide, talc and gum arabic. The coated tablets are glazed with beeswax to give 1000 coated tablets.

Formulation Example 2

| (1) Compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Melatonin Receptor Binding Inhibitory Test
(1) Preparation of CHO-hMelR7 Cells expressing Human Melatonin 1 Receptors A cDNA fragment (SEQ ID NO: 1) encoding full-length of human melatonin 1 receptors (human $MT_1$ receptors) was incorporated into expression vector pAKKO-111H (former name pAKKO1.11H; Biochim Biophys Acta. Vol. 1219(2), pp. 251-259, 1994) to give plasmid pAKKO-hMelR7 for animal cell expression. CHO/dhfr-cells (ATCC, #CRL-9096) were plated at a concentration of $0.3 \times 10^6$ cells/dish in a 6 cm culture dish (Becton Dickinson), and cultured under the conditions of 37° C., 5% $CO_2$ for 48 hr. The cells were transfected with pAKKO-hMelR7 plasmid DNA (5 μg) using Cellphect Transfection Kit (Amersham, #27-9268-01). The transfected cells were cultured in Dulbecco's modified Eagle medium (DMEM) (Sigma, #D6046) containing 10% dialyzed FBS (Biowest, #S180D), 1× Non-Essential Amino Acid (Invitrogen, #11140-050) and 50 μg/mL Gentamycin (Invitrogen, #15750-060), and the cell line that stably expressed the plasmid gene was selected. By a receptor binding assay using 2-[$^{125}$I] Iodomelatonin, CHO-hMelR7 cell line showing specific binding of 2-[$^{125}$I] Iodomelatonin was selected from the obtained clones.
(2) Preparation of CHO-hMT2 Cells Expressing Human Melatonin 2 Receptors A cDNA fragment (SEQ ID NO: 2) encoding full-length of human melatonin 2 receptors (human $MT_2$ receptors) was incorporated into expression vector pCMV-Script (Stratagene, #212220) to give the plasmid that was pCMV-human MT2 receptors expression vector for animal cell expression. CHO-K1 cells (ATCC, #CCL-61) were plated at the concentration of $1.5 \times 10^5$ cells/cm² in a 6 well plate (ASAHI TECHNO GLASS), and cultured under the conditions of 37° C., 5% $CO_2$ for 24 hr. For gene transfection, solution obtained by blending pCMV-human MT2 receptors expression vector (1.9 μg), Lipofectamine Transfection Reagent (Invitrogen, #18324-012) (11.3 μL) and Minimum Essential Medium Eagle (MEM) medium (Sigma, M8042) (93.8 μL), and reacting at room temperature for 20 min was added to the cells per one well. The transfected cells were cultured in MEM medium containing 10% FBS (Life Technology) and 300 μg/mL Geneticin (GIBCO, #10131), and the cell line that stably expressed the plasmid gene was selected. By a receptor binding assay using 2-[$^{125}$I] Iodomelatonin, CHO-hMT2 cell line showing specific binding of 2-[$^{125}$I] Iodomelatonin was selected from the obtained clones.
(3) Preparation of Cellular Membrane Fraction of CHO Cell (CHO-hMelR7 and CHO-hMT2) Stably Expressing Human $MT_1$ and $MT_2$ Receptors CHO-hMelR7 and CHO-hMT2 cells were plated using Cellfactory (Nunc, #170009) under the conditions of $1 \times 10^8$ cells/2000 mL/flask. The cells were grown to confluent, and recovered by the following method. As the medium for CHO-hMelR7 and CHO-hMT2, MEM a containing 10% FBS and penicillin/streptomycin was used. 300 ng/mL of geneticin was added to the medium for CHO-hMT2.

The medium was discarded, cells were washed twice with 200 mL of EDTA/PBS(−), 200 mL of EDTA/PBS(−) was further added, and the cells were stood still at room temperature for 20 min until they were released. The cells were recovered in four 50 mL tubes (Becton Dickinson, #352070), and centrifuged at 1,500 rpm for 10 min at 4° C. using a low speed cooling centrifuge (Hitachi, CF7D2). The supernatant was discarded, the pellets in the four tubes were suspended in 10 mL of PBS(−), and combined in one tube (Becton Dickinson, #352070). The mixture was further centrifuged at 1,500 rpm for 10 min at 4° C., and the obtained pellets were suspended in 20 mL of ice-cooled homogenizing buffer [10 mM $NaHCO_3$, 5 mM EDTA, Protease inhibitor Complete (Roche), pH 7.4]. The cell suspension was homogenized 3 times using a polytron homogenizer at 20,000 rpm for 30 sec. The obtained homogenate was centrifuged (2,000 rpm, 10 min, 4° C.) using a low speed cooling centrifuge. The supernatant was recovered in an ultracentrifugation tube and ultracentrifuged (40,000 rpm, 60 min, 4° C.) using an ultracentrifuge (Beckman, L-90K). To the obtained pellets was added a suspending buffer [50 mM Tris-HCl, 1 mM EDTA, Protease inhibitor Complete (Roche), pH 7.4], and the pellets were suspended by pipetting. The protein concentration of this suspension was measured, diluted to 2 mg/mL to give cellular membrane fractions of CHO-hMelR7 and CHO-hMT2 cells. The membrane fractions were dispensed to 1.5 mL tubes (Eppendorf, #0030120.086) by 100 μL, preserved in a freezer (−80° C.) and used for a binding assay. Protein was quantified using BCA protein assay kit (Pierce) with BSA as the standard.
(4) Preparation of Membrane Fraction Suspension Immediately before use, the membrane fractions of CHO-hMelR7 and CHO-hMT2 cells of the above-mentioned (3) were diluted 20-fold with assay buffer (50 mM Tris-HCl, pH 7.7).
(5) Preparation of 2-[$^{125}$I] Iodomelatonin Solution 2-[$^{125}$I] Iodomelatonin (#NEX236, PerkinElmer) was diluted with the assay buffer to 400 pM for $MT_1$ and 1 nM for $MT_2$.
(6) Binding Reaction The assay buffer (80 μL) of the above-mentioned (4) was added to each well of a 96-well plate (type 3363, Corning). Then, a test compound (compound solution diluted with DMSO to 200-fold of the final measurement concentration) was added by 2 μL. 2 μL of DMSO was added to each well of the total binding control section, and 100 μM cold Melatonin solution (Sigma, diluted with DMSO to 100 μM) was added to each well of the nonspecific binding control section by 2 μL. Then, the membrane fraction suspension (100 μL) was added. 2-[$^{125}$I] Iodomelatonin solution of the above-mentioned (5) was added to each well mentioned above by 20 μL, and a binding reaction was carried out at 25° C. for 2.5 hr in a micromixer (TAITEC, Bioshaker M.BR-024).

(7) Measurement

Using a cell harvester (PerkinElmer), the binding reaction mixture in each well of the 96-well plate was transferred to a treated (immersed in 50 mM Tris, pH 7.7 in advance) filter plate (UniFilter GF/C, PerkinElmer) and filtered. After filtration, the plate was washed 4 times with the assay buffer, and dried in a dryer (42° C.) for 2 hr or more. 25 μL of a liquid scintillator (MicroScint O, PerkinElmer) was added to each well of the filter plate after drying, and the luminescence of scintillator was measured by TopCount (PerkinElmer) for 1 min.

Specific binding is a value obtained by subtracting nonspecific binding from the total binding. The binding inhibitory activity of the test compound is shown by the ratio of the value obtained by subtracting the measurement value when the test compound was added from the total binding, to the specific binding. The compound concentration ($IC_{50}$ value) showing 50% of binding inhibitory activity was calculated from the dose reaction curve.

The binding inhibitory activity of the compound of Examples 1, 2, 3, 4, 5, 6, 10, 11, 12, 13, 14, 16, 17, 18, 19, 23, 24, 25, 26, 27, 28, 29, 30, 31, 32, 33, 34, 35, 36, 37, 38, 39, 43, 44, 45, 46, 47, 48, 49, 51, 52, 53, 56, 57, 58, 59, 60, 61, 62 and 63 was not more than 100 nM as $IC_{50}$ value for $MT_1$.

The binding inhibitory activity of the compound of Examples 1, 2, 4, 5, 6, 10, 11, 12, 13, 14, 16, 17, 18, 19, 23, 24, 25, 26, 27, 28, 29, 30, 31, 32, 33, 34, 35, 36, 37, 38, 39, 43, 44, 45, 46, 47, 48, 49, 51, 52, 53, 56, 57, 58, 59, 60, 61, 62 and 63 was not more than 100 nM as $IC_{50}$ value for $MT_2$.

This application is based on application No. 2007-117676 filed in Japan, the contents of which are incorporated hereinto by reference.

---

The invention claimed is:
1. A compound represented by the formula:

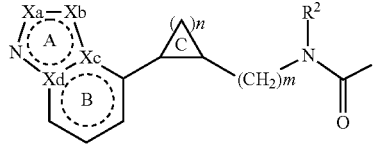

(I)

wherein
R¹ is a hydrocarbon group optionally having substituent(s), amino optionally having substituent(s), hydroxy optionally having a substituent or a heterocyclic group optionally having substituent(s),
R² is a hydrogen atom or a hydrocarbon group optionally having substituent(s),
Xa and Xb are each a carbon atom, a nitrogen atom, an oxygen atom or a sulfur atom,
Xc and Xd are each a carbon atom or a nitrogen atom,
m is 0, 1 or 2,
n is 1, 2 or 3,
ring A is a 5-membered ring optionally having substituent(s),
ring B is a 6-membered ring optionally having substituent(s),
ring C is a 3- to 5-membered ring optionally having substituent(s), and
------ is a single bond or a double bond,
provided that when Xa, Xc and Xd are carbon atoms, then Xb is a nitrogen atom or a sulfur atom, or a salt thereof.

2. The compound of claim 1, wherein the bicyclic ring consisting of ring A and ring B is a ring represented by the formula

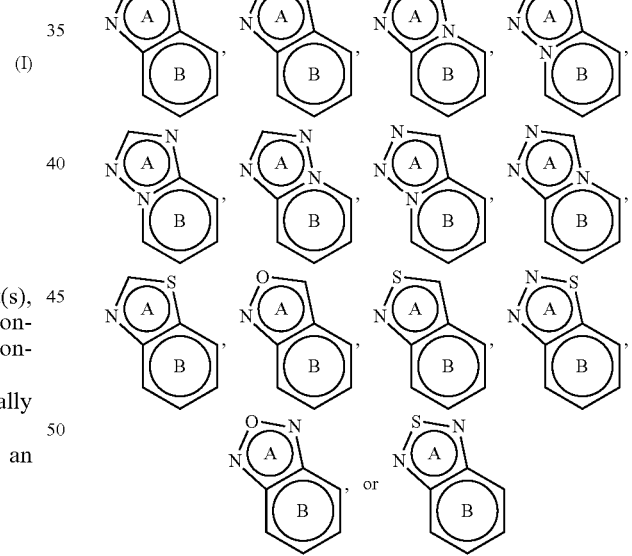

wherein each symbol is as defined in claim 1.

3. The compound of claim 1, wherein R¹ is $C_{1-6}$ alkyl optionally having substituent(s), $C_{3-6}$ cycloalkyl optionally having substituent(s), $C_{2-6}$ alkenyl optionally having substituent(s), $C_{6-14}$ aryl optionally having substituent(s), amino optionally having substituent(s) or hydroxy optionally having a substituent.

4. The compound of claim 1, wherein R² is a hydrogen atom or $C_{1-6}$ alkyl optionally having substituent(s).

5. The compound of claim 1, wherein m is 1.

6. The compound of claim 1, wherein n is 1.

7. The compound of claim 1, wherein ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent.

8. The compound of claim 1, wherein ring B is a 6-membered ring optionally having 1 to 3 substituents selected from a halogen atom, cyano, a hydrocarbon group optionally having substituent(s), amino optionally having substituent(s), hydroxy optionally having a substituent, mercapto optionally having a substituent and a heterocyclic group optionally having substituent(s).

9. The compound of claim 1, wherein ring C is $C_{3-5}$ cycloalkane optionally having 1 to 4 substituents selected from a hydrocarbon group optionally having substituent(s) and a halogen atom.

10. N-{[2-(2-Methyl-2H-indazol-4-yl)cyclopropyl]methyl}acetamide, N-{[2-(2-methyl-2H-indazol-4-yl)cyclopropyl]methyl}propanamide, N-{[2-(2-methylpyrazolo[1,5-a]pyridin-4-yl)cyclopropyl]methyl}acetamide, N-{[2-(2-methylpyrazolo[1,5-a]pyridin-4-yl)cyclopropyl]methyl}propanamide, N-{[2-(3-fluoro-2-methyl-2H-indazol-4-yl)cyclopropyl]methyl}acetamide, N-{[2-(5-fluoro-2-methyl-2H-indazol-4-yl)cyclopropyl]methyl}acetamide, N-{[2-(7-fluoro-2-methyl-2H-indazol-4-yl)cyclopropyl]methyl}acetamide, N-{[2-(2-methylpyrazolo[1,5-a]pyridin-4-yl)cyclopropyl]methyl}cyclopropanecarboxamide, or N-{[2-(2-methyl-1,3-benzothiazol-7-yl)cyclopropyl]methyl}acetamide, or a salt thereof.

11. A prodrug of the compound of claim 1.

12. A pharmaceutical composition comprising the compound of claim 1 or a prodrug thereof.

13. The pharmaceutical composition of claim 12, which is a melatonin receptor agonist.

14. The pharmaceutical composition of claim 12, which is an agent for the treatment of sleep disorder.

15. A compound represented by the formula

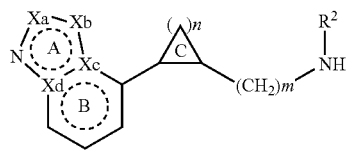

wherein each symbol is as defined in claim 1, or a salt thereof.

16. A method for treating sleep disorder in a mammal, comprising administering an effective amount of the compound of claim 1 or a salt thereof or a prodrug thereof to the mammal.

17. A method for treating bipolar disorder in a mammal, comprising administering an effective amount of the compound of claim 1 or a salt thereof or a prodrug thereof to the mammal.

* * * * *

SEQUENCE LISTING

```
<160> NUMBER OF SEQ ID NOS: 2

<210> SEQ ID NO 1
<211> LENGTH: 1053
<212> TYPE: DNA
<213> ORGANISM: Homo sapiens

<400> SEQUENCE: 1
atgcagggca acggcagcgc gctgcccaac gcctcccagc ccgtgctccg cggggacggc      60
gcgcggccct cgtggctggc gtccgccctg gcctgcgtcc tcatcttcac catcgtggtg     120
gacatcctgg gcaacctcct ggtcatcctg tcggtgtatc ggaacaagaa gctcaggaac     180
gcaggaaaca tctttgtggt gagcttagcg gtggcagacc tggtggtggc catttatccg     240
tacccgttgg tgctgatgtc gatatttaac aacgggtgga acctgggcta tctgcactgc     300
caagtcagtg ggttcctgat gggcctgagc gtcatcggcc ccatattcaa catcaccggc     360
atcgccatca accgctactg ctacatctgc cacagtctca agtacgacaa actgtacagc     420
agcaagaact ccctctgcta cgtgctcctc atatggctcc tgacgctggc ggccgtcctg     480
cccaacctcc gtgcagggac tctccagtac gacccgagga tctactcgtg caccttcgcc     540
cagtccgtca gctccgccta caccatcgcc gtggtggttt tccacttcct cgtccccatg     600
atcatagtca tcttctgtta cctgagaata tggatcctgg ttctccaggt cagacagagg     660
gtgaaacctg accgcaaacc caaactgaaa ccacaggact tcaggaattt tgtcaccatg     720
tttgtggttt ttgtcctttt tgccatttgc tgggctcctc tgaacttcat tggcctggcc     780
gtggcctctg accccgccag catggtgcct aggatcccag agtggctgtt tgtggccagt     840
tactacatgg cgtatttcaa cagctgcctc aatgccatta tacgggct actgaaccaa     900 aatttcagga aggaatacag gagaattata gtctcgctct gtacagccag ggtgttcttt     960
gtggacagct ctaacgacgt ggccgatagg gttaaatgga aaccgtctcc actgatgacc    1020
aacaataatg tagtaaaggt ggactccgtt taa                                  1053

<210> SEQ ID NO 2
<211> LENGTH: 1089
<212> TYPE: DNA
<213> ORGANISM: Homo sapiens

<400> SEQUENCE: 2
atgtcagaga acgctccttt cgccaactgc tgcgaggcgg gcgggtgggc agtgcgcccg       60
ggctggtcgg gggctggcag cgcgcggccc tccaggaccc ctcgacctcc ctgggtggct     120
```

```
ccagcgctgt ccgcggtgct catcgtcacc accgccgtgg acgtcgtggg caacctcctg    180
gtgatcctct ccgtgctcag gaaccgcaag ctccggaacg caggtaattt gttcttggtg    240
agtctggcat tggctgacct ggtggtggcc ttctacccct acccgctaat cctcgtggcc    300
atcttctatg acggctgggc cctggggag gagcactgca aggccagcgc ctttgtgatg    360
ggcctgagcg tcatcggctc tgtcttcaat atcactgcca tcgccattaa ccgctactgc    420
tacatctgcc acagcatggc ctaccaccga atctaccggc gctggcacac ccctctgcac    480
atctgcctca tctggctcct caccgtggtg gccttgctgc ccaacttctt tgtggggtcc    540
ctggagtacg acccacgcat ctattcctgc accttcatcc agaccgccag cacccagtac    600
acggcggcag tggtggtcat ccacttcctc ctccctatcg ctgtcgtgtc cttctgctac    660
ctgcgcatct gggtgctggt gcttcaggcc cgcaggaaag ccaagccaga gagcaggctg    720
tgcctgaagc ccagcgactt gcggagcttt ctaaccatgt ttgtggtgtt tgtgatcttt    780
gccatctgct gggctccact taactgcatc ggcctcgctg tggccatcaa cccccaagaa    840
atggctcccc agatccctga ggggctattt gtcactagct acttactggc ttatttcaac    900
agctgcctga atgccattgt ctatgggctc ttgaaccaaa acttccgcag ggaatacaag    960
aggatcctct tggccctttg gaacccacgg cactgcattc aagatgcttc caagggcagc   1020
cacgcggagg ggctgcagag cccagctcca cccatcattg gtgtgcagca ccaggcagat   1080
gctctctag                                                            1089
```